United States Patent
Byrne et al.

(10) Patent No.: US 10,808,247 B2
(45) Date of Patent: Oct. 20, 2020

(54) METHODS FOR TREATING NEUROLOGICAL DISORDERS USING A SYNERGISTIC SMALL MOLECULE AND NUCLEIC ACIDS THERAPEUTIC APPROACH

(71) Applicants: Phio Pharmaceuticals Corp., Marlborough, MA (US); Synaerion Therapeutics, Berwyn, PA (US)

(72) Inventors: Michael Byrne, Natick, MA (US); Antonella Favit-VanPelt, Norwell, MA (US)

(73) Assignees: Phio Pharmaceuticals Corp., Marlborough, MA (US); Synaerion Therapeutics, Berwyn, PA (US)

( * ) Notice: Subject to any disclaimer, the term of this patent is extended or adjusted under 35 U.S.C. 154(b) by 0 days.

(21) Appl. No.: 15/742,117

(22) PCT Filed: Jul. 6, 2016

(86) PCT No.: PCT/US2016/041147
§ 371 (c)(1),
(2) Date: Jan. 5, 2018

(87) PCT Pub. No.: WO2017/007825
PCT Pub. Date: Jan. 12, 2017

(65) Prior Publication Data
US 2018/0195066 A1 Jul. 12, 2018

Related U.S. Application Data

(60) Provisional application No. 62/189,142, filed on Jul. 6, 2015.

(51) Int. Cl.
| | |
|---|---|
| *C12N 15/113* | (2010.01) |
| *C12N 15/11* | (2006.01) |
| *A61P 25/28* | (2006.01) |
| *A61K 31/713* | (2006.01) |
| *A61K 31/36* | (2006.01) |
| *A61K 31/444* | (2006.01) |

(52) U.S. Cl.
CPC ......... *C12N 15/113* (2013.01); *A61K 31/713* (2013.01); *A61P 25/28* (2018.01); *C12N 15/111* (2013.01); *A61K 31/36* (2013.01); *A61K 31/444* (2013.01); *A61K 2300/00* (2013.01); *C12N 2310/11* (2013.01); *C12N 2310/315* (2013.01); *C12N 2320/31* (2013.01)

(58) Field of Classification Search
CPC ............. C12N 15/113; C12N 2310/31; C12N 15/315; C12N 15/321; C12N 15/3515; C12N 15/3521; C12N 2320/30
USPC ..... 424/450; 435/6.1, 91.1, 91.31, 455, 458; 514/7.4, 17.7, 17.8, 44 A, 44 R; 536/23.1, 24.5; 530/350
See application file for complete search history.

(56) References Cited

U.S. PATENT DOCUMENTS

| | | |
|---|---|---|
| 3,687,808 A | 8/1972 | Merigan et al. |
| 4,201,860 A | 5/1980 | Naito et al. |
| 4,235,871 A | 11/1980 | Papahadjopoulos et al. |
| 4,415,732 A | 11/1983 | Caruthers et al. |
| 4,426,330 A | 1/1984 | Sears |
| 4,501,728 A | 2/1985 | Geho et al. |
| 4,737,323 A | 4/1988 | Martin et al. |
| 4,810,646 A | 3/1989 | Jamas et al. |
| 4,837,028 A | 6/1989 | Allen |
| 4,853,386 A | 8/1989 | Friebe et al. |
| 4,897,355 A | 1/1990 | Eppstein et al. |
| 4,904,582 A | 2/1990 | Tullis |
| 4,958,013 A | 9/1990 | Letsinger |
| 4,992,540 A | 2/1991 | Jamas et al. |
| 5,023,243 A | 6/1991 | Tullis |
| 5,028,703 A | 7/1991 | Jamas et al. |
| 5,032,401 A | 7/1991 | Jamas et al. |
| 5,082,936 A | 1/1992 | Jamas et al. |
| 5,112,963 A | 5/1992 | Pieles et al. |
| 5,151,510 A | 9/1992 | Stec et al. |
| 5,188,897 A | 2/1993 | Suhadolnik et al. |
| 5,264,423 A | 11/1993 | Cohen et al. |
| 5,264,562 A | 11/1993 | Matteucci |
| 5,322,841 A | 6/1994 | Jamas et al. |
| 5,401,727 A | 3/1995 | Rorstad et al. |
| 5,405,939 A | 4/1995 | Suhadolnik |

(Continued)

FOREIGN PATENT DOCUMENTS

| | | |
|---|---|---|
| AU | 2004206255 B2 | 8/2004 |
| CN | 1 568 373 S | 1/2005 |

(Continued)

OTHER PUBLICATIONS

Fassio et al, Human Molec. Genetics, vol. 20, No. 12, pp. 2297-2307 (Year: 2011).*
[No Author Listed] RedChip Small-Cap Investor Conference. RXI Pharmaceuticals (Nasdaq RXII). Jun. 16, 2009 Presentation. 22 pages.
[No Author Listed] Rxi Pharmaceutical Corporation. Ex 99.1. OTC: RXII. Mar. 2013. 38 pages.
[No Author Listed], Rxi Pharmaceuticals Presents Self-Delivering RNAi Data at Scar Club Meeting in France. Drugs.com. Mar. 26, 2010. http://www.drugs.com/clinical_trials/rxi-pharmaceuticals-presents-self-delivering-rnai-data-scar-club-meeting-france-9093.html [last accessed Aug. 19, 2014].

(Continued)

*Primary Examiner* — Jane J Zara
(74) *Attorney, Agent, or Firm* — Wolf, Greenfield & Sacks, P.C.

(57) ABSTRACT

In one aspect, the disclosure provides methods for treating a neurodegenerative disorder, comprising administering to a subject in need thereof a therapeutically effective amount of a nucleic acid molecule and a therapeutically effective amount of a small molecule that activates NF-κB p65 and increases expression of manganese superoxide dismutase (MnSOD/SOD2) and/or expression of a related protein or enzyme.

14 Claims, 6 Drawing Sheets
Specification includes a Sequence Listing.

(56) References Cited

U.S. PATENT DOCUMENTS

| | | |
|---|---|---|
| 5,414,077 A | 5/1995 | Lin et al. |
| 5,416,203 A | 5/1995 | Letsinger |
| 5,417,978 A | 5/1995 | Tari et al. |
| 5,419,966 A | 5/1995 | Reed et al. |
| 5,432,272 A | 7/1995 | Benner |
| 5,453,496 A | 9/1995 | Caruthers et al. |
| 5,459,255 A | 10/1995 | Cook et al. |
| 5,466,786 A | 11/1995 | Buhr et al. |
| 5,470,967 A | 11/1995 | Huie et al. |
| 5,486,603 A | 1/1996 | Buhr |
| 5,489,677 A | 2/1996 | Sanghvi et al. |
| 5,495,009 A | 2/1996 | Matteucci et al. |
| 5,504,079 A | 4/1996 | Jamas et al. |
| 5,512,667 A | 4/1996 | Reed et al. |
| 5,514,786 A | 5/1996 | Cook et al. |
| 5,532,130 A | 7/1996 | Alul |
| 5,534,259 A | 7/1996 | Zalipsky et al. |
| 5,556,948 A | 9/1996 | Tagawa et al. |
| 5,561,225 A | 10/1996 | Maddry et al. |
| 5,578,718 A | 11/1996 | Cook et al. |
| 5,580,731 A | 12/1996 | Chang et al. |
| 5,580,972 A | 12/1996 | Tu et al. |
| 5,587,469 A | 12/1996 | Cook et al. |
| 5,591,721 A | 1/1997 | Agrawal et al. |
| 5,591,722 A | 1/1997 | Montgomery et al. |
| 5,591,843 A | 1/1997 | Eaton |
| 5,594,121 A | 1/1997 | Froehler et al. |
| 5,596,086 A | 1/1997 | Matteucci et al. |
| 5,596,091 A | 1/1997 | Switzer |
| 5,599,797 A | 2/1997 | Cook et al. |
| 5,602,240 A | 2/1997 | De Mesmaeker et al. |
| 5,607,677 A | 3/1997 | Jamas et al. |
| 5,607,923 A | 3/1997 | Cook et al. |
| 5,614,617 A | 3/1997 | Cook et al. |
| 5,614,621 A | 3/1997 | Ravikumar et al. |
| 5,623,070 A | 4/1997 | Cook et al. |
| 5,625,050 A | 4/1997 | Beaton et al. |
| 5,633,360 A | 5/1997 | Bischofberger et al. |
| 5,643,889 A | 7/1997 | Suhadolnik et al. |
| 5,646,126 A | 7/1997 | Cheng et al. |
| 5,646,265 A | 7/1997 | McGee |
| 5,652,359 A | 7/1997 | Meyer, Jr. et al. |
| 5,658,731 A | 8/1997 | Sproat et al. |
| 5,661,134 A | 8/1997 | Cook et al. |
| 5,663,312 A | 9/1997 | Chaturvedula |
| 5,670,633 A | 9/1997 | Cook et al. |
| 5,681,940 A | 10/1997 | Wang et al. |
| 5,681,941 A | 10/1997 | Cook et al. |
| 5,684,143 A | 11/1997 | Gryaznov et al. |
| 5,700,920 A | 12/1997 | Altmann et al. |
| 5,736,392 A | 4/1998 | Hawley-Nelson et al. |
| 5,750,666 A | 5/1998 | Caruthers et al. |
| 5,767,099 A | 6/1998 | Harris et al. |
| 5,770,713 A | 6/1998 | Imbach et al. |
| 5,777,153 A | 7/1998 | Lin et al. |
| 5,780,053 A | 7/1998 | Ashley et al. |
| 5,789,416 A | 8/1998 | Lum et al. |
| 5,792,847 A | 8/1998 | Buhr et al. |
| 5,808,023 A | 9/1998 | Sanghvi et al. |
| 5,814,014 A | 9/1998 | Elsberry et al. |
| 5,817,781 A | 10/1998 | Swaminathan et al. |
| 5,830,430 A | 11/1998 | Unger et al. |
| 5,830,653 A | 11/1998 | Froehler et al. |
| 5,849,902 A | 12/1998 | Arrow et al. |
| 5,851,548 A | 12/1998 | Dattagupta et al. |
| 5,855,910 A | 1/1999 | Ashley et al. |
| 5,856,455 A | 1/1999 | Cook |
| 5,914,396 A | 6/1999 | Cook et al. |
| 5,945,521 A | 8/1999 | Just et al. |
| 5,948,767 A | 9/1999 | Scheule et al. |
| 5,968,811 A | 10/1999 | Greenshields |
| 5,969,116 A | 10/1999 | Martin |
| 5,976,567 A | 11/1999 | Wheeler et al. |
| 5,981,501 A | 11/1999 | Wheeler et al. |
| 5,986,083 A | 11/1999 | Dwyer et al. |
| 6,001,841 A | 12/1999 | Cook et al. |
| 6,005,096 A | 12/1999 | Matteucci et al. |
| 6,015,886 A | 1/2000 | Dale et al. |
| 6,020,475 A | 2/2000 | Capaldi et al. |
| 6,020,483 A | 2/2000 | Beckvermit et al. |
| 6,028,183 A | 2/2000 | Lin et al. |
| 6,043,352 A | 3/2000 | Manoharan et al. |
| 6,051,699 A | 4/2000 | Ravikumar |
| 6,093,180 A | 7/2000 | Elsberry |
| 6,107,094 A | 8/2000 | Crooke |
| 6,111,085 A | 8/2000 | Cook et al. |
| 6,121,437 A | 9/2000 | Guzaev |
| 6,153,737 A | 11/2000 | Manoharan et al. |
| 6,207,819 B1 | 3/2001 | Manoharan et al. |
| 6,242,594 B1 | 6/2001 | Kelly |
| 6,248,878 B1 | 6/2001 | Matulic-Adamic et al. |
| 6,271,358 B1 | 8/2001 | Manoharan et al. |
| 6,326,358 B1 | 12/2001 | Manoharan |
| 6,331,617 B1 | 12/2001 | Weeks et al. |
| 6,335,434 B1 | 1/2002 | Guzaev et al. |
| 6,344,323 B1 | 2/2002 | Seifert |
| 6,355,787 B1 | 3/2002 | Beckvermit et al. |
| 6,358,931 B1 | 3/2002 | Cook et al. |
| 6,395,492 B1 | 5/2002 | Manoharan et al. |
| 6,399,754 B1 | 6/2002 | Cook |
| 6,410,702 B1 | 6/2002 | Swaminathan et al. |
| 6,420,549 B1 | 7/2002 | Cook et al. |
| 6,432,963 B1 | 8/2002 | Hisamichi et al. |
| 6,440,943 B1 | 8/2002 | Cook et al. |
| 6,444,448 B1 | 9/2002 | Wheatcroft et al. |
| 6,444,806 B1 | 9/2002 | Veerapanani et al. |
| 6,455,586 B1 | 9/2002 | Kaplan et al. |
| 6,465,628 B1 | 10/2002 | Ravikumar et al. |
| 6,476,003 B1 | 11/2002 | Jordan et al. |
| 6,476,205 B1 | 11/2002 | Buhr et al. |
| 6,506,559 B1 | 1/2003 | Fire et al. |
| 6,528,631 B1 | 3/2003 | Cook et al. |
| 6,531,584 B1 | 3/2003 | Cook et al. |
| 6,673,611 B2 | 1/2004 | Thompson et al. |
| 6,683,167 B2 | 1/2004 | Meteley et al. |
| 6,815,432 B2 | 11/2004 | Wheeler et al. |
| 6,849,726 B2 | 2/2005 | Usman et al. |
| 6,858,225 B2 | 2/2005 | Semple et al. |
| 7,041,824 B2 | 5/2006 | Bordon-Pallier et al. |
| 7,056,704 B2 | 6/2006 | Tuschl et al. |
| 7,078,196 B2 | 7/2006 | Tuschl et al. |
| 7,132,530 B2 | 11/2006 | Bennett et al. |
| 7,205,297 B2 | 4/2007 | Beauchamp et al. |
| 7,432,250 B2 | 10/2008 | Crooke |
| 7,538,095 B2 | 5/2009 | Fire et al. |
| 7,560,438 B2 | 7/2009 | Fire et al. |
| 7,595,387 B2 | 9/2009 | Leake et al. |
| 7,622,455 B2 | 11/2009 | Bennett et al. |
| 7,622,633 B2 | 11/2009 | Fire et al. |
| 7,629,321 B2 | 12/2009 | Crooke |
| 7,695,902 B2 | 4/2010 | Crooke |
| 7,745,608 B2 | 6/2010 | Manoharan et al. |
| 7,750,144 B2 | 7/2010 | Zamore et al. |
| 7,786,290 B2 | 8/2010 | Woppmann et al. |
| 7,829,693 B2 | 11/2010 | Kreutzer et al. |
| 7,902,163 B2 | 3/2011 | Bennett et al. |
| 8,110,674 B2 | 2/2012 | Manoharan et al. |
| 8,263,569 B2 | 9/2012 | Baulcombe et al. |
| 8,664,189 B2 | 3/2014 | Khvorova et al. |
| 8,796,443 B2 | 8/2014 | Khvorova et al. |
| 8,815,818 B2 | 8/2014 | Samarsky et al. |
| 9,074,211 B2 | 7/2015 | Woolf et al. |
| 9,080,171 B2 | 7/2015 | Khvorova et al. |
| 9,095,504 B2 | 8/2015 | Libertine et al. |
| 9,175,289 B2 | 11/2015 | Khvorova et al. |
| 9,222,092 B2 | 12/2015 | Giese et al. |
| 9,303,259 B2 | 4/2016 | Khvorova et al. |
| 9,340,786 B2 | 5/2016 | Khvorova et al. |
| 9,493,774 B2 | 11/2016 | Kamens et al. |
| 9,745,574 B2 | 8/2017 | Woolf et al. |
| 9,938,530 B2 | 4/2018 | Khvorova et al. |
| 9,963,702 B2 | 5/2018 | Khvorova et al. |
| 10,041,073 B2 | 8/2018 | Khvorova et al. |
| 10,131,904 B2 | 11/2018 | Pavco et al. |

(56) References Cited

U.S. PATENT DOCUMENTS

| | | |
|---|---|---|
| 10,138,485 B2 | 11/2018 | Khvorova et al. |
| 10,167,471 B2 | 1/2019 | Kamens et al. |
| 10,184,124 B2 | 1/2019 | Libertine et al. |
| 10,240,149 B2 | 3/2019 | Khvorova et al. |
| 10,300,027 B2 | 5/2019 | Levis et al. |
| 10,479,992 B2 | 11/2019 | Woolf et al. |
| 10,633,654 B2 | 4/2020 | Pavco et al. |
| 2002/0132788 A1 | 9/2002 | Lewis et al. |
| 2002/0147332 A1 | 10/2002 | Kaneko et al. |
| 2002/0160393 A1 | 10/2002 | Symonds et al. |
| 2002/0162126 A1 | 10/2002 | Beach et al. |
| 2003/0004325 A1 | 1/2003 | Cook et al. |
| 2003/0077829 A1 | 4/2003 | MacLachlan |
| 2003/0108923 A1 | 6/2003 | Tuschl et al. |
| 2003/0139585 A1 | 7/2003 | Uhlmann et al. |
| 2003/0157030 A1 | 8/2003 | Davis et al. |
| 2003/0158403 A1 | 8/2003 | Manoharan et al. |
| 2003/0166282 A1 | 9/2003 | Brown et al. |
| 2003/0190635 A1 | 10/2003 | McSwiggen |
| 2003/0216346 A1 | 11/2003 | Sakurai et al. |
| 2004/0009938 A1 | 1/2004 | Manoharan et al. |
| 2004/0014715 A1 | 1/2004 | Ostroff |
| 2004/0014957 A1 | 1/2004 | Eldrup et al. |
| 2004/0018999 A1 | 1/2004 | Beach et al. |
| 2004/0054155 A1 | 3/2004 | Woolf et al. |
| 2004/0063654 A1 | 4/2004 | Davis et al. |
| 2004/0072785 A1 | 4/2004 | Wolff et al. |
| 2004/0137471 A1 | 7/2004 | Vickers et al. |
| 2004/0162235 A1 | 8/2004 | Trubetskoy et al. |
| 2004/0167090 A1 | 8/2004 | Monahan et al. |
| 2004/0171033 A1 | 9/2004 | Baker et al. |
| 2004/0180351 A1 | 9/2004 | Giese et al. |
| 2004/0192629 A1 | 9/2004 | Xu et al. |
| 2004/0204377 A1 | 10/2004 | Rana |
| 2004/0229266 A1 | 11/2004 | Tuschl et al. |
| 2004/0241845 A1 | 12/2004 | Desgroseillers et al. |
| 2004/0248839 A1 | 12/2004 | Kowalik |
| 2004/0259247 A1 | 12/2004 | Tuschl et al. |
| 2005/0020521 A1 | 1/2005 | Rana |
| 2005/0026286 A1 | 2/2005 | Chi et al. |
| 2005/0032733 A1 | 2/2005 | McSwiggen et al. |
| 2005/0037496 A1 | 2/2005 | Rozema et al. |
| 2005/0042227 A1 | 2/2005 | Zankel et al. |
| 2005/0064595 A1 | 3/2005 | MacLachlan et al. |
| 2005/0080246 A1 | 4/2005 | Allerson et al. |
| 2005/0107325 A1 | 5/2005 | Manoharan et al. |
| 2005/0142535 A1 | 6/2005 | Damha et al. |
| 2005/0181382 A1 | 8/2005 | Zamore et al. |
| 2005/0245474 A1 | 11/2005 | Baker et al. |
| 2005/0246794 A1 | 11/2005 | Khvorova et al. |
| 2005/0255487 A1 | 11/2005 | Khvorova et al. |
| 2005/0265957 A1 | 12/2005 | Monahan et al. |
| 2005/0281781 A1 | 12/2005 | Ostroff |
| 2006/0008910 A1 | 1/2006 | MacLachlan et al. |
| 2006/0009409 A1 | 1/2006 | Woolf |
| 2006/0069050 A1 | 3/2006 | Rana |
| 2006/0142228 A1 | 6/2006 | Ford et al. |
| 2006/0178324 A1 | 8/2006 | Hadwiger et al. |
| 2006/0178327 A1 | 8/2006 | Yeung |
| 2006/0211766 A1 | 9/2006 | Kaplan et al. |
| 2006/0229268 A1 | 10/2006 | Benjamin et al. |
| 2006/0240093 A1 | 10/2006 | MacLachlan et al. |
| 2007/0032441 A1 | 2/2007 | McSwiggen et al. |
| 2007/0166734 A1 | 7/2007 | Bhat et al. |
| 2007/0173476 A1 | 7/2007 | Leake et al. |
| 2007/0231392 A1 | 10/2007 | Wagner et al. |
| 2007/0269889 A1 | 11/2007 | Leake et al. |
| 2008/0038296 A1 | 2/2008 | Brahmbhatt et al. |
| 2008/0071068 A1 | 3/2008 | Oba et al. |
| 2008/0085869 A1 | 4/2008 | Yamada et al. |
| 2008/0107694 A1 | 5/2008 | Trogden et al. |
| 2008/0112916 A1 | 5/2008 | Wagner et al. |
| 2008/0125386 A1 | 5/2008 | Rana et al. |
| 2008/0152661 A1 | 6/2008 | Rozema et al. |
| 2008/0311040 A1 | 12/2008 | Berry et al. |
| 2009/0023216 A1 | 1/2009 | Woolf |
| 2009/0042828 A1 | 2/2009 | Xu et al. |
| 2009/0131360 A1 | 5/2009 | Woolf et al. |
| 2009/0208564 A1 | 8/2009 | Li et al. |
| 2009/0247608 A1 | 10/2009 | Manoharan et al. |
| 2010/0040656 A1 | 2/2010 | Franklin et al. |
| 2010/0069620 A1 | 3/2010 | Zon |
| 2010/0081705 A1 | 4/2010 | Bennett et al. |
| 2010/0136695 A1 | 6/2010 | Woolf |
| 2011/0039914 A1 | 2/2011 | Pavco et al. |
| 2011/0237522 A1 | 9/2011 | Khvorova et al. |
| 2011/0250300 A1 | 10/2011 | Biswal et al. |
| 2011/0251258 A1 | 10/2011 | Samarsky et al. |
| 2011/0268761 A1 | 11/2011 | Levis et al. |
| 2011/0294869 A1 | 12/2011 | Petersen |
| 2014/0242699 A1 | 8/2014 | Zhang |
| 2015/0057362 A1 | 2/2015 | Levis et al. |
| 2015/0174267 A1* | 6/2015 | Castaigne .............. C07K 7/083 424/450 |
| 2016/0115482 A1 | 4/2016 | Libertine et al. |
| 2016/0115484 A1 | 4/2016 | Woolf et al. |
| 2016/0130578 A1 | 5/2016 | Khvorova et al. |
| 2016/0244765 A1 | 8/2016 | Khvorova et al. |
| 2016/0304873 A1 | 10/2016 | Wolfson et al. |
| 2016/0304875 A1 | 10/2016 | Cauwenbergh et al. |
| 2016/0319278 A1 | 11/2016 | Khvorova et al. |
| 2016/0355808 A1 | 12/2016 | Khvorova et al. |
| 2016/0355826 A1 | 12/2016 | Khvorova et al. |
| 2017/0051288 A1 | 2/2017 | Byrne et al. |
| 2017/0051290 A1 | 2/2017 | Byrne et al. |
| 2017/0137823 A1 | 5/2017 | Kamens et al. |
| 2018/0030451 A1 | 2/2018 | Cauwenbergh |
| 2018/0155718 A1 | 6/2018 | Woolf et al. |
| 2018/0195072 A1 | 7/2018 | Cardia et al. |
| 2018/0263925 A1 | 9/2018 | Cauwenbergh et al. |
| 2018/0327748 A1 | 11/2018 | Khvorova et al. |
| 2018/0371464 A1 | 12/2018 | Khvorova et al. |
| 2019/0029974 A1 | 1/2019 | Cauwenbergh et al. |
| 2019/0048341 A1 | 2/2019 | Cardia et al. |
| 2019/0161757 A1 | 5/2019 | Khvorova et al. |
| 2019/0169608 A1 | 6/2019 | Pavco et al. |
| 2019/0211337 A1 | 7/2019 | Khvorova et al. |
| 2019/0218557 A1 | 7/2019 | Kamens et al. |
| 2019/0233826 A1 | 8/2019 | Libertine et al. |
| 2020/0002701 A1 | 1/2020 | Khvorova et al. |
| 2020/0085764 A1 | 3/2020 | Maxwell et al. |
| 2020/0101028 A1 | 4/2020 | Levis et al. |

FOREIGN PATENT DOCUMENTS

| | | |
|---|---|---|
| CN | 103380145 A | 10/2013 |
| EP | 0 552766 A2 | 7/1993 |
| EP | 1 214 945 A2 | 6/2002 |
| EP | 1 144 623 B9 | 3/2003 |
| EP | 1 352 061 B1 | 10/2003 |
| EP | 0 928 290 B9 | 3/2005 |
| EP | 1 407 044 B1 | 9/2007 |
| EP | 1 605 978 A1 | 9/2010 |
| JP | 4 095 895 B2 | 9/2004 |
| JP | 2007-525169 A | 9/2007 |
| JP | 2007-531520 A | 11/2007 |
| JP | 2009-519033 | 5/2009 |
| JP | 2009-538279 A | 11/2009 |
| WO | WO 90/14074 A1 | 11/1990 |
| WO | WO 91/16024 A1 | 10/1991 |
| WO | WO 91/17424 A1 | 11/1991 |
| WO | WO 92/03464 A1 | 3/1992 |
| WO | WO 94/08003 A1 | 4/1994 |
| WO | WO 94/23028 A2 | 10/1994 |
| WO | WO 95/11910 A1 | 5/1995 |
| WO | WO 95/22553 A1 | 8/1995 |
| WO | WO 95/23162 A1 | 8/1995 |
| WO | WO 96/40964 A2 | 12/1996 |
| WO | WO 02/12348 A2 | 2/2002 |
| WO | WO 03/012052 A2 | 2/2003 |
| WO | WO 2003/064626 A2 | 8/2003 |
| WO | WO 2004/042027 A2 | 5/2004 |
| WO | WO 2004/065600 A2 | 8/2004 |
| WO | WO 2004/065601 A2 | 8/2004 |

(56) References Cited

FOREIGN PATENT DOCUMENTS

| WO | WO 2004/090105 A2 | 10/2004 |
|---|---|---|
| WO | WO 2005/019430 A2 | 3/2005 |
| WO | WO 2005/019453 A2 | 3/2005 |
| WO | WO 2005/078096 A2 | 8/2005 |
| WO | WO 2005/079533 A2 | 9/2005 |
| WO | WO 2005/097992 A2 | 10/2005 |
| WO | WO 2006/007372 A2 | 1/2006 |
| WO | WO 2006/019430 A2 | 2/2006 |
| WO | WO 2006/039656 A2 | 4/2006 |
| WO | WO 2006/065601 A2 | 6/2006 |
| WO | WO 2006/128141 A2 | 11/2006 |
| WO | WO 2007/022470 A2 | 2/2007 |
| WO | WO 2007/030167 A1 | 3/2007 |
| WO | WO 2007/044362 A2 | 4/2007 |
| WO | WO 2007/050643 A2 | 5/2007 |
| WO | WO 2007/069068 A2 | 6/2007 |
| WO | WO 2007/089607 A2 | 8/2007 |
| WO | WO 2008/021157 A1 | 2/2008 |
| WO | WO 2008/036825 A2 | 3/2008 |
| WO | WO 2008/109353 A1 | 9/2008 |
| WO | WO 2008/125902 | 10/2008 |
| WO | WO 2009/020344 A2 | 2/2009 |
| WO | WO 2009/021157 A1 | 2/2009 |
| WO | WO 2009/029688 A3 | 3/2009 |
| WO | WO 2009/029690 A1 | 3/2009 |
| WO | WO 2009/044392 A2 | 4/2009 |
| WO | WO 2009/078685 A2 | 6/2009 |
| WO | WO 2009/126933 A2 | 10/2009 |
| WO | WO 2009/134487 A2 | 11/2009 |
| WO | WO 2010/006237 A2 | 1/2010 |
| WO | WO 2010/011346 A2 | 1/2010 |
| WO | WO 2010/027830 A2 | 3/2010 |
| WO | WO 2010/042281 A2 | 4/2010 |
| WO | WO 2011/047129 A1 | 4/2011 |
| WO | WO 2014/191493 A1 | 12/2014 |
| WO | WO 2015/031392 A1 | 3/2015 |
| WO | WO-2015031392 A1 * | 3/2015 |

OTHER PUBLICATIONS

Alahari et al., Inhibition of expression of the multidrug resistance-associated P-glycoprotein of by phosphorothioate and 5' cholesterol-conjugated phosphorothioate antisense oligonucleotides. Mol Pharmacol. Oct. 1996;50(4):808-19.

Albensi et al., Evidence for the involvement of TNF and NF-kappaB in hippocampal synaptic plasticity. Synapse. Feb. 2000;35(2):151-9.

Aleckovic et al., J RNAi Gene Silencing. May 27, 2008;27;4(1):266-8.

Andersen et al., Amyotrophic lateral sclerosis associated with homozygosity for an Asp90A1a mutation in CuZn-superoxide dismutase. Nat Genet. 1995;10:61-6.

Augustyns et al., Incorporation of hexose nucleoside analogues into oligonucleotides: synthesis, base-pairing properties and enzymatic stability. Nucleic Acids Res. Sep. 25, 1992;20(18):4711-6.

Baigude et al., Design and creation of new nanomaterials for therapeutic RNAi. ACS Chem Biol. Apr. 24, 2007;2(4):237-41.

Bergan et al., Electroporation enhances c-myc antisense oligodeoxynucleotide efficacy. Nucleic Acids Res. Jul. 25, 1993;21(15):3567-73.

Boutorin et al., Synthesis of alkylating oligonucleotide derivatives containing cholesterol or phenazinium residues at their 3'-terminus and their interaction with DNA within mammalian cells. FEBS Lett. Aug. 28, 1989;254(1-2):129-32.

Braasch et al., RNA interference in mammalian cells by chemically-modified RNA. Biochemistry. Jul. 8, 2003;42(26):7967-75.

Brown et al., RNAi off-targeting: Light at the end of the tunnel. J RNAi Gene Silencing. Jul. 28, 2006;2(2):175-7.

Cardia et al., Novel self-delivering RNAi compounds with enhanced cellular updatake and distribution properties. Keystone RNAi Silencing Conference. Jan 14-19, 2010. Poster. 1 Page.

Cardia et al., Self-Delivering RNAi Compounds. Drug Delivery Technology. Sep. 2010;10(7):1-4.

Caruthers et al., Chemical and biochemical studies with dithioate DNA. Nucleosides & Nucleotides. 1991;10(1-3):47-59.

Chen et al., Nanoparticles modified with tumor-targeting scFv deliver siRNA and miRNA for cancer therapy. Mol Ther. Sep. 2010;18(9):1650-6. doi: 10.1038/mt.2010.136. Epub Jul. 6, 2010.

Chen et al., Functionalization of single-walled carbon nanotubes enables efficient intracellular delivery of siRNA targeting MDM2 to inhibit breast cancer cells growth. Biomed Pharmacother. Jul. 2012;66(5):334-8. doi: 10.1016/j.biopha.2011.12.005. Epub Feb. 17, 2012.

Chiang et al., Antisense oligonucleotides inhibit intercellular adhesion molecule 1 expression by two distinct mechanisms. J Biol Chem. Sep. 25, 1991;266(27):18162-71.

Chiu et al., siRNA function in RNAi: a chemical modification analysis. RNA. Sep. 2003;9(9):1034-48.

Chiurchiu et al., Chronic inflammatory disorders and their redox control: from molecular mechanisms to therapeutic opportunities. Antioxid Redox Signal. Nov. 1, 2011;15(9):2605-41. doi: 10.1089/ars.2010.3547. Epub Jun. 6, 2011. Review.

Choung et al., Chemical modification of siRNAs to improve serum stability without loss of efficacy. Biochem Biophys Res Commun. Apr. 14, 2006;342(3):919-27.

Chu et al., Potent RNAi by short RNA triggers. RNA. 2008;14:1714-9.

Chung et al., Immunohistochemical study on the aggregation of ubiquitin in the central nervous system of the transgenic mice expressing a human Cu/Zn SOD mutation. Neurol Res. Jun. 2003;25(4):395-400.

Constantinides et al., Formulation and intestinal absorption enhancement evaluation of water-in-oil microemulsions incorporating medium-chain glycerides. Pharm Res. Oct. 1994;11(10):1385-90.

Cruthirds et al., Mitochondrial targets of oxidative stress during renal ischemia/reperfusion. Arch Biochem Biophys. Apr. 1, 2003;412(1):27-33.

Cudkowicz et al., Epidemiology of mutations in superoxide dismutase in amyotrophic lateral sclerosis. Ann Neurol. Feb. 1997;41(2):210-21.

Czauderna et al., Structural variations and stabilising modifications of synthetic siRNAs in mammalian cells. Nucleic Acids Res. Jun. 1, 2003;31(11):2705-16.

De Belleroche et al, Familial amyotrophic lateral sclerosis/motor neurone disease (FALS): a review of current developments. J Med Genet. Nov. 1995;32(11):841-7.

De Smidt et al., Association of antisense oligonucleotides with lipoproteins prolongs the plasma half-life and modifies the tissue distribution. Nucleic Acids Res. Sep. 11, 1991;19(17):4695-700.

Debart et al., Chemical modifications to improve the cellular uptake of oligonucleotides. Curr Top Med Chem. 2007;7(7):727-37.

Del Signore et al., Combined riluzole and sodium phenylbutyrate therapy in transgenic amyotrophic lateral sclerosis mice. Amyotroph Lateral Scler. Apr. 2009;10(2):85-94. doi: 10.1080/17482960802226148.

Deng et al., Amyotrophic lateral sclerosis and structural defects in Cu,Zn superoxide dismutase. Science. Aug. 20, 1993;261(5124):1047-51.

Dykxhoorn et al., The silent treatment: siRNAs as small molecule drugs. Gene Ther. Mar. 2006;13(6):541-52. Review.

Elbashir et al., Duplexes of 21-nucleotide RNAs mediate RNA interference in cultured mammalian cells. Nature. May 24, 2001;411(6836):494-8.

Elbashir et al., Functional anatomy of siRNAs for mediating efficient RNAi in *Drosophila melanogaster* embryo lysate. EMBO J. Dec. 3, 2001;20(23):6877-88.

Fedorov et al., Off-target effects by siRNA can induce toxic phenotype. RNA. Jul. 2006;12(7):1188-96. Epub May 8, 2006.

Ferentz et al., Disulfide-crosslinked oligonucleotides. Journal of the American Chemical Society. 1991;113 (10): 4000-4002.

Fisher et al., Intracellular disposition and metabolism of fluorescently-labeled unmodified and modified oligonucleotides microinjected into mammalian cells. Nucleic Acids Res. Aug. 11, 1993;21(16):3857-65.

(56) References Cited

OTHER PUBLICATIONS

Flanagan et al., Overexpression of manganese superoxide dismutase attenuates neuronal death in human cells expressing mutant (G37R) Cu/Zn-superoxide dismutase. J Neurochem. Apr. 2002;81(1):170-7.
GenBank Submission; NIH/NCBI, Accession No. NM_000454.4. *Homo sapiens* superoxide dismutase 1, soluble (SOD1), mRNA. Mar. 15, 2015. 5 pages.
GenBank Submission; NIH/NCBI, Accession No. NM_000454.4. *Homo sapiens* superoxide dismutase 1 (SOD1), mRNA. May 12, 2019. 6 pages.
Ginobbi et al., Folic acid-polylysine carrier improves efficacy of c-myc antisense oligodeoxynucleotides on human melanoma (M14) cells. Anticancer Res. Jan.-Feb. 1997;17(1A):29-35.
Glaser, Oligonucleotide therapies move toward efficacy trials to treav HIV CMV, cancer. Genetic Engineering News. Feb. 1, 2016;16:1-21.
Ho et al., Preparation of microemulsions using polyglycerol fatty acid esters as surfactant for the delivery of protein drugs. J Pharm Sci. Feb. 1996;85(2):138-43.
Holmes et al., Syntheses and oligonucleotide incorporation of nucleoside analogues containing pendant imidazolyl or amino functionalities—the search for sequence-specific artificial ribonucleases. Eur J Org Chem. Apr. 13, 2005;5171-83. DOI; 10.1002/ejoc.20050413.
Hope et al., Cationic lipids, phosphatidylethanolamine and the intracellular delivery of polymeric, nucleic acid-based drugs (review). Mol Membr Biol. Jan.-Mar. 1998;15(1):1-14.
Hudziak et al., Resistance of morpholino phosphorodiamidate oligomers to enzymatic degradation. Antisense Nucleic Acid Drug Dev. 1996 Winter;6(4):267-72.
Jaarsma et al., Human Cu/Zn superoxide dismutase (SOD1) overexpression in mice causes mitochondrial vacuolization, axonal degeneration, and premature motoneuron death and accelerates motoneuron disease in mice expressing a familial amyotrophic lateral sclerosis mutant SOD1. Neurobiol Dis. Dec. 2000;7(6 Pt B):623-43.
Jackson et al., Position-specific chemical modification of siRNAs reduces "off-target" transcript silencing. RNA. Jul. 2006;12(7):1197-1205. Epub May 8, 2006.
Jones et al., Cu/Zn superoxide dismutase (SOD1) mutations and sporadic amyotrophic lateral sclerosis. Lancet. Oct. 23, 1993;342(8878):1050-1.
Kamata et al., Amphiphilic peptides enhance the efficiency of liposome-mediated DNA transfection. Nucleic Acids Res. Feb. 11, 1994;22(3):536-7.
Kamens et al., Novel, chemically modified RNAi compounds with improved potency, stability and specificity. Keystone RNAi Silencing: Mechanism, Biology and Application Conference. Jan. 14-19, 2010. Poster. 1 Page.
Kim et al., Systemic and specific delivery of small interfering RNAs to the liver mediated by apolipoprotein A-I. Mol Ther. Jun. 2007;15(6):1145-52. Epub Apr. 17, 2007.
Kiningham et al., All-trans-retinoic acid induces manganese superoxide dismutase in human neuroblastoma through NF-kappaB. Free Radic Biol Med. Apr. 15, 2008;44(8):1610-6. doi: 10.1016/j.freeradbiomed.2008.01.015. Epub Jan. 30, 2008. Author manuscript.
Kovacs, Molecular Pathological Classification of Neurodegenerative Diseases: Turning towards Precision Medicine. Int J Mol Sci. Feb. 2, 2016;17(2). pii: E189. doi: 10.3390/ijms17020189.
Kraynack et al., Small interfering RNAs containing full 2'-O-methylribonucleotide-modified sense strands display Argonaute2/eIF2C2-dependent activity. RNA. Jan. 2006;12(1):163-76. Epub Nov. 21, 2005.
Kubo et al., Modified 27-nt dsRNAs with dramatically enhanced stability in serum and long-term RNAi activity. Oligonucleotides. 2007 Winter;17(4):445-64.
Layzer et al., In vivo activity of nuclease-resistant siRNAs. RNA. May 2004;10(5):766-71.
Lebovitz et al., Neurodegeneration, myocardial injury, and perinatal death in mitochondrial superoxide dismutase-deficient mice. Proc Natl Acad Sci U S A. Sep. 3, 1996;93(18):9782-7.
Lee et al., Contributions of 3'-overhang to the dissociation of small interfering RNAs from the PAZ domain: molecular dynamics simulation study. J Mol Graph Model. Mar. 2007;25(6):784-93. Epub Jul. 11, 2006.
Letsinger et al., Cholesteryl-conjugated oligonucleotides: synthesis, properties, and activity as inhibitors of replication of human immunodeficiency virus in cell culture. Proc Natl Acad Sci U S A. Sep. 1989;86(17):6553-6.
Leuschner et al., Cleavage of the siRNA passenger strand during RISC assembly in human cells. EMBO Reports 2006;7(3):314-20.
Lewis et al., A serum-resistant cytofectin for cellular delivery of antisense oligodeoxynucleotides and plasmid DNA. Proc Natl Acad Sci U S A. Apr. 16, 1996;93(8):3176-81.
Li et al., Surface-modified LPD nanoparticles for tumor targeting. Ann N Y Acad Sci. Oct. 2006;1082:1-8.
Li et al., Yeast glucan particles activate murine resident macrophages to secrete proinflammatory cytokines via MyD88-and Syk kinase-dependent pathways. Clin Immunol. Aug. 2007;124(2):170-81. Epub Jun. 14, 2007. Author manuscript.
Liang et al., Oligonucleotide delivery: a cellular prospective. Pharmazie. Aug. 1999;54(8):559-66.
Maehara et al., A NF-kappaB p65 subunit is indispensable for activating manganese superoxide: dismutase gene transcription mediated by tumor necrosis factor-alpha. J Cell Biochem. Apr. 2000;77(3):474-86.
Manoharan et al., Chemical modifications to improve uptake and bioavailability of antisense oligonucleotides. Ann N Y Acad Sci. Oct. 28, 1992;660:306-9.
Manoharan, Oligonucleotide conjugates as potential antisense drugs with improved uptake, biodistribution, targeted delivery, and mechanism of action. Antisense Nucleic Acid Drug Dev. Apr. 2002;12(2):103-28.
Manuvakhova et al., Identification of novel small molecule activators of nuclear factor-κB with neuroprotective action via high-throughput screening. J Neurosci Res. Jan. 2011;89(1):58-72. doi: 10.1002/jnr.22526. Author manuscript.
Martins et al., Sterol side chain length and structure affect the clearance of chylomicron-like lipid emulsions in rats and mice. J Lipid Res. Feb. 1998;39(2):302-12.
Mathews et al., Incorporating chemical modification constraints into a dynamic programming algorithm for prediction of RNA secondary structure. Proc Natl Acad Sci U S A. May 11, 2004;101(19):7287-92. Epub May 3, 2004.
Maxwell et al., RNA interference-mediated silencing of mutant superoxide dismutase rescues cyclosporin A—induced death in cultured neuroblastoma cells. Proc Natl Acad Sci U S A Mar. 2, 2004;101(9):3178-83. Epub Feb. 23, 2004.
Meberg et al., Gene expression of the transcription factor NF-kappa B in hippocampus: regulation by synaptic activity. Brain Res Mol Brain Res. Jun. 1996;38(2):179-90.
Mescalchin et al., Cellular uptake and intracellular release are major obstacles to the therapeutic application of siRNA: novel options by phosphorothioate-stimulated delivery. Expert Opin Biol Ther. Oct. 2007;7(10):1531-8. Review.
Oberhauser et al., Effective incorporation of 2'-O-methyl-oligoribonucleotides into liposomes and enhanced cell association through modification with thiocholesterol. Nucleic Acids Res. Feb. 11, 1992;20(3):533-8.
Orrell et al., Familial ALS is associated with mutations in all exons of SOD1: a novel mutation in exon 3 (Gly72Ser). J Neurol Sci. Dec. 9, 1997;153(1):46-9.
Ortigão et al., Antisense effect of oligodeoxynucleotides with inverted terminal internucleotidic linkages: a minimal modification protecting against nucleolytic degradation. Antisense Res Dev. 1992 Summer;2(2):129-46.
Overhoff et al., Phosphorothioate-stimulated uptake of short interfering RNA by human cells. Embo Rep. Dec. 2005;6(12):1176-81.
Palomo et al., Exploring new pathways of neurodegeneration in ALS: the role of mitochondria quality control. Brain Res. May 14, 2015;1607:36-46. doi: 10.1016/j.brainres.2014.09.065. Epub Oct. 6, 2014. Author manuscript.
Parone et al., Enhancing mitochondrial calcium buffering capacity reduces aggregation of misfolded SOD1 and motor neuron cell

(56) References Cited

OTHER PUBLICATIONS death without extending survival in mouse models of inherited amyotrophic lateral sclerosis. J Neurosci. Mar. 13, 2013;33(11):4657-71. doi: 10.1523/JNEUROSCI.1119-12.2013.
Parrish et al., Functional anatomy of a dsRNA trigger: differential requirement for the two trigger strands in RNA interference. Mol Cell. Nov. 2000;6(5):1077-87.
Pavco et al., Robust Intradermal efficacy with novel chemically modified self-delivering RNAi compounds. Keystone RNAi Silencing Conference: Mechanism, Biology and Application Conference. Jan. 14-19, 2010. Poster. 1 Page.
Rajeev et al., 2'-modified-2-thiothymidine oligonucleotides. Org Lett. Aug. 21, 2003;5(17):3005-8.
Reichhart et al., Splice-activated UAS hairpin vector gives complete RNAi knockout of single or double target transcripts in *Drosophila melanogaster*. Genesis. Sep.-Oct. 2002;34(1-2):160-4.
Rosen et al., Mutations in Cu/Zn superoxide dismutase gene are associated with familial amyotrophic lateral sclerosis. Nature. Mar. 4, 1993;362(6415):59-62. Erratum in: Nature. Jul. 22, 1993;364(6435):362.
Rozners et al., Expanding functionality of RNA: synthesis and properties of RNA containing imidazole modified tandem G-U wobble base pairs. Chem Commun (Camb). Dec. 14, 2005;(46):5778-80.
Rump et al., Preparation of conjugates of oligodeoxynucleotides and lipid structures and their interaction with low-density lipoprotein. Bioconjug Chem. May-Jun. 1998;9(3):341-9.
Ryu et al., Sodium phenylbutyrate prolongs survival and regulates expression of anti-apoptotic genes in transgenic amyotrophic lateral sclerosis mice. J Neurochem. Jun. 2005;93(5):1087-98.
Salomon et al., Modified dsRNAs that are not processed by Dicer maintain potency and are incorporated into the RISC. Nucleic Acids Res. Jun. 2010;38(11):3771-9. doi: 10.1093/nar/gkq055. Epub Feb. 18, 2010.
Sato et al., Tumor targeting and imaging of intraperitoneal tumors by use of antisense oligo-DNA complexed with dendrimers and/or avidin in mice. Clin Cancer Res. Nov. 2001;7(11):3606-12.
Seela et al., Oligodeoxyribonucleotides containing 1,3-propanediol as nucleoside substitute. Nucleic Acids Res. Apr. 10, 1987;15(7):3113-29.
Shi, Mammalian RNAi for the masses. Trends Genet. Jan. 2003;19(1):9-12.
Shoeman et al., Fluorescence microscopic comparison of the binding of phosphodiester and phosphorothioate (antisense) oligodeoxyribonucleotides to subcellular structures, including intermediate filaments, the endoplasmic reticulum, and the nuclear interior. Antisense Nucleic Acid Drug Dev. Aug. 1997;7(4):291-308.
Smith et al., Antisense oligonucleotide therapy for neurodegenerative disease. J Clin Invest. Aug. 2006;116(8):2290-6. Epub Jul. 27, 2006.
Snead et al., RNA interference trigger variants: getting the most out of RNA for RNA interference-based therapeutics. Nucleic Acid Ther. Jun. 2012;22(3):139-46. doi: 10.1089/nat.2012.0361. Review.
Soto et al., Characterization of multilayered nanoparticles encapsulated in yeast cell wall particles for DNA delivery. Bioconjug Chem. Apr. 2008;19(4):840-8. doi: 10.1021/bc700329p. Epub Apr. 1, 2008.
Soto et al., Oral Macrophage Mediated Gene Delivery System. 2007 NSTI Nanotechnology Conference and Trade Show, May 20-24, 2007, Santa Clara, CA. NSTI Nanotech 2007 Proceedings; 2:378-81.
Soutschek et al., Therapeutic silencing of an endogenous gene by systemic administration of modified siRNAs. Nature. Nov. 11, 2004;432(7014):173-8.
Stein et al., A specificity comparison of four antisense types: morpholino, 2'-O-methyl RNA, DNA, and phosphorothioate DNA. Antisense Nucleic Acid Drug Dev. Jun. 1997;7(3):151-7.
Strong et al., The pathobiology of amyotrophic lateral sclerosis: a proteinopathy? J Neuropathol Exp Neurol. Aug. 2005;64(8):649-64.

Sui et al., A DNA vector-based RNAi technology to suppress gene expression in mammalian cells. Proc Natl Acad Sci U S A. Apr. 16, 2002;99(8):5515-20.
Summerton et al., Morpholino and phosphorothioate antisense oligomers compared in cell-free and in-cell systems. Antisense Nucleic Acid Drug Dev. Apr. 1997;7(2):63-70.
Summerton et al., Morpholino antisense oligomers: design, preparation, and properties. Antisense Nucleic Acid Drug Dev. Jun. 1997;7(3):187-95. Review.
Summerton, Morpholino antisense oligomers: the case for an RNase H-independent structural type. Biochim Biophys Acta. Dec. 1999;1489(1):141-58. Review.
Sun et al., Asymmetric RNA duplexes mediate RNA interference in mammalian cells. Nat Biotechnol. Dec. 2008;26(12):1379-82. doi: 10.1038/nbt.1512. Epub Nov. 23, 2008. 4 Pages.
Swarup et al., ALS pathogenesis: recent insights from genetics and mouse models. Prog Neuropsychopharmacol Biol Psychiatry. Mar. 30, 2011;35(2):363-9. doi: 10.1016/j.pnpbp.2010.08.006. Epub Aug. 20, 2010.
Taylor et al., Curbing activation: proprotein convertases in homeostasis and pathology. FASEB J. Jul. 2003;17(10):1215-27.
Uhlmann et al., Antisense oligonucleotides: a new therapeutic principle. Chem Rev. 1990;90(4):543-84.
Vaught et al., Expanding the chemistry of DNA for in vitro selection. J Am Chem Soc. Mar. 31, 2010;132(12):4141-51. doi: 10.1021/ja908035g.
Visner et al., Regulation of manganese superoxide dismutase by lipopolysaccharide, interleukin-1, and tumor necrosis factor. Role in the acute inflammatory response. J Biol Chem. Feb. 15, 1990;265(5):2856-64.
Vlassov et al., Transport of oligonucleotides across natural and model membranes. Biochim Biophys Acta. Jun. 29, 1994;1197(2):95-108.
Wagner et al., Transferrin-polycation-DNA complexes: the effect of polycations on the structure of the complex and DNA delivery to cells. Proc Natl Acad Sci U S A. May 15, 1991;88(10):4255-9.
Wang et al., Therapeutic gene silencing delivered by a chemically modified small interfering RNA against mutant SOD1 slows amyotrophic lateral sclerosis progression. J Biol Chem. Jun 6, 2008;283(23):15845-52. doi: 10.1074/jbc.M800834200. Epub Mar. 26, 2008.
Wolfrum et al., Mechanisms and optimization of in vivo delivery of lipophilic siRNAs. Nat Biotechnol. Oct. 2007;25(10):1149-57. Epub Sep. 16, 2007.
Wright et al., Screening for inhibitors of the SOD1 gene promoter: pyrimethamine does not reduce SOD1 levels in cell and animal models. Neurosci Lett. Oct. 4, 2010;482(3):188-92. doi: 10.1016/j.neulet.2010.07.020. Epub Jul. 16, 2010. Author manuscript.
Xia et al., Allele-specific RNAi selectively silences mutant SOD1 and achieves significant therapeutic benefit in vivo. Neurobiol Dis. Sep. 2006;23(3):578-86. Epub Jul. 20, 2006.
Yamada et al., Lysophosphatidic acid stimulates the proliferation and motility of malignant pleural mesothelioma cells through lysophosphatidic acid receptors, LPA1 and LPA2. Cancer Sci. Aug. 2008;99(8):1603-10.
Yamada et al., Synthesis and properties of oligonucleotides having a chemically stable 2-(trimethylsilyl)benzoyl group. Nucleic Acids Symp Ser (Oxf). 2008;(52):301-2. doi: 10.1093/nass/nrn152.
Yu et al., RNA interference by expression of short-interfering RNAs and hairpin RNAs in mammalian cells. Proc Natl Acad Sci U S A. Apr. 30, 2002;99(9):6047-52. Epub Apr. 23, 2002.
U.S. Appl. No. 16/270,524, filed Feb. 7, 2019, Khvorova et al.
U.S. Appl. No. 16/377,617, filed Apr. 8, 2019, Levis et al.
PCT/US2016/041147, Oct. 4, 2016, International Search Report and Written Opinion.
PCT/US2016/041147, Jan. 18, 2018, International Preliminary Report on Patentability.
Vickers et al., Efficient reduction of target RNAs by small interfering RNA and RNase H-dependent antisense agents. A comparative analysis. J Biol Chem. Feb. 28, 2003;278(9):7108-18. Epub Dec. 23, 2002.
U.S. Appl. No. 16/680,101, filed Nov. 11, 2019, Woolf et al.
U.S. Appl. No. 16/850,912, filed Apr. 16, 2020, Cauwenbergh et al.

(56) References Cited

OTHER PUBLICATIONS

U.S. Appl. No. 16/852,328, filed Apr. 17, 2020, Byrne et al.
U.S. Appl. No. 16/637,514, filed Feb. 7, 2020, Eliseev.

* cited by examiner

Reducing Chemistry Content Results in Active
sd-rxRNA Variants with Reduced Cellular Toxicity
*in vitro*
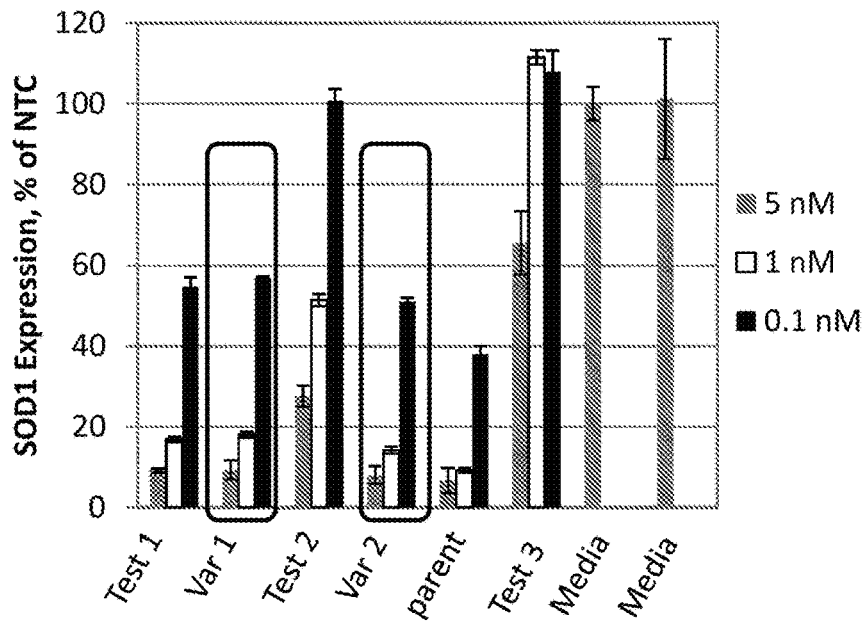
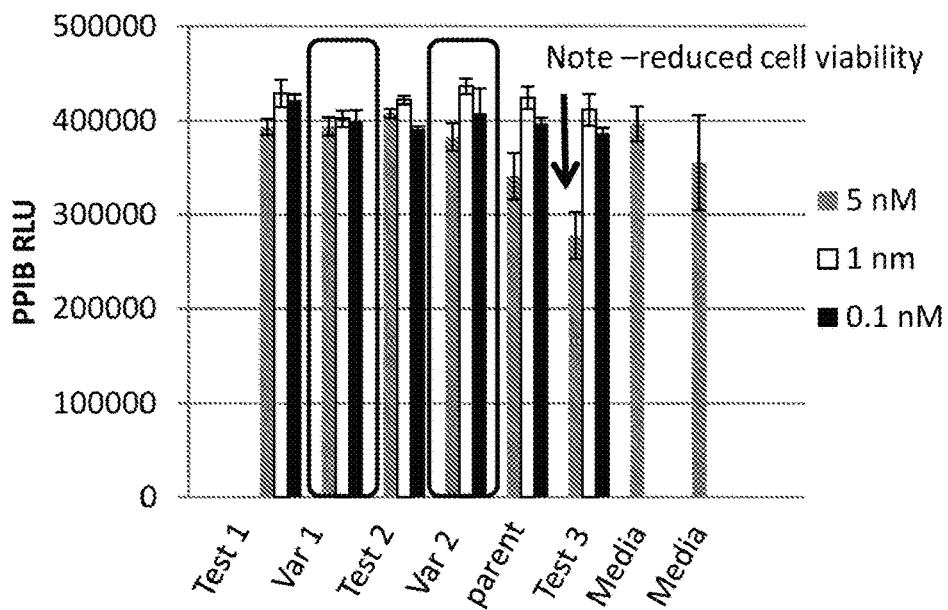
FIG. 1

Reducing Chemistry Content Results in Active sd-rxRNA Variants with Reduced Cellular Toxicity *in vitro*
SOD1 Silencing (HeLa cells)
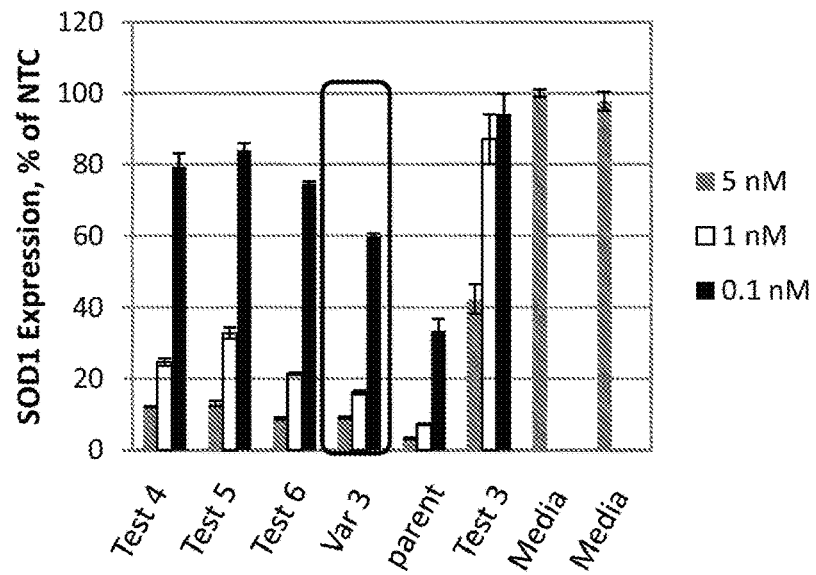
Cell Viability
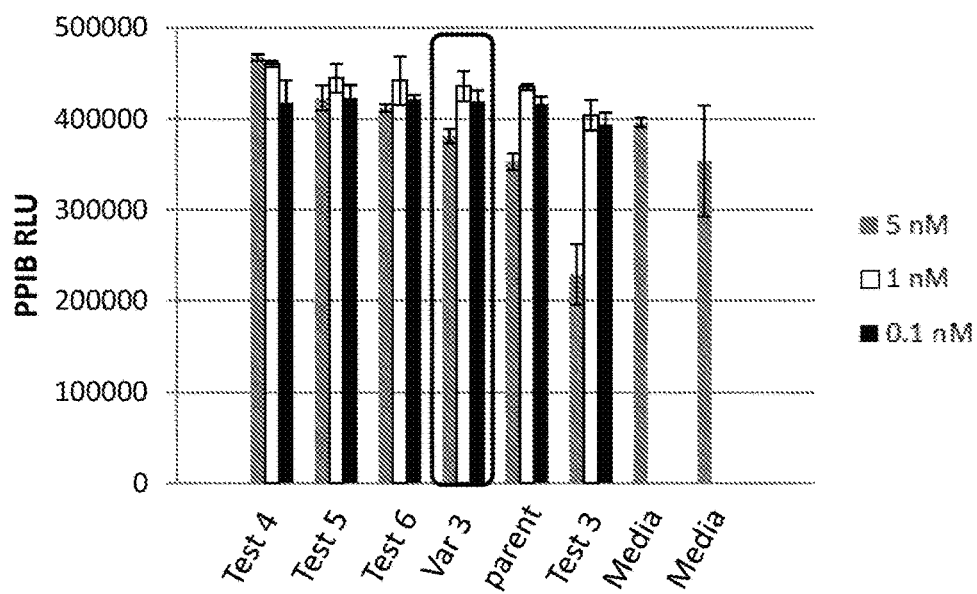
FIG. 2

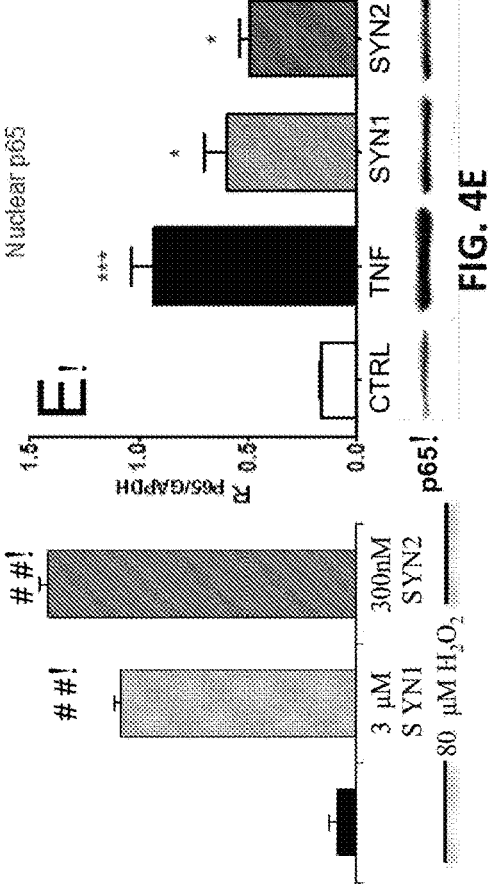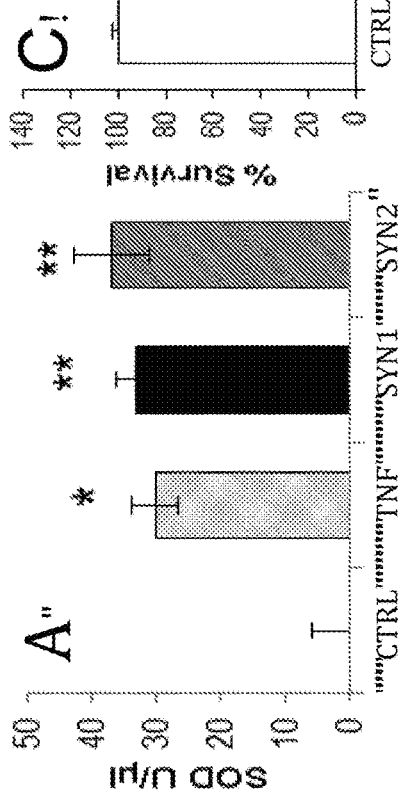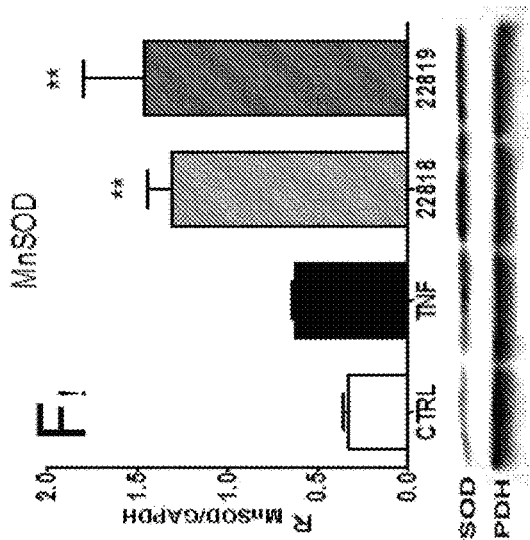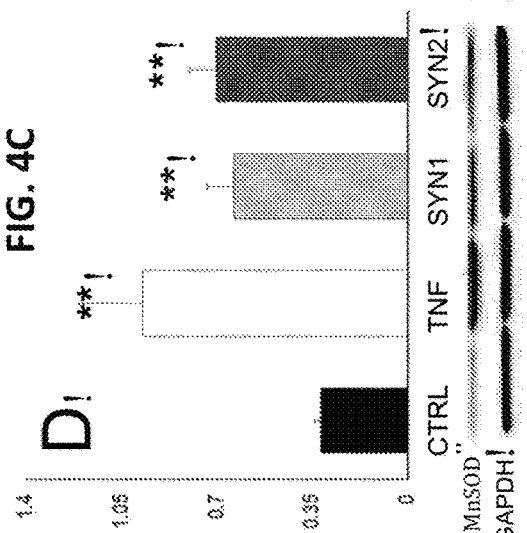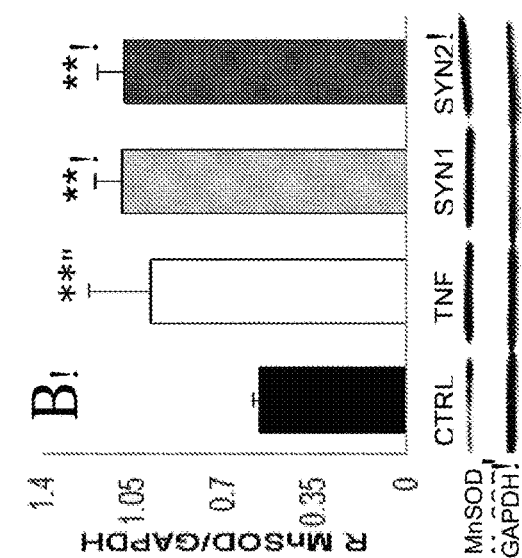

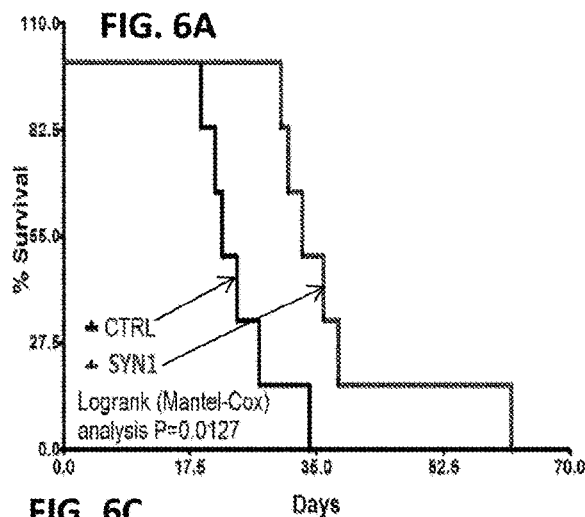
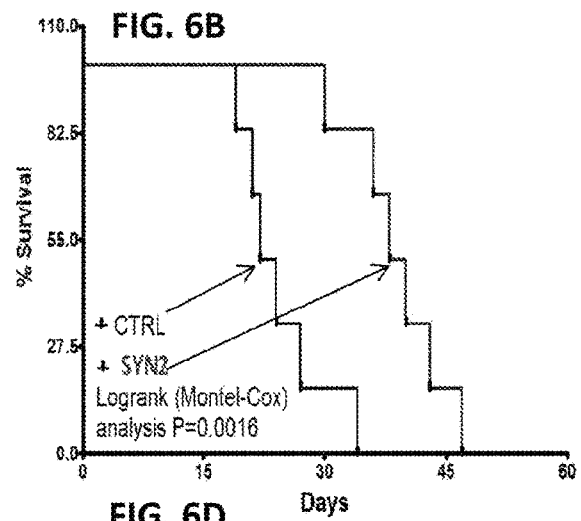
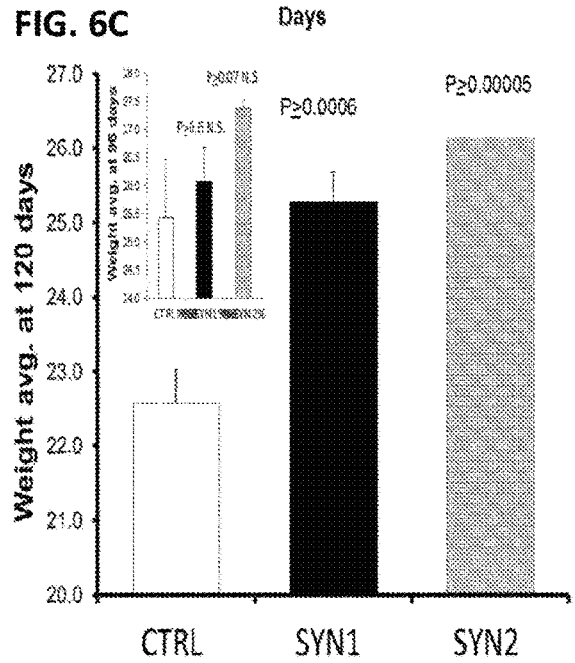
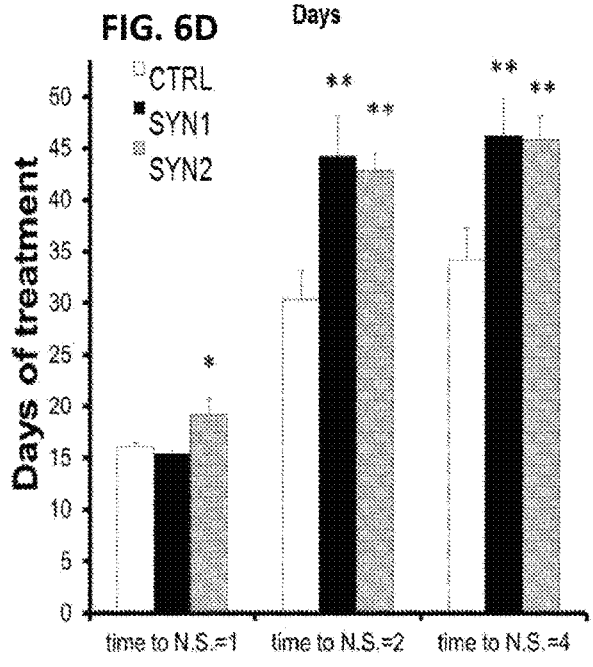

METHODS FOR TREATING NEUROLOGICAL DISORDERS USING A SYNERGISTIC SMALL MOLECULE AND NUCLEIC ACIDS THERAPEUTIC APPROACH

RELATED APPLICATIONS

This application is a national stage filing under 35 U.S.C. § 371 of International Application No. PCT/US2016/041147, entitled "METHODS FOR TREATING NEUROLOGICAL DISORDERS USING A SYNERGISTIC SMALL MOLECULE AND NUCLEIC ACIDS THERAPEUTIC APPROACH," filed Jul. 6, 2016, which was published under PCT Article 21(2) in English and which claims the benefit under 35 U.S.C. § 119(e) of U.S. Provisional Application Ser. No. 62/189,142, filed on Jul. 6, 2015, entitled "METHODS FOR TREATING NEUROLOGICAL DISORDERS USING A SYNERGISTIC SMALL MOLECULE AND NUCLEIC ACIDS THERAPEUTIC APPROACH", the entire contents of each of which are incorporated herein by reference.

FIELD OF THE INVENTION

The disclosure relates, at least in part, to methods and compositions for treating neurological disorders. The disclosure further relates, at least in part, to a non-genetic gene silencing animal model for screening therapeutic and diagnostic approaches for neurological disorders.

BACKGROUND OF THE INVENTION

Complementary oligonucleotide sequences are promising therapeutic agents and useful research tools in elucidating gene functions. However, prior art oligonucleotide molecules suffer from several problems that may impede their clinical development, and frequently make it difficult to achieve intended efficient inhibition of gene expression (including protein synthesis) using such compositions in vivo.

A major problem has been the delivery of these compounds to cells and tissues. Conventional double-stranded RNAi compounds, 19-29 bases long, form a highly negatively-charged rigid helix of approximately 1.5 by 10-15 nm in size. This rod type molecule cannot get through the cell-membrane and as a result has very limited efficacy both in vitro and in vivo. As a result, all conventional RNAi compounds require some kind of delivery vehicle to promote their tissue distribution and cellular uptake. This is considered to be a major limitation of the RNAi technology.

There have been previous attempts to apply chemical modifications to oligonucleotides to improve their cellular uptake properties. One such modification was the attachment of a cholesterol molecule to the oligonucleotide. A first report on this approach was by Letsinger et al., in 1989. Subsequently, ISIS Pharmaceuticals, Inc. (Carlsbad, Calif.) reported on more advanced techniques in attaching the cholesterol molecule to the oligonucleotide (Manoharan, 1992).

With the discovery of siRNAs in the late nineties, similar types of modifications were attempted on these molecules to enhance their delivery profiles. Cholesterol molecules conjugated to slightly modified (Soutschek, 2004) and heavily modified (Wolfrum, 2007) siRNAs appeared in the literature. Yamada et al., 2008 also reported on the use of advanced linker chemistries which further improved cholesterol mediated uptake of siRNAs. In spite of all this effort, the uptake of these types of compounds appeared to be inhibited in the presence of biological fluids resulting in highly limited efficacy in gene silencing in vivo, limiting the applicability of these compounds in a clinical setting.

SUMMARY OF THE INVENTION

In some aspects, the disclosure relates to a method for treating a neurodegenerative disorder, comprising administering to a subject in need thereof a therapeutically effective amount of a nucleic acid molecule and a therapeutically effective amount of at least one small molecule that activates NF-κB p65.

In some embodiments, the small molecule that activates NF-κB p65 increases expression of manganese superoxide dismutase (MnSOD/Sod2) and/or expression of a protein selected from the group consisting of Heat Shock Protein 27 (Hsp27), Hsp70-2, DNAJ Heat Shock Protein Family (Hsp40) Member B9 (DNAJB9), T-complex protein 1 subunit zeta-2 (CCT6B), DNAJ Heat Shock Protein Family (Hsp40) Member 5 Gamma (DNAJC5G), and Heme Oxygenase 1 (HMOX1).

In some embodiments, the neurodegenerative disorder is Alzheimer Disease, Amyotrophic Lateral Sclerosis (ALS), Argyrophilic Grain Disease, Basophilic Inclusion Body Disease, Sporadic Cerebral Amyloid Angiopathy, Corticobasal Degeneration, Creutzfeldt-Jakob Disease, a degenerative proteinopathy associated with Traumatic Brain Injury (TBI), dementia, dementia with Lewy Bodies, Dentatorubral-Pallidoluysian Atrophy, Sporadic Fatal Insomnia, Fatal Familial Insomnia, Fragile X Mental Retardation, Frontotemporal Dementia (FD), Frontotemporal Lobar Degeneration, Atypical Frontotemporal Lobar Degeneration with Ubiquitinated Inclusions, Frontotemporal Lobar Degeneration with Inclusions Immunoreactive only for the Components of the Ubiquitine Proteasome System, Frontotemporal Lobar Degeneration with No Inclusion Specified, Frontotemporal Dementia and Parkinsonism Linked to Chromosome 17 Caused by Mutations in the MAPT (Tau) Gene, Fragile X Associated Tremor and Ataxia Syndrome, Globular Glial Tauopathies, Gerstmann-Sträussler-Scheinker Disease, Huntington Disease (HD), Neuronal/Glial Intranuclear Inclusion Body Diseases, a movement disorder, Motor Neuron Disease, Multiple System Atrophy, Neurodegeneration with Brain Iron Accumulation, Neurodegeneration Associated with Traumatic Brain Injury (TBI); Neurofilament Intermediate Filament Inclusion Disease, Parkinson Disease, Pick Disease, Prion Protein, Progressive Supranuclear Palsy, Spinocerebellar Ataxia (SCA), Spinal and Bulbar Muscular Atrophy, Trinucleotide Repeat Expansion Disorder, or Variably Protease-Sensitive Prionopathy.

In some embodiments, the neurodegenerative disorder is ALS.

Aspects of the invention relate to methods for treating amyotrophic lateral sclerosis (ALS) comprising administering to a subject in need thereof a therapeutically effective amount of a nucleic acid molecule that is directed against a gene encoding copper/zinc superoxide dismutase 1 (SOD1) and a therapeutically effective amount of at least one small molecule that activates NF-κB p65.

In some embodiments, the small molecule that activates NF-κB p65 increases expression of manganese superoxide dismutase (MnSOD/Sod2) and/or expression of a protein selected from the group consisting of Heat Shock Protein 27 (Hsp27), Hsp70-2, DNAJ Heat Shock Protein Family (Hsp40) Member B9 (DNAJB9), T-complex protein 1 subunit zeta-2 (CCT6B), DNAJ Heat Shock Protein Family (Hsp40) Member 5 Gamma (DNAJC5G), and Heme Oxygenase 1 (HMOX1)

In some embodiments, the nucleic acid molecule is a chemically modified oligonucleotide. In some embodiments, the nucleic acid molecule is a double stranded nucleic acid molecule.

In some embodiments, the nucleic acid molecule is an isolated double stranded nucleic acid molecule that includes a double stranded region and a single stranded region, wherein the region of the molecule that is double stranded is from 8-15 nucleotides long, wherein the guide strand contains a single stranded region that is 2-14 nucleotides long, wherein the guide strand contains 2, 3, 4, 5, 6, 7, 8, 9, 10, 11, 12, 13, 14, 15, 16, 17, 18, 19, 20, 21 or 22 phosphorothioate modifications, and wherein the passenger strand is 8 to 15 nucleotides long, wherein the passenger strand contains 3, 4, 5, 6, 7, 8, 9, 10, 11, 12, 13 or 14 phosphorothioate modifications and wherein at least 40% of the nucleotides of the isolated double stranded nucleic acid molecule are modified.

In some embodiments, at least one of the nucleotides of the isolated double stranded nucleic acid molecule that is modified comprises a 2'O-methyl or a 2'-fluoro modification.

In some embodiments, a plurality of the U's and/or C's of the isolated double stranded nucleic acid molecule include a hydrophobic modification, selected from the group consisting of methyl, isobutyl, octyl, imidazole or thiophene and wherein the modifications are located on positions 4 or 5 of U's and/or C's.

In some embodiments, the isolated double stranded nucleic acid comprises a completely phosphorothioated backbone. In some embodiments, at least one strand of the isolated double stranded nucleic acid molecule is completely phosphorothioated, or is completely phosphorothioated with the exception of one residue.

In some embodiments, the isolated double stranded nucleic acid molecule does not comprise the modification pattern of SEQ ID NO: 40 described in PCT Publication number WO2010/033247.

In some embodiments, the isolated double stranded nucleic acid does not form a hairpin.

In some embodiments, the isolated double stranded nucleic acid molecule comprises at least 12 contiguous nucleotides of a sequence selected from the sequences within Table 1 or Table 2. In some embodiments, the isolated double stranded nucleic acid molecule that comprises at least 12 contiguous nucleotides of a sequence selected from the sequences within Table 1 or Table 2 has the chemical modification pattern provided in Table 1 or Table 2.

In some embodiments, if the isolated double stranded nucleic acid comprises at least 12 contiguous nucleotides of a sequence selected from SEQ ID NOs: 70, 71, 72, 73, 79, 80, 81, or 84 in Table 2, then the guide strand contains more than 6 phosphorothioate modifications.

In some embodiments, the sense strand of the isolated nucleic acid molecule comprises at least 12 consecutive nucleotides of SEQ ID NO: 2, SEQ ID NO: 32, or SEQ ID NO: 122, and the guide strand comprises at least 12 consecutive nucleotides of SEQ ID NO: 61, SEQ ID NO: 91, or SEQ ID NO: 123.

In some embodiments, the sense strand of the isolated nucleic acid molecule comprises SEQ ID NO: 2, SEQ ID NO: 32, or SEQ ID NO: 122, and the guide strand comprises SEQ ID NO: 61, SEQ ID NO: 91, or SEQ ID NO: 123.

In some embodiments, the sense strand of the isolated nucleic acid molecule comprises at least 12 consecutive nucleotides of SEQ ID NO: 4, SEQ ID NO: 34, or SEQ ID NO: 126, and the guide strand comprises at least 12 consecutive nucleotides of SEQ ID NO: 63 or SEQ ID NO: 93.

In some embodiments, the sense strand of the isolated nucleic acid molecule comprises SEQ ID NO: 4, SEQ ID NO: 34, or SEQ ID NO: 126, and the guide strand comprises SEQ ID NO: 63 or SEQ ID NO: 93.

In some embodiments, the sense strand of the isolated nucleic acid molecule comprises at least 12 consecutive nucleotides of SEQ ID NO: 9, SEQ ID NO: 38, or SEQ ID NO:135, and the guide strand comprises at least 12 consecutive nucleotides of SEQ ID NO: 68, SEQ ID NO: 97, or SEQ ID NO: 136.

In some embodiments, the sense strand of the isolated nucleic acid molecule comprises SEQ ID NO: 9, SEQ ID NO: 38, or SEQ ID NO:135, and the guide strand comprises SEQ ID NO: 68, SEQ ID NO: 97, or SEQ ID NO: 136.

In some embodiments, the sense strand of the isolated nucleic acid molecule comprises at least 12 consecutive nucleotides of SEQ ID NO: 10 or SEQ ID NO: 39, and the guide strand comprises at least 12 consecutive nucleotides of SEQ ID NO: 69 or SEQ ID NO: 98.

In some embodiments, the sense strand of the isolated nucleic acid molecule comprises SEQ ID NO: 10 or SEQ ID NO: 39, and the guide strand comprises SEQ ID NO: 69 or SEQ ID NO: 98.

In some embodiments, the sense strand of the isolated double stranded nucleic acid molecule comprises at least 12 consecutive nucleotides of SEQ ID NO: 5, SEQ ID NO: 127 or SEQ ID NO: 137, and the guide strand comprises at least 12 consecutive nucleotides of SEQ ID NO: 64, SEQ ID NO: 128 or SEQ ID NO: 138.

In some embodiments, the sense strand of the isolated nucleic acid molecule comprises SEQ ID NO: 5, SEQ ID NO: 127 or SEQ ID NO: 137, and the guide strand comprises SEQ ID NO: 64, SEQ ID NO: 128 or SEQ ID NO: 138.

In some embodiments, the isolated double stranded nucleic acid molecule further comprises a hydrophobic conjugate that is attached to the isolated double stranded nucleic acid molecule.

In some embodiments, the isolated double stranded nucleic acid molecule is formulated for delivery to the central nervous system.

In some embodiments, the small molecule that activates NF-κB p65 and increases SOD2 expression is selected from the group consisting of: SYN1, SYN2, SYN-NCE and/or SYN-GL.

In some embodiments, more than one small molecule selected from the group consisting of: SYN1, SYN2, SYN-NCE and/or SYN-GL is administered.

In some embodiments, of methods described by the disclosure, the nucleic acid molecule and the small molecule that activates NF-κB p65 are administered together (e.g., simultaneously). In some embodiments, the nucleic acid molecule and the small molecule that activates NF-κB p65 are administered together (e.g., simultaneously) as a single composition. In some embodiments, the composition further comprises a pharmaceutically acceptable carrier.

In some aspects, the disclosure relates to a method for generating non-genetic models of neurodegenerative diseases based on silencing of target proteins responsible for the pathogenic effects, comprising administering an effective amount of an agent that reduces the level or activity of SOD1 protein and/or mRNA, resulting in phenotypes that mimic neurodegenerative diseases. In some embodiments, the agent that reduces the level or activity of SOD1 protein and/or mRNA is a chemically modified oligonucleotide. In some embodiments, the chemically modified oligonucleotide is an isolated double stranded nucleic acid molecule as described by the disclosure.

In some aspects, the disclosure relates to a method for generating a model of sporadic ALS, comprising administering an effective amount of an agent that reduces the level or activity of SOD1 protein and/or mRNA, resulting in a phenotype that mimics ALS. In some embodiments, the agent that reduces the level or activity of SOD1 protein and/or mRNA is a chemically modified oligonucleotide. In some embodiments, the chemically modified oligonucleotide is an isolated double stranded nucleic acid molecule as described by the disclosure.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways.

BRIEF DESCRIPTION OF THE DRAWINGS

FIG. 1. Reducing chemistry content results in active sd-rxRNA variants with reduced cellular toxicity in vitro. The upper panel shows SOD1 silencing (Hela cells) and the lower panel shows cell viability. These data revealed that sd-rxRNA variants 1 and 2 were potent and had a more favorable cellular toxicity profile (in vitro) compared to parent.

FIG. 2. Reducing chemistry content results in active sd-rxRNA variants with reduced cellular toxicity in vitro. The upper panel shows SOD1 silencing (Hela cells) and the lower panel shows cell viability. These data revealed that sd-rxRNA variant 3 was potent and had a slightly more favorable cellular toxicity profile (in vitro) compared to parent.

FIGS. 4A-4F. SYN1 and SYN2 increase the expression and activity of NF-κB target genes, such as MnSOD in neurons. FIG. 4A shows SYN1 and SYN2 increase MnSOD activity. A commercially available kit, modified to detect MnSOD activity in primary neurons, was used. Neurons were exposed to 3 mM SYN1 or 300 nM SYN2 for 24 h. Both compounds significantly increased MnSOD activity in primary neurons. TNF-α was included as a reference. FIGS. 4B, 4D and 4F show SYN1 and SYN2 increase MnSOD protein expression. Mature primary neurons (FIG. 4B), SH-SY5Y cells (FIG. 4D), and NSC-34 cells (FIG. 4F) were treated for 24 h with the compounds. Thereafter, cells were lysed, and proteins were extracted and subjected to SDS-PAGE. Immunoblots were then performed following the instructions of the antibody manufacturer. ECL was used for detection. Both compounds increased MnSOD expression in all three kinds of neurons. The effect of TNF exposure is provided for reference. FIG. 4C shows the effects of SYN1 and SYN2 on neurotoxicity induced by $H_2O_2$. Primary cortical neurons at 6 D.I.V. were pretreated for 24 h with compounds and then challenged with 80 µM of $H_2O_2$. Neurons pretreated with the compounds showed a marked reduction in the toxic effect of $H_2O_2$. SYN1 at 3 µM inhibited cell death by 100%. SYN2 had a peak effect at 300 nM, showing a high potency. The protection exceeded 60% and extended up to a concentration of 1 µM. FIG. 4E shows that SYN1 and SYN2 translocate NF-κB in NSC-34 immortalized motoneurons. NSC-34 cells were treated for 24 h with the compounds. Thereafter, cells were lysed, and cytosolic and nuclear fractions were separated. Subsequently, SDS-PAGE and immunoblots were performed. ECL was used for detection. Both compounds increased p65 nuclear presence. The effect of TNF exposure was provided for reference. FIG. 4F shows SYN1 and SYN2 increased MnSOD expression in immortalized motoneurons. NSC-34 cells treated for 24 h with the compounds showed increased expression of MnSOD as probed by Western blot. *, . * $P>0.5, 0.01, 0.001$ vs. VEH; ## $P>0.01$ vs. $H_2O_2$. ANOVA+ Bonferroni's.

FIGS. 6A-6D. Effect of SYN1 and SYN2 in SOD-1-G93A ALS mouse. The animals were received at day 70 and kept until day 96, at which time daily IP treatment was started with 25 mg/kg of the compounds. Weight and standard neurologic scores (N.S.) were assessed on alternate days. A N.S. of 4 triggered the exception (euthanized accordingly to humane practices). Kaplan-Meier survival analysis indicated that SYN1 and SYN2 administration at the time of onset significantly extended survival. Data in FIGS. 6A and 6B document a 66% and an 81% lifespan extension for SYN1 and SYN2, respectively, at 50% survival in male mice. A similar trend was observed in female mice. Animal weight, which reflects muscle atrophy and metabolic weight waste, was also significantly reduced by the treatments. The average weight within the groups before the treatment was similar (inset to FIG. 6C). However, at 120 days, control animals lost on average 12% of the body weight (FIG. 6C). SYN1 and SYN2 treated mice lost only 3% (75% inhibition) and 4% (65% inhibition) of the body weight, respectively. N.S. were also improved by the compounds. Although progression from N.S. 0 to 1 was delayed only by SYN1 (2 day delay, +30%), progression to higher N.S. was delayed by both agents (FIG. 6D). SYN1 and SYN2 administration increased the time spent at N.S.1 (the animal is still able to move around and has minimal motor impairment). Control animals reached N.S.=2 at 30 days on average; treated animals reached N.S.=2 at day 46 or later on average. *$P<0.05$; **$P<0.01$.

DETAILED DESCRIPTION

Figure 3:
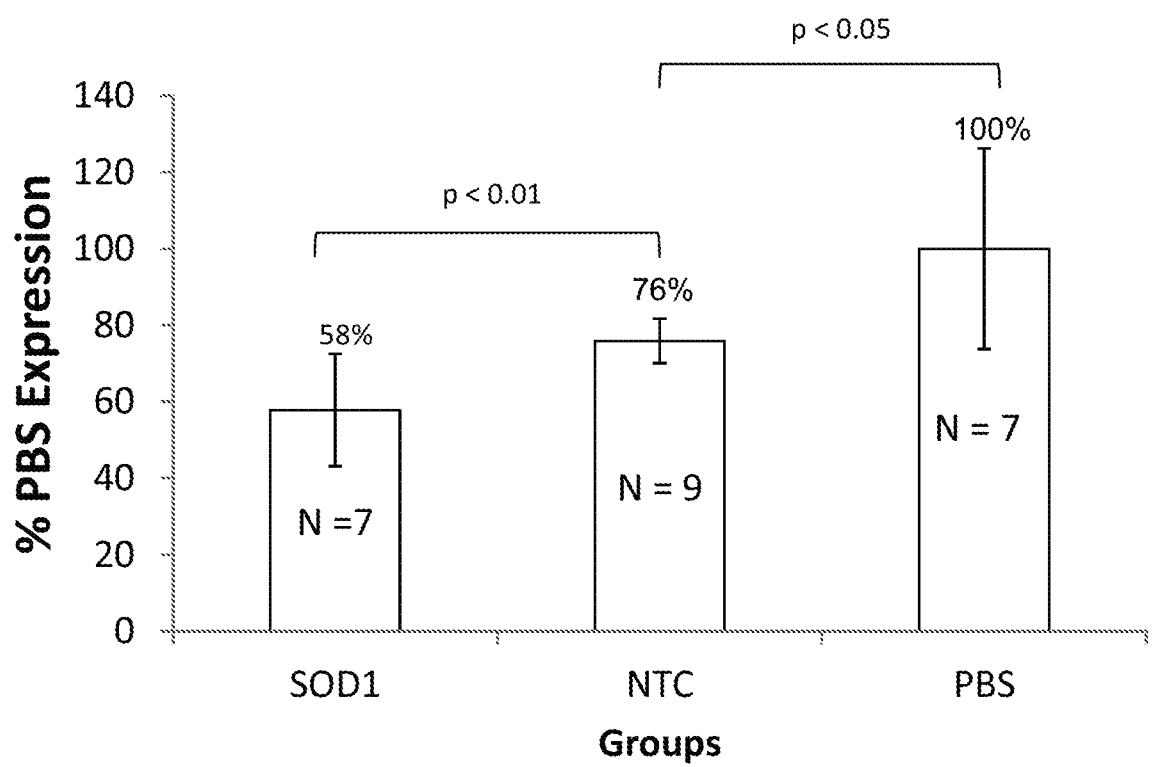
FIG. 3. Reduction of SOD1 mRNA following a 14-day intrathecal infusion of SOD1 targeting sd-rxRNA variant 3 in normal mice. A 14 day intrathecal infusion with implanted osmotic pump in C57BL/6 normal (non-transgenic) mice was implemented. 14 day osmotic pumps were filled with 100 ul of 10 mg/ml of each compound. The pump flow rate was 0.25 ul/hr. 60 µg of SOD1 targeting or non-targeting control (NTC) sd-rxRNA variant was administered per day for 14 days (840 ug total). Gene expression analysis by qPCR was performed and normalized to a PPIB housekeeping gene and plotted relative to SOD1 expression in the PBS group. Silencing was observed in the lumbar region of the spinal cord only (region of catheter placement). 100% of the SOD1 ps-rxRNA treated animals exhibited adverse advents (hind limb lameness or paralysis). 30 C57BL/6J mice were used for this study including: Fl-SOD1 targeting ps-rxRNA Gen 2: n=10; NTC ps-rxRNA: n=10; and PBS n=10.

Aspects of the invention relate to the use of small molecule regenerative compounds in combination with nucleic acid molecules with improved in vivo delivery properties, which target SOD1 and other neurological genes of interest, for the treatment of neurological disorders such as amyotrophic lateral sclerosis (ALS), traumatic brain injury (TBI), and Alzheimer's disease (AD).

As used herein, "neurodegenerative disease" or "neurodegenerative disorder" refers to disorders, diseases or conditions that are caused by the deterioration of cell and/or tissue components of the nervous system, whether now known or discovered in the future. In some embodiments, neurodegenerative disorders are associated with pathologically altered proteins that deposit in the human brain and in peripheral organs. Examples of NDD include but are not limited to Alzheimer Disease (AD), Amyotrophic Lateral Sclerosis (ALS), Argyrophilic Grain Disease, Basophilic Inclusion Body Disease, Sporadic Cerebral Amyloid Angiopathy, Corticobasal Degeneration, Creutzfeldt-Jakob Disease (e.g., Iatrogenic, Sporadic, Variant, and Genetic Creutzfeldt-Jakob Disease), Degenerative Proteinopaties associated with Traumatic Brain Injury (TBI), dementia, dementia with Lewy Bodies, Dentatorubral-Pallidoluysian Atrophy, Sporadic Fatal Insomnia, Fatal Familial Insomnia, Fragile X Mental Retardation, Frontotemporal Dementia (FD), Frontotemporal Lobar Degeneration. Atypical Frontotemporal Lobar Degeneration with Ubiquitinated Inclusions, Frontotemporal Lobar Degeneration with Inclusions Immunoreactive only for the Components of the Ubiquitine Proteasome System, Frontotemporal Lobar Degeneration with No Inclusion Specified, Frontotemporal Dementia and Parkinsonism Linked to Chromosome 17 Caused by Mutations in the MAPT (Tau) Gene, Fragile X Associated Tremor and Ataxia Syndrome (FXTAS), Globular Glial Tauopathies, Gerstmann-Sträussler-Scheinker Disease, Huntington Disease (HD), Neuronal/Glial Intranuclear Inclusion Body Diseases, movement disorders, motor neuron diseases (e.g., Motor Neuron Disease), Multiple System Atrophy, Neurodegeneration with Brain Iron Accumulation, Neurodegeneration Associated with Traumatic Brain Injury; Neurofilament Intermediate Filament Inclusion Disease, Parkinson Disease, Pick Disease, Prion Protein, Progressive Supranuclear Palsy, Spinocerebellar Ataxia (SA), Spinal and Bulbar Muscular Atrophy, Trinucleotide Repeat Expansion Disorder, Variably Protease-Sensitive Prionopathy. Additional NDD and characterization thereof are disclosed, for example, in Kovacs, G. (2016). *Molecular Pathological Classification of Neurodegenerative Diseases: Turning towards Precision Medicine.* Int. J. Mol. Sci. 17, 189; doi:10.3390/ijms17020189.

Further aspects of the invention relate to a non-genetic gene silencing animal model for the screening of potential ALS and TBI therapeutics and diagnostic approaches.

NF-κB and MnSOD/SOD2 Activation Effects

Cellular damage in several central nervous system diseases including, but not limited to, ALS and TBI, is associated with increased ROS and decreased neurotrophic factors, which ultimately results in cell death and brain function degeneration (Strong, M. J., S. Kesavapany, and H. C. Pant, *The pathobiology of amyotrophic lateral sclerosis: a proteinopathy?* J Neuropathol Exp Neurol, 2005; 64(8):649-64; Palomo, G. M. and G. Manfredi (2015). *Exploring new pathways of neurodegeneration in ALS: the role of mitochondria quality control.* Brain Res, 2015; 1607:36-46). Without wishing to be bound by any theory, neurodegenerative diseases like ALS and TBI are multifactorial diseases involving three main pathogenic features: 1) imbalance of reactive oxygen species (ROS), 2) mitochondrial malady and 3) intraneuronal inclusions composed of many proteins including SOD1, TDP43, FUS, ribosomal components and RNA, ultimately resulting in protein transcription failure.

Nuclear Factor κB (NF-κB)

NF-κB is involved in a cell-signaling pathway particularly important in the central nervous system (CNS). The most common form of NF-κB (up to 75%) is a dimer of p50/p65, with p65 representing 75% of the dimer in neurons and responsible for key neuronal and neurotrophic functions (Meberg, P. J., et al., *Gene expression of the transcription factor NF-kappa B in hippocampus: regulation by synaptic activity.* Brain Res Mol Brain Res, 1996; 38(2):179-90; Albensi, B. C. and M. P. Mattson, *Evidence for the involvement of TNF and NF-kappaB in hippocampal synaptic plasticity.* Synapse, 2000; 35(2):151-9).

Enhancement of general protein transcription via inhibition of histone deacetylase (HDAC) enzymes, a process mediated by NF-κB activation, has been associated with impressive improvement of symptoms and prolonged survival in the ALS animal model (Del Signore, S. J., et al., *Combined riluzole and sodium phenylbutyrate therapy in transgenic amyotrophic lateral sclerosis mice.* Amyotroph Lateral Scler, 2009; 10(2):85-94; Ryu, H., et al., *Sodium phenylbutyrate prolongs survival and regulates expression of anti-apoptotic genes in transgenic amyotrophic lateral sclerosis mice.* J Neurochem, 2005; 93(5):087-98).

ROS increase in ALS has been implicated in both decreased DNA acetylation and mRNA transcription that affects the expression of important neurotrophic factors (Swarup V, Julien J P. *ALS pathogenesis: Recent insights from genetics and mouse models.* Prog. Neuropsychopharmacol. Biol. Psychiatry. 2011; 35(2):363-9. PubMed PMID: 20728492). It was initially hypothesized that introduction of non-mutated SOD1 in cells would rescue the mitochondrial functions and maintain cell viability. Studies in vitro have shown that co-expression of wild type SOD1 in the presence of mutated SOD1 results in failure of the normal SOD activity, possibly by inducing the misfolding of the normal exogenously introduced SOD1, and is accompanied by more fragile neurons, faster disease progression and worsening of symptoms (Jaarsma, D., et al., *Human Cu/Zn superoxide dismutase (SOD1) overexpression in mice causes mitochondrial vacuolization, axonal degeneration, and premature motoneuron death and accelerates motoneuron disease in mice expressing a familial amyotrophic lateral sclerosis mutant SOD1.* Neurobiol Dis, 2000; 7(6 Pt B):623-43).

SOD1 (Copper/Zinc Superoxide Dismutase)

As used herein, "SOD1" refers to the Superoxide Dismutase 1 enzyme, which is one of three superoxide dismutases involved in converting harmful superoxide radicals to water. Approximately 10% of all ALS cases are dominantly inherited, and of these ~20% are due to defects in cytosolic superoxide dismutase 1 (SOD1). In addition, SOD1 has been implicated in non-familial (e.g. sporadic) forms of ALS (Jones, C. T., Brock, D. J. H., Chancellor, A. M., Warlow, C. P., Swingler, R. J. *Cu/Zn superoxide dismutase (SOD1) mutations and sporadic amyotrophic lateral sclerosis.* Lancet 342: 1050-1051, 1993). Without wishing to be bound by any theory, several lines of investigation have suggested that the mutations in SOD1 do not cause ALS through loss of the dismutase activity of this enzyme. Rather, mutant SOD1 is neurotoxic through multiple alternate mechanisms, many of which entail conformational instability and aberrant binding and aggregation of the mutant protein. It was initially hypothesized that introduction of non-mutated SOD1 in the cells would rescue the mitochondrial functions and maintain cell viability. Studies in vitro have shown that co-expression of wild type SOD1 in the presence of mutated SOD1 results in failure of the normal SOD1 activity, possibly by inducing the misfolding of the normal exogenously introduced SOD1, and is accompanied by more fragile neurons, faster disease progression and worsening of symptoms (Jaarsma, D., et al., *Human Cu/Zn superoxide dismutase (SOD1) overexpression in mice causes mitochondrial vacuolization, axonal degeneration, and premature motoneuron death and accelerates motoneuron disease in mice expressing a familial amyotrophic lateral sclerosis mutant SOD1*. Neurobiol Dis, 2000; 7(6 Pt B):623-43). While the precise details of the toxicity of mutant SOD1 are not fully defined, it is abundantly clear that reduction of the burden of mutant SOD1 protein in animal models significantly delays death. This has been achieved using both antisense oligonucleotides (ASO) (Smith et al) and siRNA (Maxwell, Pasinelli et al. 2004) (Xia, Zhou et al. 2006) (Wang, Ghosh et al. 2008). These studies illustrate the principle that siRNA-based drugs represent a potentially significant therapeutic advance for the treatment of ALS and many other CNS disorders. In both cases, efficacy was achieved by delivery of high amounts of material over long periods of time; these studies illustrate the point that a major limitation of ASO and siRNA therapies in their present forms is the lack of optimally efficient and non-toxic in vivo delivery systems (Smith, Miller et al. 2006; Wang, Ghosh et al. 2008).

Aspects of the invention relate to the use of an agent that decreases SOD1 expression (e.g., nucleic acid molecules) in combination with an agent that increases expression of manganese superoxide dismutase (MnSOD/Sod2) and/or related proteins and enzymes for treatment of neurological disorders (e.g., neurodegenerative disorders). In some embodiments, the agent that decreases SOD1 expression is a nucleic acid (e.g., a chemically modified nucleic acid). In some embodiments, the chemically modified nucleic acid is a double stranded isolated nucleic acid selected from the sequences listed in Tables 1 and 2. In some embodiments, the double stranded isolated nucleic acid selected from the sequences listed in Tables 1 and 2 has the chemical modification pattern provided in Tables 1 and 2.

MnSOD/SOD2 (Manganese Superoxide Dismutase)

As used herein, "MnSOD" and "SOD2" are used interchangeably and both refer to Superoxide dismutase 2, mitochondrial (also called Manganese superoxide dismutase), which is a critical highly inducible enzyme localized in the mitochondria. Studies in MnSOD knockout mice have demonstrated unequivocally that this enzyme is required for neuronal well-being and organism survival (Lebovitz, R. M., et al., *Neurodegeneration, myocardial injury, and perinatal death in mitochondrial superoxide dismutase-deficient mice*. Proc Natl Acad Sci USA, 1996; 93(18):9782-7; Chung, Y. H., et al., *Immunohistochemical study on the aggregation of ubiquitin in the central nervous system of the transgenic mice expressing a human Cu/Zn SOD mutation*. Neurol Res, 2003; 25(4):395-400; Flanagan, S. W., et al., *Overexpression of manganese superoxide dismutase attenuates neuronal death in human cells expressing mutant (G37R) Cu/Zn-superoxide dismutase*. J Neurochem, 2002; 81(1): 170-7; Cruthirds, D. L., et al., *Mitochondrial targets of oxidative stress during renal ischemia/reperfusion*. Arch Biochem Biophys, 2003; 412(1):27-33). MnSOD, although expressed in resting conditions, can be strongly induced by several factors including NF-κB activation (Kiningham, K. K., et al., *All-trans-retinoic acid induces manganese superoxide dismutase in human neuroblastoma through NF-kappaB*. Free Radic Biol Med, 2008; 44(8):1610-6). This is particularly noteworthy since MnSOD is unaffected in ALS. Studies demonstrate that MnSOD immunoreactivity is moderately increased in the spinal cord of SOD1 transgenic mice at pre-symptomatic and symptomatic stage and, in a cellular model of ROS toxicity, based on SOD1 mutation G37R expression, molecular over-expression of MnSOD reduced the enhancement of sensitivity to stressors caused by the SOD1 abnormality in cultures of differentiated human neurons (Chung, Y. H., et al., *Immunohistochemical study on the aggregation of ubiquitin in the central nervous system of the transgenic mice expressing a human Cu/Zn SOD mutation*. Neurol Res, 2003; 25(4):395-400; Flanagan, S. W., et al., *Overexpression of manganese superoxide dismutase attenuates neuronal death in human cells expressing mutant (G37R) Cu/Zn-superoxide dismutase*. J Neurochem, 2002; 81(1):170-7) suggesting that MnSOD is a likely pharmacologic target for the treatment of neurodegenerative diseases.

In some aspects, the disclosure relates to the use of an agent that decreases SOD1 expression (e.g., nucleic acid molecules) in combination with an agent that increases expression of manganese superoxide dismutase (MnSOD/Sod2) and/or related proteins and enzymes for treatment of neurological disorders (e.g., neurodegenerative disorders). Examples of proteins and enzymes that are related to MnSOD/SOD2 include but are not limited to Heat Shock Protein 27 (Hsp27), Hsp70-2, DNAJ Heat Shock Protein Family (Hsp40) Member B9 (DNAJB9), T-complex protein 1 subunit zeta-2 (CCT6B), DNAJ Heat Shock Protein Family (Hsp40) Member 5 Gamma (DNAJC5G), and Heme Oxygenase 1 (HMOX1).

An "agent that increases expression of manganese superoxide dismutase (MnSOD/Sod2) and/or related proteins" can be, for example, a nucleic acid, small molecule, peptide, or polypeptide (e.g., antibody). In some embodiments, the agent is a small molecule. In some embodiments, the small molecule is an activator of Nuclear Factor-κB (NF-κB), for example as described in Manuvakhova et al. (2011). *Identification of Novel Small Molecule Activators of Nuclear Factor-κB with Neuroprotective Action Via High-Throughput Screening*. J Neurosci. Res. 89(1); 58-72.

SYN1 and SYN2

As used herein, "SYN1" and "SYN2" and related chemical entities (e.g., SYN-NCE and SYN-GL), which are described in and incorporated by reference from PCT Publication No. WO/2011/047129 (PCT/US10/52624), refer to small molecules with neuro-regenerative activity, which act through the selective up-regulation of NF-κB p65 expression exclusively in neurons, with a mechanism completely devoid of any inflammatory or other evident toxicity. The main target of this mechanism of action is the activation of the MnSOD/SOD2 pathway. Increased SOD2 expression leads to disease-modifying effects, enhancing the quenching of ROS and expression/release of several neurotrophic factors, ameliorating overall neuronal survival in response to mechanic and biochemical insults. In addition, SYN1 has been shown to ameliorate protein misfolding, a known pathogenic cause of several neurodegenerative diseases including, but not limited to ALS, TBI, and Alzheimer's disease.

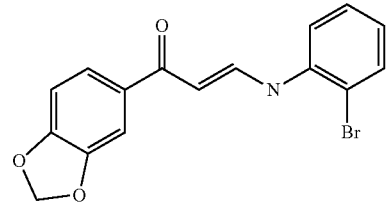

SYN1

-continued

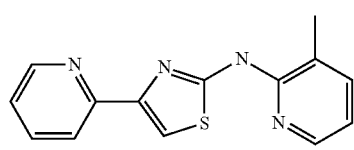

SYN2

Neurogenerative Disorders

Aspects of the invention relate to treatment of neurodegenerative diseases, including the use of compounds that are described in and incorporated by reference from PCT Publication No. WO/2011/047129. Methods described herein include methods for treating a patient suffering from a neurodegenerative disease such as Alzheimer's, Parkinson's, and ALS (also called "Lou Gehrig's disease"). Further aspects of the invention relate to treating patients who have a learning or memory impairment or who are predisposed to having such an impairment. It should be appreciated that methods described herein could be applied to any type of neurodegeneration. Further aspects of the invention relate to enhancing memory performance. Methods involve administering to a subject an effective amount of certain heterocyclic and aromatic compounds as described in and incorporated by reference from PCT Publication No. WO/2011/047129. Methods involve treating subjects in situations where modifying NF-κB signaling can result in improvement of a condition affecting the subject, including but not limited to conditions affecting the central nervous system. Aspects of the invention encompass the use of a neuronal human cell-based assay that assesses NF-κB gene up-regulation using a luciferase reporter for screening for compounds for use in treating neurodegenerative diseases as described in and incorporated by reference from PCT Publication No. WO/2011/047129.

Neurodegenerative diseases, such as Alzheimer's, Parkinson's, and ALS, which impact millions of people throughout the world, are still lacking effective treatments. The only treatments available marginally improve symptoms. It is expected that the burden on society caused by these diseases will continue to increase as human life span increases.

As discussed in and incorporated by reference from PCT Publication No. WO2011047129, the NF-κB pathway has been linked to neuronal resilience and cellular learning. Reducing expression of NF-κB in the brain has been reported to lead to negative effects including sensitization to toxic stimuli, whereas activation of NF-κB has been reported to positive effects related to learning and memory. It should be appreciated that methods and compositions described herein can be applied to any system or condition in which modulation of NF-κB signaling is beneficial.

Aspects of the invention relate to methods of treating neurodegenerative disease, memory impairments or learning impairments and/or protecting neurons and/or enhancing memory performance in a subject by administering to the subject at least one compound disclosed in and incorporated by reference from FIG. 11 of PCT Publication No. WO2011047129, represented by the structures:

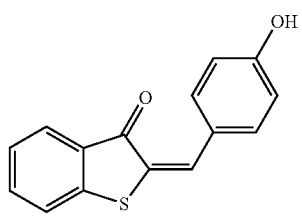

1

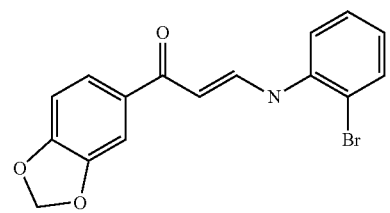

2

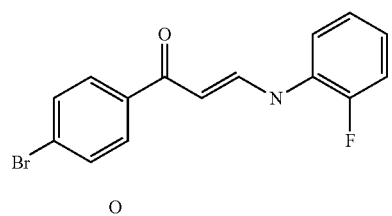

3

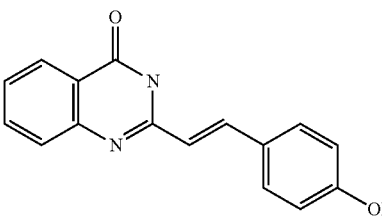

4

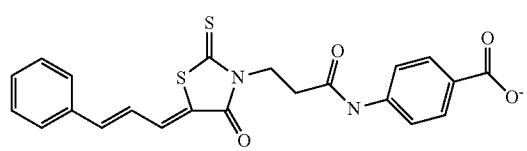

5

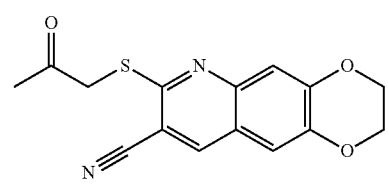

6

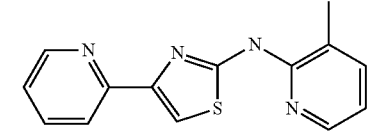

10

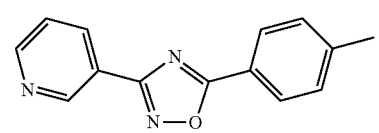

11

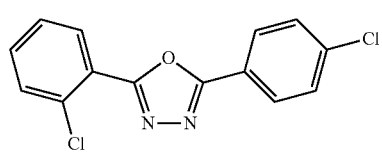

12

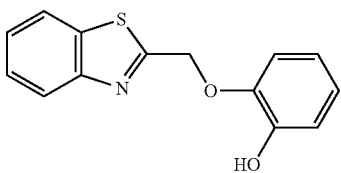
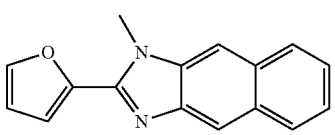
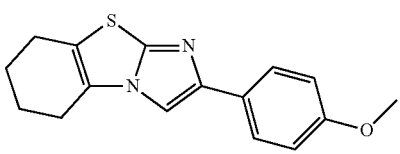
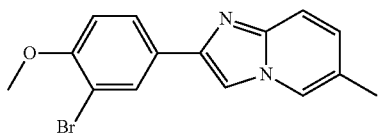
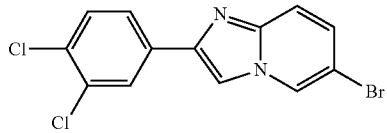
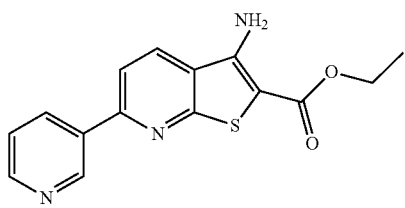
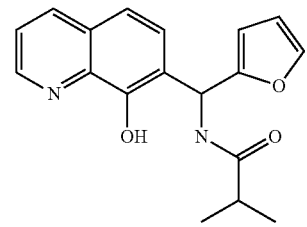
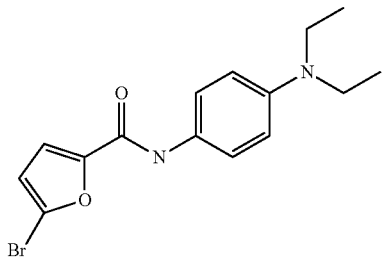

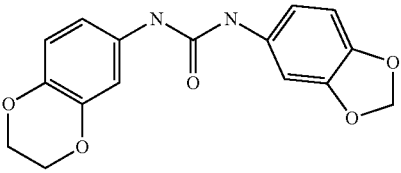

In some embodiments, a subject has a neurodegenerative disorder or an impairment affecting learning or memory. In other embodiments a subject is predisposed to having a neurodegenerative disorder or a disorder affecting learning or memory. In some embodiments methods are directed to improving memory or learning.

Amyotrophic Lateral Sclerosis (ALS)

ALS is a progressive neurodegenerative disease affecting motor neurons in the central nervous system. Degeneration of the motor neurons results in paralysis and eventual death, usually due to respiratory failure. In a subset of cases, ALS is caused by dominantly transmitted mutations in the gene encoding cytosolic superoxide dismutase (SOD1). Transgenic expression of mutant SOD1 causes ALS in mice.

Nucleic Acid Molecules

As used herein, "nucleic acid molecule" includes but is not limited to: sd-rxRNA, sd-rxRNA variant, rxRNAori, oligonucleotides, ASO, siRNA, shRNA, miRNA, ncRNA, cp-lasiRNA, aiRNA, single-stranded nucleic acid molecules, double-stranded nucleic acid molecules, RNA and DNA. In some embodiments, the nucleic acid molecule is a chemically modified nucleic acid molecule, such as a chemically modified oligonucleotide.

Sd-rxRNA Molecules

Aspects of the invention relate to sd-rxRNA molecules. As used herein, an "sd-rxRNA" or an "sd-rxRNA molecule" refers to a self-delivering RNA molecule such as those described in, and incorporated by reference from, U.S. Pat. No. 8,796,443, granted on Aug. 5, 2014, entitled "REDUCED SIZE SELF-DELIVERING RNAI COMPOUNDS", U.S. Pat. No. 9,175,289, granted on Nov. 3, 2015, entitled "REDUCED SIZE SELF-DELIVERING RNAI COMPOUNDS", and PCT Publication No. WO2010/033247 (Application No. PCT/US2009/005247), filed on Sep. 22, 2009, and entitled "REDUCED SIZE SELF-DELIVERING RNAI COMPOUNDS." Briefly, an sd-rxRNA, (also referred to as an sd-rxRNA$^{nano}$) is an isolated asymmetric double stranded nucleic acid molecule comprising a guide strand, with a minimal length of 16 nucleotides, and a passenger strand of 8-18 nucleotides in length, wherein the double stranded nucleic acid molecule has a double stranded region and a single stranded region, the single stranded region having 4-12 nucleotides in length and having at least three nucleotide backbone modifications. In preferred embodiments, the double stranded nucleic acid molecule has one end that is blunt or includes a one or two nucleotide overhang. sd-rxRNA molecules can be optimized through chemical modification, and in some instances through attachment of hydrophobic conjugates.

In some embodiments, an sd-rxRNA comprises an isolated double stranded nucleic acid molecule comprising a guide strand and a passenger strand, wherein the region of the molecule that is double stranded is from 8-15 nucleotides long, wherein the guide strand contains a single stranded region that is 4-12 nucleotides long, wherein the single stranded region of the guide strand contains 3, 4, 5, 6, 7, 8, 9, 10, 11 or 12 phosphorothioate modifications, and wherein at least 40% of the nucleotides of the double stranded nucleic acid are modified.

In some embodiments, an sd-rxRNA variant comprises an sd-rxRNA that contains an 18 to 23 nucleotide long guide strand (antisense strand) and a 10 to 15 nucleotide long passenger strand (sense strand). The guide strand and passenger strand can form an asymmetric duplex. In some embodiments, the guide strand contains between 6 to 22 backbone modifications, including phosphorothioate modifications. In some embodiments, the passenger strand contains between 2 to 14 backbone modifications, including phosphorothioate modifications. In some embodiments, the passenger strand is attached to a hydrophobic conjugate. The term "sd-rxRNA variant" is used interchangeably herein with "ps-rxRNA".

In some embodiments, the guide strand contains 2, 3, 4, 5, 6, 7, 8, 9, 10, 11, 12, 13, 14, 15, 16, 17, 18, 19, 20, 21 or 22 phosphorothioate modifications. In some embodiments, the guide strand is completely phosphorothioated. In some embodiments, the passenger strand contains 3, 4, 5, 6, 7, 8, 9, 10, 11, 12, 13 or 14 phosphorothioate modifications. In some embodiments, the passenger strand is completely phosphorothioated. It was surprisingly found herein that high levels of phosphorothioate modifications can lead to increased delivery of isolated double stranded nucleic acid molecules.

Nucleic acid molecules associated with the invention are also referred to herein as polynucleotides, isolated double stranded or duplex nucleic acids, oligonucleotides, nano molecules, nano RNA, sd-rxRNA$^{nano}$, sd-rxRNA or RNA molecules of the invention.

sd-rxRNAs are much more effectively taken up by cells compared to conventional siRNAs. These molecules are highly efficient in silencing of target gene expression and offer significant advantages over previously described RNAi molecules including high activity in the presence of serum, efficient self delivery, compatibility with a wide variety of linkers, and reduced presence or complete absence of chemical modifications that are associated with toxicity.

In contrast to single-stranded polynucleotides, duplex polynucleotides have traditionally been difficult to deliver to a cell as they have rigid structures and a large number of negative charges which makes membrane transfer difficult. sd-rxRNAs however, although partially double-stranded, are recognized in vivo as single-stranded and, as such, are capable of efficiently being delivered across cell membranes. As a result the polynucleotides of the invention are capable in many instances of self delivery. Thus, the polynucleotides of the invention may be formulated in a manner similar to conventional RNAi agents or they may be delivered to the cell or subject alone (or with non-delivery type carriers) and allowed to self deliver. In one embodiment of the present invention, self delivering asymmetric double-stranded RNA molecules are provided in which one portion of the molecule resembles a conventional RNA duplex and a second portion of the molecule is single stranded.

The oligonucleotides of the invention in some aspects have a combination of asymmetric structures including a double stranded region and a single stranded region of 5 nucleotides or longer, specific chemical modification patterns and are conjugated to lipophilic or hydrophobic molecules. This class of RNAi like compounds have superior efficacy in vitro and in vivo. It is believed that the reduction in the size of the rigid duplex region in combination with phosphorothioate modifications applied to a single stranded region contribute to the observed superior efficacy.

In some embodiments an RNAi compound associated with the invention comprises an asymmetric compound comprising a duplex region (required for efficient RISC entry of 8-15 bases long) and single stranded region of 4-12 nucleotides long. In some embodiments, the duplex region is 13 or 14 nucleotides long. A 6 or 7 nucleotide single stranded region is preferred in some embodiments. In some embodiments, the RNAi compound comprises 2-12 phosphorothioate internucleotide linkages (referred to as phosphorothioate modifications). 6-8 phosphorothioate internucleotide linkages are preferred in some embodiments. In some embodiments, the RNAi compounds include a unique chemical modification pattern, which provides stability and is compatible with RISC entry. The combination of these elements has resulted in unexpected properties which are highly useful for delivery of RNAi reagents in vitro and in vivo.

The chemical modification pattern, which provides stability and is compatible with RISC entry includes modifications to the sense, or passenger, strand as well as the antisense, or guide, strand. For instance the passenger strand can be modified with any chemical entities which confirm stability and do not interfere with activity. Such modifications include 2' ribo modifications (O-methyl, 2' F, 2 deoxy and others) and backbone modification like phosphorothioate modifications. A preferred chemical modification pattern in the passenger strand includes Omethyl modification of C and U nucleotides within the passenger strand or alternatively the passenger strand may be completely Omethyl modified.

The guide strand, for example, may also be modified by any chemical modification which confirms stability without interfering with RISC entry. A preferred chemical modification pattern in the guide strand includes the majority of C and U nucleotides being 2' F modified and the 5' end being phosphorylated. Another preferred chemical modification pattern in the guide strand includes 2'Omethyl modification of position 1 and C/U in positions 11-18 and 5' end chemical phosphorylation. Yet another preferred chemical modification pattern in the guide strand includes 2'Omethyl modification of position 1 and C/U in positions 11-18 and 5' end chemical phosphorylation and 2'F modification of C/U in positions 2-10. In some embodiments the passenger strand and/or the guide strand contains at least one 5-methyl C or U modifications.

In some embodiments, at least 30% of the nucleotides in the sd-rxRNA are modified. For example, at least 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the nucleotides in the sd-rxRNA are modified. In some embodiments, 100% of the nucleotides in the sd-rxRNA are modified.

The above-described chemical modification patterns of the oligonucleotides of the invention are well tolerated and actually improved efficacy of asymmetric RNAi compounds.

In some embodiments, elimination of any of the described components (Guide strand stabilization, phosphorothioate stretch, sense strand stabilization and hydrophobic conjugate) or increase in size in some instances results in sub-optimal efficacy and in some instances complete lost of efficacy. The combination of elements results in development of a compound, which is fully active following passive delivery to cells such as HeLa cells.

The sd-rxRNA can be further improved in some instances by improving the hydrophobicity of compounds using of novel types of chemistries. For example, one chemistry is related to use of hydrophobic base modifications. Any base in any position might be modified, as long as modification results in an increase of the partition coefficient of the base. The preferred locations for modification chemistries are positions 4 and 5 of the pyrimidines. The major advantage of these positions is (a) ease of synthesis and (b) lack of interference with base-pairing and A form helix formation, which are essential for RISC complex loading and target recognition. A version of sd-rxRNA compounds where multiple deoxy Uridines are present without interfering with overall compound efficacy was used. In addition major improvement in tissue distribution and cellular uptake might be obtained by optimizing the structure of the hydrophobic conjugate. In some of the preferred embodiment the structure of sterol is modified to alter (increase/decrease) C17 attached chain. This type of modification results in significant increase in cellular uptake and improvement of tissue uptake properties in vivo.

dsRNA formulated according to the invention also includes rxRNAori. rxRNAori refers to a class of RNA molecules described in and incorporated by reference from PCT Publication No. WO2009/102427 (Application No. PCT/US2009/000852), filed on Feb. 11, 2009, and entitled, "MODIFIED RNAI POLYNUCLEOTIDES AND USES THEREOF" and US Patent Publication No. US 2011-0039914 entitled "MODIFIED RNAI POLYNUCLEOTIDES AND USES THEREOF."

In some embodiments, an rxRNAori molecule comprises a double-stranded RNA (dsRNA) construct of 12-35 nucleotides in length, for inhibiting expression of a target gene, comprising: a sense strand having a 5'-end and a 3'-end, wherein the sense strand is highly modified with 2'-modified ribose sugars, and wherein 3-6 nucleotides in the central portion of the sense strand are not modified with 2'-modified ribose sugars and, an antisense strand having a 5'-end and a 3'-end, which hybridizes to the sense strand and to mRNA of the target gene, wherein the dsRNA inhibits expression of the target gene in a sequence-dependent manner.

rxRNAori can contain any of the modifications described herein. In some embodiments, at least 30% of the nucleotides in the rxRNAori are modified. For example, at least 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the nucleotides in the rxRNAori are modified. In some embodiments, 100% of the nucleotides in the sd-rxRNA are modified. In some embodiments, only the passenger strand of the rxRNAori contains modifications.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Aspects of the invention relate to isolated double stranded nucleic acid molecules comprising a guide (antisense) strand and a passenger (sense) strand. As used herein, the term "double-stranded" refers to one or more nucleic acid molecules in which at least a portion of the nucleomonomers are complementary and hydrogen bond to form a double-stranded region. In some embodiments, the length of the guide strand ranges from 16-29 nucleotides long. In certain embodiments, the guide strand is 16, 17, 18, 19, 20, 21, 22, 23, 24, 25, 26, 27, 28, or 29 nucleotides long. The guide strand has complementarity to a target gene. Complementarity between the guide strand and the target gene may exist over any portion of the guide strand. Complementarity as used herein may be perfect complementarity or less than perfect complementarity as long as the guide strand is sufficiently complementary to the target that it mediates RNAi. In some embodiments complementarity refers to less than 25%, 20%, 15%, 10%, 5%, 4%, 3%, 2%, or 1% mismatch between the guide strand and the target. Perfect complementarity refers to 100% complementarity. In some embodiments, siRNA sequences with insertions, deletions, and single point mutations relative to the target sequence have also been found to be effective for inhibition. Moreover, not all positions of a siRNA contribute equally to target recognition. Mismatches in the center of the siRNA are most critical and essentially abolish target RNA cleavage. Mismatches upstream of the center or upstream of the cleavage site referencing the antisense strand are tolerated but significantly reduce target RNA cleavage. Mismatches downstream of the center or cleavage site referencing the antisense strand, preferably located near the 3' end of the antisense strand, e.g. 1, 2, 3, 4, 5 or 6 nucleotides from the 3' end of the antisense strand, are tolerated and reduce target RNA cleavage only slightly.

While not wishing to be bound by any particular theory, in some embodiments, the guide strand is at least 16 nucleotides in length and anchors the Argonaute protein in RISC. In some embodiments, when the guide strand loads into RISC it has a defined seed region and target mRNA cleavage takes place across from position 10-11 of the guide strand. In some embodiments, the 5' end of the guide strand is or is able to be phosphorylated. The nucleic acid molecules described herein may be referred to as minimum trigger RNA.

In some embodiments, the length of the passenger strand ranges from 8-15 nucleotides long. In certain embodiments, the passenger strand is 8, 9, 10, 11, 12, 13, 14 or 15 nucleotides long. The passenger strand has complementarity to the guide strand. Complementarity between the passenger strand and the guide strand can exist over any portion of the passenger or guide strand. In some embodiments, there is 100% complementarity between the guide and passenger strands within the double stranded region of the molecule.

Aspects of the invention relate to double stranded nucleic acid molecules with minimal double stranded regions. In some embodiments the region of the molecule that is double stranded ranges from 8-15 nucleotides long. In certain embodiments, the region of the molecule that is double stranded is 8, 9, 10, 11, 12, 13, 14 or 15 nucleotides long. In certain embodiments the double stranded region is 13 or 14 nucleotides long. There can be 100% complementarity between the guide and passenger strands, or there may be one or more mismatches between the guide and passenger strands. In some embodiments, on one end of the double stranded molecule, the molecule is either blunt-ended or has a one-nucleotide overhang. The single stranded region of the molecule is in some embodiments between 4-12 nucleotides long. For example the single stranded region can be 4, 5, 6, 7, 8, 9, 10, 11 or 12 nucleotides long. However, in certain embodiments, the single stranded region can also be less than 4 or greater than 12 nucleotides long. In certain embodiments, the single stranded region is at least 6 or at least 7 nucleotides long.

RNAi constructs associated with the invention can have a thermodynamic stability (ΔG) of less than −13 kkal/mol. In some embodiments, the thermodynamic stability (ΔG) is less than −20 kkal/mol. In some embodiments there is a loss of efficacy when (ΔG) goes below −21 kkal/mol. In some embodiments a (ΔG) value higher than −13 kkal/mol is compatible with aspects of the invention. Without wishing to be bound by any theory, in some embodiments a molecule with a relatively higher (ΔG) value may become active at a relatively higher concentration, while a molecule with a relatively lower (ΔG) value may become active at a relatively lower concentration. In some embodiments, the (ΔG) value may be higher than −9 kkcal/mol. The gene silencing effects mediated by the RNAi constructs associated with the invention, containing minimal double stranded regions, are unexpected because molecules of almost identical design but lower thermodynamic stability have been demonstrated to be inactive (Rana et al 2004).

Without wishing to be bound by any theory, a stretch of 8-10 bp of dsRNA or dsDNA may be structurally recognized by protein components of RISC or co-factors of RISC. Additionally, there is a free energy requirement for the triggering compound that it may be either sensed by the protein components and/or stable enough to interact with such components so that it may be loaded into the Argonaute protein. If optimal thermodynamics are present and there is a double stranded portion that is preferably at least 8 nucleotides then the duplex will be recognized and loaded into the RNAi machinery.

In some embodiments, thermodynamic stability is increased through the use of LNA bases. In some embodiments, additional chemical modifications are introduced. Several non-limiting examples of chemical modifications include: 5' Phosphate, 2'-O-methyl, 2'-O-ethyl, 2'-fluoro, ribothymidine, C-5 propynyl-dC (pdC) and C-5 propynyl-dU (pdU); C-5 propynyl-C(pC) and C-5 propynyl-U (pU); 5-methyl C, 5-methyl U, 5-methyl dC, 5-methyl dU methoxy, (2,6-diaminopurine), 5'-Dimethoxytrityl-N4-ethyl-2'-deoxyCytidine and MGB (minor groove binder). It should be appreciated that more than one chemical modification can be combined within the same molecule.

Molecules associated with the invention are optimized for increased potency and/or reduced toxicity. For example, nucleotide length of the guide and/or passenger strand, and/or the number of phosphorothioate modifications in the guide and/or passenger strand, can in some aspects influence potency of the RNA molecule, while replacing 2'-fluoro (2'F) modifications with 2'-O-methyl (2'OMe) modifications can in some aspects influence toxicity of the molecule. Specifically, reduction in 2'F content of a molecule is predicted to reduce toxicity of the molecule. Furthermore, the number of phosphorothioate modifications in an RNA molecule can influence the uptake of the molecule into a cell, for example the efficiency of passive uptake of the molecule into a cell. Preferred embodiments of molecules described herein have no 2'F modification and yet are characterized by equal efficacy in cellular uptake and tissue penetration. Such molecules represent a significant improvement over prior art, such as molecules described by Accell and Wolfrum, which are heavily modified with extensive use of 2'F.

In some embodiments, a guide strand is approximately 18-19 nucleotides in length and has approximately 2-14 phosphate modifications. For example, a guide strand can contain 2, 3, 4, 5, 6, 7, 8, 9, 10, 11, 12, 13, 14 or more than 14 nucleotides that are phosphate-modified. The guide strand may contain one or more modifications that confer increased stability without interfering with RISC entry. The phosphate modified nucleotides, such as phosphorothioate modified nucleotides, can be at the 3' end, 5' end or spread throughout the guide strand. In some embodiments, the 3' terminal 10 nucleotides of the guide strand contains 1, 2, 3, 4, 5, 6, 7, 8, 9 or 10 phosphorothioate modified nucleotides. The guide strand can also contain 2'F and/or 2'OMe modifications, which can be located throughout the molecule. In some embodiments, the nucleotide in position one of the guide strand (the nucleotide in the most 5' position of the guide strand) is 2'OMe modified and/or phosphorylated. C and U nucleotides within the guide strand can be 2'F modified. For example, C and U nucleotides in positions 2-10 of a 19 nt guide strand (or corresponding positions in a guide strand of a different length) can be 2'F modified. C and U nucleotides within the guide strand can also be 2'OMe modified. For example, C and U nucleotides in positions 11-18 of a 19 nt guide strand (or corresponding positions in a guide strand of a different length) can be 2'OMe modified. In some embodiments, the nucleotide at the most 3' end of the guide strand is unmodified. In certain embodiments, the majority of Cs and Us within the guide strand are 2'F modified and the 5' end of the guide strand is phosphorylated. In other embodiments, position 1 and the Cs or Us in positions 11-18 are 2'OMe modified and the 5' end of the guide strand is phosphorylated. In other embodiments, position 1 and the Cs or Us in positions 11-18 are 2'OMe modified, the 5' end of the guide strand is phosphorylated, and the Cs or Us in position 2-10 are 2'F modified.

In some aspects, an optimal passenger strand is approximately 11-14 nucleotides in length. The passenger strand may contain modifications that confer increased stability. One or more nucleotides in the passenger strand can be 2'OMe modified. In some embodiments, one or more of the C and/or U nucleotides in the passenger strand is 2'OMe modified, or all of the C and U nucleotides in the passenger strand are 2'OMe modified. In certain embodiments, all of the nucleotides in the passenger strand are 2'OMe modified. One or more of the nucleotides on the passenger strand can also be phosphate-modified such as phosphorothioate modified. The passenger strand can also contain 2' ribo, 2'F and 2 deoxy modifications or any combination of the above. Chemical modification patterns on both the guide and passenger strand can be well tolerated and a combination of chemical modifications can lead to increased efficacy and self-delivery of RNA molecules.

Aspects of the invention relate to RNAi constructs that have extended single-stranded regions relative to double stranded regions, as compared to molecules that have been used previously for RNAi. The single stranded region of the molecules may be modified to promote cellular uptake or gene silencing. In some embodiments, phosphorothioate modification of the single stranded region influences cellular uptake and/or gene silencing. The region of the guide strand that is phosphorothioate modified can include nucleotides within both the single stranded and double stranded regions of the molecule. In some embodiments, the single stranded region includes 2-12 phosphorothioate modifications. For example, the single stranded region can include 2, 3, 4, 5, 6, 7, 8, 9, 10, 11, or 12 phosphorothioate modifications. In some instances, the single stranded region contains 6-8 phosphorothioate modifications.

Molecules associated with the invention are also optimized for cellular uptake. In RNA molecules described herein, the guide and/or passenger strands can be attached to a conjugate. In certain embodiments the conjugate is hydrophobic. The hydrophobic conjugate can be a small molecule with a partition coefficient that is higher than 10. The conjugate can be a sterol-type molecule such as cholesterol, or a molecule with an increased length polycarbon chain attached to C17, and the presence of a conjugate can influence the ability of an RNA molecule to be taken into a cell with or without a lipid transfection reagent. The conjugate can be attached to the passenger or guide strand through a hydrophobic linker. In some embodiments, a hydrophobic linker is 5-12C in length, and/or is hydroxypyrrolidine-based. In some embodiments, a hydrophobic conjugate is attached to the passenger strand and the CU residues of either the passenger and/or guide strand are modified. In some embodiments, at least 50%, 55%, 60%, 65%, 70%, 75%, 80%, 85%, 90% or 95% of the CU residues on the passenger strand and/or the guide strand are modified. In some aspects, molecules associated with the invention are self-delivering (sd). As used herein, "self-delivery" refers to the ability of a molecule to be delivered into a cell without the need for an additional delivery vehicle such as a transfection reagent.

Aspects of the invention relate to selecting molecules for use in RNAi. In some embodiments, molecules that have a double stranded region of 8-15 nucleotides can be selected for use in RNAi. In some embodiments, molecules are selected based on their thermodynamic stability ($\Delta G$). In some embodiments, molecules will be selected that have a ($\Delta G$) of less than −13 kkal/mol. For example, the ($\Delta G$) value may be −13, −14, −15, −16, −17, −18, −19, −21, −22 or less than −22 kkal/mol. In other embodiments, the ($\Delta G$) value may be higher than −13 kkal/mol. For example, the ($\Delta G$) value may be −12, −11, −10, −9, −8, −7 or more than −7 kkal/mol. It should be appreciated that $\Delta G$ can be calculated using any method known in the art. In some embodiments $\Delta G$ is calculated using Mfold, available through the Mfold internet site (mfold.bioinfo.rpi.edu/cgi-bin/rna-form1.cgi). Methods for calculating $\Delta G$ are described in, and are incorporated by reference from, the following references: Zuker, M. (2003) Nucleic Acids Res., 31(13):3406-15; Mathews, D. H., *Sabina*, J., Zuker, M. and Turner, D. H. (1999) J. Mol. Biol. 288:911-940; Mathews, D. H., Disney, M. D., Childs, J. L., Schroeder, S. J., Zuker, M., and Turner, D. H. (2004) Proc. Natl. Acad. Sci. 101:7287-7292; Duan, S., Mathews, D. H., and Turner, D. H. (2006) Biochemistry 45:9819-9832; Wuchty, S., Fontana, W., Hofacker, I. L., and Schuster, P. (1999) Biopolymers 49:145-165.

In certain embodiments, the polynucleotide contains 5'- and/or 3'-end overhangs. The number and/or sequence of nucleotides overhang on one end of the polynucleotide may be the same or different from the other end of the polynucleotide. In certain embodiments, one or more of the overhang nucleotides may contain chemical modification(s), such as phosphorothioate or 2'-OMe modification.

In certain embodiments, the polynucleotide is unmodified. In other embodiments, at least one nucleotide is modified. In further embodiments, the modification includes a 2'-H or 2'-modified ribose sugar at the 2nd nucleotide from the 5'-end of the guide sequence. The "2nd nucleotide" is defined as the second nucleotide from the 5'-end of the polynucleotide.

As used herein, "2'-modified ribose sugar" includes those ribose sugars that do not have a 2'—OH group. "2'-modified ribose sugar" does not include 2'-deoxyribose (found in unmodified canonical DNA nucleotides). For example, the 2'-modified ribose sugar may be 2'-O-alkyl nucleotides, 2'-deoxy-2'-fluoro nucleotides, 2'-deoxy nucleotides, or combination thereof.

In certain embodiments, the 2'-modified nucleotides are pyrimidine nucleotides (e.g., C/U). Examples of 2'-O-alkyl nucleotides include 2'-O-methyl nucleotides, or 2'-O-allyl nucleotides.

In certain embodiments, the sd-rxRNA polynucleotide of the invention with the above-referenced 5'-end modification exhibits significantly (e.g., at least about 25%, 30%, 35%, 40%, 45%, 50%, 55%, 60%, 65%, 70%, 75%, 80%, 85%, 90% or more) less "off-target" gene silencing when compared to similar constructs without the specified 5'-end modification, thus greatly improving the overall specificity of the RNAi reagent or therapeutics.

As used herein, "off-target" gene silencing refers to unintended gene silencing due to, for example, spurious sequence homology between the antisense (guide) sequence and the unintended target mRNA sequence.

According to this aspect of the invention, certain guide strand modifications further increase nuclease stability, and/or lower interferon induction, without significantly decreasing RNAi activity (or no decrease in RNAi activity at all).

Certain combinations of modifications may result in further unexpected advantages, as partly manifested by enhanced ability to inhibit target gene expression, enhanced serum stability, and/or increased target specificity, etc.

In certain embodiments, the guide strand comprises a 2'-O-methyl modified nucleotide at the $2^{nd}$ nucleotide on the 5'-end of the guide strand and no other modified nucleotides.

In other aspects, the sd-rxRNA structures of the present invention mediates sequence-dependent gene silencing by a microRNA mechanism. As used herein, the term "microRNA" ("miRNA"), also referred to in the art as "small temporal RNAs" ("stRNAs"), refers to a small (10-50 nucleotide) RNA which are genetically encoded (e.g., by viral, mammalian, or plant genomes) and are capable of directing or mediating RNA silencing. An "miRNA disorder" shall refer to a disease or disorder characterized by an aberrant expression or activity of an miRNA.

microRNAs are involved in down-regulating target genes in critical pathways, such as development and cancer, in mice, worms and mammals. Gene silencing through a microRNA mechanism is achieved by specific yet imperfect base-pairing of the miRNA and its target messenger RNA (mRNA). Various mechanisms may be used in microRNA-mediated down-regulation of target mRNA expression.

miRNAs are noncoding RNAs of approximately 22 nucleotides which can regulate gene expression at the post transcriptional or translational level during plant and animal development. One common feature of miRNAs is that they are all excised from an approximately 70 nucleotide precursor RNA stem-loop termed pre-miRNA, probably by Dicer, an RNase III-type enzyme, or a homolog thereof. Naturally-occurring miRNAs are expressed by endogenous genes in vivo and are processed from a hairpin or stem-loop precursor (pre-miRNA or pri-miRNAs) by Dicer or other RNAses. miRNAs can exist transiently in vivo as a double-stranded duplex but only one strand is taken up by the RISC complex to direct gene silencing.

In some embodiments a version of sd-rxRNA compounds, which are effective in cellular uptake and inhibiting of miRNA activity are described. Essentially the compounds are similar to RISC entering version but large strand chemical modification patterns are optimized in the way to block cleavage and act as an effective inhibitor of the RISC action. For example, the compound might be completely or mostly Omethyl modified with the phosphorothioate content described previously. For these types of compounds the 5' phosphorylation is not necessary in some embodiments. The presence of double stranded region is preferred as it is promotes cellular uptake and efficient RISC loading.

Another pathway that uses small RNAs as sequence-specific regulators is the RNA interference (RNAi) pathway, which is an evolutionarily conserved response to the presence of double-stranded RNA (dsRNA) in the cell. The dsRNAs are cleaved into ~20-base pair (bp) duplexes of small-interfering RNAs (siRNAs) by Dicer. These small RNAs get assembled into multiprotein effector complexes called RNA-induced silencing complexes (RISCs). The siRNAs then guide the cleavage of target mRNAs with perfect complementarity.

Some aspects of biogenesis, protein complexes, and function are shared between the siRNA pathway and the miRNA pathway. Single-stranded polynucleotides may mimic the dsRNA in the siRNA mechanism, or the microRNA in the miRNA mechanism.

In certain embodiments, the modified RNAi constructs may have improved stability in serum and/or cerebral spinal fluid compared to an unmodified RNAi constructs having the same sequence.

In certain embodiments, the structure of the RNAi construct does not induce interferon response in primary cells, such as mammalian primary cells, including primary cells from human, mouse and other rodents, and other non-human mammals. In certain embodiments, the RNAi construct may also be used to inhibit expression of a target gene in an invertebrate organism.

To further increase the stability of the subject constructs in vivo, the 3'-end of the structure may be blocked by protective group(s). For example, protective groups such as inverted nucleotides, inverted abasic moieties, or amino-end modified nucleotides may be used. Inverted nucleotides may comprise an inverted deoxynucleotide. Inverted abasic moieties may comprise an inverted deoxyabasic moiety, such as a 3',3'-linked or 5',5'-linked deoxyabasic moiety.

The RNAi constructs of the invention are capable of inhibiting the synthesis of any target protein encoded by target gene(s). The invention includes methods to inhibit expression of a target gene either in a cell in vitro, or in vivo. As such, the RNAi constructs of the invention are useful for treating a patient with a disease characterized by the overexpression of a target gene.

The target gene can be endogenous or exogenous (e.g., introduced into a cell by a virus or using recombinant DNA technology) to a cell. Such methods may include introduction of RNA into a cell in an amount sufficient to inhibit expression of the target gene. By way of example, such an RNA molecule may have a guide strand that is complementary to the nucleotide sequence of the target gene, such that the composition inhibits expression of the target gene.

The invention also relates to vectors expressing the nucleic acids of the invention, and cells comprising such vectors or the nucleic acids. The cell may be a mammalian cell in vivo or in culture, such as a human cell.

The invention further relates to compositions comprising the subject RNAi constructs, and a pharmaceutically acceptable carrier or diluent. In some embodiments, the composition comprises an additional therapeutic agent. Non-limiting examples of additional therapeutic agents include but are not limited to nucleic acids (e.g., sd-rxRNA, etc.), small molecules (e.g., small molecules useful for treating cancer, neurodegenerative diseases, infectious diseases, autoimmune diseases, etc.), peptides (e.g., peptides useful for treating cancer, neurodegenerative diseases, infectious diseases, autoimmune diseases, etc.), and polypeptides (e.g., antibodies useful for treating cancer, neurodegenerative diseases, infectious diseases, autoimmune diseases, etc.). Compositions of the disclosure can have, in some embodiments, 2, 3, 4, 5, 6, 7, 8, 9, 10, or more additional therapeutic agents. In some embodiments, a composition comprises more than 10 additional therapeutic agents.

The method may be carried out in vitro, ex vivo, or in vivo, in, for example, mammalian cells in culture, such as a human cell in culture.

The target cells (e.g., mammalian cell) may be contacted in the presence of a delivery reagent, such as a lipid (e.g., a cationic lipid) or a liposome.

Another aspect of the invention provides a method for inhibiting the expression of a target gene in a mammalian cell, comprising contacting the mammalian cell with a vector expressing the subject RNAi constructs.

In one aspect of the invention, a longer duplex polynucleotide is provided, including a first polynucleotide that ranges in size from about 16 to about 30 nucleotides; a second polynucleotide that ranges in size from about 26 to about 46 nucleotides, wherein the first polynucleotide (the antisense strand) is complementary to both the second polynucleotide (the sense strand) and a target gene, and wherein both polynucleotides form a duplex and wherein the first polynucleotide contains a single stranded region longer than 6 bases in length and is modified with alternative chemical modification pattern, and/or includes a conjugate moiety that facilitates cellular delivery. In this embodiment, between about 40% to about 90% of the nucleotides of the passenger strand between about 40% to about 90% of the nucleotides of the guide strand, and between about 40% to about 90% of the nucleotides of the single stranded region of the first polynucleotide are chemically modified nucleotides.

In an embodiment, the chemically modified nucleotide in the polynucleotide duplex may be any chemically modified nucleotide known in the art, such as those discussed in detail above. In a particular embodiment, the chemically modified nucleotide is selected from the group consisting of 2' F modified nucleotides, 2'-O-methyl modified and 2'deoxy nucleotides. In another particular embodiment, the chemically modified nucleotides results from "hydrophobic modifications" of the nucleotide base. In another particular embodiment, the chemically modified nucleotides are phosphorothioates. In an additional particular embodiment, chemically modified nucleotides are combination of phosphorothioates, 2'-O-methyl, 2'deoxy, hydrophobic modifications and phosphorothioates. As these groups of modifications refer to modification of the ribose ring, back bone and nucleotide, it is feasible that some modified nucleotides will carry a combination of all three modification types.

In another embodiment, the chemical modification is not the same across the various regions of the duplex. In a particular embodiment, the first polynucleotide (the passenger strand), has a large number of diverse chemical modifications in various positions. For this polynucleotide up to 90% of nucleotides might be chemically modified and/or have mismatches introduced.

In another embodiment, chemical modifications of the first or second polynucleotide include, but not limited to, 5' position modification of Uridine and Cytosine (4-pyridyl, 2-pyridyl, indolyl, phenyl ($C_6H_5OH$); tryptophanyl (C8H6N)CH2CH(NH2)CO), isobutyl, butyl, aminobenzyl; phenyl; naphthyl, etc), where the chemical modification might alter base pairing capabilities of a nucleotide. For the guide strand an important feature of this aspect of the invention is the position of the chemical modification relative to the 5' end of the antisense and sequence. For example, chemical phosphorylation of the 5' end of the guide strand is usually beneficial for efficacy. O-methyl modifications in the seed region of the sense strand (position 2-7 relative to the 5' end) are not generally well tolerated, whereas 2'F and deoxy are well tolerated. The mid part of the guide strand and the 3' end of the guide strand are more permissive in a type of chemical modifications applied. Deoxy modifications are not tolerated at the 3' end of the guide strand.

A unique feature of this aspect of the invention involves the use of hydrophobic modification on the bases. In one embodiment, the hydrophobic modifications are preferably positioned near the 5' end of the guide strand, in other embodiments, they localized in the middle of the guides strand, in other embodiment they localized at the 3' end of the guide strand and yet in another embodiment they are distributed thought the whole length of the polynucleotide. The same type of patterns is applicable to the passenger strand of the duplex.

The other part of the molecule is a single stranded region. In some embodiments, the single stranded region is expected to range from 7 to 40 nucleotides.

In one embodiment, the single stranded region of the first polynucleotide contains modifications selected from the group consisting of between 40% and 90% hydrophobic base modifications, between 40%-90% phosphorothioates, between 40%-90% modification of the ribose moiety, and any combination of the preceding.

Efficiency of guide strand (first polynucleotide) loading into the RISC complex might be altered for heavily modified polynucleotides, so in one embodiment, the duplex polynucleotide includes a mismatch between nucleotide 9, 11, 12, 13, or 14 on the guide strand (first polynucleotide) and the opposite nucleotide on the sense strand (second polynucleotide) to promote efficient guide strand loading.

More detailed aspects of the invention are described in the sections below.

Duplex Characteristics

Double-stranded oligonucleotides of the invention may be formed by two separate complementary nucleic acid strands. Duplex formation can occur either inside or outside the cell containing the target gene.

As used herein, the term "duplex" includes the region of the double-stranded nucleic acid molecule(s) that is (are) hydrogen bonded to a complementary sequence. Double-stranded oligonucleotides of the invention may comprise a nucleotide sequence that is sense to a target gene and a complementary sequence that is antisense to the target gene. The sense and antisense nucleotide sequences correspond to the target gene sequence, e.g., are identical or are sufficiently identical to effect target gene inhibition (e.g., are about at least about 98% identical, 96% identical, 94%, 90% identical, 85% identical, or 80% identical) to the target gene sequence.

In certain embodiments, the double-stranded oligonucleotide of the invention is double-stranded over its entire length, i.e., with no overhanging single-stranded sequence at either end of the molecule, i.e., is blunt-ended. In other embodiments, the individual nucleic acid molecules can be of different lengths. In other words, a double-stranded oligonucleotide of the invention is not double-stranded over its entire length. For instance, when two separate nucleic acid molecules are used, one of the molecules, e.g., the first molecule comprising an antisense sequence, can be longer than the second molecule hybridizing thereto (leaving a portion of the molecule single-stranded). Likewise, when a single nucleic acid molecule is used a portion of the molecule at either end can remain single-stranded.

In one embodiment, a double-stranded oligonucleotide of the invention contains mismatches and/or loops or bulges, but is double-stranded over at least about 70% of the length of the oligonucleotide. In another embodiment, a double-stranded oligonucleotide of the invention is double-stranded over at least about 80% of the length of the oligonucleotide. In another embodiment, a double-stranded oligonucleotide of the invention is double-stranded over at least about 90%-95% of the length of the oligonucleotide. In another embodiment, a double-stranded oligonucleotide of the invention is double-stranded over at least about 96%-98% of the length of the oligonucleotide. In certain embodiments, the double-stranded oligonucleotide of the invention contains at least or up to 1, 2, 3, 4, 5, 6, 7, 8, 9, 10, 11, 12, 13, 14, or 15 mismatches.

Modifications

The nucleotides of the invention may be modified at various locations, including the sugar moiety, the phosphodiester linkage, and/or the base.

In some embodiments, the base moiety of a nucleoside may be modified. For example, a pyrimidine base may be modified at the 2, 3, 4, 5, and/or 6 position of the pyrimidine ring. In some embodiments, the exocyclic amine of cytosine may be modified. A purine base may also be modified. For example, a purine base may be modified at the 1, 2, 3, 6, 7, or 8 position. In some embodiments, the exocyclic amine of adenine may be modified. In some cases, a nitrogen atom in a ring of a base moiety may be substituted with another atom, such as carbon. A modification to a base moiety may be any suitable modification. Examples of modifications are known to those of ordinary skill in the art. In some embodiments, the base modifications include alkylated purines or pyrimidines, acylated purines or pyrimidines, or other heterocycles.

In some embodiments, a pyrimidine may be modified at the 5 position. For example, the 5 position of a pyrimidine may be modified with an alkyl group, an alkynyl group, an alkenyl group, an acyl group, or substituted derivatives thereof. In other examples, the 5 position of a pyrimidine may be modified with a hydroxyl group or an alkoxyl group or substituted derivative thereof. Also, the $N^4$ position of a pyrimidine may be alkylated. In still further examples, the pyrimidine 5-6 bond may be saturated, a nitrogen atom within the pyrimidine ring may be substituted with a carbon atom, and/or the $O^2$ and $O^4$ atoms may be substituted with sulfur atoms. It should be understood that other modifications are possible as well.

In other examples, the $N^7$ position and/or $N^2$ and/or $N^3$ position of a purine may be modified with an alkyl group or substituted derivative thereof. In further examples, a third ring may be fused to the purine bicyclic ring system and/or a nitrogen atom within the purine ring system may be substituted with a carbon atom. It should be understood that other modifications are possible as well.

Non-limiting examples of pyrimidines modified at the 5 position are disclosed in U.S. Pat. Nos. 5,591,843, 7,205, 297, 6,432,963, and 6,020,483; non-limiting examples of pyrimidines modified at the N⁴ position are disclosed in U.S. Pat. No. 5,580,731; non-limiting examples of purines modified at the 8 position are disclosed in U.S. Pat. Nos. 6,355,787 and 5,580,972; non-limiting examples of purines modified at the N⁶ position are disclosed in U.S. Pat. Nos. 4,853,386, 5,789,416, and 7,041,824; and non-limiting examples of purines modified at the 2 position are disclosed in U.S. Pat. Nos. 4,201,860 and 5,587,469, all of which are incorporated herein by reference.

Non-limiting examples of modified bases include N,N⁴-ethanocytosine, 7-deazaxanthosine, 7-deazaguanosine, 8-oxo-N⁶-methyladenine, 4-acetylcytosine, 5-(carboxyhydroxylmethyl) uracil, 5-fluorouracil, 5-bromouracil, 5-carboxymethylaminomethyl-2-thiouracil, 5-carboxymethylaminomethyl uracil, dihydrouracil, inosine, N-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N⁶-methyladenine, 7-methylguanine, 5-methylaminomethyl uracil, 5-methoxy aminomethyl-2-thiouracil, 5-methoxyuracil, 2-methylthio-N⁶-isopentenyladenine, pseudouracil, 5-methyl-2-thiouracil, 2-thiouracil, 4-thiouracil, 5-methyluracil, 2-thiocytosine, and 2,6-diaminopurine. In some embodiments, the base moiety may be a heterocyclic base other than a purine or pyrimidine. The heterocyclic base may be optionally modified and/or substituted.

Sugar moieties include natural, unmodified sugars, e.g., monosaccharide (such as pentose, e.g., ribose, deoxyribose), modified sugars and sugar analogs. In general, possible modifications of nucleomonomers, particularly of a sugar moiety, include, for example, replacement of one or more of the hydroxyl groups with a halogen, a heteroatom, an aliphatic group, or the functionalization of the hydroxyl group as an ether, an amine, a thiol, or the like.

One particularly useful group of modified nucleomonomers are 2'-O-methyl nucleotides. Such 2'-O-methyl nucleotides may be referred to as "methylated," and the corresponding nucleotides may be made from unmethylated nucleotides followed by alkylation or directly from methylated nucleotide reagents. Modified nucleomonomers may be used in combination with unmodified nucleomonomers. For example, an oligonucleotide of the invention may contain both methylated and unmethylated nucleomonomers.

Some exemplary modified nucleomonomers include sugar- or backbone-modified ribonucleotides. Modified ribonucleotides may contain a non-naturally occurring base (instead of a naturally occurring base), such as uridines or cytidines modified at the 5'-position, e.g., 5'-(2-amino)propyl uridine and 5'-bromo uridine; adenosines and guanosines modified at the 8-position, e.g., 8-bromo guanosine; deaza nucleotides, e.g., 7-deaza-adenosine; and N-alkylated nucleotides, e.g., N6-methyl adenosine. Also, sugar-modified ribonucleotides may have the 2'—OH group replaced by a H, alkoxy (or OR), R or alkyl, halogen, SH, SR, amino (such as NH₂, NHR, NR₂), or CN group, wherein R is lower alkyl, alkenyl, or alkynyl.

Modified ribonucleotides may also have the phosphodiester group connecting to adjacent ribonucleotides replaced by a modified group, e.g., of phosphorothioate group. More generally, the various nucleotide modifications may be combined.

Although the antisense (guide) strand may be substantially identical to at least a portion of the target gene (or genes), at least with respect to the base pairing properties, the sequence need not be perfectly identical to be useful, e.g., to inhibit expression of a target gene's phenotype. Generally, higher homology can be used to compensate for the use of a shorter antisense gene. In some cases, the antisense strand generally will be substantially identical (although in antisense orientation) to the target gene.

The use of 2'-O-methyl modified RNA may also be beneficial in circumstances in which it is desirable to minimize cellular stress responses. RNA having 2'-O-methyl nucleomonomers may not be recognized by cellular machinery that is thought to recognize unmodified RNA. The use of 2'-O-methylated or partially 2'-O-methylated RNA may avoid the interferon response to double-stranded nucleic acids, while maintaining target RNA inhibition. This may be useful, for example, for avoiding the interferon or other cellular stress responses, both in short RNAi (e.g., siRNA) sequences that induce the interferon response, and in longer RNAi sequences that may induce the interferon response.

Overall, modified sugars may include D-ribose, 2'-O-alkyl (including 2'-O-methyl and 2'-O-ethyl), i.e., 2'-alkoxy, 2'-amino, 2'-S-alkyl, 2'-halo (including 2'-fluoro), 2'-methoxyethoxy, 2'-allyloxy (—OCH₂CH═CH₂), 2'-propargyl, 2'-propyl, ethynyl, ethenyl, propenyl, and cyano and the like. In one embodiment, the sugar moiety can be a hexose and incorporated into an oligonucleotide as described (Augustyns, K., et al., *Nucl. Acids. Res.* 18:4711 (1992)). Exemplary nucleomonomers can be found, e.g., in U.S. Pat. No. 5,849,902, incorporated by reference herein.

Definitions of specific functional groups and chemical terms are described in more detail below. For purposes of this invention, the chemical elements are identified in accordance with the Periodic Table of the Elements, CAS version, *Handbook of Chemistry and Physics*, 75ᵗʰ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito: 1999, the entire contents of which are incorporated herein by reference.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are all contemplated by the present invention. Those of ordinary skill in the art will readily appreciate that analogous ratios are contemplated for more complex isomer mixtures.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

In certain embodiments, oligonucleotides of the invention comprise 3' and 5' termini (except for circular oligonucleotides). In one embodiment, the 3' and 5' termini of an oligonucleotide can be substantially protected from nucleases e.g., by modifying the 3' or 5' linkages (e.g., U.S. Pat. No. 5,849,902 and WO 98/13526). For example, oligonucleotides can be made resistant by the inclusion of a "blocking group." The term "blocking group" as used herein refers to substituents (e.g., other than OH groups) that can be attached to oligonucleotides or nucleomonomers, either as protecting groups or coupling groups for synthesis (e.g., FITC, propyl ($CH_2$—$CH_2$—$CH_3$), glycol (—O—$CH_2$—$CH_2$—O—) phosphate ($PO_3^{2-}$), hydrogen phosphonate, or phosphoramidite). "Blocking groups" also include "end blocking groups" or "exonuclease blocking groups" which protect the 5' and 3' termini of the oligonucleotide, including modified nucleotides and non-nucleotide exonuclease resistant structures.

Exemplary end-blocking groups include cap structures (e.g., a 7-methylguanosine cap), inverted nucleomonomers, e.g., with 3'-3' or 5'-5' end inversions (see, e.g., Ortiagao el al. 1992. *Antisense Res. Dev.* 2:129), methylphosphonate, phosphoramidite, non-nucleotide groups (e.g., non-nucleotide linkers, amino linkers, conjugates) and the like. The 3' terminal nucleomonomer can comprise a modified sugar moiety. The 3' terminal nucleomonomer comprises a 3'-O that can optionally be substituted by a blocking group that prevents 3'-exonuclease degradation of the oligonucleotide. For example, the 3'-hydroxyl can be esterified to a nucleotide through a 3'-3' internucleotide linkage. For example, the alkyloxy radical can be methoxy, ethoxy, or isopropoxy, and preferably, ethoxy. Optionally, the 3'-31'linked nucleotide at the 3' terminus can be linked by a substitute linkage. To reduce nuclease degradation, the 5' most 3'-5' linkage can be a modified linkage, e.g., a phosphorothioate or a P-alkyloxyphosphotriester linkage. Preferably, the two 5' most 3'-5' linkages are modified linkages. Optionally, the 5' terminal hydroxy moiety can be esterified with a phosphorus containing moiety, e.g., phosphate, phosphorothioate, or P-ethoxyphosphate.

One of ordinary skill in the art will appreciate that the synthetic methods, as described herein, utilize a variety of protecting groups. By the term "protecting group," as used herein, it is meant that a particular functional moiety, e.g., O, S, or N, is temporarily blocked so that a reaction can be carried out selectively at another reactive site in a multifunctional compound. In certain embodiments, a protecting group reacts selectively in good yield to give a protected substrate that is stable to the projected reactions; the protecting group should be selectively removable in good yield by readily available, preferably non-toxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen, and carbon protecting groups may be utilized. Hydroxyl protecting groups include methyl, methoxylmethyl (MOM), methylthiomethyl (MTM), 1-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), 1-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, 1-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis (4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napthhyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate. Amino-protecting groups include methyl carbamate, ethyl carbamate, 9-fluorenylmethyl carbamate (Fmoc), 9-(2-sulfo)fluorenylmethyl carbamate, 9-(2,7-dibromo)fluorenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido) propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo) benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl) ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino) acetamide, 3-(p-hydroxyphenyl)propanamide, 3-(o-nitrophenyl)propanamide, 2-methyl-2-(o-nitrophenoxy) propanamide, 2-methyl-2-(o-phenylazophenoxy) propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N-(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide. Exemplary protecting groups are detailed herein. However, it will be appreciated that the present invention is not intended to be limited to these protecting groups; rather, a variety of additional equivalent protecting groups can be readily identified using the above criteria and utilized in the method of the present invention. Additionally, a variety of protecting groups are described in Protective Groups in Organic Synthesis, Third Ed. Greene. T.W. and Wuts, P. G., Eds., John Wiley & Sons, New York: 1999, the entire contents of which are hereby incorporated by reference.

It will be appreciated that the compounds, as described herein, may be substituted with any number of substituents or functional moieties. In general, the term "substituted" whether proceeded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment, for example, of infectious diseases or proliferative disorders. The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

The term "aliphatic," as used herein, includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl," "alkynyl," and the like. Furthermore, as used herein, the terms "alkyl," "alkenyl," "alkynyl," and the like encompass both substituted and unsubstituted groups. In certain embodiments, as used herein, "lower alkyl" is used to indicate those alkyl groups (cyclic, acyclic, substituted, unsubstituted, branched, or unbranched) having 1-6 carbon atoms.

In certain embodiments, the alkyl, alkenyl, and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, cyclopropyl, —$CH_2$-cyclopropyl, vinyl, allyl, n-butyl, sec-butyl, isobutyl, tert-butyl, cyclobutyl, —$CH_2$-cyclobutyl, n-pentyl, sec-pentyl, isopentyl, tert-pentyl, cyclopentyl, —$CH_2$-cyclopentyl, n-hexyl, sec-hexyl, cyclohexyl, —$CH_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

Some examples of substituents of the above-described aliphatic (and other) moieties of compounds of the invention include, but are not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —C(O)R$_x$; —$CO_2$(R$_x$); —CON(R$_x$)$_2$; —OC(O)R$_x$; —$OCO_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments described herein.

The term "heteroaliphatic," as used herein, refers to aliphatic moieties that contain one or more oxygen, sulfur, nitrogen, phosphorus, or silicon atoms, e.g., in place of carbon atoms. Heteroaliphatic moieties may be branched, unbranched, cyclic or acyclic and include saturated and unsaturated heterocycles such as morpholino, pyrrolidinyl, etc. In certain embodiments, heteroaliphatic moieties are substituted by independent replacement of one or more of the hydrogen atoms thereon with one or more moieties including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —$NO_2$; —CN; —$CF_3$; —$CH_2CF_3$; —$CHCl_2$; —$CH_2OH$; —$CH_2CH_2OH$; —$CH_2NH$; —$CH_2SO_2CH_3$; —C(O)R$_x$; —$CO_2$(R$_x$); —CON(R$_x$)$_2$; —OC(O)R$_x$; —$OCO_2$R$_x$; —OCON(R$_x$)$_2$; —N(R$_x$)$_2$; —S(O)$_2$R$_x$; —NR$_x$(CO)R$_x$, wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments described herein.

The terms "halo" and "halogen" as used herein refer to an atom selected from fluorine, chlorine, bromine, and iodine.

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. In certain embodiments, a straight chain or branched chain alkyl has 6 or fewer carbon atoms in its backbone (e.g., $C_1$-$C_6$ for straight chain, $C_3$-$C_6$ for branched chain), and more preferably 4 or fewer. Likewise, preferred cycloalkyls have from 3-8 carbon atoms in their ring structure, and more preferably have 5 or 6 carbons in the ring structure. The term $C_1$-$C_6$ includes alkyl groups containing 1 to 6 carbon atoms.

Moreover, unless otherwise specified, the term alkyl includes both "unsubstituted alkyls" and "substituted alkyls," the latter of which refers to alkyl moieties having independently selected substituents replacing a hydrogen on one or more carbons of the hydrocarbon backbone. Such substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "arylalkyl" moiety is an alkyl substituted with an aryl (e.g., phenylmethyl (benzyl)). The term "alkyl" also includes the side chains of natural and unnatural amino acids. The term "n-alkyl" means a straight chain (i.e., unbranched) unsubstituted alkyl group.

The term "alkenyl" includes unsaturated aliphatic groups analogous in length and possible substitution to the alkyls described above, but that contain at least one double bond. For example, the term "alkenyl" includes straight-chain alkenyl groups (e.g., ethylenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. In certain embodiments, a straight chain or branched chain alkenyl group has 6 or fewer carbon atoms in its backbone (e.g., $C_2$-$C_6$ for straight chain, $C_3$-$C_6$ for branched chain). Likewise, cycloalkenyl groups may have from 3-8 carbon atoms in their ring structure, and more preferably have 5 or 6 carbons in the ring structure. The term $C_2$-$C_6$ includes alkenyl groups containing 2 to 6 carbon atoms.

Moreover, unless otherwise specified, the term alkenyl includes both "unsubstituted alkenyls" and "substituted alkenyls," the latter of which refers to alkenyl moieties having independently selected substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkynyl" includes unsaturated aliphatic groups analogous in length and possible substitution to the alkyls described above, but which contain at least one triple bond. For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. In certain embodiments, a straight chain or branched chain alkynyl group has 6 or fewer carbon atoms in its backbone (e.g., $C_2$-$C_6$ for straight chain, $C_3$-$C_6$ for branched chain). The term $C_2$-$C_6$ includes alkynyl groups containing 2 to 6 carbon atoms.

Moreover, unless otherwise specified, the term alkynyl includes both "unsubstituted alkynyls" and "substituted alkynyls," the latter of which refers to alkynyl moieties having independently selected substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless the number of carbons is otherwise specified, "lower alkyl" as used herein means an alkyl group, as defined above, but having from one to five carbon atoms in its backbone structure. "Lower alkenyl" and "lower alkynyl" have chain lengths of, for example, 2-5 carbon atoms.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups. Examples of substituted alkoxy groups include halogenated alkoxy groups. The alkoxy groups can be substituted with independently selected groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfmyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc.

The term "heteroatom" includes atoms of any element other than carbon or hydrogen. Preferred heteroatoms are nitrogen, oxygen, sulfur and phosphorus.

The term "hydroxy" or "hydroxyl" includes groups with an —OH or —O⁻ (with an appropriate counterion).

The term "halogen" includes fluorine, bromine, chlorine, iodine, etc. The term "perhalogenated" generally refers to a moiety wherein all hydrogens are replaced by halogen atoms.

The term "substituted" includes independently selected substituents which can be placed on the moiety and which allow the molecule to perform its intended function. Examples of substituents include alkyl, alkenyl, alkynyl, aryl, $(CR'R'')_{0-3}NR'R''$, $(CR'R'')_{0-3}CN$, $NO_2$, halogen, $(CR'R'')_{0-3}C(halogen)_3$, $(CR'R'')_{0-3}CH(halogen)_2$, $(CR'R'')_{0-3}CH_2(halogen)$, $(CR'R'')_{0-3}CONR'R''$, $(CR'R'')_{0-3}S(O)_{1-2}NR'R''$, $(CR'R'')_{0-3}CHO$, $(CR'R'')_{0-3}(CR'R'')_{0-3}H$, $(CR'R'')_{0-3}S(O)_{0-2}R'$, $(CR'R'')_{0-3}O(CR'R'')_{0-3}H$, $(CR'R'')_{0-3}COR'$, $(CR'R'')_{0-3}CO_2R'$, or $(CR'R'')_{0-3}OR'$ groups; wherein each R' and R" are each independently hydrogen, a $C_1$-$C_5$ alkyl, $C_2$-$C_5$ alkenyl, $C_2$-$C_5$ alkynyl, or aryl group, or R' and R" taken together are a benzylidene group or a —$(CH_2)_2O(CH_2)_2$— group.

The term "amine" or "amino" includes compounds or moieties in which a nitrogen atom is covalently bonded to at least one carbon or heteroatom. The term "alkyl amino" includes groups and compounds wherein the nitrogen is bound to at least one additional alkyl group. The term "dialkyl amino" includes groups wherein the nitrogen atom is bound to at least two additional alkyl groups.

The term "ether" includes compounds or moieties which contain an oxygen bonded to two different carbon atoms or heteroatoms. For example, the term includes "alkoxyalkyl," which refers to an alkyl, alkenyl, or alkynyl group covalently bonded to an oxygen atom which is covalently bonded to another alkyl group.

The terms "polynucleotide," "nucleotide sequence," "nucleic acid," "nucleic acid molecule," "nucleic acid sequence," and "oligonucleotide" refer to a polymer of two or more nucleotides. The polynucleotides can be DNA, RNA, or derivatives or modified versions thereof. The polynucleotide may be single-stranded or double-stranded. The polynucleotide can be modified at the base moiety, sugar moiety, or phosphate backbone, for example, to improve stability of the molecule, its hybridization parameters, etc. The polynucleotide may comprise a modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N-2-carboxypropyl) uracil, and 2,6-diaminopurine. The olynucleotide may comprise a modified sugar moiety (e.g., 2'-fluororibose, ribose, 2'-deoxyribose, 2'-O-methylcytidine, arabinose, and hexose), and/or a modified phosphate moiety (e.g., phosphorothioates and 5'-N-phosphoramidite linkages). A nucleotide sequence typically carries genetic information, including the information used by cellular machinery to make proteins and enzymes. These terms include double- or single-stranded genomic and cDNA, RNA, any synthetic and genetically manipulated polynucleotide, and both sense and antisense polynucleotides. This includes single- and double-stranded molecules, i.e., DNA-DNA, DNA-RNA, and RNA-RNA hybrids, as well as "protein nucleic acids" (PNA) formed by conjugating bases to an amino acid backbone.

The term "base" includes the known purine and pyrimidine heterocyclic bases, deazapurines, and analogs (including heterocyclic substituted analogs, e.g., aminoethyoxy phenoxazine), derivatives (e.g., 1-alkyl-, 1-alkenyl-, heteroaromatic- and 1-alkynyl derivatives) and tautomers thereof. Examples of purines include adenine, guanine, inosine, diaminopurine, and xanthine and analogs (e.g., 8-oxo-$N^6$-methyladenine or 7-diazaxanthine) and derivatives thereof. Pyrimidines include, for example, thymine, uracil, and cytosine, and their analogs (e.g., 5-methylcytosine, 5-methyluracil, 5-(1-propynyl)uracil, 5-(1-propynyl) cytosine and 4,4-ethanocytosine). Other examples of suitable bases include non-purinyl and non-pyrimidinyl bases such as 2-aminopyridine and triazines.

In a preferred embodiment, the nucleomonomers of an oligonucleotide of the invention are RNA nucleotides. In another preferred embodiment, the nucleomonomers of an oligonucleotide of the invention are modified RNA nucleotides. Thus, the oligunucleotides contain modified RNA nucleotides.

The term "nucleoside" includes bases which are covalently attached to a sugar moiety, preferably ribose or deoxyribose. Examples of preferred nucleosides include ribonucleosides and deoxyribonucleosides. Nucleosides also include bases linked to amino acids or amino acid analogs which may comprise free carboxyl groups, free amino groups, or protecting groups. Suitable protecting groups are well known in the art (see P. G. M. Wuts and T. W. Greene, "Protective Groups in Organic Synthesis", $2^{nd}$ Ed., Wiley-Interscience, New York, 1999).

The term "nucleotide" includes nucleosides which further comprise a phosphate group or a phosphate analog.

The nucleic acid molecules may be associated with a hydrophobic moiety for targeting and/or delivery of the molecule to a cell. In certain embodiments, the hydrophobic moiety is associated with the nucleic acid molecule through a linker. In certain embodiments, the association is through non-covalent interactions. In other embodiments, the association is through a covalent bond. Any linker known in the art may be used to associate the nucleic acid with the hydrophobic moiety. Linkers known in the art are described in published international PCT applications, WO 92/03464, WO 95/23162, WO 2008/021157, WO 2009/021157, WO 2009/134487, WO 2009/126933, U.S. Patent Application Publication 2005/0107325, U.S. Pat. Nos. 5,414,077, 5,419, 966, 5,512,667, 5,646,126, and 5,652,359, which are incorporated herein by reference. The linker may be as simple as a covalent bond to a multi-atom linker. The linker may be cyclic or acyclic. The linker may be optionally substituted. In certain embodiments, the linker is capable of being cleaved from the nucleic acid. In certain embodiments, the linker is capable of being hydrolyzed under physiological conditions. In certain embodiments, the linker is capable of being cleaved by an enzyme (e.g., an esterase or phosphodiesterase). In certain embodiments, the linker comprises a spacer element to separate the nucleic acid from the hydrophobic moiety. The spacer element may include one to thirty carbon or heteroatoms. In certain embodiments, the linker and/or spacer element comprises protonatable functional groups. Such protonatable functional groups may promote the endosomal escape of the nucleic acid molecule. The protonatable functional groups may also aid in the delivery of the nucleic acid to a cell, for example, neutralizing the overall charge of the molecule. In other embodiments, the linker and/or spacer element is biologically inert (that is, it does not impart biological activity or function to the resulting nucleic acid molecule).

In certain embodiments, the nucleic acid molecule with a linker and hydrophobic moiety is of the formulae described herein. In certain embodiments, the nucleic acid molecule is of the formula:

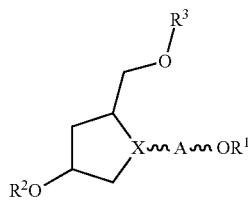

wherein

X is N or CH;

A is a bond; substituted or unsubstituted, cyclic or acyclic, branched or unbranched aliphatic; or substituted or unsubstituted, cyclic or acyclic, branched or unbranched heteroaliphatic;

$R^1$ is a hydrophobic moiety;

$R^2$ is hydrogen; an oxygen-protecting group; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; and $R^3$ is a nucleic acid.

In certain embodiments, the molecule is of the formula:

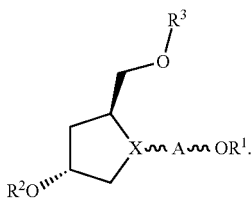

In certain embodiments, the molecule is of the formula:

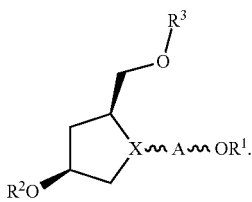

In certain embodiments, the molecule is of the formula:

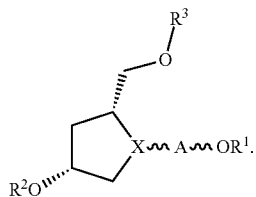

In certain embodiments, the molecule is of the formula:

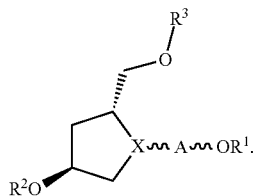

In certain embodiments, X is N. In certain embodiments, X is CH.

In certain embodiments, A is a bond. In certain embodiments, A is substituted or unsubstituted, cyclic or acyclic, branched or unbranched aliphatic. In certain embodiments, A is acyclic, substituted or unsubstituted, branched or unbranched aliphatic. In certain embodiments, A is acyclic, substituted, branched or unbranched aliphatic. In certain embodiments, A is acyclic, substituted, unbranched aliphatic. In certain embodiments, A is acyclic, substituted, unbranched alkyl. In certain embodiments, A is acyclic, substituted, unbranched $C_{1-20}$ alkyl. In certain embodiments, A is acyclic, substituted, unbranched $C_{1-12}$ alkyl. In certain embodiments, A is acyclic, substituted, unbranched $C_{1-10}$ alkyl. In certain embodiments, A is acyclic, substituted, unbranched $C_{1-8}$ alkyl. In certain embodiments, A is acyclic, substituted, unbranched $C_{1-6}$ alkyl. In certain embodiments, A is substituted or unsubstituted, cyclic or acyclic, branched or unbranched heteroaliphatic. In certain embodiments, A is acyclic, substituted or unsubstituted, branched or unbranched heteroaliphatic. In certain embodiments, A is acyclic, substituted, branched or unbranched heteroaliphatic. In certain embodiments, A is acyclic, substituted, unbranched heteroaliphatic.

In certain embodiments, A is of the formula:

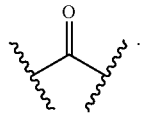

In certain embodiments, A is of one of the formulae:

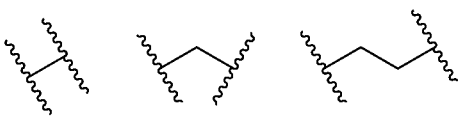

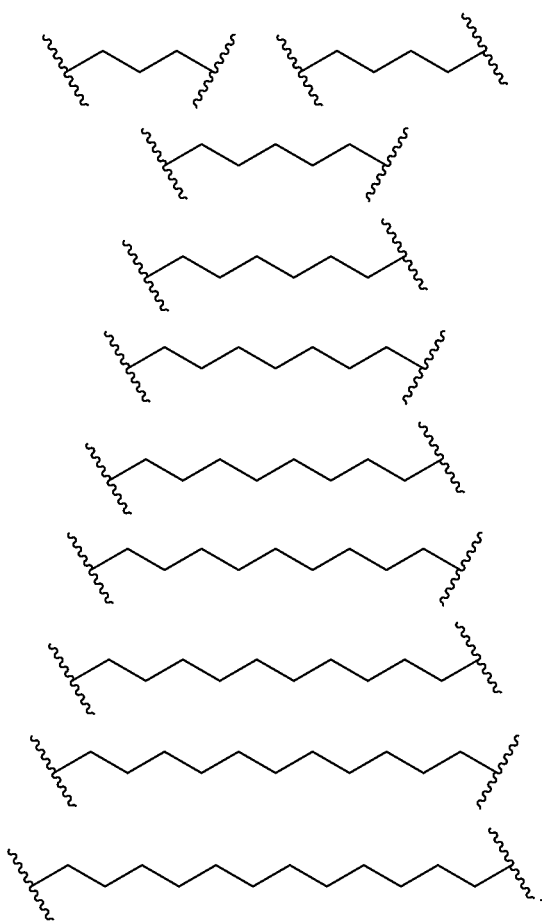
In certain embodiments, A is of one of the formulae:
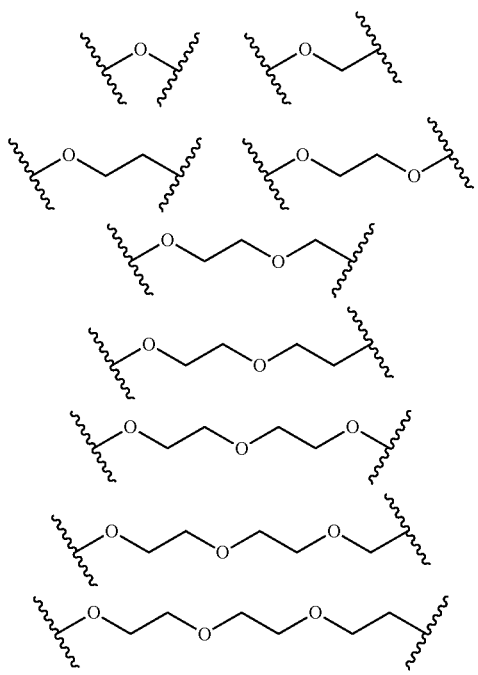
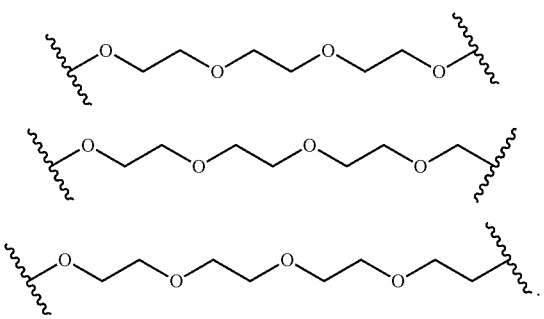
In certain embodiments, A is of one of the formulae:
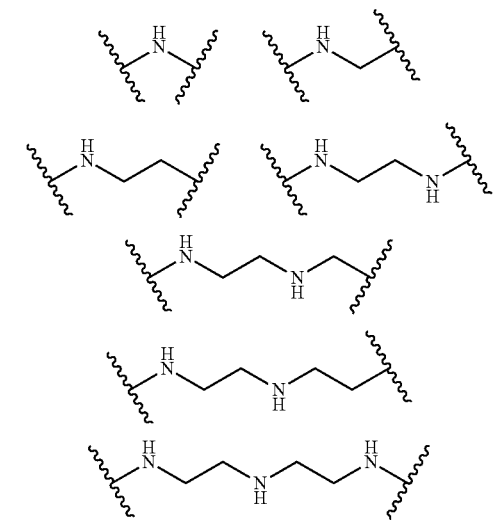
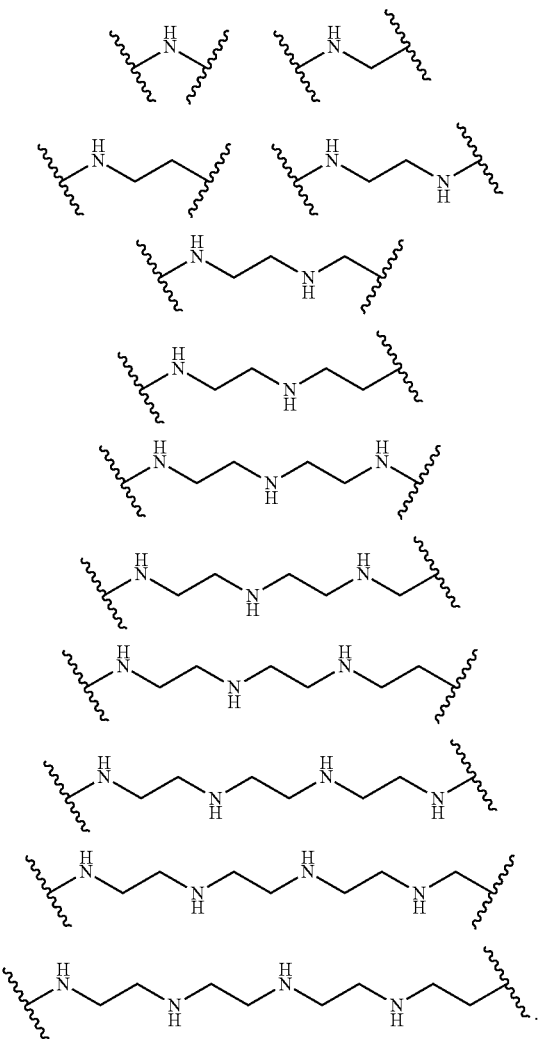
In certain embodiments, A is of the formula:
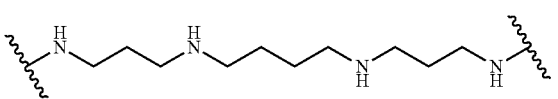

In certain embodiments, A is of the formula:

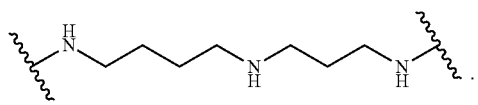 [SMILES: *NCCCCNCCCN*]

In certain embodiments, A is of the formula:

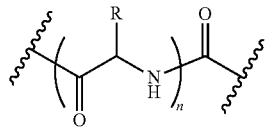

wherein
each occurrence of R is independently the side chain of a natural or unnatural amino acid; and
n is an integer between 1 and 20, inclusive. In certain embodiments, A is of the formula:

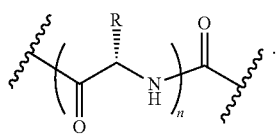

In certain embodiments, each occurrence of R is independently the side chain of a natural amino acid. In certain embodiments, n is an integer between 1 and 15, inclusive. In certain embodiments, n is an integer between 1 and 10, inclusive. In certain embodiments, n is an integer between 1 and 5, inclusive.

In certain embodiments, A is of the formula:

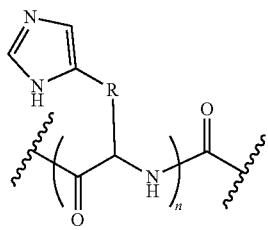

wherein n is an integer between 1 and 20, inclusive. In certain embodiments, A is of the formula:

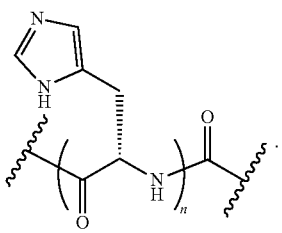

In certain embodiments, n is an integer between 1 and 15, inclusive. In certain embodiments, n is an integer between 1 and 10, inclusive. In certain embodiments, n is an integer between 1 and 5, inclusive.

In certain embodiments, A is of the formula:

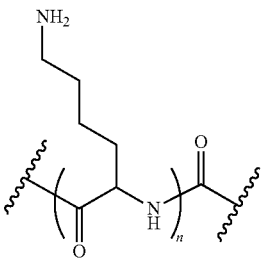

wherein n is an integer between 1 and 20, inclusive. In certain embodiments, A is of the formula:

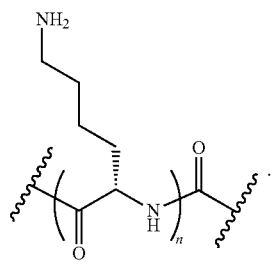

In certain embodiments, n is an integer between 1 and 15, inclusive. In certain embodiments, n is an integer between 1 and 10, inclusive. In certain embodiments, n is an integer between 1 and 5, inclusive.

In certain embodiments, the molecule is of the formula:

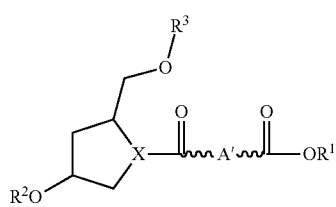

wherein X, $R^1$, $R^2$, and $R^3$ are as defined herein; and
A' is substituted or unsubstituted, cyclic or acyclic, branched or unbranched aliphatic; or substituted or unsubstituted, cyclic or acyclic, branched or unbranched heteroaliphatic.

In certain embodiments, A' is of one of the formulae:

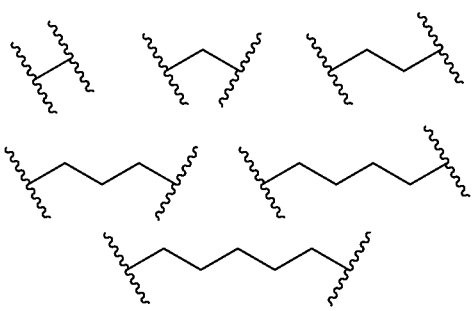

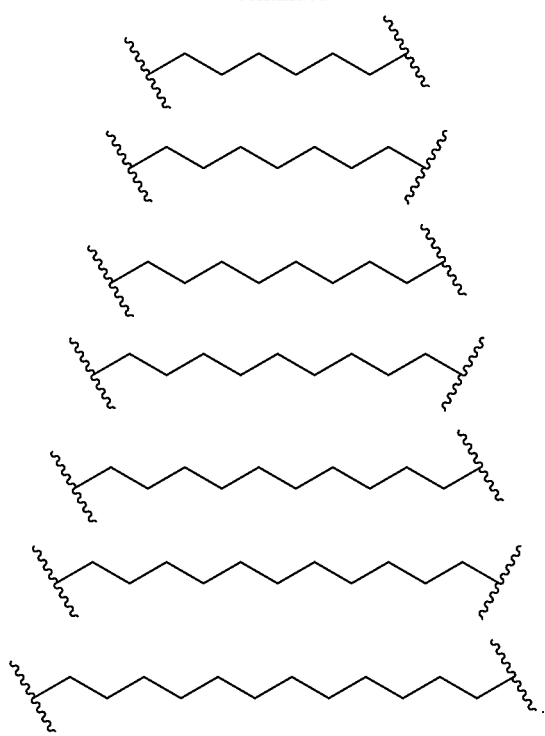
In certain embodiments, A is of one of the formulae:
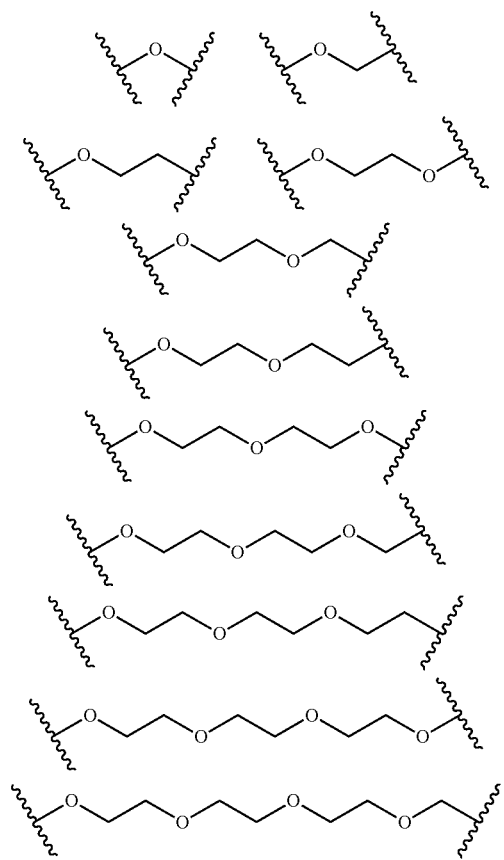
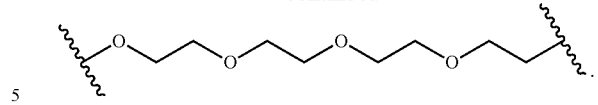
In certain embodiments, A is of one of the formulae:
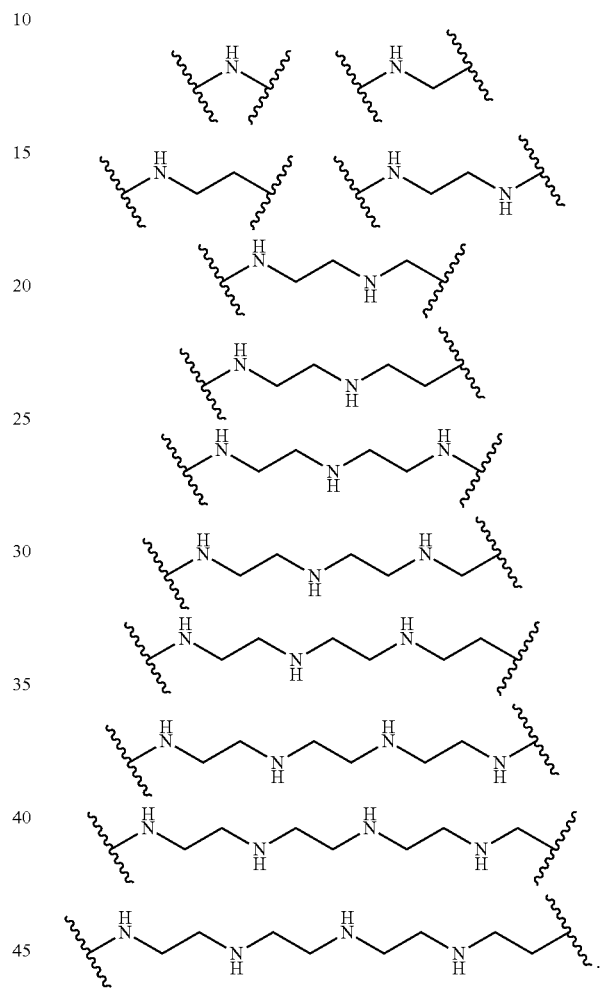
In certain embodiments, A is of the formula:
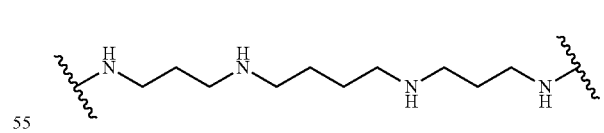
In certain embodiments, A is of the formula:
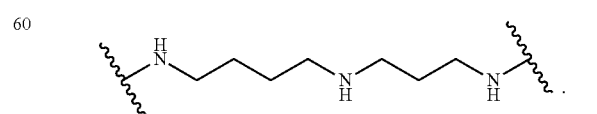
In certain embodiments, $R^1$ is a steroid. In certain embodiments, $R^1$ is a cholesterol.

In certain embodiments, R¹ is a lipophilic vitamin. In certain embodiments, R¹ is a vitamin A. In certain embodiments, R¹ is a vitamin E.

In certain embodiments, R¹ is of the formula:

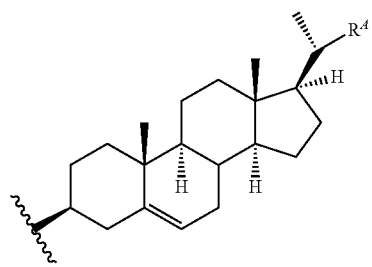

wherein R⁴ is substituted or unsubstituted, cyclic or acyclic, branched or unbranched aliphatic; or substituted or unsubstituted, cyclic or acyclic, branched or unbranched heteroaliphatic.

In certain embodiments, R¹ is of the formula:

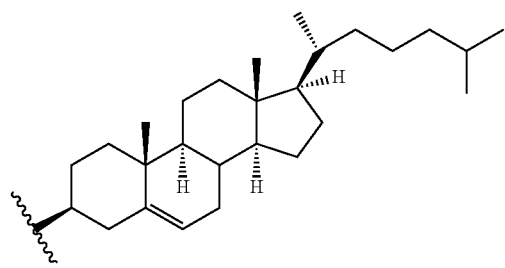

In certain embodiments, R¹ is of the formula:

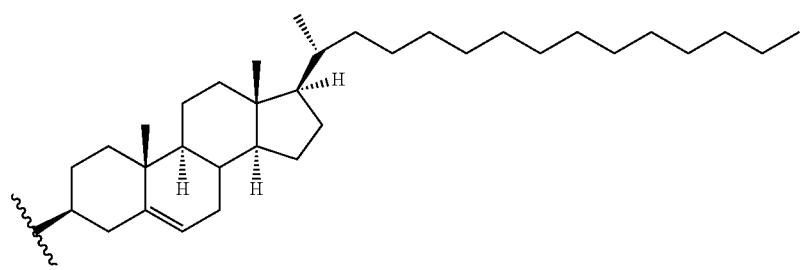

In certain embodiments, R¹ is of the formula:

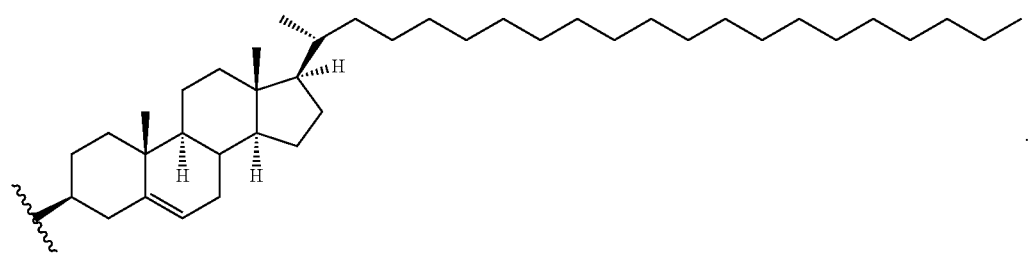

In certain embodiments, R¹ is of the formula:

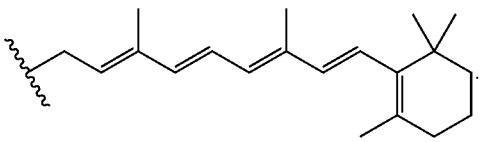 [SMILES: *C/C=C(C)/C=C/C=C(C)/C=C/C1=C(C)CCCC1(C)C]

In certain embodiments, R¹ is of the formula:

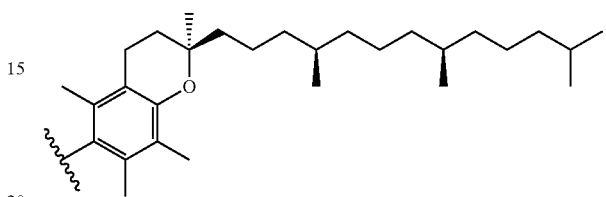

In certain embodiments, the nucleic acid molecule is of the formula:

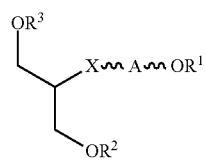

wherein
X is N or CH;
A is a bond; substituted or unsubstituted, cyclic or acyclic, branched or unbranched aliphatic; or substituted or unsubstituted, cyclic or acyclic, branched or unbranched heteroaliphatic;
R¹ is a hydrophobic moiety;

49

R² is hydrogen; an oxygen-protecting group; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; and R³ is a nucleic acid.

In certain embodiments, the nucleic acid molecule is of the formula:

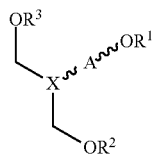

wherein

X is N or CH;

A is a bond; substituted or unsubstituted, cyclic or acyclic, branched or unbranched aliphatic; or substituted or unsubstituted, cyclic or acyclic, branched or unbranched heteroaliphatic;

R¹ is a hydrophobic moiety;

R² is hydrogen; an oxygen-protecting group; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; and R³ is a nucleic acid.

In certain embodiments, the nucleic acid molecule is of the formula:

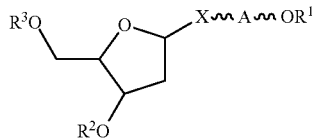

50 wherein

X is N or CH;

A is a bond; substituted or unsubstituted, cyclic or acyclic, branched or unbranched aliphatic; or substituted or unsubstituted, cyclic or acyclic, branched or unbranched heteroaliphatic;

R¹ is a hydrophobic moiety;

R² is hydrogen; an oxygen-protecting group; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; and R³ is a nucleic acid. In certain embodiments, the nucleic acid molecule is of the formula:

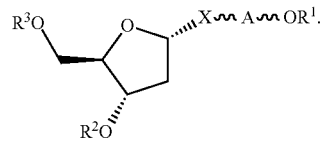

In certain embodiments, the nucleic acid molecule is of the formula:

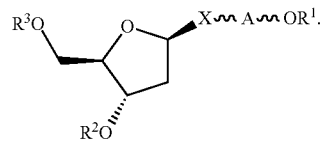

In certain embodiments, the nucleic acid molecule is of the formula:

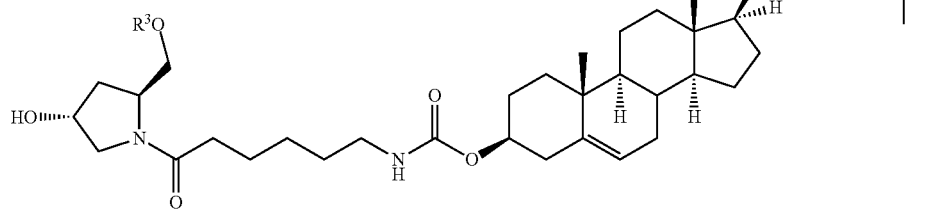

wherein R³ is a nucleic acid.

In certain embodiments, the nucleic acid molecule is of the formula:

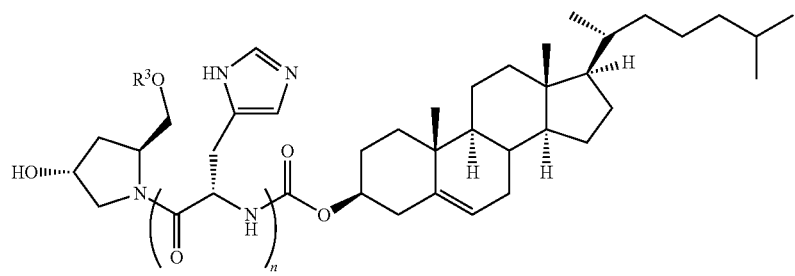
wherein R³ is a nucleic acid; and
n is an integer between 1 and 20, inclusive.
In certain embodiments, the nucleic acid molecule is of the formula:
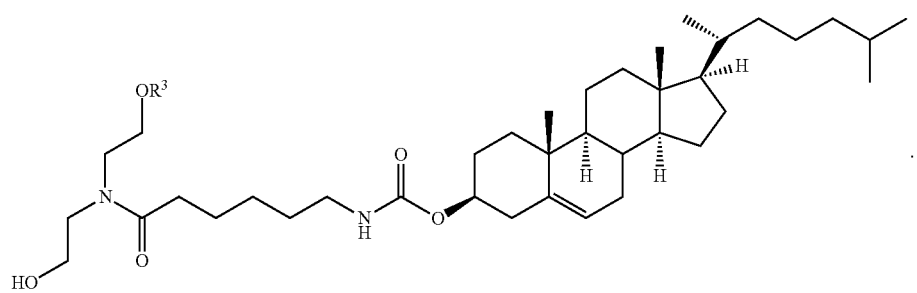
In certain embodiments, the nucleic acid molecule is of the formula:
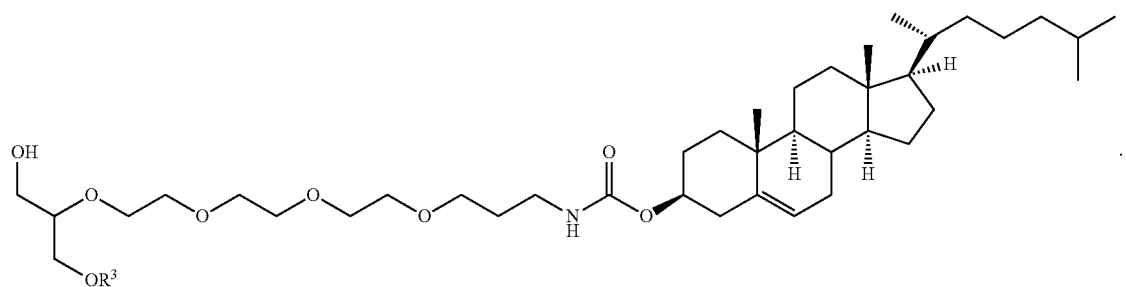
In certain embodiments, the nucleic acid molecule is of the formula:
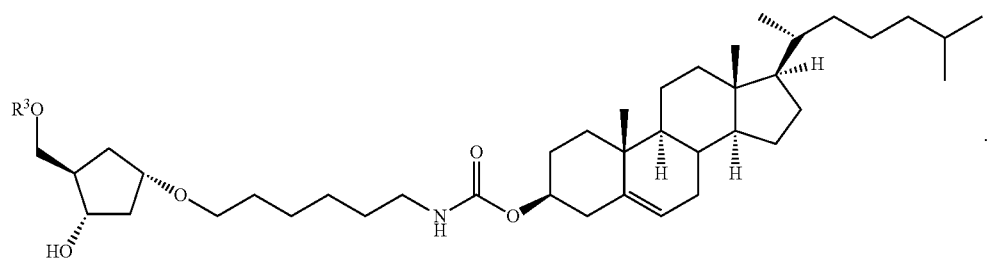
In certain embodiments, the nucleic acid molecule is of the formula:

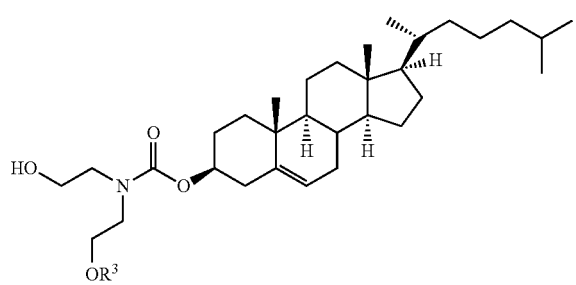

In certain embodiments, the nucleic acid molecule is of the formula:

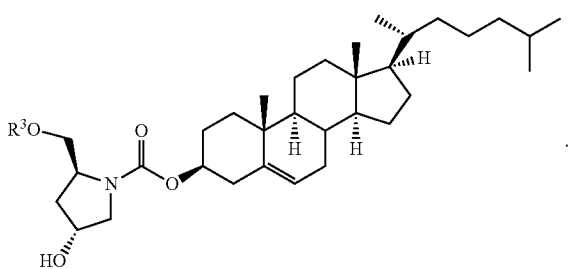

As used herein, the term "linkage" includes a naturally occurring, unmodified phosphodiester moiety (—O—(PO$^{2-}$)—O—) that covalently couples adjacent nucleomonomers. As used herein, the term "substitute linkage" includes any analog or derivative of the native phosphodiester group that covalently couples adjacent nucleomonomers. Substitute linkages include phosphodiester analogs, e.g., phosphorothioate, phosphorodithioate, and P-ethyoxyphosphodiester, P-ethoxyphosphodiester, P-alkyloxyphosphotriester, methylphosphonate, and nonphosphorus containing linkages, e.g., acetals and amides. Such substitute linkages are known in the art (e.g., Bjergarde et al. 1991. Nucleic Acids Res. 19:5843; Caruthers et al. 1991. Nucleosides Nucleotides. 10:47). In certain embodiments, non-hydrolizable linkages are preferred, such as phosphorothiate linkages.

In certain embodiments, oligonucleotides of the invention comprise hydrophobicly modified nucleotides or "hydrophobic modifications." As used herein "hydrophobic modifications" refers to bases that are modified such that (1) overall hydrophobicity of the base is significantly increased, and/or (2) the base is still capable of forming close to regular Watson-Crick interaction. Several non-limiting examples of base modifications include 5-position uridine and cytidine modifications such as phenyl, 4-pyridyl, 2-pyridyl, indolyl, and isobutyl, phenyl (C6H5OH); tryptophanyl (C8H6N) CH2CH(NH2)CO), Isobutyl, butyl, aminobenzyl; phenyl; and naphthyl.

Another type of conjugates that can be attached to the end (3' or 5' end), the loop region, or any other parts of the sd-rxRNA might include a sterol, sterol type molecule, peptide, small molecule, protein, etc. In some embodiments, a sdrxRNA may contain more than one conjugates (same or different chemical nature). In some embodiments, the conjugate is cholesterol.

Another way to increase target gene specificity, or to reduce off-target silencing effect, is to introduce a 2'-modification (such as the 2'-O methyl modification) at a position corresponding to the second 5'-end nucleotide of the guide sequence. Antisense (guide) sequences of the invention can be "chimeric oligonucleotides" which comprise an RNA-like and a DNA-like region.

The language "RNase H activating region" includes a region of an oligonucleotide, e.g., a chimeric oligonucleotide, that is capable of recruiting RNase H to cleave the target RNA strand to which the oligonucleotide binds. Typically, the RNase activating region contains a minimal core (of at least about 3-5, typically between about 3-12, more typically, between about 5-12, and more preferably between about 5-10 contiguous nucleomonomers) of DNA or DNA-like nucleomonomers. (See, e.g., U.S. Pat. No. 5,849,902). Preferably, the RNase H activating region comprises about nine contiguous deoxyribose containing nucleomonomers.

The language "non-activating region" includes a region of an antisense sequence, e.g., a chimeric oligonucleotide, that does not recruit or activate RNase H. Preferably, a non-activating region does not comprise phosphorothioate DNA. The oligonucleotides of the invention comprise at least one non-activating region. In one embodiment, the non-activating region can be stabilized against nucleases or can provide specificity for the target by being complementary to the target and forming hydrogen bonds with the target nucleic acid molecule, which is to be bound by the oligonucleotide.

In one embodiment, at least a portion of the contiguous polynucleotides are linked by a substitute linkage, e.g., a phosphorothioate linkage.

In certain embodiments, most or all of the nucleotides beyond the guide sequence (2'-modified or not) are linked by phosphorothioate linkages. Such constructs tend to have improved pharmacokinetics due to their higher affinity for serum proteins. The phosphorothioate linkages in the non-guide sequence portion of the polynucleotide generally do not interfere with guide strand activity, once the latter is loaded into RISC.

Antisense (guide) sequences of the present invention may include "morpholino oligonucleotides." Morpholino oligonucleotides are non-ionic and function by an RNase H-independent mechanism. Each of the 4 genetic bases (Adenine, Cytosine, Guanine, and Thymine/Uracil) of the morpholino oligonucleotides is linked to a 6-membered morpholine ring. Morpholino oligonucleotides are made by joining the 4 different subunit types by, e.g., non-ionic phosphorodiamidate inter-subunit linkages. Morpholino oligonucleotides have many advantages including: complete resistance to nucleases (Antisense & Nucl. Acid Drug Dev. 1996. 6:267); predictable targeting (Biochemica Biophysica Acta. 1999. 1489:141); reliable activity in cells (Antisense & Nucl. Acid Drug Dev. 1997. 7:63); excellent sequence specificity (Antisense & Nucl. Acid Drug Dev. 1997. 7:151); minimal non-antisense activity (Biochemica Biophysica Acta. 1999. 1489:141); and simple osmotic or scrape delivery (Antisense & Nucl. Acid Drug Dev. 1997. 7:291). Morpholino oligonucleotides are also preferred because of their non-toxicity at high doses. A discussion of the preparation of morpholino oligonucleotides can be found in Antisense & Nucl. Acid Drug Dev. 1997. 7:187.

The chemical modifications described herein are believed, based on the data described herein, to promote single stranded polynucleotide loading into the RISC. Single stranded polynucleotides have been shown to be active in loading into RISC and inducing gene silencing. However, the level of activity for single stranded polynucleotides appears to be 2 to 4 orders of magnitude lower when compared to a duplex polynucleotide.

The present invention provides a description of the chemical modification patterns, which may (a) significantly increase stability of the single stranded polynucleotide (b) promote efficient loading of the polynucleotide into the RISC complex and (c) improve uptake of the single stranded nucleotide by the cell. The chemical modification patterns may include combination of ribose, backbone, hydrophobic nucleoside and conjugate type of modifications. In addition, in some of the embodiments, the 5' end of the single polynucleotide may be chemically phosphorylated.

In yet another embodiment, the present invention provides a description of the chemical modifications patterns, which improve functionality of RISC inhibiting polynucleotides. Single stranded polynucleotides have been shown to inhibit activity of a preloaded RISC complex through the substrate competition mechanism. For these types of molecules, conventionally called antagomers, the activity usually requires high concentration and in vivo delivery is not very effective. The present invention provides a description of the chemical modification patterns, which may (a) significantly increase stability of the single stranded polynucleotide (b) promote efficient recognition of the polynucleotide by the RISC as a substrate and/or (c) improve uptake of the single stranded nucleotide by the cell. The chemical modification patterns may include combination of ribose, backbone, hydrophobic nucleoside and conjugate type of modifications.

The modifications provided by the present invention are applicable to all polynucleotides. This includes single stranded RISC entering polynucleotides, single stranded RISC inhibiting polynucleotides, conventional duplexed polynucleotides of variable length (15-40 bp), asymmetric duplexed polynucleotides, and the like. Polynucleotides may be modified with wide variety of chemical modification patterns, including 5' end, ribose, backbone and hydrophobic nucleoside modifications.

Aspects of the invention relate to nucleic acid molecules that are highly modified with phosphorothioate backbone modifications. Completely phosphorothioated compounds (21552) that are highly active were disclosed in PCT Publication No. WO2011/119852, incorporated by reference herein. Interestingly, compounds that contained a 21 mer guide strand that was completely phosphorothioate modified were active, however, reducing the guide strand length by two nucleotides, e.g., 19 mer guide strand (21550), resulted in reduced activity. Without wishing to be bound by any theory, increasing the guide strand from 19 to 21 nucleotides (fully phosphorothioated guide strands) may increase the melting temperature between the guide strand and mRNA, resulting in enhanced silencing activity. Varying phosphorothioate content on the 13 mer passenger strand such that it was either completely phosphorothioate modified or contained 6 phosphorothioate modifications did not result in altered activity (21551 vs 21556 as disclosed in PCT Publication No. WO2011/119852).

Several past groups have tried to develop completely phosphorothioated RNAi compounds. Completely phosphorothioated duplexes, lacking single stranded regions, have been designed and tested before, however, these compounds did not demonstrate acceptable pharmacokinetic profiles. Completely phosphorothioated single stranded RNAi compound shave also been designed previously, however, these compounds did not efficiently enter RISC. PCT Publication No. WO2011/119852, incorporated by reference herein in its entirety, disclosed hybrid RNAi compounds that efficiently enter RISC and contain complete phosphorothioated backbones.

In some aspects, the disclosure relates to the discovery of isolated double stranded nucleic acid molecules having highly phosphorothioated backbones (e.g., having at least one strand with a completely phosphorothioated backbone, or almost completely phosphorothioated backbone (e.g., having one un-phosphorothioated residue)) that mediate increased levels of cellular uptake of the isolated double stranded nucleic acid molecule in the central nervous system (CNS) relative to isolated double stranded nucleic acid molecules having less phosphorothioate modifications (e.g., not having at least one strand that is fully phosphorothioated or almost completely phosphorothioated).

Synthesis

Oligonucleotides of the invention can be synthesized by any method known in the art, e.g., using enzymatic synthesis and/or chemical synthesis. The oligonucleotides can be synthesized in vitro (e.g., using enzymatic synthesis and chemical synthesis) or in vivo (using recombinant DNA technology well known in the art).

In a preferred embodiment, chemical synthesis is used for modified polynucleotides. Chemical synthesis of linear oligonucleotides is well known in the art and can be achieved by solution or solid phase techniques. Preferably, synthesis is by solid phase methods. Oligonucleotides can be made by any of several different synthetic procedures including the phosphoramidite, phosphite triester, H-phosphonate, and phosphotriester methods, typically by automated synthesis methods.

Oligonucleotide synthesis protocols are well known in the art and can be found, e.g., in U.S. Pat. No. 5,830,653; WO 98/13526; Stec et al. 1984. *J. Am. Chem. Soc.* 106:6077; Stec et al. 1985. *J. Org. Chem.* 50:3908; Stec et al. J. Chromatog. 1985. 326:263; LaPlanche et al. 1986. *Nucl. Acid. Res.* 1986. 14:9081; Fasman G. D., 1989. Practical Handbook of Biochemistry and Molecular Biology. 1989. CRC Press, Boca Raton, Fla.; Lamone. 1993. *Biochem. Soc. Trans.* 21:1; U.S. Pat. Nos. 5,013,830; 5,214,135; 5,525,719; Kawasaki et al. 1993. *J. Med. Chem.* 36:831; WO 92/03568; U.S. Pat. Nos. 5,276,019; and 5,264,423.

The synthesis method selected can depend on the length of the desired oligonucleotide and such choice is within the skill of the ordinary artisan. For example, the phosphoramidite and phosphite triester method can produce oligonucleotides having 175 or more nucleotides, while the H-phosphonate method works well for oligonucleotides of less than 100 nucleotides. If modified bases are incorporated into the oligonucleotide, and particularly if modified phosphodiester linkages are used, then the synthetic procedures are altered as needed according to known procedures. In this regard, Uhlmann et al. (1990, *Chemical Reviews* 90:543-584) provide references and outline procedures for making oligonucleotides with modified bases and modified phosphodiester linkages. Other exemplary methods for making oligonucleotides are taught in Sonveaux. 1994. "Protecting Groups in Oligonucleotide Synthesis"; Agrawal. *Methods in Molecular Biology* 26:1. Exemplary synthesis methods are also taught in "Oligonucleotide Synthesis—A Practical Approach" (Gait, M. J. IRL Press at Oxford University Press. 1984). Moreover, linear oligonucleotides of defined sequence, including some sequences with modified nucleotides, are readily available from several commercial sources.

The oligonucleotides may be purified by polyacrylamide gel electrophoresis, or by any of a number of chromatographic methods, including gel chromatography and high pressure liquid chromatography. To confirm a nucleotide sequence, especially unmodified nucleotide sequences, oligonucleotides may be subjected to DNA sequencing by any of the known procedures, including Maxam and Gilbert sequencing, Sanger sequencing, capillary electrophoresis sequencing, the wandering spot sequencing procedure or by using selective chemical degradation of oligonucleotides bound to Hybond paper. Sequences of short oligonucleotides can also be analyzed by laser desorption mass spectroscopy or by fast atom bombardment (McNeal, et al., 1982, *J. Am. Chem. Soc.* 104:976; Viari, et al., 1987, *Biomed. Environ. Mass Spectrom.* 14:83; Grotjahn et al., 1982, *Nuc. Acid Res.* 10:4671). Sequencing methods are also available for RNA oligonucleotides.

The quality of oligonucleotides synthesized can be verified by testing the oligonucleotide by capillary electrophoresis and denaturing strong anion HPLC (SAX-HPLC) using, e.g., the method of Bergot and Egan. 1992. *J. Chrom.* 599:35.

Other exemplary synthesis techniques are well known in the art (see, e.g., Sambrook et al., Molecular Cloning: a Laboratory Manual, Second Edition (1989); DNA Cloning, Volumes I and II (DN Glover Ed. 1985); Oligonucleotide Synthesis (M J Gait Ed, 1984; Nucleic Acid Hybridisation (B D Hames and S J Higgins eds. 1984); A Practical Guide to Molecular Cloning (1984); or the series, Methods in Enzymology (Academic Press, Inc.)).

In certain embodiments, the subject RNAi constructs or at least portions thereof are transcribed from expression vectors encoding the subject constructs. Any art recognized vectors may be use for this purpose. The transcribed RNAi constructs may be isolated and purified, before desired modifications (such as replacing an unmodified sense strand with a modified one, etc.) are carried out.

Uptake of Oligonucleotides by Cells

Oligonucleotides and oligonucleotide compositions are contacted with (i.e., brought into contact with, also referred to herein as administered or delivered to) and taken up by one or more cells or a cell lysate. The term "cells" includes prokaryotic and eukaryotic cells, preferably vertebrate cells, and, more preferably, mammalian cells. In a preferred embodiment, the oligonucleotide compositions of the invention are contacted with human cells.

Oligonucleotide compositions of the invention can be contacted with cells in vitro, e.g., in a test tube or culture dish, (and may or may not be introduced into a subject) or in vivo, e.g., in a subject such as a mammalian subject. In some embodiments, Oligonucleotides are administered topically or through electroporation. Oligonucleotides are taken up by cells at a slow rate by endocytosis, but endocytosed oligonucleotides are generally sequestered and not available, e.g., for hybridization to a target nucleic acid molecule. In one embodiment, cellular uptake can be facilitated by electroporation or calcium phosphate precipitation. However, these procedures are only useful for in vitro or ex vivo embodiments, are not convenient and, in some cases, are associated with cell toxicity.

In another embodiment, delivery of oligonucleotides into cells can be enhanced by suitable art recognized methods including calcium phosphate, DMSO, glycerol or dextran, electroporation or by transfection, e.g., using cationic, anionic, or neutral lipid compositions or liposomes using methods known in the art (see e.g., WO 90/14074; WO 91/16024; WO 91/17424; U.S. Pat. No. 4,897,355; Bergan et al. 1993. *Nucleic Acids Research.* 21:3567). Enhanced delivery of oligonucleotides can also be mediated by the use of vectors (See e.g., Shi, Y. 2003. Trends Genet 2003 Jan. 19:9; Reichhart J M et al. Genesis. 2002. 34(1-2):1604, Yu et al. 2002. Proc. Natl. Acad Sci. USA 99:6047; Sui et al. 2002. Proc. Natl. Acad Sci. USA 99:5515) viruses, polyamine or polycation conjugates using compounds such as polylysine, protamine, or Ni, N12-bis (ethyl) spermine (see, e.g., Bartzatt, R. et al. 1989. *Biotechnol. Appl. Biochem.* 11:133; Wagner E. et al. 1992. *Proc. Natl. Acad. Sci.* 88:4255).

In certain embodiments, the sd-rxRNA of the invention may be delivered by using various beta-glucan containing particles, referred to as GeRPs (glucan encapsulated RNA loaded particle), described in, and incorporated by reference from, U.S. Provisional Application No. 61/310,611, filed on Mar. 4, 2010 and entitled "Formulations and Methods for Targeted Delivery to Phagocyte Cells." Such particles are also described in, and incorporated by reference from US Patent Publications US 2005/0281781 A1, and US 2010/0040656, U.S. Pat. No. 8,815,818 and in PCT publications WO 2006/007372, and WO 2007/050643. The sd-rxRNA molecule may be hydrophobically modified and optionally may be associated with a lipid and/or amphiphilic peptide. In certain embodiments, the beta-glucan particle is derived from yeast. In certain embodiments, the payload trapping molecule is a polymer, such as those with a molecular weight of at least about 1000 Da, 10,000 Da, 50,000 Da, 100 kDa, 500 kDa, etc. Preferred polymers include (without limitation) cationic polymers, chitosans, or PEI (polyethylenimine), etc.

Glucan particles can be derived from insoluble components of fungal cell walls such as yeast cell walls. In some embodiments, the yeast is Baker's yeast. Yeast-derived glucan molecules can include one or more of β-(1,3)-Glucan, β-(1,6)-Glucan, mannan and chitin. In some embodiments, a glucan particle comprises a hollow yeast cell wall whereby the particle maintains a three dimensional structure resembling a cell, within which it can complex with or encapsulate a molecule such as an RNA molecule. Some of the advantages associated with the use of yeast cell wall particles are availability of the components, their biodegradable nature, and their ability to be targeted to phagocytic cells.

In some embodiments, glucan particles can be prepared by extraction of insoluble components from cell walls, for example by extracting Baker's yeast (Fleischmann's) with 1M NaOH/pH 4.0 H2O, followed by washing and drying. Methods of preparing yeast cell wall particles are discussed in, and incorporated by reference from U.S. Pat. Nos. 4,810,646, 4,992,540, 5,082,936, 5,028,703, 5,032,401, 5,322,841, 5,401,727, 5,504,079, 5,607,677, 5,968,811, 6,242,594, 6,444,448, 6,476,003, US Patent Publications 2003/0216346, 2004/0014715 and 2010/0040656, and PCT published application WO02/12348.

Protocols for preparing glucan particles are also described in, and incorporated by reference from, the following references: Soto and Ostroff (2008), "Characterization of multilayered nanoparticles encapsulated in yeast cell wall particles for DNA delivery." *Bioconjug Chem* 19(4):840-8; Soto and Ostroff (2007), "Oral Macrophage Mediated Gene Delivery System," *Nanotech, Volume* 2, Chapter 5 ("Drug Delivery"), pages 378-381; and Li et al. (2007), "Yeast glucan particles activate murine resident macrophages to secrete proinflammatory cytokines via MyD88- and Syk kinase-dependent pathways." *Clinical Immunology* 124(2): 170-181.

Glucan containing particles such as yeast cell wall particles can also be obtained commercially. Several non-limiting examples include: Nutricell MOS 55 from Biorigin (Sao Paolo, Brazil), SAF-Mannan (SAF Agri, Minneapolis, Minn.), Nutrex (Sensient Technologies, Milwaukee, Wis.), alkali-extracted particles such as those produced by Nutricepts (Nutricepts Inc., Burnsville, Minn.) and ASA Biotech, acid-extracted WGP particles from Biopolymer Engineering, and organic solvent-extracted particles such as Adjuvax™ from Alpha-beta Technology, Inc. (Worcester, Mass.) and microparticulate glucan from Novogen (Stamford, Conn.).

Glucan particles such as yeast cell wall particles can have varying levels of purity depending on the method of production and/or extraction. In some instances, particles are alkali-extracted, acid-extracted or organic solvent-extracted to remove intracellular components and/or the outer mannoprotein layer of the cell wall. Such protocols can produce particles that have a glucan (w/w) content in the range of 50%-90%. In some instances, a particle of lower purity, meaning lower glucan w/w content may be preferred, while in other embodiments, a particle of higher purity, meaning higher glucan w/w content may be preferred.

Glucan particles, such as yeast cell wall particles, can have a natural lipid content. For example, the particles can contain 1%, 2%, 3%, 4%, 5%, 6%, 7%, 8%, 9%, 10%, 11%, 12%, 13%, 14%, 15%, 16%, 17%, 18%, 19%, 20% or more than 20% w/w lipid. In the Examples section, the effectiveness of two glucan particle batches are tested: YGP SAF and YGP SAF+L (containing natural lipids). In some instances, the presence of natural lipids may assist in complexation or capture of RNA molecules.

Glucan containing particles typically have a diameter of approximately 2-4 microns, although particles with a diameter of less than 2 microns or greater than 4 microns are also compatible with aspects of the invention.

The RNA molecule(s) to be delivered are complexed or "trapped" within the shell of the glucan particle. The shell or RNA component of the particle can be labeled for visualization, as described in, and incorporated by reference from, Soto and Ostroff (2008) *Bioconjug Chem* 19:840. Methods of loading GeRPs are discussed further below.

The optimal protocol for uptake of oligonucleotides will depend upon a number of factors, the most crucial being the type of cells that are being used. Other factors that are important in uptake include, but are not limited to, the nature and concentration of the oligonucleotide, the confluence of the cells, the type of culture the cells are in (e.g., a suspension culture or plated) and the type of media in which the cells are grown.

Encapsulating Agents

Encapsulating agents entrap oligonucleotides within vesicles. In another embodiment of the invention, an oligonucleotide may be associated with a carrier or vehicle, e.g., liposomes or micelles, although other carriers could be used, as would be appreciated by one skilled in the art. Liposomes are vesicles made of a lipid bilayer having a structure similar to biological membranes. Such carriers are used to facilitate the cellular uptake or targeting of the oligonucleotide, or improve the oligonucleotide's pharmacokinetic or toxicologic properties.

For example, the oligonucleotides of the present invention may also be administered encapsulated in liposomes, pharmaceutical compositions wherein the active ingredient is contained either dispersed or variously present in corpuscles consisting of aqueous concentric layers adherent to lipidic layers. The oligonucleotides, depending upon solubility, may be present both in the aqueous layer and in the lipidic layer, or in what is generally termed a liposomic suspension. The hydrophobic layer, generally but not exclusively, comprises phopholipids such as lecithin and sphingomyelin, steroids such as cholesterol, more or less ionic surfactants such as diacetylphosphate, stearylamine, or phosphatidic acid, or other materials of a hydrophobic nature. The diameters of the liposomes generally range from about 15 nm to about 5 microns.

The use of liposomes as drug delivery vehicles offers several advantages. Liposomes increase intracellular stability, increase uptake efficiency and improve biological activity. Liposomes are hollow spherical vesicles composed of lipids arranged in a similar fashion as those lipids which make up the cell membrane. They have an internal aqueous space for entrapping water soluble compounds and range in size from 0.05 to several microns in diameter. Several studies have shown that liposomes can deliver nucleic acids to cells and that the nucleic acids remain biologically active. For example, a lipid delivery vehicle originally designed as a research tool, such as Lipofectin or LIPOFECTAMINE™ 2000, can deliver intact nucleic acid molecules to cells.

Specific advantages of using liposomes include the following: they are non-toxic and biodegradable in composition; they display long circulation half-lives; and recognition molecules can be readily attached to their surface for targeting to tissues. Finally, cost-effective manufacture of liposome-based pharmaceuticals, either in a liquid suspension or lyophilized product, has demonstrated the viability of this technology as an acceptable drug delivery system.

In some aspects, formulations associated with the invention might be selected for a class of naturally occurring or chemically synthesized or modified saturated and unsaturated fatty acid residues. Fatty acids might exist in a form of triglycerides, diglycerides or individual fatty acids. In another embodiment, the use of well-validated mixtures of fatty acids and/or fat emulsions currently used in pharmacology for parenteral nutrition may be utilized.

Liposome based formulations are widely used for oligonucleotide delivery. However, most of commercially available lipid or liposome formulations contain at least one positively charged lipid (cationic lipids). The presence of this positively charged lipid is believed to be essential for obtaining a high degree of oligonucleotide loading and for enhancing liposome fusogenic properties. Several methods have been performed and published to identify optimal positively charged lipid chemistries. However, the commercially available liposome formulations containing cationic lipids are characterized by a high level of toxicity. In vivo limited therapeutic indexes have revealed that liposome formulations containing positive charged lipids are associated with toxicity (i.e. elevation in liver enzymes) at concentrations only slightly higher than concentration required to achieve RNA silencing.

Nucleic acids associated with the invention can be hydrophobically modified and can be encompassed within neutral nanotransporters. Further description of neutral nanotransporters is incorporated by reference from PCT Application PCT/US2009/005251, filed on Sep. 22, 2009, and entitled "Neutral Nanotransporters." Such particles enable quantitative oligonucleotide incorporation into non-charged lipid mixtures. The lack of toxic levels of cationic lipids in such neutral nanotransporter compositions is an important feature.

As demonstrated in PCT/US2009/005251, oligonucleotides can effectively be incorporated into a lipid mixture that is free of cationic lipids and such a composition can effectively deliver a therapeutic oligonucleotide to a cell in a manner that it is functional. For example, a high level of activity was observed when the fatty mixture was composed of a phosphatidylcholine base fatty acid and a sterol such as a cholesterol. For instance, one preferred formulation of neutral fatty mixture is composed of at least 20% of DOPC or DSPC and at least 20% of sterol such as cholesterol. Even as low as 1:5 lipid to oligonucleotide ratio was shown to be sufficient to get complete encapsulation of the oligonucleotide in a non charged formulation.

The neutral nanotransporters compositions enable efficient loading of oligonucleotide into neutral fat formulation. The composition includes an oligonucleotide that is modified in a manner such that the hydrophobicity of the molecule is increased (for example a hydrophobic molecule is attached (covalently or no-covalently) to a hydrophobic molecule on the oligonucleotide terminus or a non-terminal nucleotide, base, sugar, or backbone), the modified oligonucleotide being mixed with a neutral fat formulation (for example containing at least 25% of cholesterol and 25% of DOPC or analogs thereof). A cargo molecule, such as another lipid can also be included in the composition. This composition, where part of the formulation is build into the oligonucleotide itself, enables efficient encapsulation of oligonucleotide in neutral lipid particles.

In some aspects, stable particles ranging in size from 50 to 140 nm can be formed upon complexing of hydrophobic oligonucleotides with preferred formulations. It is interesting to mention that the formulation by itself typically does not form small particles, but rather, forms agglomerates, which are transformed into stable 50-120 nm particles upon addition of the hydrophobic modified oligonucleotide.

The neutral nanotransporter compositions of the invention include a hydrophobic modified polynucleotide, a neutral fatty mixture, and optionally a cargo molecule. A "hydrophobic modified polynucleotide" as used herein is a polynucleotide of the invention (i.e. sd-rxRNA) that has at least one modification that renders the polynucleotide more hydrophobic than the polynucleotide was prior to modification. The modification may be achieved by attaching (covalently or non-covalently) a hydrophobic molecule to the polynucleotide. In some instances the hydrophobic molecule is or includes a lipophilic group.

The term "lipophilic group" means a group that has a higher affinity for lipids than its affinity for water. Examples of lipophilic groups include, but are not limited to, cholesterol, a cholesteryl or modified cholesteryl residue, adamantine, dihydrotesterone, long chain alkyl, long chain alkenyl, long chain alkynyl, olely-lithocholic, cholenic, oleoyl-cholenic, palmityl, heptadecyl, myrisityl, bile acids, cholic acid or taurocholic acid, deoxycholate, oleyl litocholic acid, oleoyl cholenic acid, glycolipids, phospholipids, sphingolipids, isoprenoids, such as steroids, vitamins, such as vitamin E, fatty acids either saturated or unsaturated, fatty acid esters, such as triglycerides, pyrenes, porphyrines, Texaphyrine, adamantane, acridines, biotin, coumarin, fluorescein, rhodamine, Texas-Red, digoxygenin, dimethoxytrityl, t-butyldimethylsilyl, t-butyldiphenylsilyl, cyanine dyes (e.g. Cy3 or Cy5), Hoechst 33258 dye, psoralen, or ibuprofen. The cholesterol moiety may be reduced (e.g. as in cholestan) or may be substituted (e.g. by halogen). A combination of different lipophilic groups in one molecule is also possible.

The hydrophobic molecule may be attached at various positions of the polynucleotide. As described above, the hydrophobic molecule may be linked to the terminal residue of the polynucleotide such as the 3' of 5'-end of the polynucleotide. Alternatively, it may be linked to an internal nucleotide or a nucleotide on a branch of the polynucleotide. The hydrophobic molecule may be attached, for instance to a 2'-position of the nucleotide. The hydrophobic molecule may also be linked to the heterocyclic base, the sugar or the backbone of a nucleotide of the polynucleotide.

The hydrophobic molecule may be connected to the polynucleotide by a linker moiety. Optionally the linker moiety is a non-nucleotidic linker moiety. Non-nucleotidic linkers are e.g. abasic residues (dSpacer), oligoethyleneglycol, such as triethyleneglycol (spacer 9) or hexaethylenegylcol (spacer 18), or alkane-diol, such as butanediol. The spacer units are preferably linked by phosphodiester or phosphorothioate bonds. The linker units may appear just once in the molecule or may be incorporated several times, e.g. via phosphodiester, phosphorothioate, methylphosphonate, or amide linkages.

Typical conjugation protocols involve the synthesis of polynucleotides bearing an aminolinker at one or more positions of the sequence, however, a linker is not required. The amino group is then reacted with the molecule being conjugated using appropriate coupling or activating reagents. The conjugation reaction may be performed either with the polynucleotide still bound to a solid support or following cleavage of the polynucleotide in solution phase. Purification of the modified polynucleotide by HPLC typically results in a pure material.

In some embodiments the hydrophobic molecule is a sterol type conjugate, a PhytoSterol conjugate, cholesterol conjugate, sterol type conjugate with altered side chain length, fatty acid conjugate, any other hydrophobic group conjugate, and/or hydrophobic modifications of the internal nucleoside, which provide sufficient hydrophobicity to be incorporated into micelles.

For purposes of the present invention, the term "sterols", refers or steroid alcohols are a subgroup of steroids with a hydroxyl group at the 3-position of the A-ring. They are amphipathic lipids synthesized from acetyl-coenzyme A via the HMG-CoA reductase pathway. The overall molecule is quite flat. The hydroxyl group on the A ring is polar. The rest of the aliphatic chain is non-polar. Usually sterols are considered to have an 8 carbon chain at position 17.

For purposes of the present invention, the term "sterol type molecules", refers to steroid alcohols, which are similar in structure to sterols. The main difference is the structure of the ring and number of carbons in a position 21 attached side chain.

For purposes of the present invention, the term "PhytoSterols" (also called plant sterols) are a group of steroid alcohols, phytochemicals naturally occurring in plants. There are more then 200 different known PhytoSterols For purposes of the present invention, the term "Sterol side chain" refers to a chemical composition of a side chain attached at the position 17 of sterol-type molecule. In a standard definition sterols are limited to a 4 ring structure carrying a 8 carbon chain at position 17. In this invention, the sterol type molecules with side chain longer and shorter than conventional are described. The side chain may branched or contain double back bones.

Thus, sterols useful in the invention, for example, include cholesterols, as well as unique sterols in which position 17 has attached side chain of 2-7 or longer then 9 carbons. In a particular embodiment, the length of the polycarbon tail is varied between 5 and 9 carbons. Such conjugates may have significantly better ii vivo efficacy, in particular delivery to liver. These types of molecules are expected to work at concentrations 5 to 9 fold lower then oligonucleotides conjugated to conventional cholesterols.

Alternatively the polynucleotide may be bound to a protein, peptide or positively charged chemical that functions as the hydrophobic molecule. The proteins may be selected from the group consisting of protamine, dsRNA binding domain, and arginine rich peptides. Exemplary positively charged chemicals include spermine, spermidine, cadaverine, and putrescine.

In another embodiment hydrophobic molecule conjugates may demonstrate even higher efficacy when it is combined with optimal chemical modification patterns of the polynucleotide (as described herein in detail), containing but not limited to hydrophobic modifications, phosphorothioate modifications, and 2' ribo modifications.

In another embodiment the sterol type molecule may be a naturally occurring PhytoSterols. The polycarbon chain may be longer than 9 and may be linear, branched and/or contain double bonds. Some PhytoSterol containing polynucleotide conjugates may be significantly more potent and active in delivery of polynucleotides to various tissues. Some PhytoSterols may demonstrate tissue preference and thus be used as a way to delivery RNAi specifically to particular tissues.

The hydrophobic modified polynucleotide is mixed with a neutral fatty mixture to form a micelle. The neutral fatty acid mixture is a mixture of fats that has a net neutral or slightly net negative charge at or around physiological pH that can form a micelle with the hydrophobic modified polynucleotide. For purposes of the present invention, the term "micelle" refers to a small nanoparticle formed by a mixture of non charged fatty acids and phospholipids. The neutral fatty mixture may include cationic lipids as long as they are present in an amount that does not cause toxicity. In preferred embodiments the neutral fatty mixture is free of cationic lipids. A mixture that is free of cationic lipids is one that has less than 1% and preferably 0% of the total lipid being cationic lipid. The term "cationic lipid" includes lipids and synthetic lipids having a net positive charge at or around physiological pH. The term "anionic lipid" includes lipids and synthetic lipids having a net negative charge at or around physiological pH.

The neutral fats bind to the oligonucleotides of the invention by a strong but non-covalent attraction (e.g., an electrostatic, van der Waals, pi-stacking, etc. interaction).

The neutral fat mixture may include formulations selected from a class of naturally occurring or chemically synthesized or modified saturated and unsaturated fatty acid residues. Fatty acids might exist in a form of triglycerides, diglycerides or individual fatty acids. In another embodiment the use of well-validated mixtures of fatty acids and/or fat emulsions currently used in pharmacology for parenteral nutrition may be utilized.

The neutral fatty mixture is preferably a mixture of a choline based fatty acid and a sterol. Choline based fatty acids include for instance, synthetic phosphocholine derivatives such as DDPC, DLPC, DMPC, DPPC, DSPC, DOPC, POPC, and DEPC. DOPC (chemical registry number 4235-95-4) is dioleoylphosphatidylcholine (also known as dielaidoylphosphatidylcholine, dioleoyl-PC, dioleoylphosphocholine, dioleoyl-sn-glycero-3-phosphocholine, dioleylphosphatidylcholine). DSPC (chemical registry number 816-94-4) is distearoylphosphatidylcholine (also known as 1,2-Distearoyl-sn-Glycero-3-phosphocholine).

The sterol in the neutral fatty mixture may be for instance cholesterol. The neutral fatty mixture may be made up completely of a choline based fatty acid and a sterol or it may optionally include a cargo molecule. For instance, the neutral fatty mixture may have at least 20% or 25% fatty acid and 20% or 25% sterol.

For purposes of the present invention, the term "Fatty acids" relates to conventional description of fatty acid. They may exist as individual entities or in a form of two- and triglycerides. For purposes of the present invention, the term "fat emulsions" refers to safe fat formulations given intravenously to subjects who are unable to get enough fat in their diet. It is an emulsion of soy bean oil (or other naturally occurring oils) and egg phospholipids. Fat emulsions are being used for formulation of some insoluble anesthetics. In this disclosure, fat emulsions might be part of commercially available preparations like Intralipid, Liposyn, Nutrilipid, modified commercial preparations, where they are enriched with particular fatty acids or fully de novo-formulated combinations of fatty acids and phospholipids.

In one embodiment, the cells to be contacted with an oligonucleotide composition of the invention are contacted with a mixture comprising the oligonucleotide and a mixture comprising a lipid, e.g., one of the lipids or lipid compositions described supra for between about 12 hours to about 24 hours. In another embodiment, the cells to be contacted with an oligonucleotide composition are contacted with a mixture comprising the oligonucleotide and a mixture comprising a lipid, e.g., one of the lipids or lipid compositions described supra for between about 1 and about five days. In one embodiment, the cells are contacted with a mixture comprising a lipid and the oligonucleotide for between about three days to as long as about 30 days. In another embodiment, a mixture comprising a lipid is left in contact with the cells for at least about five to about 20 days. In another embodiment, a mixture comprising a lipid is left in contact with the cells for at least about seven to about 15 days.

50%-60% of the formulation can optionally be any other lipid or molecule. Such a lipid or molecule is referred to herein as a cargo lipid or cargo molecule. Cargo molecules include but are not limited to intralipid, small molecules, fusogenic peptides or lipids or other small molecules might be added to alter cellular uptake, endosomal release or tissue distribution properties. The ability to tolerate cargo molecules is important for modulation of properties of these particles, if such properties are desirable. For instance the presence of some tissue specific metabolites might drastically alter tissue distribution profiles. For example use of Intralipid type formulation enriched in shorter or longer fatty chains with various degrees of saturation affects tissue distribution profiles of these type of formulations (and their loads).

An example of a cargo lipid useful according to the invention is a fusogenic lipid. For instance, the zwiterionic lipid DOPE (chemical registry number 4004-5-1, 1,2-Dioleoyl-sn-Glycero-3-phosphoethanolamine) is a preferred cargo lipid.

Intralipid may be comprised of the following composition: 1 000 mL contain: purified soybean oil 90 g, purified egg phospholipids 12 g, glycerol anhydrous 22 g, water for injection q.s. ad 1 000 mL. pH is adjusted with sodium hydroxide to pH approximately 8. Energy content/L: 4.6 MJ (190 kcal). Osmolality (approx.): 300 mOsm/kg water. In another embodiment fat emulsion is Liposyn that contains 5% safflower oil, 5% soybean oil, up to 1.2% egg phosphatides added as an emulsifier and 2.5% glycerin in water for injection. It may also contain sodium hydroxide for pH adjustment. pH 8.0 (6.0-9.0). Liposyn has an osmolarity of 276 m Osmol/liter (actual).

Variation in the identity, amounts and ratios of cargo lipids affects the cellular uptake and tissue distribution characteristics of these compounds. For example, the length of lipid tails and level of saturability will affect differential uptake to liver, lung, fat and cardiomyocytes. Addition of special hydrophobic molecules like vitamins or different forms of sterols can favor distribution to special tissues which are involved in the metabolism of particular compounds. In some embodiments, vitamin A or E is used. Complexes are formed at different oligonucleotide concentrations, with higher concentrations favoring more efficient complex formation.

In another embodiment, the fat emulsion is based on a mixture of lipids. Such lipids may include natural compounds, chemically synthesized compounds, purified fatty acids or any other lipids. In yet another embodiment the composition of fat emulsion is entirely artificial. In a particular embodiment, the fat emulsion is more then 70% linoleic acid. In yet another particular embodiment the fat emulsion is at least 1% of cardiolipin. Linoleic acid (LA) is an unsaturated omega-6 fatty acid. It is a colorless liquid made of a carboxylic acid with an 18-carbon chain and two cis double bonds.

In yet another embodiment of the present invention, the alteration of the composition of the fat emulsion is used as a way to alter tissue distribution of hydrophobicly modified polynucleotides. This methodology provides for the specific delivery of the polynucleotides to particular tissues.

In another embodiment the fat emulsions of the cargo molecule contain more then 70% of Linoleic acid (C18H32O2) and/or cardiolipin.

Fat emulsions, like intralipid have been used before as a delivery formulation for some non-water soluble drugs (such as Propofol, re-formulated as Diprivan). Unique features of the present invention include (a) the concept of combining modified polynucleotides with the hydrophobic compound(s), so it can be incorporated in the fat micelles and (b) mixing it with the fat emulsions to provide a reversible carrier. After injection into a blood stream, micelles usually bind to serum proteins, including albumin, HDL, LDL and other. This binding is reversible and eventually the fat is absorbed by cells. The polynucleotide, incorporated as a part of the micelle will then be delivered closely to the surface of the cells. After that cellular uptake might be happening though variable mechanisms, including but not limited to sterol type delivery.

Complexing Agents

Complexing agents bind to the oligonucleotides of the invention by a strong but non-covalent attraction (e.g., an electrostatic, van der Waals, pi-stacking, etc. interaction). In one embodiment, oligonucleotides of the invention can be complexed with a complexing agent to increase cellular uptake of oligonucleotides. An example of a complexing agent includes cationic lipids. Cationic lipids can be used to deliver oligonucleotides to cells. However, as discussed above, formulations free in cationic lipids are preferred in some embodiments.

The term "cationic lipid" includes lipids and synthetic lipids having both polar and non-polar domains and which are capable of being positively charged at or around physiological pH and which bind to polyanions, such as nucleic acids, and facilitate the delivery of nucleic acids into cells. In general cationic lipids include saturated and unsaturated alkyl and alicyclic ethers and esters of amines, amides, or derivatives thereof. Straight-chain and branched alkyl and alkenyl groups of cationic lipids can contain, e.g., from 1 to about 25 carbon atoms. Preferred straight chain or branched alkyl or alkene groups have six or more carbon atoms. Alicyclic groups include cholesterol and other steroid groups. Cationic lipids can be prepared with a variety of counterions (anions) including, e.g., Cl$^-$, Br$^-$, I$^-$, F$^-$, acetate, trifluoroacetate, sulfate, nitrite, and nitrate.

Examples of cationic lipids include polyethylenimine, polyamidoamine (PAMAM) starburst dendrimers, Lipofectin (a combination of DOTMA and DOPE), Lipofectase, LIPOFECTAMINE™ (e.g., LIPOFECTAMINE™ 2000), DOPE, Cytofectin (Gilead Sciences, Foster City, Calif.), and Eufectins (JBL, San Luis Obispo, Calif.). Exemplary cationic liposomes can be made from N-[1-(2,3-dioleoloxy)-propyl]-N,N,N-trimethylammonium chloride (DOTMA), N-[1-(2,3-dioleoloxy)-propyl]-N,N,N-trimethylammonium methylsulfate (DOTAP), 3β-[N-(N',N'-dimethylaminoethane)carbamoyl]cholesterol (DC-Chol), 2,3,-dioleyloxy-N-[2 (sperminecarboxamido)ethyl]-N,N-dimethyl-1-propanaminium trifluoroacetate (DOSPA), 1,2-dimyristyloxypropyl-3-dimethyl-hydroxyethyl ammonium bromide; and dimethyldioctadecylammonium bromide (DDAB). The cationic lipid N-(1-(2,3-dioleyloxy)propyl)-N,N,N-trimethylammonium chloride (DOTMA), for example, was found to increase 1000-fold the antisense effect of a phosphorothioate oligonucleotide. (Vlassov el al., 1994, Biochimica et Biophysica Acta 1197:95-108). Oligonucleotides can also be complexed with, e.g., poly (L-lysine) or avidin and lipids may, or may not, be included in this mixture, e.g., steryl-poly (L-lysine).

Cationic lipids have been used in the art to deliver oligonucleotides to cells (see, e.g., U.S. Pat. Nos. 5,855,910; 5,851,548; 5,830,430; 5,780,053; 5,767,099; Lewis et al. 1996. *Proc. Natl. Acad. Sci. USA* 93:3176; Hope et al. 1998. *Molecular Membrane Biology* 15:1). Other lipid compositions which can be used to facilitate uptake of the instant oligonucleotides can be used in connection with the claimed methods. In addition to those listed supra, other lipid compositions are also known in the art and include, e.g., those taught in U.S. Pat. Nos. 4,235,871; 4,501,728; 4,837,028; 4,737,323.

In one embodiment lipid compositions can further comprise agents, e.g., viral proteins to enhance lipid-mediated transfections of oligonucleotides (Kamata, et al., 1994. *Nucl. Acids. Res.* 22:536). In another embodiment, oligonucleotides are contacted with cells as part of a composition comprising an oligonucleotide, a peptide, and a lipid as taught, e.g., in U.S. Pat. No. 5,736,392. Improved lipids have also been described which are serum resistant (Lewis, et al., 1996. *Proc. Natl. Acad. Sci.* 93:3176). Cationic lipids and other complexing agents act to increase the number of oligonucleotides carried into the cell through endocytosis.

In another embodiment N-substituted glycine oligonucleotides (peptoids) can be used to optimize uptake of oligonucleotides. Peptoids have been used to create cationic lipid-like compounds for transfection (Murphy, et al., 1998. *Proc. Natl. Acad. Sci.* 95:1517). Peptoids can be synthesized using standard methods (e.g., Zuckermann, R. N., et al. 1992. *J. Am. Chem. Soc.* 114:10646; Zuckermann, R. N., et al. 1992. *Int. J. Peptide Protein Res.* 40:497). Combinations of cationic lipids and peptoids, liptoids, can also be used to optimize uptake of the subject oligonucleotides (Hunag, et al., 1998. *Chemistry and Biology.* 5:345). Liptoids can be synthesized by elaborating peptoid oligonucleotides and coupling the amino terminal submonomer to a lipid via its amino group (Hunag, et al., 1998. *Chemistry and Biology.* 5:345).

It is known in the art that positively charged amino acids can be used for creating highly active cationic lipids (Lewis et al. 1996. *Proc. Natl. Acad. Sci. US.A.* 93:3176). In one embodiment, a composition for delivering oligonucleotides of the invention comprises a number of arginine, lysine, histidine or ornithine residues linked to a lipophilic moiety (see e.g., U.S. Pat. No. 5,777,153).

In another embodiment, a composition for delivering oligonucleotides of the invention comprises a peptide having from between about one to about four basic residues. These basic residues can be located, e.g., on the amino terminal, C-terminal, or internal region of the peptide. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine (can also be considered non-polar), asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Apart from the basic amino acids, a majority or all of the other residues of the peptide can be selected from the non-basic amino acids, e.g., amino acids other than lysine, arginine, or histidine. Preferably a preponderance of neutral amino acids with long neutral side chains are used.

In one embodiment, a composition for delivering oligonucleotides of the invention comprises a natural or synthetic polypeptide having one or more gamma carboxyglutamic acid residues, or γ-Gla residues. These gamma carboxyglutamic acid residues may enable the polypeptide to bind to each other and to membrane surfaces. In other words, a polypeptide having a series of γ-Gla may be used as a general delivery modality that helps an RNAi construct to stick to whatever membrane to which it comes in contact. This may at least slow RNAi constructs from being cleared from the blood stream and enhance their chance of homing to the target.

The gamma carboxyglutamic acid residues may exist in natural proteins (for example, prothrombin has 10 γ-Gla residues). Alternatively, they can be introduced into the purified, recombinantly produced, or chemically synthesized polypeptides by carboxylation using, for example, a vitamin K-dependent carboxylase. The gamma carboxyglutamic acid residues may be consecutive or non-consecutive, and the total number and location of such gamma carboxyglutamic acid residues in the polypeptide can be regulated/fine tuned to achieve different levels of "stickiness" of the polypeptide.

In one embodiment, the cells to be contacted with an oligonucleotide composition of the invention are contacted with a mixture comprising the oligonucleotide and a mixture comprising a lipid, e.g., one of the lipids or lipid compositions described supra for between about 12 hours to about 24 hours. In another embodiment, the cells to be contacted with an oligonucleotide composition are contacted with a mixture comprising the oligonucleotide and a mixture comprising a lipid, e.g., one of the lipids or lipid compositions described supra for between about 1 and about five days. In one embodiment, the cells are contacted with a mixture comprising a lipid and the oligonucleotide for between about three days to as long as about 30 days. In another embodiment, a mixture comprising a lipid is left in contact with the cells for at least about five to about 20 days. In another embodiment, a mixture comprising a lipid is left in contact with the cells for at least about seven to about 15 days.

For example, in one embodiment, an oligonucleotide composition can be contacted with cells in the presence of a lipid such as cytofectin CS or GSV (available from Glen Research; Sterling, Va.), GS3815, GS2888 for prolonged incubation periods as described herein.

In one embodiment, the incubation of the cells with the mixture comprising a lipid and an oligonucleotide composition does not reduce the viability of the cells. Preferably, after the transfection period the cells are substantially viable. In one embodiment, after transfection, the cells are between at least about 70% and at least about 100% viable. In another embodiment, the cells are between at least about 80% and at least about 95% viable. In yet another embodiment, the cells are between at least about 85% and at least about 90% viable.

In one embodiment, oligonucleotides are modified by attaching a peptide sequence that transports the oligonucleotide into a cell, referred to herein as a "transporting peptide." In one embodiment, the composition includes an oligonucleotide which is complementary to a target nucleic acid molecule encoding the protein, and a covalently attached transporting peptide.

The language "transporting peptide" includes an amino acid sequence that facilitates the transport of an oligonucleotide into a cell. Exemplary peptides which facilitate the transport of the moieties to which they are linked into cells are known in the art, and include, e.g., HIV TAT transcription factor, lactoferrin, Herpes VP22 protein, and fibroblast growth factor 2 (Pooga et al. 1998. *Nature Biotechnology.* 16:857; and Derossi et al. 1998. *Trends in Cell Biology.* 8:84; Elliott and O'Hare. 1997. Cell 88:223).

Oligonucleotides can be attached to the transporting peptide using known techniques, e.g., (Prochiantz, A. 1996. *Curr. Opin. Neurobiol.* 6:629; Derossi et al. 1998. *Trends Cell Biol.* 8:84; Troy et al. 1996. *J. Neurosci.* 16:253), Vives et al. 1997. *J. Biol. Chem.* 272:16010). For example, in one embodiment, oligonucleotides bearing an activated thiol group are linked via that thiol group to a cysteine present in a transport peptide (e.g., to the cysteine present in the β turn between the second and the third helix of the antennapedia homeodomain as taught, e.g., in Derossi et al. 1998. *Trends Cell Biol.* 8:84; Prochiantz. 1996. *Current Opinion in Neurobiol.* 6:629; Allinquant et al. 1995. J Cell Biol. 128:919). In another embodiment, a Boc-Cys-(Npys)OH group can be coupled to the transport peptide as the last (N-terminal) amino acid and an oligonucleotide bearing an SH group can be coupled to the peptide (Troy et al. 1996. *J. Neurosci.* 16:253).

In one embodiment, a linking group can be attached to a nucleomonomer and the transporting peptide can be covalently attached to the linker. In one embodiment, a linker can function as both an attachment site for a transporting peptide and can provide stability against nucleases. Examples of suitable linkers include substituted or unsubstituted $C_1$-$C_{20}$ alkyl chains, $C_2$-$C_{20}$ alkenyl chains, $C_2$-$C_{20}$ alkynyl chains, peptides, and heteroatoms (e.g., S. O, NH, etc.). Other exemplary linkers include bifunctional crosslinking agents such as sulfosuccinimidyl-4-(maleimidophenyl)-butyrate (SMPB) (see, e.g., Smith et al. Biochem J 1991. 276: 417-2).

In one embodiment, oligonucleotides of the invention are synthesized as molecular conjugates which utilize receptor-mediated endocytotic mechanisms for delivering genes into cells (see, e.g., Bunnell et al. 1992. *Somatic Cell and Molecular Genetics.* 18:559, and the references cited therein).

Targeting Agents

The delivery of oligonucleotides can also be improved by targeting the oligonucleotides to a cellular receptor. The targeting moieties can be conjugated to the oligonucleotides or attached to a carrier group (i.e., poly(L-lysine) or liposomes) linked to the oligonucleotides. This method is well suited to cells that display specific receptor-mediated endocytosis.

For instance, oligonucleotide conjugates to 6-phosphomannosylated proteins are internalized 20-fold more efficiently by cells expressing mannose 6-phosphate specific receptors than free oligonucleotides. The oligonucleotides may also be coupled to a ligand for a cellular receptor using a biodegradable linker. In another example, the delivery construct is mannosylated streptavidin which forms a tight complex with biotinylated oligonucleotides. Mannosylated streptavidin was found to increase 20-fold the internalization of biotinylated oligonucleotides. (Vlassov et al. 1994. *Biochimica et Biophysica Acta* 1197:95-108).

In addition specific ligands can be conjugated to the polylysine component of polylysine-based delivery systems. For example, transferrin-polylysine, adenovirus-polylysine, and influenza virus hemagglutinin HA-2 N-terminal fusogenic peptides-polylysine conjugates greatly enhance receptor-mediated DNA delivery in eucaryotic cells. Mannosylated glycoprotein conjugated to poly(L-lysine) in aveolar macrophages has been employed to enhance the cellular uptake of oligonucleotides. Liang et al. 1999. *Pharmazie* 54:559-566.

Because malignant cells have an increased need for essential nutrients such as folic acid and transferrin, these nutrients can be used to target oligonucleotides to cancerous cells. For example, when folic acid is linked to poly(L-lysine) enhanced oligonucleotide uptake is seen in promyelocytic leukaemia (HL-60) cells and human melanoma (M-14) cells. Ginobbi et al. 1997. *Anticancer Res.* 17:29. In another example, liposomes coated with maleylated bovine serum albumin, folic acid, or ferric protoporphyrin IX, show enhanced cellular uptake of oligonucleotides in murine macrophages, KB cells, and 2.2.15 human hepatoma cells. Liang et al. 1999. *Pharmazie* 54:559-566.

Liposomes naturally accumulate in the liver, spleen, and reticuloendothelial system (so-called, passive targeting). By coupling liposomes to various ligands such as antibodies are protein A, they can be actively targeted to specific cell populations. For example, protein A-bearing liposomes may be pretreated with H-2K specific antibodies which are targeted to the mouse major histocompatibility complex-encoded H-2K protein expressed on L cells. (Vlassov et al. 1994. *Biochimica el Biophysica Acta* 1197:95-108).

Other in vitro and/or in vivo delivery of RNAi reagents are known in the art, and can be used to deliver the subject RNAi constructs. See, for example, U.S. patent application publications 20080152661, 20080112916, 20080107694, 20080038296, 20070231392, 20060240093, 20060178327, 20060008910, 20050265957, 20050064595, 20050042227, 20050037496, 20050026286, 20040162235, 20040072785, 20040063654, 20030157030, WO 2008/036825, WO04/065601, and AU2004206255B2, just to name a few (all incorporated by reference).

Administration

The optimal course of administration or delivery of agents associated with the invention, such as oligonucleotides and/or small molecules, may vary depending upon the desired result and/or on the subject to be treated. As used herein "administration" refers to contacting cells with oligonucleotides and can be performed in vitro or in vivo. The dosage of oligonucleotides may be adjusted to optimally reduce expression of a protein translated from a target nucleic acid molecule, e.g., as measured by a readout of RNA stability or by a therapeutic response, without undue experimentation.

For example, expression of the protein encoded by the nucleic acid target can be measured to determine whether or not the dosage regimen needs to be adjusted accordingly. In addition, an increase or decrease in RNA or protein levels in a cell or produced by a cell can be measured using any art recognized technique. By determining whether transcription has been decreased, the effectiveness of the oligonucleotide in inducing the cleavage of a target RNA can be determined.

Any of the above-described oligonucleotide compositions can be used alone or in conjunction with a pharmaceutically acceptable carrier. As used herein, "pharmaceutically acceptable carrier" includes appropriate solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredient, it can be used in the therapeutic compositions. Supplementary active ingredients can also be incorporated into the compositions.

Oligonucleotides may be incorporated into liposomes or liposomes modified with polyethylene glycol or admixed with cationic lipids for parenteral administration. Incorporation of additional substances into the liposome, for example, antibodies reactive against membrane proteins found on specific target cells, can help target the oligonucleotides to specific cell types.

With respect to in vivo applications, the formulations of the present invention can be administered to a patient in a variety of forms adapted to the chosen route of administration, e.g., parenterally, orally, or intraperitoneally, infusion, intrathecal delivery, parenchymal delivery, intravenous delivery or direct injection into the brain or spinal cord.

Aspects of the invention relate to delivery of nucleic acid molecules, such as sd-rxRNA or sd-rxRNA variants to the nervous system. For example, an sd-rxRNA or sd-rxRNA variant can be delivered to the brain or to the spinal cord. Any appropriate delivery mechanism for delivering an sd-rxRNA variant to the brain or spinal cord can be applied. In some embodiments, delivery to the brain or spinal cord occurs by infusion, intrathecal delivery, parenchymal delivery, intravenous delivery or direct injection into the brain or spinal cord. In some embodiments, an sd-rxRNA or an sd-rxRNA variant is delivered to a specific region of the brain. An sd-rxRNA or an sd-rxRNA variant can be modified or formulated appropriately to pass the blood-brain barrier. In other embodiments, an sd-rxRNA or an sd-rxRNA variant is administered in such a way that it does not need to cross the blood-brain barrier. In some embodiments, the sd-rxRNA or an sd-rxRNA variant is delivered by a pump or catheter system into the brain or spinal cord. Examples of such delivery are incorporated by reference from U.S. Pat. No. 6,093,180 (Elsberry). Techniques for infusing drugs into the brain are also incorporated by reference from U.S. Pat. No. 5,814,014 (Elsberry et al.).

In some embodiments, the sd-rxRNA molecules are administered by parenteral routes. Parenteral administration includes administration by the following routes: intravenous; intramuscular; interstitially; intraarterially; subcutaneous; intra ocular; intrasynovial; trans epithelial, including transdermal; pulmonary via inhalation; ophthalmic; sublingual and buccal; topically, including ophthalmic; dermal; ocular; rectal; and nasal inhalation via insufflation. In some embodiments, the sd-rxRNA molecules are administered by intradermal injection or subcutaneously.

Pharmaceutical preparations associated with the invention can include aqueous solutions of the active compounds in water-soluble or water-dispersible form. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, or dextran, optionally, the suspension may also contain stabilizers. The oligonucleotides of the invention can be formulated in liquid solutions, preferably in physiologically compatible buffers such as Hank's solution or Ringer's solution. In addition, the oligonucleotides may be formulated in solid form and redissolved or suspended immediately prior to use. Lyophilized forms are also included in the invention.

Pharmaceutical preparations associated with the invention can include transdermal patches, ointments, lotions, creams, gels, drops, sprays, suppositories, liquids and powders. In addition, conventional pharmaceutical carriers, aqueous, powder or oily bases, or thickeners may be used in pharmaceutical preparations for topical administration.

Pharmaceutical preparations associated with the invention can include powders or granules, suspensions or solutions in water or non-aqueous media, capsules, sachets or tablets. In addition, thickeners, flavoring agents, diluents, emulsifiers, dispersing aids, or binders may be used in pharmaceutical preparations for oral administration.

For transmucosal or transdermal administration, penetrants appropriate to the barrier to be permeated are used in the formulation. Such penetrants are known in the art, and include, for example, for transmucosal administration bile salts and fusidic acid derivatives, and detergents. Transmucosal administration may be through nasal sprays or using suppositories. For oral administration, the oligonucleotides are formulated into conventional oral administration forms such as capsules, tablets, and tonics. For topical administration, the oligonucleotides of the invention are formulated into ointments, salves, gels, or creams as known in the art.

Drug delivery vehicles can be chosen e.g., for in vitro, for systemic, or for topical administration. These vehicles can be designed to serve as a slow release reservoir or to deliver their contents directly to the target cell. An advantage of using some direct delivery drug vehicles is that multiple molecules are delivered per uptake. Such vehicles have been shown to increase the circulation half-life of drugs that would otherwise be rapidly cleared from the blood stream. Some examples of such specialized drug delivery vehicles which fall into this category are liposomes, hydrogels, cyclodextrins, biodegradable nanocapsules, and bioadhesive microspheres.

The described oligonucleotides may be administered systemically to a subject. Systemic absorption refers to the entry of drugs into the blood stream followed by distribution throughout the entire body. Administration routes which lead to systemic absorption include: intravenous, subcutaneous, intraperitoneal, and intranasal. Each of these administration routes delivers the oligonucleotide to accessible diseased cells. Following subcutaneous administration, the therapeutic agent drains into local lymph nodes and proceeds through the lymphatic network into the circulation. The rate of entry into the circulation has been shown to be a function of molecular weight or size. The use of a liposome or other drug carrier localizes the oligonucleotide at the lymph node. The oligonucleotide can be modified to diffuse into the cell, or the liposome can directly participate in the delivery of either the unmodified or modified oligonucleotide into the cell.

The chosen method of delivery will result in entry into cells. In some embodiments, preferred delivery methods include liposomes (10-400 nm), hydrogels, controlled-release polymers, and other pharmaceutically applicable vehicles, and microinjection or electroporation (for ex vivo treatments).

The pharmaceutical preparations of the present invention may be prepared and formulated as emulsions. Emulsions are usually heterogeneous systems of one liquid dispersed in another in the form of droplets usually exceeding 0.1 µm in diameter. The emulsions of the present invention may contain excipients such as emulsifiers, stabilizers, dyes, fats, oils, waxes, fatty acids, fatty alcohols, fatty esters, humectants, hydrophilic colloids, preservatives, and anti-oxidants may also be present in emulsions as needed. These excipients may be present as a solution in either the aqueous phase, oily phase or itself as a separate phase.

Examples of naturally occurring emulsifiers that may be used in emulsion formulations of the present invention include lanolin, beeswax, phosphatides, lecithin and acacia. Finely divided solids have also been used as good emulsifiers especially in combination with surfactants and in viscous preparations. Examples of finely divided solids that may be used as emulsifiers include polar inorganic solids, such as heavy metal hydroxides, nonswelling clays such as bentonite, attapulgite, hectorite, kaolin, montrnorillonite, colloidal aluminum silicate and colloidal magnesium aluminum silicate, pigments and nonpolar solids such as carbon or glyceryl tristearate.

Examples of preservatives that may be included in the emulsion formulations include methyl paraben, propyl paraben, quaternary ammonium salts, benzalkonium chloride, esters of p-hydroxybenzoic acid, and boric acid. Examples of antioxidants that may be included in the emulsion formulations include free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

In one embodiment, the compositions of oligonucleotides are formulated as microemulsions. A microemulsion is a system of water, oil and amphiphile which is a single optically isotropic and thermodynamically stable liquid solution. Typically microemulsions are prepared by first dispersing an oil in an aqueous surfactant solution and then adding a sufficient amount of a 4th component, generally an intermediate chain-length alcohol to form a transparent system.

Surfactants that may be used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (S0750), decaglycerol decaoleate (DA0750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules.

Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain ($C_8$-$C_{12}$) mono, di, and tri-glycerides, polyoxyethylated glyceryl fatty acid esters, fatty alcohols, polyglycolized glycerides, saturated polyglycolized $C_8$-$C_{10}$ glycerides, vegetable oils and silicone oil.

Microemulsions are particularly of interest from the standpoint of drug solubilization and the enhanced absorption of drugs. Lipid based microemulsions (both oil/water and water/oil) have been proposed to enhance the oral bioavailability of drugs.

Microemulsions offer improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides el al., Pharmaceutical Research, 1994, 11:1385; Ho et al., J. Pharm. Sci., 1996, 85:138-143). Microemulsions have also been effective in the transdermal delivery of active components in both cosmetic and pharmaceutical applications. It is expected that the microemulsion compositions and formulations of the present invention will facilitate the increased systemic absorption of oligonucleotides from the gastrointestinal tract, as well as improve the local cellular uptake of oligonucleotides within the gastrointestinal tract, vagina, buccal cavity and other areas of administration.

In an embodiment, the present invention employs various penetration enhancers to affect the efficient delivery of nucleic acids, particularly oligonucleotides, to the skin of animals. Even non-lipophilic drugs may cross cell membranes if the membrane to be crossed is treated with a penetration enhancer. In addition to increasing the diffusion of non-lipophilic drugs across cell membranes, penetration enhancers also act to enhance the permeability of lipophilic drugs.

Five categories of penetration enhancers that may be used in the present invention include: surfactants, fatty acids, bile salts, chelating agents, and non-chelating non-surfactants. Other agents may be utilized to enhance the penetration of the administered oligonucleotides include: glycols such as ethylene glycol and propylene glycol, pyrrols such as 2-15 pyrrol, azones, and terpenes such as limonene, and menthone.

The oligonucleotides, especially in lipid formulations, can also be administered by coating a medical device, for example, a catheter, such as an angioplasty balloon catheter, with a cationic lipid formulation. Coating may be achieved, for example, by dipping the medical device into a lipid formulation or a mixture of a lipid formulation and a suitable solvent, for example, an aqueous-based buffer, an aqueous solvent, ethanol, methylene chloride, chloroform and the like. An amount of the formulation will naturally adhere to the surface of the device which is subsequently administered to a patient, as appropriate. Alternatively, a lyophilized mixture of a lipid formulation may be specifically bound to the surface of the device. Such binding techniques are described, for example, in K. Ishihara et al., Journal of Biomedical Materials Research, Vol. 27, pp. 1309-1314 (1993), the disclosures of which are incorporated herein by reference in their entirety.

The useful dosage to be administered and the particular mode of administration will vary depending upon such factors as the cell type, or for in vivo use, the age, weight and the particular animal and region thereof to be treated, the particular oligonucleotide and delivery method used, the therapeutic or diagnostic use contemplated, and the form of the formulation, for example, suspension, emulsion, micelle or liposome, as will be readily apparent to those skilled in the art. Typically, dosage is administered at lower levels and increased until the desired effect is achieved. When lipids are used to deliver the oligonucleotides, the amount of lipid compound that is administered can vary and generally depends upon the amount of oligonucleotide agent being administered. For example, the weight ratio of lipid compound to oligonucleotide agent is preferably from about 1:1 to about 15:1, with a weight ratio of about 5:1 to about 10:1 being more preferred. Generally, the amount of cationic lipid compound which is administered will vary from between about 0.1 milligram (mg) to about 1 gram (g). By way of general guidance, typically between about 0.1 mg and about 10 mg of the particular oligonucleotide agent, and about 1 mg to about 100 mg of the lipid compositions, each per kilogram of patient body weight, is administered, although higher and lower amounts can be used.

The agents of the invention are administered to subjects or contacted with cells in a biologically compatible form suitable for pharmaceutical administration. By "biologically compatible form suitable for administration" is meant that the oligonucleotide is administered in a form in which any toxic effects are outweighed by the therapeutic effects of the oligonucleotide. In one embodiment, oligonucleotides can be administered to subjects. Examples of subjects include mammals, e.g., humans and other primates; cows, pigs, horses, and farming (agricultural) animals; dogs, cats, and other domesticated pets; mice, rats, and transgenic non-human animals.

Administration of an active amount of an oligonucleotide of the present invention is defined as an amount effective, at dosages and for periods of time necessary to achieve the desired result. For example, an active amount of an oligonucleotide may vary according to factors such as the type of cell, the oligonucleotide used, and for in vivo uses the disease state, age, sex, and weight of the individual, and the ability of the oligonucleotide to elicit a desired response in the individual. Establishment of therapeutic levels of oligonucleotides within the cell is dependent upon the rates of uptake and efflux or degradation. Decreasing the degree of degradation prolongs the intracellular half-life of the oligonucleotide. Thus, chemically-modified oligonucleotides, e.g., with modification of the phosphate backbone, may require different dosing.

The exact dosage of an oligonucleotide and number of doses administered will depend upon the data generated experimentally and in clinical trials. Several factors such as the desired effect, the delivery vehicle, disease indication, and the route of administration, will affect the dosage. Dosages can be readily determined by one of ordinary skill in the art and formulated into the subject pharmaceutical compositions. Preferably, the duration of treatment will extend at least through the course of the disease symptoms.

Dosage regimens may be adjusted to provide the optimum therapeutic response. For example, the oligonucleotide may be repeatedly administered, e.g., several doses may be administered daily or the dose may be proportionally reduced as indicated by the exigencies of the therapeutic situation. One of ordinary skill in the art will readily be able to determine appropriate doses and schedules of administration of the subject oligonucleotides, whether the oligonucleotides are to be administered to cells or to subjects.

Administration of sd-rxRNAs can be optimized through testing of dosing regimens. In some embodiments, a single administration is sufficient. To further prolong the effect of the administered sd-rxRNA, the sd-rxRNA can be administered in a slow-release formulation or device, as would be familiar to one of ordinary skill in the art. The hydrophobic nature of sd-rxRNA compounds can enable use of a wide variety of polymers, some of which are not compatible with conventional oligonucleotide delivery.

In other embodiments, the sd-rxRNA is administered multiple times. In some instances it is administered daily, bi-weekly, weekly, every two weeks, every three weeks, monthly, every two months, every three months, every four months, every five months, every six months or less frequently than every six months. In some instances, it is administered multiple times per day, week, month and/or year. For example, it can be administered approximately every hour, 2 hours, 3 hours, 4 hours, 5 hours, 6 hours, 7 hours, 8 hours, 9 hours 10 hours, 12 hours or more than twelve hours. It can be administered 1, 2, 3, 4, 5, 6, 7, 8, 9, 10 or more than 10 times per day.

Aspects of the invention relate to administering sd-rxRNA molecules to a subject. In some instances the subject is a patient and administering the sd-rxRNA molecule involves administering the sd-rxRNA molecule in a doctor's office.

In some embodiments, more than one sd-rxRNA molecule is administered simultaneously. For example a composition may be administered that contains 1, 2, 3, 4, 5, 6, 7, 8, 9, 10 or more than 10 different sd-rxRNA molecules. In certain embodiments, a composition comprises 2 or 3 different sd-rxRNA molecules. When a composition comprises more than one sd-rxRNA, the sd-rxRNA molecules within the composition can be directed to the same gene or to different genes.

In some instances, the effective amount of sd-rxRNA that is delivered is at least approximately 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more than 100 mg/kg including any intermediate values.

In some instances, the effective amount of sd-rxRNA that is delivered is at least approximately 1, 5, 10, 15, 20, 25, 30, 35, 40, 45, 50, 55, 60, 65, 70, 75, 80, 85, 90, 95, 100, 125, 150, 200, 250, 300, 350, 400, 450, 500, 550, 600, 650, 700, 750, 800, 850, 900, 950 or more than 950 µg including any intermediate values.

sd-rxRNA molecules administered through methods described herein are effectively targeted to all the cell types in the nervous system.

It should be appreciated that the formulations and methods for delivery or administration discussed herein for sd-rxRNA molecules are also applicable to small molecules or other agents associated with the invention. Small molecules described herein can be formulated and administered according to methods known in the art.

In some embodiments of methods described by the disclosure, a nucleic acid molecule (e.g., a sd-rxRNA) and an agent that activates NF-κB p65 (e.g., increases expression of manganese superoxide dismutase (MnSOD/Sod2) and/or expression of a related protein) are co-administered. In some embodiments, the nucleic acid molecule (e.g., a sd-rxRNA) and the agent that activates NF-κB p65 (e.g., increases expression of manganese superoxide dismutase (MnSOD/Sod2) and/or expression of a related protein) are co-administered as separate compositions. In some embodiments, the nucleic acid and the agent are administered to a subject within 0 seconds (e.g., simultaneous co-administration) and 24 hours of each other. In some embodiments, the time between the administration of the nucleic acid molecule and the agent that activates NF-κB p65 ranges from about 0 seconds to about 6 hours. In some embodiments, the administration of the nucleic acid molecule and the agent that activates NF-κB p65 ranges from about 0 seconds to about 1 hour. In some embodiments, the administration of the nucleic acid molecule occurs within one hour of administration of the agent that activates NF-κB p65. In some embodiments, the nucleic acid molecule (e.g., a sd-rxRNA) and the agent that activates NF-κB p65 are co-administered as a single composition.

Various modalities of introducing nucleic acids into a subject (e.g., a cell of a subject) are contemplated by the disclosure. For example, nucleic acids (e.g., a solution containing the nucleic acids) can be injected into a subject (e.g., injected into a cell) or a subject (e.g., a cell) can be bombarded by particles covered by the nucleic acids. In some embodiments, the cell or organism is soaked in a solution of the nucleic acid. In some embodiments, a nucleic acid is introduced into an organism or cell by electroporation of cell membranes in the presence of the nucleic acid. In some embodiments, a viral construct comprising the nucleic acid is packaged into a viral particle and accomplishes introduction of the nucleic acid into the cell and transcription of nucleic acid. Further examples of modalities for introducing nucleic acids into a subject (e.g., a cell of a subject) include but are not limited to lipid-mediated carrier transport, chemical-mediated transport (e.g., calcium phosphate), etc.

Nucleic acids can be introduced with additional components. For example, in some embodiments, the nucleic acid is introduced with a component that enhances nucleic acid uptake by the cell. In some embodiments, the nucleic acid is introduced with a component that inhibits annealing of single strands. In some embodiments, the nucleic acid is introduced with a component that stabilizes the nucleic acid molecule, or other-wise increases inhibition of the target gene.

Nucleic acid may be directly introduced into the cell (i.e., intracellularly); or introduced extracellularly into a cavity, interstitial space, into the circulation of an organism, introduced orally, or may be introduced by bathing a cell or organism in a solution containing the nucleic acid. Vascular or extravascular circulation, the blood or lymph system, and the cerebrospinal fluid are sites where the nucleic acid may be introduced.

In some embodiments, the cell with the target gene may be derived from any organism. In some embodiments, the cell with the target gene may be contained in (e.g., housed by, or present within) any organism. For example, the organism may a plant, animal, protozoan, bacterium, virus, or fungus. The plant may be a monocot, dicot or gymnosperm; the animal may be a vertebrate or invertebrate. Preferred microbes are those used in agriculture or by industry, and those that are pathogenic for plants or animals.

Alternatively, vectors, e.g., transgenes encoding a siRNA of the invention can be engineered into a host cell or transgenic animal using art recognized techniques.

A further preferred use for the agents of the present invention (or vectors or transgenes encoding same) is a functional analysis to be carried out in eukaryotic cells, or eukaryotic non-human organisms, preferably mammalian cells or organisms and most preferably human cells, e.g. cell lines such as HeLa or 293 or rodents, e.g. rats and mice. By administering a suitable priming agent/RNAi agent which is sufficiently complementary to a target mRNA sequence to direct target-specific RNA interference, a specific knockout or knockdown phenotype can be obtained in a target cell, e.g. in cell culture or in a target organism.

Thus, a further subject matter of the invention is a eukaryotic cell or a eukaryotic non-human organism exhibiting a target gene-specific knockout or knockdown phenotype comprising a fully or at least partially deficient expression of at least one endogenous target gene wherein said cell or organism is transfected with at least one vector comprising DNA encoding an RNAi agent capable of inhibiting the expression of the target gene. It should be noted that the present invention allows a target-specific knockout or knockdown of several different endogenous genes due to the specificity of the RNAi agent.

Gene-specific knockout or knockdown phenotypes of cells or non-human organisms, particularly of human cells or non-human mammals may be used in analytic to procedures, e.g. in the functional and/or phenotypical analysis of complex physiological processes such as analysis of gene expression profiles and/or proteomes. Preferably the analysis is carried out by high throughput methods using oligonucleotide based chips.

Therapeutic Use

By inhibiting the expression of a gene, the oligonucleotide compositions of the present invention can be used to treat any disease involving the expression of a protein, such as neurodegenerative disease.

Aspects of the invention relate to the use of nucleic acid molecules, such as sd-rxRNA or sd-rxRNA variants sd-rxRNA in treatment of disorders affecting the nervous system. In some embodiments, the sd-rxRNA is used to treat a neurodegenerative disorder. Some non-limiting examples of neurodegenerative disorders include stroke, Alzheimer's disease, Parkinson's disease, Huntington's disease, Peri ventricular leukomalacia (PVL), amyotrophic lateral sclerosis (ALS, "Lou Gehrig's disease"), ALS-Parkinson's-Dementia complex of Guam, Friedrich's Ataxia, Wilson's disease, multiple sclerosis, cerebral palsy, progressive supranuclear palsy (Steel-Richardson syndrome), bulbar and pseudobulbar palsy, diabetic retinopathy, multi-infarct dementia, macular degeneration, Pick's disease, diffuse Lewy body disease, prion diseases such as Creutzfeldt-Jakob, Gerstmann-Straussler-Scheinker disease, Kuru and fatal familial insomnia, primary lateral sclerosis, degenerative ataxias, Machado-Joseph disease/spinocerebellar ataxia type 3 and olivopontocerebellar degenerations, spinal and spinobulbar muscular atrophy (Kennedy's disease), familial spastic paraplegia, Wohlfart-Kugelberg-Welander disease, Tay-Sach's disease, multisystem degeneration (Shy-Drager syndrome), Gilles De La Tourette's disease, familial dysautonomia (Riley-Day syndrome), Kugelberg-Welander disease, subacute sclerosing panencephalitis, Werdnig-Hoffinann disease, synucleinopathies (including multiple system atrophy), Sandhoffdisease, cortical basal degeneration, spastic paraparesis, primary progressive aphasia, progressive multifocal leukoencephalopathy, striatonigral degeneration, familial spastic disease, chronic epileptic conditions associated with neurodegeneration, Binswanger's disease, and dementia (including all underlying etiologies of dementia).

Non-limiting examples of genes associated with CNS disease include: DRD2, GRIA1, GRIA2, GRIN1, SLC1A1, SYP, SYT1, CHRNA7, 3Rtau/4rTUS, APP, BAX, BCL-2, GRIK1, GFAP, IL-1, AGER, associated with Alzheimer's Disease; UCH-L1, SKP1, EGLN1, Nurr-1, BDNF, TrkB, gstm1, S10613, associated with Parkinson's Disease; IT15, PRNP, JPH3, TBP, ATXN1, ATXN2, ATXN3, Atrophin 1, FTL, TITF-1, associated with Huntington's Disease; FXN, associated with Freidrich's ataxia; ASPA, associated with Canavan's Disease; DMD, associated with muscular dystrophy, and SMN1, UBE1, DYNC1H1 associated with spinal muscular atrophy.

In some embodiments, the disorder is Parkinson's disease Huntington's or ALS. In certain embodiments, the disorder is ALS and the sd-rxRNA or sd-rxRNA variant targets SOD1, a superoxide dismutase.

Neurodegenerative disorders may also be the result of a brain injury or trauma including that which is caused by a stroke, an injury to the head or spinal cord, or acute ischemic injury. Ischemic injuries refer to conditions that arise when the brain receives insufficient blood flow. In some embodiments, injury to the brain or nervous system can result from a traumatic injury, or could be the result of infection, radiation, chemical or toxic damage. Injury within the brain and nervous system, which may be diffuse or localized, includes an intracranial or intra vertebral lesion or hemorrhage, cerebral ischemia or infarction including embolic occlusion and thrombotic occlusion, perinatal hypoxic-ischemic injury, whiplash, shaken infant syndrome, reperfusion following acute ischemia, or cardiac arrest.

In one embodiment, in vitro treatment of cells with oligonucleotides can be used for ex vivo therapy of cells removed from a subject (e.g., for treatment of leukemia or viral infection) or for treatment of cells which did not originate in the subject, but are to be administered to the subject (e.g., to eliminate transplantation antigen expression on cells to be transplanted into a subject). In addition, in vitro treatment of cells can be used in nontherapeutic settings, e.g., to evaluate gene function, to study gene regulation and protein synthesis or to evaluate improvements made to oligonucleotides designed to modulate gene expression or protein synthesis. In vivo treatment of cells can be useful in certain clinical settings where it is desirable to inhibit the expression of a protein. There are numerous medical conditions for which antisense therapy is reported to be suitable (see, e.g., U.S. Pat. No. 5,830,653) as well as respiratory syncytial virus infection (WO 95/22,553) influenza virus (WO 94/23,028), and malignancies (WO 94/08, 003). Other examples of clinical uses of antisense sequences are reviewed, e.g., in Glaser. 1996. Genetic Engineering News 16:1. Exemplary targets for cleavage by oligonucleotides include, e.g., protein kinase Ca, ICAM-1, c-rafkinase, p53, c-myb, and the bcr/ab1 fusion gene found in chronic myelogenous leukemia.

Aspects of the invention relate to reduction of SOD1 activity, protein level and/or mRNA level. It should be appreciated that any means of reducing SOD1 activity, protein level and/or mRNA level can be compatible with aspects of the invention. In some embodiments, SOD mRNA is reduced by a nucleic acid associated with the invention.

In other embodiments, SOD1 activity, protein level and/or mRNA level is reduced by an antagonist, antibody or small molecules. Non-limiting examples of small molecules include ATN-224, cycloheximide, desipramine, methotrexate, puromycin, qunacrine, tamoxifen, and minocycline. In some embodiments, a small molecule may inhibit the SOD1 promoter (Wright P D et al., Screening for inhibitors of the SOD1 gene promoter: pyrimethamine does not reduce SOD1 levels in cell and animal models. Neurosci Lett. 2010 Oct. 4; 482(3):188-92.). Loss of mitochondrial Ca(2+)-buffering capacity has also been linked to the inhibition of SOD1 (Parone P A et al., Enhancing mitochondrial calcium buffering capacity reduces aggregation of misfolded SOD1 and motor neuron cell death without extending survival in mouse models of inherited amyotrophic lateral sclerosis. J Neurosci. 2013 Mar. 13; 33(11):4657-71).

The subject nucleic acids can be used in RNAi-based therapy in any animal having RNAi pathway, such as human, non-human primate, non-human mammal, non-human vertebrates, rodents (mice, rats, hamsters, rabbits, etc.), domestic livestock animals, pets (cats, dogs, etc.), *Xenopus*, fish, insects (*Drosophila*, etc.), and worms (*C. elegans*), etc.

The invention provides methods for preventing in a subject, a disease or condition associated with an aberrant or unwanted target gene expression or activity, by administering to the subject a therapeutic agent (e.g., a RNAi agent or vector or transgene encoding same). If appropriate, subjects are first treated with a priming agent so as to be more responsive to the subsequent RNAi therapy. Subjects at risk for a disease which is caused or contributed to by aberrant or unwanted target gene expression or activity can be identified by, for example, any or a combination of diagnostic or prognostic assays as described herein. Administration of a prophylactic agent can occur prior to the manifestation of symptoms characteristic of the target gene aberrancy, such that a disease or disorder is prevented or, alternatively, delayed in its progression. Depending on the type of target gene aberrancy, for example, a target gene, target gene agonist or target gene antagonist agent can be used for treating the subject.

In another aspect, the invention pertains to methods of modulating target gene expression, protein expression or activity for therapeutic purposes. Accordingly, in an exemplary embodiment, the modulatory method of the invention involves contacting a cell capable of expressing target gene with a therapeutic agent of the invention that is specific for the target gene or protein (e.g., is specific for the mRNA encoded by said gene or specifying the amino acid sequence of said protein) such that expression or one or more of the activities of target protein is modulated. These modulatory methods can be performed in vitro (e.g., by culturing the cell with the agent), in vivo (e.g., by administering the agent to a subject), or ex vivo. Typically, subjects are first treated with a priming agent so as to be more responsive to the subsequent RNAi therapy. As such, the present invention provides methods of treating an individual afflicted with a disease or disorder characterized by aberrant or unwanted expression or activity of a target gene polypeptide or nucleic acid molecule. Inhibition of target gene activity is desirable in situations in which target gene is abnormally unregulated and/or in which decreased target gene activity is likely to have a beneficial effect.

The therapeutic agents of the invention can be administered to individuals to treat (prophylactically or therapeutically) disorders associated with aberrant or unwanted target gene activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a therapeutic agent as well as tailoring the dosage and/or therapeutic regimen of treatment with a therapeutic agent. Pharmacogenomics deals with clinically significant hereditary variations in the response to drugs due to altered drug disposition and abnormal action in affected persons. See, for example, Eichelbaum, M. et al. (1996) Clin. Exp. Pharmacol. Physiol. 23(10-11): 983-985 and Linder, M. W. et al. (1997) Clin. Chem. 43(2):254-266.

The present invention is further illustrated by the following Examples, which in no way should be construed as further limiting. The entire contents of all of the references (including literature references, issued patents, published patent applications, and co pending patent applications) cited throughout this application are hereby expressly incorporated by reference.

EXAMPLES

Example 1: Identification of SOD1-Targeting Sd-rxRNA Variants sd-rxRNA variants targeting SOD1 were designed, synthesized and screened in vitro to determine the ability of the sd-rxRNA variant to reduce target gene mRNA levels. The sd-rxRNA variants were tested for activity in HeLa cells (human cervical carcinoma cell line, 10,000 cells/well, 96 well plate). HeLa cells were treated with varying concentrations of a panel of SOD1-targeting sd-rxRNA variants or non-targeting control in serum containing media. Concentrations tested were 5, 1 and 0.1 µM. The non-targeting control sd-rxRNA is of similar structure to the SOD1-targeting sd-rxRNA variants and contains similar stabilizing modifications throughout both strands. Forty eight hours post administration, cells were lysed and mRNA levels determined by the Quantigene branched DNA assay according to the manufacture's protocol using gene-specific probes (Affymetrix, Santa Clara, Calif.). Exemplary sense and antisense sequences are presented in Tables 1 and 2 below. FIGS. 1 and 2 demonstrate the SOD1-targeting sd-rxRNA variants significantly reduce target gene mRNA levels in vitro in HeLa cells. Data were normalized to a house keeping gene (PPIB) and graphed with respect to the non-targeting control. Error bars represent the standard deviation from the mean of biological duplicates.

TABLE 1

Exemplary sense oligonucleotides

| Oligo Number | Gene symbol | Sense sequence | SEQ ID NO: | Sense Chemistry | Sense Backbone | Notes |
|---|---|---|---|---|---|---|
| 25634 | SOD1 | GAGAGGCAUGUUA | 1 | DY547mm0m00m0m0mmm | oooooooooosso | |
| 25635 | SOD1 | GAGAGGCAUGUUA | 2 | DY547mm0m00m0m0mmm | oooooooooosso | |
| 25636 | SOD1 | GAGAGGCAUGUUA | 3 | DY547mm0m00m0m0mmm | oooooooooosso | |

TABLE 1-continued

Exemplary sense oligonucleotides

| Oligo Number | Gene symbol | Sense sequence | SEQ ID NO: | Sense Chemistry | Sense Backbone | Notes |
|---|---|---|---|---|---|---|
| 25637 | SOD1 | GAGAGGCAUGUUA | 4 | DY547mm0m00m0m0mmm | sssssssssssso | |
| 25600 | SOD1 | GAGAGGCAUGUUA | 5 | mm00oom0m0mmm | sssssssssssso | |
| 25638 | SOD1 | GAGAGGCAUGUUA | 6 | DY547mm0m00m0m0mmm | sssssssssssso | |
| 25643 | SOD1 | GAGAGGCAUGUUA | 7 | DY547mm0m00m0m0mmm | ooooooooosso | |
| 25644 | SOD1 | GAGAGGCAUGUUA | 8 | DY547mm0m00m0m0mmm | sssssssssssso | |
| 25645 | SOD1 | GAGAGGCAUGUUA | 9 | DY547mm0m00m0m0mmm | ooooooooosso | |
| 25652 | SOD1 | GAGAGGCAUGUUA | 10 | DY547mm0m0000m0m0mmm | sssssssssssso | |
| 25568 | SOD1 | AGGZGGAAAZGAA | 11 | DY547mm0m00000m0mm | ssssssssssso | Z = octyl, x = 5 methyl C, Y = 5 methyl U |
| 25569 | SOD1 | AGGYGGAAAZGAA | 12 | DY547mm0m00000m0mm | ssssssssssso | Z = octyl, x = 5 methyl C, Y = 5 methyl U |
| 25570 | SOD1 | AGGZGGAAAYGAA | 13 | DY547mm0m00000m0mm | ssssssssssso | Z = octyl, x = 5 methyl C, Y = 5 methyl U |
| 25571 | SOD1 | AGGYGGAAAYGAA | 14 | DY547mm0m00000m0mm | ssssssssssso | Z = octyl, x = 5 methyl C, Y = 5 methyl U |
| 25572 | SOD1 | AGGUGGAAAUGAA | 15 | DY547mm0m00000m0mm | ssssssssssso | Z = octyl, x = 5 methyl C, Y = 5 methyl U |
| 25573 | SOD1 | AGGUGGAAAUGAA | 16 | DY547mm0m00000m0mm | ssssssssssso | Z = octyl, x = 5 methyl C, Y = 5 methyl U |
| 25574 | SOD1 | AGGUGGAAAUGAA | 17 | DY547mm0m00000m0mm | ssssssssssso | Z = octyl, x = 5 methyl C, Y = 5 methyl U |
| 25575 | SOD1 | AGGUGGAAAUGAA | 18 | DY547mm0m00000m0mm | ssssssssssso | Z = octyl, x = 5 methyl C, Y = 5 methyl U |
| 25576 | SOD1 | AGGUGGAAAUGAA | 19 | DY547mm0m00000m0mm | ssssssssssso | x = 5 methyl C, Y = 5 methyl U |
| 25578 | SOD1 | AGGYGGAAAZGAA | 20 | DY547mm0m00000m0mm | ssssssssssso | Z = thiophene, x = 5 methyl C, Y = 5 methyl U |
| 25579 | SOD1 | AGGZGGAAAYGAA | 21 | DY547mm0m00000m0mm | ssssssssssso | Z = thiophene, x = 5 methyl C, |

TABLE 1-continued

Exemplary sense oligonucleotides

| Oligo Number | Gene symbol | Sense sequence | SEQ ID NO: | Sense Chemistry | Sense Backbone | Notes |
|---|---|---|---|---|---|---|
| | | | | | | Y = 5 methyl U |
| 25580 | SOD1 | AGGYGGAAAYGAA | 22 | DY547mm0m00000m0mm | sssssssssssso | Z = thiophene, x = 5 methyl C, Y = 5 methyl U |
| 25584 | SOD1 | AGGUGGAAAUGAA | 23 | DY547mm0m00000m0mm | sssssssssssso | Z = thiophene, x = 5 methyl C, Y = 5 methyl U |
| 25585 | SOD1 | AGGUGGAAAUGAA | 24 | DY547mm0m00000m0mm | sssssssssssso | Z = thiophene, x = 5 methyl C, Y = 5 methyl U |
| 25586 | SOD1 | AGGZGGAAAZGAA | 25 | DY547mm0m0d00000d0mm | sssssssssssso | Z = isobutyl, x = 5 methyl C, Y = 5 methyl U |
| 25587 | SOD1 | AGGYGGAAAZGAA | 26 | DY547mm0m00000d0mm | sssssssssssso | Z = isobutyl, x = 5 methyl C, Y = 5 methyl U |
| 25588 | SOD1 | AGGZGGAAAYGAA | 27 | DY547mm0m0d00000m0mm | sssssssssssso | Z = isobutyl, x = 5 methyl C, Y = 5 methyl U |
| 25589 | SOD1 | AGGUGGAAAUGAA | 28 | DY547mm0m00000m0mm | sssssssssssso | Z = isobutyl, x = 5 methyl C, Y = 5 methyl U |
| 25590 | SOD1 | AGGUGGAAAUGAA | 29 | DY547mm0m00000m0mm | sssssssssssso | Z = isobutyl, x = 5 methyl C, Y = 5 methyl U |
| 24560 | SOD1 | AGGUGGAAAUGAA | 30 | DY547mm0m00000m0mm | sssssssssssso | |
| 25634 no Fl label | SOD1 | GAGAGGCAUGUUA | 31 | mm0m00m0m0mmm | ooooooooosso | |
| 25635 no Fl label | SOD1 | GAGAGGCAUGUUA | 32 | mm0m00m0m0mmm | ooooooooosso | |
| 25636 no Fl label | SOD1 | GAGAGGCAUGUUA | 33 | mm0m00m0m0mmm | ooooooooosso | |
| 25637 no Fl label | SOD1 | GAGAGGCAUGUUA | 34 | mm0m00m0m0mmm | sssssssssssso | |
| 25638 no Fl label | SOD1 | GAGAGGCAUGUUA | 35 | mm0m00m0m0mmm | sssssssssssso | |
| 25643 no Fl label | SOD1 | GAGAGGCAUGUUA | 36 | mm0m00m0m0mmm | ooooooooosso | |
| 25644 no Fl label | SOD1 | GAGAGGCAUGUUA | 37 | mm0m00m0m0mmm | sssssssssssso | |
| 25645 no Fl label | SOD1 | GAGAGGCAUGUUA | 38 | mm0m00m0m0mmm | ooooooooosso | |

TABLE 1-continued

Exemplary sense oligonucleotides

| Oligo Number | Gene symbol | Sense sequence | SEQ ID NO: | Sense Chemistry | Sense Backbone | Notes |
|---|---|---|---|---|---|---|
| 25652 no Fl label | SOD1 | GAGAGGCAUGUUA | 39 | mm0000m0m0mmm | sssssssssssso | |
| 25568 no Fl label | SOD1 | AGGZGGAAAZGAA | 40 | mm0m00000m0mm | sssssssssssso | Z = octyl, x = 5 methyl C, Y = 5 methyl U |
| 25569 no Fl label | SOD1 | AGGYGGAAAZGAA | 41 | mm0m00000m0mm | sssssssssssso | Z = octyl, x = 5 methyl C, Y = 5 methyl U |
| 25570 no Fl label | SOD1 | AGGZGGAAAYGAA | 42 | mm0m00000m0mm | sssssssssssso | Z = octyl, x = 5 methyl C, Y = 5 methyl U |
| 25571 no Fl label | SOD1 | AGGYGGAAAYGAA | 43 | mm0m00000m0mm | sssssssssssso | Z = octyl, x = 5 methyl C, Y = 5 methyl U |
| 25572 no Fl label | SOD1 | AGGUGGAAAUGAA | 44 | mm0m00000m0mm | sssssssssssso | Z = octyl, x = 5 methyl C, Y = 5 methyl U |
| 25573 no Fl label | SOD1 | AGGUGGAAAUGAA | 45 | mm0m00000m0mm | sssssssssssso | Z = octyl, x = 5 methyl C, Y = 5 methyl U |
| 25574 no Fl label | SOD1 | AGGUGGAAAUGAA | 46 | mm0m00000m0mm | sssssssssssso | Z = octyl, x = 5 methyl C, Y = 5 methyl U |
| 25575 no Fl label | SOD1 | AGGUGGAAAUGAA | 47 | mm0m00000m0mm | sssssssssssso | Z = octyl, x = 5 methyl C, Y = 5 methyl U |
| 25576 no Fl label | SOD1 | AGGUGGAAAUGAA | 48 | mm0m00000m0mm | sssssssssssso | x = 5 methyl C, Y = 5 methyl U |
| 25578 no Fl label | SOD1 | AGGYGGAAAZGAA | 49 | mm0m00000m0mm | sssssssssssso | Z = thiophene, x = 5 methyl C, Y = 5 methyl U |
| 25579 no Fl label | SOD1 | AGGZGGAAAYGAA | 50 | mm0m00000m0mm | sssssssssssso | Z = thiophene, x = 5 methyl C, Y = 5 methyl U |
| 25580 no Fl label | SOD1 | AGGYGGAAAYGAA | 51 | mm0m00000m0mm | sssssssssssso | Z = thiophene, x = 5 methyl C, Y = 5 methyl U |
| 25584 no Fl label | SOD1 | AGGUGGAAAUGAA | 52 | mm0m00000m0mm | sssssssssssso | Z = thiophene, x = 5 methyl C, Y = 5 methyl U |
| 25585 no Fl label | SOD1 | AGGUGGAAAUGAA | 53 | mm0m00000m0mm | sssssssssssso | Z = thiophene, x = 5 methyl C, |

TABLE 1-continued

Exemplary sense oligonucleotides

| Oligo Number | Gene symbol | Sense sequence | SEQ ID NO: | Sense Chemistry | Sense Backbone | Notes |
|---|---|---|---|---|---|---|
| | | | | | | Y = 5 methyl U |
| 25586 no Fl label | SOD1 | AGGZGGAAAZGAA | 54 | mm0d00000d0mm | sssssssssso | Z = isobutyl, x = 5 methyl C, Y = 5 methyl U |
| 25587 no Fl label | SOD1 | AGGYGGAAAZGAA | 55 | mm0m00000d0mm | sssssssssso | Z = isobutyl, x = 5 methyl C, Y = 5 methyl U |
| 25588 no Fl label | SOD1 | AGGZGGAAAYGAA | 56 | mm0d00000m0mm | sssssssssso | Z = isobutyl, x = 5 methyl C, Y = 5 methyl U |
| 25589 no Fl label | SOD1 | AGGUGGAAAUGAA | 57 | mm0m00000m0mm | sssssssssso | Z = isobutyl, x = 5 methyl C, Y = 5 methyl U |
| 25590 no Fl label | SOD1 | AGGUGGAAAUGAA | 58 | mm0m00000m0mm | sssssssssso | Z = isobutyl, x = 5 methyl C, Y = 5 methyl U |
| 24560 no Fl label | SOD1 | AGGUGGAAAUGAA | 59 | mm0m00000m0mm | sssssssssso | |

TABLE 2

Exemplary antisense oligonucleotides

| Oligo Number | Antisense sequence | SEQ ID NO: | AntiSense Chemistry | AntiSense Backbone | Notes |
|---|---|---|---|---|---|
| 25634 | UAACAUGCCUCUCUUCAUCCU | 60 | Pm00f0f0fffff0fff0fff0 | sssssssssssssssssso | |
| 25635 | UAACAUGCCUCUCUUCAUCCU | 61 | Pm00f0f0ffffffffg0fff0 | ooooooooooosssssso | |
| 25636 | UAACAUGCCUCUCUUCAUC | 62 | Pm00f0f0ffffffffff0f0 | ooooooooooossssso | |
| 25637 | UAACAUGCCUCUCUUCAUCCU | 63 | Pm00f0f0ffffffffff0fff0 | ooooooooooosssssso | |
| 25600 | UAACAUGCCUCUCUUCAUCCU | 64 | Pm00f0f0fffff0fff0fff0 | sssssssssssssssssso | |
| 25638 | UAACAUGCCUCUCUUCAUCCU | 65 | Pm00f0f0ffffffffff00 | ooooooooooossssso | |
| 25643 | UAACAUGCCUCUCUUCAUC | 66 | Pm00f0f0ffffffffff0f0 | sssssssssssssssso | |
| 25644 | UAACAUGCCUCUCUUCAUC | 67 | Pm00f0f0ffffffffff0f0 | sssssssssssssssso | |
| 25645 | UAACAUGCCUCUCUUCAUCCU | 68 | Pm00f0f0ffffffffff0ff0 | sssssssssssssssssso | |
| 25652 | UAACAUGCCUCUCUUCAUCCU | 69 | Pm00f0f0fffff0fff0fff0 | sssssssssssssssssso | |
| 25568 | UUCAUUUCCACCUUUGCCCAA | 70 | Pmff0fffff0fmmmm0mmf00 | sssssssssssssssssso | Z = octyl, x = 5 methyl C, Y = 5 methyl U |

TABLE 2-continued

Exemplary antisense oligonucleotides

| Oligo Number | Antisense sequence | SEQ ID NO: | AntiSense Chemistry | AntiSense Backbone | Notes |
|---|---|---|---|---|---|
| 25569 | UUCAUUCCACCU UUGCCCAA | 71 | Pmff0fffff0fmmmm0m mf00 | sssssssssssssssssss o | Z = octyl, x = 5 methyl C, Y = 5 methyl U |
| 25570 | UUCAUUCCACCU UUGCCCAA | 72 | Pmff0fffff0fmmmm0m mf00 | sssssssssssssssssss o | Z = octyl, x = 5 methyl C, Y = 5 methyl U |
| 25571 | UUCAUUCCACCU UUGCCCAA | 73 | Pmff0fffff0fmmmm0m mf00 | sssssssssssssssssss o | Z = octyl, x = 5 methyl C, Y = 5 methyl U |
| 25572 | YZXAYYZXXAXXZYY GXXXAA | 74 | Pmff0fffff0fmmmm0m mf00 | sssssssssssssssssss o | Z = octyl, x = 5 methyl C, Y = 5 methyl U |
| 25573 | YYXAYYZXXAXXZYY GXXXAA | 75 | Pmff0fffff0fmmmm0m mf00 | sssssssssssssssssss o | Z = octyl, x = 5 methyl C, Y = 5 methyl U |
| 25574 | YZXAYYYXXAXXZYY GXXXAA | 76 | Pmff0fffff0fmmmm0m mf00 | sssssssssssssssssss o | Z = octyl, x = 5 methyl C, Y = 5 methyl U |
| 25575 | YZXAYYZXXAXXYYY GXXXAA | 77 | Pmff0fffff0fmmmm0m mf00 | sssssssssssssssssss o | Z = octyl, x = 5 methyl C, Y = 5 methyl U |
| 25576 | YYXAYYYXXAXXYYY GXXXAA | 78 | Pmff0fffff0fmmmm0m mf00 | sssssssssssssssssss o | x = 5 methyl C, Y = 5 methyl U |
| 25578 | UUCAUUCCACCU UUGCCCAA | 79 | Pmff0fffff0fmmmm0m mf00 | sssssssssssssssssss o | Z = thiophene, x = 5 methyl C, Y = 5 methyl U |
| 25579 | UUCAUUCCACCU UUGCCCAA | 80 | Pmff0fffff0fmmmm0m mf00 | sssssssssssssssssss a | Z = thiophene, x = 5 methyl C, Y = 5 methyl U |
| 25580 | UUCAUUCCACCU UUGCCCAA | 81 | Pmff0fffff0fmmmm0m mf00 | sssssssssssssssssss o | Z = thiophene, x = 5 methyl C, Y = 5 methyl U |
| 25584 | YZXAYYZXXAXXYYY GXXXAA | 82 | Pmff0fffff0fmmmm0m mf00 | sssssssssssssssssss o | Z = thiophene, x = 5 methyl C, Y = 5 methyl U |
| 25585 | YYXAYYYXXAXXYYY GXXXAA | 83 | Pmff0fffff0fmmmm0m mf00 | sssssssssssssssssss a | Z = thiophene, x = 5 methyl C, Y = 5 methyl U |
| 25586 | UUCAUUCCACCU UUGCCCAA | 84 | Pmff0fffff0fmmmm0m mf00 | sssssssssssssssssss o | Z = isobutyl, x = 5 methyl C, Y = 5 methyl U |
| 25587 | UUCAUUCCACCU UUGCCCAA | 85 | Pmff0fffff0fmmmm0m mf00 | sssssssssssssssssss o | Z = isobutyl, x = 5 methyl C, Y = 5 methyl U |
| 25588 | UUCAUUCCACCU UUGCCCAA | 86 | Pmff0fffff0fmmmm0m mf00 | sssssssssssssssssss o | Z = isobutyl, x = 5 methyl C, Y = 5 methyl U |
| 25589 | YZXAYYZXXAXXZYY GXXXAA | 87 | Pmdf0ffdff0fmdmm0m mf00 | sssssssssssssssssss o | Z = isobutyl, x = 5 methyl C, Y = 5 methyl U |
| 25590 | YYXAYYZXXAXXZYY GXXXAA | 88 | Pmff0ffdff0fmdmm0m mf00 | sssssssssssssssssss o | Z = isobutyl, x = 5 methyl C, Y = 5 methyl U |
| 24560 | UUCAUUCCACCU UUGCCCAA | 89 | Pmff0fffff0fmmmm0m mf00 | sssssssssssssssssss o | |

TABLE 2-continued

Exemplary antisense oligonucleotides

| Oligo Number | Antisense sequence | SEQ ID NO: | AntiSense Chemistry | AntiSense Backbone | Notes |
|---|---|---|---|---|---|
| 25634 no Fl label | UAACAUGCCUCUC UUCAUCCU | 90 | Pm00f0f0fffff0fff0fff0 | sssssssssssssssssssss o | |
| 25635 no Fl label | UAACAUGCCUCUC UUCAUCCU | 91 | Pm00f0f0ffffffffff0fff0 | ooooooooooooosss ssso | |
| 25636 no Fl label | UAACAUGCCUCUC UUCAUC | 92 | Pm00f0f0ffffffffff0f0 | ooooooooooooosss sso | |
| 25637 no Fl label | UAACAUGCCUCUC UUCAUCCU | 93 | Pm00f0f0ffffffffff0fff0 | ooooooooooooosss ssso | |
| 25638 no Fl label | UAACAUGCCUCUC UUCAUCCU | 94 | Pm00f0f0ffffffffff00 | ooooooooooooosss sso | |
| 25643 no Fl label | UAACAUGCCUCUC UUCAUC | 95 | Pm00f0f0ffffffffff0f0 | ssssssssssssssssso | |
| 25644 no Fl label | UAACAUGCCUCUC UUCAUC | 96 | Pm00f0f0ffffffffff0f0 | ssssssssssssssssso | |
| 25645 no Fl label | UAACAUGCCUCUC UUCAUCCU | 97 | Pm00f0f0ffffffffff0fff0 | sssssssssssssssss o | |
| 25652 no Fl label | UAACAUGCCUCUC UUCAUCCU | 98 | Pm00f0f0fffff0fff0fff0 | sssssssssssssssss o | |
| 25568 no Fl label | UUCAUUCCACCU UUGCCAA | 99 | Pmff0fffff0fmmmm0m mf00 | sssssssssssssssss o | Z = octyl, x = 5 methyl C, Y = 5 methyl U |
| 25569 no Fl label | UUCAUUCCACCU UUGCCAA | 100 | Pmff0fffff0fmmmm0m mf00 | sssssssssssssssss o | Z = octyl, x = 5 methyl C, Y = 5 methyl U |
| 25570 no Fl label | UUCAUUCCACCU UUGCCAA | 101 | Pmff0fffff0fmmmm0m mf00 | sssssssssssssssss o | Z = octyl, x = 5 methyl C, Y = 5 methyl U |
| 25571 no Fl label | UUCAUUCCACCU UUGCCAA | 102 | Pmff0fffff0fmmmm0m mf00 | sssssssssssssssss o | Z = octyl, x = 5 methyl C, Y = 5 methyl U |
| 25572 no Fl label | YZXAYYZXXAXXZYY GXXXAA | 103 | Pmff0fffff0fmmmm0m mf00 | sssssssssssssssss o | Z = octyl, x = 5 methyl C, Y = 5 methyl U |
| 25573 no Fl label | YYXAYYZXXAXXZYY GXXXAA | 104 | Pmff0fffff0fmmmm0m mf00 | sssssssssssssssss o | Z = octyl, x = 5 methyl C, Y = 5 methyl U |
| 25574 no Fl label | YZXAYYYXXAXXZYY GXXXAA | 105 | Pmff0fffff0fmmmm0m mf00 | sssssssssssssssss o | Z = octyl, x = 5 methyl C, Y = 5 methyl U |
| 25575 no Fl label | YZXAYYZXXAXXYYY GXXXAA | 106 | Pmff0fffff0fmmmm0m mf00 | sssssssssssssssss o | Z = octyl, x = 5 methyl C, Y = 5 methyl U |
| 25576 no Fl label | YYXAYYYXXAXXYYY GXXXAA | 107 | Pmff0fffff0fmmmm0m mf00 | sssssssssssssssss o | x = 5 methyl C, Y = 5 methyl U |
| 25578 no Fl label | UUCAUUCCACCU UUGCCAA | 108 | Pmffafffff0fmmmm0m mf00 | sssssssssssssssss o | Z = thiophene, x = 5 methyl C, Y = 5 methyl U |
| 25579 no Fl label | UUCAUUCCACCU UUGCCAA | 109 | Pmff0fffff0fmmmm0m mf00 | sssssssssssssssss o | Z = thiophene, x = 5 methyl C, Y = 5 methyl U |
| 25580 no Fl label | UUCAUUCCACCU UUGCCAA | 110 | Pmff0fffff0fmmmm0m mf00 | sssssssssssssssss o | Z = thiophene, x = 5 methyl C, Y = 5 methyl U |

TABLE 2-continued

Exemplary antisense oligonucleotides

| Oligo Number | Antisense sequence | SEQ ID NO: | AntiSense Chemistry | AntiSense Backbone | Notes |
|---|---|---|---|---|---|
| 25584 no Fl label | YZXAYYZXXAXXYYY GXXXAA | 111 | Pmff0fffff0fmmmm0m mf00 | sssssssssssssssssss o | Z = thiophene, x = 5 methyl C, Y = 5 methyl U |
| 25585 no Fl label | YYXAYYYXXAXXYYY GXXXAA | 112 | Pmff0fffff0fmmmm0rn mf00 | sssssssssssssssssss o | Z = thiophene, x = 5 methyl C, Y = 5 methyl U |
| 25586 no Fl label | UUCAUUUCCACCU UUGCCCAA | 113 | Pmff0fffff0fmmmm0m m100 | sssssssssssssssssss o | Z = isobutyl, x = 5 methyl C, Y = 5 methyl U |
| 25587 no Fl label | UUCAUUUCCACCU UUGCCCAA | 114 | Pmff0fffff0fmmmm0m mf00 | sssssssssssssssssss o | Z = isobutyl, x = 5 methyl C, Y = 5 methyl U |
| 25588 no Fl label | UUCAUUUCCACCU UUGCCCAA | 115 | Pmff0fffff0fmmmm0rn mf00 | sssssssssssssssssss o | Z = isobutyl, x = 5 methyl C, Y = 5 methyl U |
| 25589 no Fl label | YZXAYYZXXAXXZYY GXXXAA | 116 | Pmdf0ffdff0fmdmm0m m100 | sssssssssssssssssss o | Z = isobutyl, x = 5 methyl C, Y = 5 methyl U |
| 25590 no Fl label | YYXAYYZXXAXXZYY GXXXAA | 117 | Pmff0ffdff0fmdmm0m mf00 | sssssssssssssssssss o | Z = isobutyl, x = 5 methyl C, Y = 5 methyl U |
| 24560 no Fl label | UUCAUUUCCACCU UUGCCCAA | 118 | Pmff0fffff0fmmmm0m mf00 | sssssssssssssssssss o | |

| Key for Tables 1 and 2: | |
|---|---|
| f = | 2'fluoro |
| m = | 2'Ome |
| P = | 5' phosphate |
| s/* = | phosphorothioate linkage |
| o/. = | phosphodiester linkage |
| DY547 = | DY547 dye |
| d = | deoxyribose |

The human SOD1 sequence is represented by GenBank accession number NM_000454.4 (SEQ ID NO: 119) listed below. Multiple mutations of the SOD1 sequence have been identified (Rosen et al (1993) Nature; Deng et al (1993) Science; De Belleroche et al. (1995) J Med Genet.; Orrel et al (1997) J Neurol.; Cudkowicz (1997) Ann. Neurol.; and Anderson et al (1995) Nature Genet.) and can also be targeted utilizing the sequences outlined in this application:

(SEQ ID NO: 119)
GTTTGGGGCCAGAGTGGGCGAGGCGCGGAGGTCTGGCCTATAAAGTAGTC

GCGGAGACGGGGTGCTGGTTTGCGTCGTAGTCTCCTGCAGCGTCTGGGGT

TTCCGTTGCAGTCCTCGGAACCAGGACCTCGGCGTGGCCTAGCGAGTTAT

GGCGACGAAGGCCGTGTGCGTGCTGAAGGGCGACGGCCCAGTGCAGGGCA

TCATCAATTTCGAGCAGAAGGAAAGTAATGGACCAGTGAAGGTGTGGGGA

AGCATTAAAGGACTGACTGAAGGCCTGCATGGATTCCATGTTCATGAGTT

TGGAGATAATACAGCAGGCTGTACCAGTGCAGGTCCTCACTTTAATCCTC

TATCCAGAAAACACGGTGGGCCAAAGGATGAAGAGAGGCATGTTGGAGAC

TTGGGCAATGTGACTGCTGACAAAGATGGTGTGGCCGATGTGTCTATTGA

AGATTCTGTGATCTCACTCTCAGGAGACCATTGCATCATTGGCCGCACAC

TGGTGGTCCATGAAAAAGCAGATGACTTGGGCAAAGGTGGAAATGAAGAA

AGTACAAAGACAGGAAACGCTGGAAGTCGTTTGGCTTGTGGTGTAATTGG

GATCGCCCAATAAACATTCCCTTGGATGTAGTCTGAGGCCCCTTAACTCA

TCTGTTATCCTGCTAGCTGTAGAAATGTATCCTGATAAACATTAAACACT

GTAATCTTAAAAGTGTAATTGTGTGACTTTTTCAGAGTTGCTTTAAAGTA

CCTGTAGTGAGAAACTGATTTATGATCACTTGGAAGATTTGTATAGTTTT

ATAAAACTCAGTTAAAATGTCTGTTTCAATGACCTGTATTTTGCCAGACT

TAAATCACAGATGGGTATTAAACTTGTCAGAATTTCTTTGTCATTCAAGC

CTGTGAATAAAAACCCTGTATGGCACTTATTATGAGGCTATTAAAAGAAT

CCAAATTCAAACTAAAAAAAAAAAAAAAAAA

It should be appreciated that while some of the sequences presented in Tables 1-2 are depicted as being attached to the dye DY547, all of the sequences presented in Tables 1-2 are also disclosed herein in the absence of DY547.

Example 2: Sd-rxRNA Variant Silencing of SOD1 in CNS

FIG. 3 demonstrates SOD1 silencing in vivo (mouse, lumbar spinal cord (LSC)) following a 14-day intrathecal administration of a SOD1 targeting ps-rxRNA. A statistically significant 24% reduction of SOD1 mRNA levels was observed in mice treated with the SOD1-targeting sd-rxRNA variant compared to the non-targeting control (FIG. 3).

Methods: SOD1-targeting sd-rxRNA variant or non-targeting control (NTC) was administered by intrathecal infusion, using an osmotic pump (filled with 100 µL of a 10 mg/mL solution of compound) for 14 days. Terminal biopsy samples of the spinal cord were harvested on Day 14. RNA was isolated and subjected to gene expression analysis by qPCR. Data were normalized to the level of the cyclophilin B (PPIB) housekeeping gene and graphed relative to the non-targeting control set at 1.0. Error bars represent standard deviation between the individual biopsy samples. P value for SOD1-targeting sd-rxRNA variant-treated group vs non-targeting control group was * p<0.01. Nine out of nine mice treated with the SOD1-targeting sd-rxRNA variant exhibited hind limb lameness, mimicking ALS symptoms. In contrast only 1 out of 10 mice in the non-targeting control group exhibited hind limb lameness.

Example 3: Sporadic Non-Genetic Model of ALS

FIG. 3 demonstrates that reduction of SOD1 mRNA levels in the spinal cord of normal mice results in adverse events that mimic ALS disease progression. Therefore, compounds that are able to reduce the activity or levels of SOD1 protein and/or mRNA, such as the SOD1-targeting sd-rxRNA variant, could be used to generate a sporadic, non-genetic model of ALS. Reduction of SOD1 enzymatic activity, protein levels or mRNA levels by compounds (such as small molecules, antibodies or nucleic acids), results in increased levels of reactive oxygen species (ROS) in the CNS. Increased levels of ROS leads to oxidative stress and ultimately, neurological disorders such as ALS.

Figure 5:
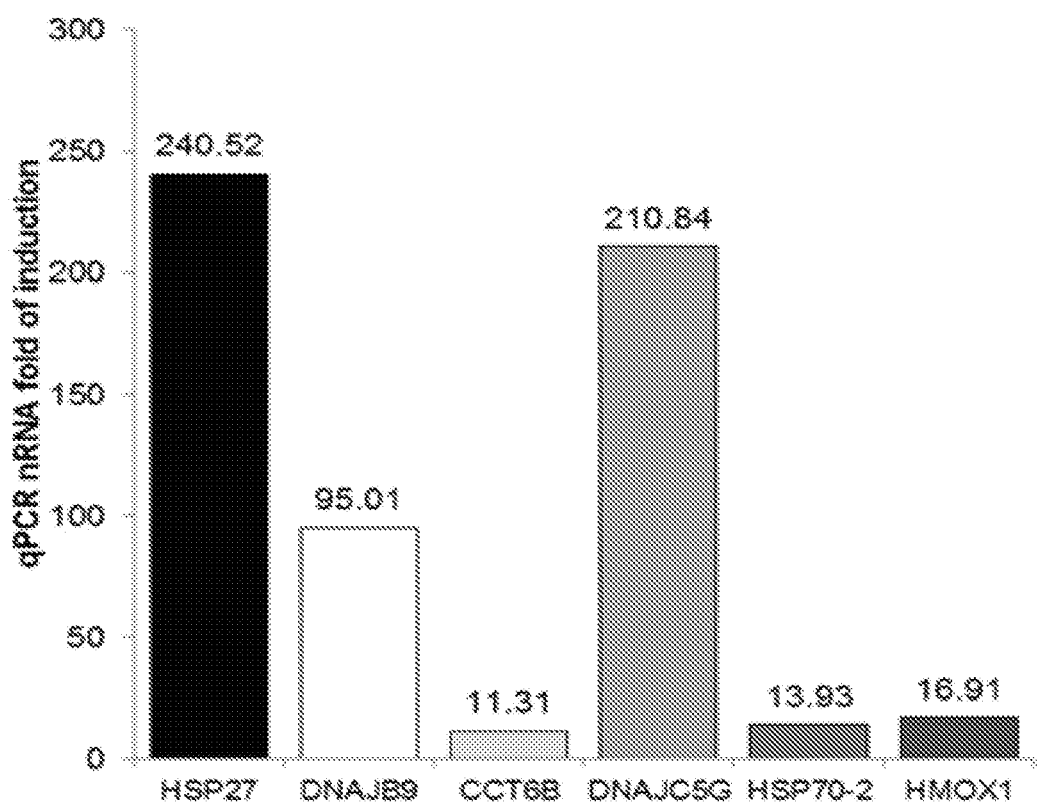
FIG. 5. Effect of SYN1 on cytoplasmic chaperones expression. The expression of the genes listed in the graph was assessed using qPCR in SH-5YSY after 24 h treatment with SYN1. Both HSP27 and HSP70-2 were significantly up-regulated by SYN1. Also, HSP-dependent mRNAs were significantly increased by the treatment.

Example 4: Synergistic Approach to Treating ALS and TBI by Reducing SOD1 Levels while Increasing SOD2 Expression As described above, reducing SOD1 activity or mRNA levels results in increased ROS in the CNS and ultimately adverse neurological outcomes. Regenerative small molecules, including but not limited to SYN1 and SYN2 act through the NF-κB p65 pathway to increase superoxide dismutase 2 (SOD2) expression (FIGS. 4A-4F) and chaperone (FIG. 5) proteins. In neurodegenerative diseases, including ALS, SOD1 activity is compromised resulting in increased levels of ROS and formation of toxic intracellular protein aggregates. In cells, decreased or lack of SOD1 activity is compensated by activation of mitochondrial SOD2. In ALS, although SOD2 function is not compromised (Kiningham, K. K., et al., *All-trans-retinoic acid induces manganese superoxide dismutase in human neuroblastoma through NF-kappaB*. Free Radic Biol Med, 2008; 44(8): 1610-6; Visner, G. A., et al., *Regulation of manganese superoxide dismutase by lipopolysaccharide, interleukin-1, and tumor necrosis factor. Role in the acute inflammation response*. J Biol Chem, 1990; 265(5):2856-64; Maehara, K., T. Hasegawa, and K. I. Isobe, *A NF-kappaB p65 subunit is indispensable for activating manganese superoxide: dismutase gene transcription mediated by tumor necrosis factor-alpha*. J Cell Biochem, 2000; 77(3):474-86), misfolded SOD1 is still perceived as a functional enzyme and the SOD2 compensatory activity is not triggered, leading to oxidative damage and a cascade of effects compromising cell viability and neuronal network viability (Chung, Y. H., et al., *Immunohistochemical study on the aggregation of ubiquitin in the central nervous system of the transgenic mice expressing a human Cu/Zn SOD mutation*. Neurol Res, 2003; 25(4):395-400). SYN1 and SYN2, two small regenerative small molecules, promote nuclear translocation of NF-κB p65 exclusively in neurons triggering expression of SOD2 (Lebovitz, R. M., et al., *Neurodegeneration, myocardial injury and perinatal death in mitochondrial superoxide dismutase-deficient mice*. Proc Natl Acad Sci USA, 1996; 93(18):9782-7). Increased SOD2 activity promotes mechanisms of mitochondrial and neuronal viability (Flanagan, S. W., et al., *Overexpression of manganese superoxide dismutase attenuates neuronal death in human cells expressing mutant (G37R) Cu/Zn-superoxide dismutase*. J Neurochem, 2002; 81(1):170-7) allowing neurons to overcome the oxidative damage resulting from reduced SOD1 activity (FIG. 3) and modify the course of disease in symptomatic ALS transgenic mice (FIGS. 6A-6D). Utilizing a synergistic approach to treat ALS by (1) reducing SOD1 levels by an RNAi mechanism and (2) enhancing SOD2 expression with small molecules, allows for:

a) reduction of the toxic effect of misfolded SOD1 by reduction of SOD1 levels by SOD1-targeting sd-rxRNA and induction of proper protein folding by the small molecules;

b) SOD2 expression compensating for lack of SOD1 oxidative function resulting from reduced transcription of normal SOD1 by the sd-rxRNA and/or overcome the toxic effect of residual misfolded SOD1;

c) maintained mitochondrial function and oxidative balance; and d) increased neurotrophin expression/release to repair and restore interneuronal network.

EQUIVALENTS

Those skilled in the art will recognize, or be able to ascertain using no more than routine experimentation, many equivalents to the specific embodiments of the invention described herein. Such equivalents are intended to be encompassed by the following claims.

All references, including patent documents, disclosed herein are incorporated by reference in their entirety. This application incorporates by reference the entire contents, including all the drawings and all parts of the specification (including sequence listing or amino acid/polynucleotide sequences) of PCT Publication No. WO2010/033247 (Application No. PCT/US2009/005247), filed on Sep. 22, 2009, and entitled "REDUCED SIZE SELF-DELIVERING RNAI COMPOUNDS," U.S. Pat. No. 8,796,443, issued on Aug. 5, 2014, published as US 2012/0040459 on Feb. 16, 2012, entitled "REDUCED SIZE SELF-DELIVERING RNAI COMPOUNDS," U.S. Pat. No. 9,175,289, issued on Nov. 3, 2015, entitled "REDUCED SIZE SELF-DELIVERING RNAI COMPOUNDS," PCT Publication No. WO2009/102427 (Application No. PCT/US2009/000852), filed on Feb. 11, 2009, and entitled, "MODIFIED RNAI POLYNUCLEOTIDES AND USES THEREOF," and US Patent Publication No. 2011/0039914, published on Feb. 17, 2011 and entitled "MODIFIED RNAI POLYNUCLEOTIDES AND USES THEREOF," PCT Publication No. WO 2011/119852, filed on Mar. 24, 2011 and entitled "REDUCED SIZE SELF-DELIVERING RNAI COMPOUNDS," and U.S. Pat. No. 9,080,171, issued on Jul. 14, 2015, and entitled "REDUCED SIZE SELF-DELIVERING RNAI COMPOUNDS."

The invention claimed is:

1. A method for treating a neurodegenerative disorder, comprising administering to a subject in need thereof:
a therapeutically effective amount of a nucleic acid molecule that is directed against a gene encoding copper/zinc superoxide dismutase 1 (SOD1), wherein the nucleic acid molecule is capable of decreasing SOD1 expression; and
a therapeutically effective amount of at least one small molecule that activates NF-κB p65.

2. The method of claim 1, wherein the small molecule that activates NF-κB p65 increases expression of manganese superoxide dismutase (MnSOD/Sod2) and/or expression of a protein selected from the group consisting of Heat Shock Protein 27 (Hsp27), Hsp70-2, DNAJ Heat Shock Protein Family (Hsp40) Member B9 (DNAJB9), T-complex protein 1 subunit zeta-2 (CCT6B), DNAJ Heat Shock Protein Family (Hsp40) Member 5 Gamma (DNAJC5G), and Heme Oxygenase 1 (HMOX1).

3. The method of claim 1, wherein the neurodegenerative disorder is Alzheimer Disease, Amyotrophic Lateral Sclerosis (ALS), Argyrophilic Grain Disease, Basophilic Inclusion Body Disease, Sporadic Cerebral Amyloid Angiopathy, Corticobasal Degeneration, Creutzfeldt-Jakob Disease, a degenerative proteinopathy associated with Traumatic Brain Injury (TBI), dementia, dementia with Lewy Bodies, Dentatorubral-Pallidoluysian Atrophy, Sporadic Fatal Insomnia, Fatal Familial Insomnia, Fragile X Mental Retardation, Frontotemporal Dementia (FD), Frontotemporal Lobar Degeneration, Atypical Frontotemporal Lobar Degeneration with Ubiquitinated Inclusions, Frontotemporal Lobar Degeneration with Inclusions Immunoreactive only for the Components of the Ubiquitine Proteasome System, Frontotemporal Lobar Degeneration with No Inclusion Specified, Frontotemporal Dementia and Parkinsonism Linked to Chromosome 17 Caused by Mutations in the MAPT (Tau) Gene, Fragile X Associated Tremor and Ataxia Syndrome, Globular Glial Tauopathies, Gerstmann-Sträussler-Scheinker Disease, Huntington Disease (HD), Neuronal/Glial Intranuclear Inclusion Body Diseases, a movement disorder, Motor Neuron Disease, Multiple System Atrophy, Neurodegeneration with Brain Iron Accumulation, Neurodegeneration Associated with Traumatic Brain Injury (TBI); Neurofilament Intermediate Filament Inclusion Disease, Parkinson Disease, Pick Disease, Prion Protein, Progressive Supranuclear Palsy, Spinocerebellar Ataxia (SCA), Spinal and Bulbar Muscular Atrophy, Trinucleotide Repeat Expansion Disorder, or Variably Protease-Sensitive Prionopathy.

4. The method of claim 1, wherein the neurodegenerative disorder is ALS.

5. The method of claim 1, wherein the nucleic acid molecule is a chemically modified oligonucleotide.

6. The method of claim 1, wherein the nucleic acid molecule is a double stranded nucleic acid molecule.

7. The method of claim 1, wherein the nucleic acid molecule is an isolated double stranded nucleic acid molecule that includes a double stranded region and a single stranded region, wherein the region of the molecule that is double stranded is from 8-15 nucleotides long, wherein the guide strand contains a single stranded region that is 2-14 nucleotides long, wherein the guide strand contains 2, 3, 4, 5, 6, 7, 8, 9, 10, 11, 12, 13, 14, 15, 16, 17, 18, 19, 20, 21 or 22 phosphorothioate modifications, and wherein the passenger strand is 8 to 15 nucleotides long, wherein the passenger strand contains 3, 4, 5, 6, 7, 8, 9, 10, 11, 12, 13 or 14 phosphorothioate modifications and wherein at least 40% of the nucleotides of the isolated double stranded nucleic acid molecule are modified.

8. The method of claim 7, wherein at least one of the nucleotides of the isolated double stranded nucleic acid molecule that is modified comprises a 2'O-methyl or a 2'-fluoro modification.

9. The method of claim 7, wherein a plurality of the U's and/or C's of the isolated double stranded nucleic acid molecule include a hydrophobic modification, selected from the group consisting of methyl, isobutyl, octyl, imidazole or thiophene and wherein the modifications are located on positions 4 or 5 of U's and/or C's.

10. The method of claim 7, wherein the isolated double stranded nucleic acid molecule comprises a completely phosphorothioated backbone.

11. The method of claim 7, wherein the isolated double stranded nucleic acid molecule further comprises a hydrophobic conjugate that is attached to the isolated double stranded nucleic acid molecule.

12. The method of claim 7, wherein the isolated double stranded nucleic acid molecule is formulated for delivery to the central nervous system.

13. The method of claim 1, wherein the at least one small molecule that activates NF-κB p65 and increases SOD2 expression is selected from the group consisting of: SYN1, SYN2, SYN-NCE and SYN-GL.

14. The method of claim 13 wherein more than one small molecule selected from the group consisting of: SYN1, SYN2, SYN-NCE and SYN-GL is administered to the subject.

* * * * *

SEQUENCE LISTING

<160> NUMBER OF SEQ ID NOS: 119

<210> SEQ ID NO 1
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: DY547 dye modified
<220> FEATURE:
<221> NAME/KEY: misc_feature
<222> LOCATION: (1)..(2)
<223> OTHER INFORMATION: 2'OMe modified
<220> FEATURE:
<221> NAME/KEY: misc_feature
<222> LOCATION: (1)..(10)
<223> OTHER INFORMATION: Phosphodiester linkage
<220> FEATURE:
<221> NAME/KEY: misc_feature
<222> LOCATION: (4)..(4)
<223> OTHER INFORMATION: 2'OMe modified
<220> FEATURE:
<221> NAME/KEY: misc_feature
<222> LOCATION: (7)..(7)
<223> OTHER INFORMATION: 2'OMe modified
<220> FEATURE:
<221> NAME/KEY: misc_feature
<222> LOCATION: (9)..(9)
<223> OTHER INFORMATION: 2'OMe modified
<220> FEATURE:
<221> NAME/KEY: misc_feature
<222> LOCATION: (11)..(13)
<223> OTHER INFORMATION: 2'OMe modified
<220> FEATURE:
<221> NAME/KEY: misc_feature
<222> LOCATION: (10)..(12)
<223> OTHER INFORMATION: Phosphorothioate linkage
<220> FEATURE:
<221> NAME/KEY: misc_feature
<222> LOCATION: (12)..(13)
<223> OTHER INFORMATION: Phosphodiester linkage

<400> SEQUENCE: 1
gagaggcaug uua                                                          13

<210> SEQ ID NO 2
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: DY547 dye modified
<220> FEATURE:
<221> NAME/KEY: misc_feature
<222> LOCATION: (1)..(2)
<223> OTHER INFORMATION: 2'OMe modified
<220> FEATURE:
<221> NAME/KEY: misc_feature
<222> LOCATION: (1)..(10)
<223> OTHER INFORMATION: Phosphodiester linkage
<220> FEATURE:
<221> NAME/KEY: misc_feature
<222> LOCATION: (4)..(4)
<223> OTHER INFORMATION: 2'OMe modified
<220> FEATURE:
<221> NAME/KEY: misc_feature
<222> LOCATION: (7)..(7)
<223> OTHER INFORMATION: 2'OMe modified
<220> FEATURE:
<221> NAME/KEY: misc_feature

```
<222> LOCATION: (9)..(9)
<223> OTHER INFORMATION: 2'OMe modified
<220> FEATURE:
<221> NAME/KEY: misc_feature
<222> LOCATION: (11)..(13)
<223> OTHER INFORMATION: 2'OMe modified
<220> FEATURE:
<221> NAME/KEY: misc_feature
<222> LOCATION: (10)..(12)
<223> OTHER INFORMATION: Phosphorothioate linkage
<220> FEATURE:
<221> NAME/KEY: misc_feature
<222> LOCATION: (12)..(13)
<223> OTHER INFORMATION: Phosphodiester linkage

<400> SEQUENCE: 2
gagaggcaug uua                                                           13

<210> SEQ ID NO 3
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: DY547 dye modified
<220> FEATURE:
<221> NAME/KEY: misc_feature
<222> LOCATION: (1)..(2)
<223> OTHER INFORMATION: 2'OMe modified
<220> FEATURE:
<221> NAME/KEY: misc_feature
<222> LOCATION: (1)..(10)
<223> OTHER INFORMATION: Phosphodiester linkage
<220> FEATURE:
<221> NAME/KEY: misc_feature
<222> LOCATION: (4)..(4)
<223> OTHER INFORMATION: 2'OMe modified
<220> FEATURE:
<221> NAME/KEY: misc_feature
<222> LOCATION: (7)..(7)
<223> OTHER INFORMATION: 2'OMe modified
<220> FEATURE:
<221> NAME/KEY: misc_feature
<222> LOCATION: (9)..(9)
<223> OTHER INFORMATION: 2'OMe modified
<220> FEATURE:
<221> NAME/KEY: misc_feature
<222> LOCATION: (11)..(13)
<223> OTHER INFORMATION: 2'OMe modified
<220> FEATURE:
<221> NAME/KEY: misc_feature
<222> LOCATION: (10)..(12)
<223> OTHER INFORMATION: Phosphorothioate linkage
<220> FEATURE:
<221> NAME/KEY: misc_feature
<222> LOCATION: (12)..(13)
<223> OTHER INFORMATION: Phosphodiester linkage

<400> SEQUENCE: 3
gagaggcaug uua                                                           13

<210> SEQ ID NO 4
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: DY547 dye modified
<220> FEATURE:
```

```
<221> NAME/KEY: misc_feature
<222> LOCATION: (1)..(2)
<223> OTHER INFORMATION: 2'OMe modified
<220> FEATURE:
<221> NAME/KEY: misc_feature
<222> LOCATION: (4)..(4)
<223> OTHER INFORMATION: 2'OMe modified
<220> FEATURE:
<221> NAME/KEY: misc_feature
<222> LOCATION: (7)..(7)
<223> OTHER INFORMATION: 2'OMe modified
<220> FEATURE:
<221> NAME/KEY: misc_feature
<222> LOCATION: (9)..(9)
<223> OTHER INFORMATION: 2'OMe modified
<220> FEATURE:
<221> NAME/KEY: misc_feature
<222> LOCATION: (11)..(13)
<223> OTHER INFORMATION: 2'OMe modified
<220> FEATURE:
<221> NAME/KEY: misc_feature
<222> LOCATION: (1)..(12)
<223> OTHER INFORMATION: Phosphorothioate linkage
<220> FEATURE:
<221> NAME/KEY: misc_feature
<222> LOCATION: (12)..(13)
<223> OTHER INFORMATION: Phosphodiester linkage

<400> SEQUENCE: 4
gagaggcaug uua                                                         13

<210> SEQ ID NO 5
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(2)
<223> OTHER INFORMATION: 2'OMe modified
<220> FEATURE:
<221> NAME/KEY: misc_feature
<222> LOCATION: (7)..(7)
<223> OTHER INFORMATION: 2'OMe modified
<220> FEATURE:
<221> NAME/KEY: misc_feature
<222> LOCATION: (9)..(9)
<223> OTHER INFORMATION: 2'OMe modified
<220> FEATURE:
<221> NAME/KEY: misc_feature
<222> LOCATION: (11)..(13)
<223> OTHER INFORMATION: 2'OMe modified
<220> FEATURE:
<221> NAME/KEY: misc_feature
<222> LOCATION: (1)..(12)
<223> OTHER INFORMATION: Phosphorothioate linkage
<220> FEATURE:
<221> NAME/KEY: misc_feature
<222> LOCATION: (12)..(13)
<223> OTHER INFORMATION: Phosphodiester linkage

<400> SEQUENCE: 5
gagaggcaug uua                                                         13

<210> SEQ ID NO 6
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: DY547 dye modified
```

```
<220> FEATURE:
<221> NAME/KEY: misc_feature
<222> LOCATION: (1)..(2)
<223> OTHER INFORMATION: 2'OMe modified
<220> FEATURE:
<221> NAME/KEY: misc_feature
<222> LOCATION: (4)..(4)
<223> OTHER INFORMATION: 2'OMe modified
<220> FEATURE:
<221> NAME/KEY: misc_feature
<222> LOCATION: (7)..(7)
<223> OTHER INFORMATION: 2'OMe modified
<220> FEATURE:
<221> NAME/KEY: misc_feature
<222> LOCATION: (9)..(9)
<223> OTHER INFORMATION: 2'OMe modified
<220> FEATURE:
<221> NAME/KEY: misc_feature
<222> LOCATION: (11)..(13)
<223> OTHER INFORMATION: 2'OMe modified
<220> FEATURE:
<221> NAME/KEY: misc_feature
<222> LOCATION: (1)..(12)
<223> OTHER INFORMATION: Phosphorothioate linkage
<220> FEATURE:
<221> NAME/KEY: misc_feature
<222> LOCATION: (12)..(13)
<223> OTHER INFORMATION: Phosphodiester linkage

<400> SEQUENCE: 6
gagaggcaug uua                                                            13

<210> SEQ ID NO 7
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: DY547 dye modified
<220> FEATURE:
<221> NAME/KEY: misc_feature
<222> LOCATION: (1)..(2)
<223> OTHER INFORMATION: 2'OMe modified
<220> FEATURE:
<221> NAME/KEY: misc_feature
<222> LOCATION: (1)..(10)
<223> OTHER INFORMATION: Phosphodiester linkage
<220> FEATURE:
<221> NAME/KEY: misc_feature
<222> LOCATION: (4)..(4)
<223> OTHER INFORMATION: 2'OMe modified
<220> FEATURE:
<221> NAME/KEY: misc_feature
<222> LOCATION: (7)..(7)
<223> OTHER INFORMATION: 2'OMe modified
<220> FEATURE:
<221> NAME/KEY: misc_feature
<222> LOCATION: (9)..(9)
<223> OTHER INFORMATION: 2'OMe modified
<220> FEATURE:
<221> NAME/KEY: misc_feature
<222> LOCATION: (11)..(13)
<223> OTHER INFORMATION: 2'OMe modified
<220> FEATURE:
<221> NAME/KEY: misc_feature
<222> LOCATION: (10)..(12)
<223> OTHER INFORMATION: Phosphorothioate linkage
<220> FEATURE:
<221> NAME/KEY: misc_feature
<222> LOCATION: (12)..(13)
<223> OTHER INFORMATION: Phosphodiester linkage

<400> SEQUENCE: 7
```
gagaggcaug uua                                                         13

<210> SEQ ID NO 8
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: DY547 dye modified
<220> FEATURE:
<221> NAME/KEY: misc_feature
<222> LOCATION: (1)..(2)
<223> OTHER INFORMATION: 2'OMe modified
<220> FEATURE:
<221> NAME/KEY: misc_feature
<222> LOCATION: (1)..(12)
<223> OTHER INFORMATION: Phosphorothioate linkage
<220> FEATURE:
<221> NAME/KEY: misc_feature
<222> LOCATION: (4)..(4)
<223> OTHER INFORMATION: 2'OMe modified
<220> FEATURE:
<221> NAME/KEY: misc_feature
<222> LOCATION: (7)..(7)
<223> OTHER INFORMATION: 2'OMe modified
<220> FEATURE:
<221> NAME/KEY: misc_feature
<222> LOCATION: (9)..(9)
<223> OTHER INFORMATION: 2'OMe modified
<220> FEATURE:
<221> NAME/KEY: misc_feature
<222> LOCATION: (11)..(13)
<223> OTHER INFORMATION: 2'OMe modified
<220> FEATURE:
<221> NAME/KEY: misc_feature
<222> LOCATION: (12)..(13)
<223> OTHER INFORMATION: Phosphodiester linkage

<400> SEQUENCE: 8
gagaggcaug uua                                                         13

<210> SEQ ID NO 9
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: DY547 dye modified
<220> FEATURE:
<221> NAME/KEY: misc_feature
<222> LOCATION: (1)..(2)
<223> OTHER INFORMATION: 2'OMe modified
<220> FEATURE:
<221> NAME/KEY: misc_feature
<222> LOCATION: (1)..(10)
<223> OTHER INFORMATION: Phosphodiester linkage
<220> FEATURE:
<221> NAME/KEY: misc_feature
<222> LOCATION: (4)..(4)
<223> OTHER INFORMATION: 2'OMe modified
<220> FEATURE:
<221> NAME/KEY: misc_feature
<222> LOCATION: (7)..(7)
<223> OTHER INFORMATION: 2'OMe modified
<220> FEATURE:
<221> NAME/KEY: misc_feature
<222> LOCATION: (9)..(9)
<223> OTHER INFORMATION: 2'OMe modified
<220> FEATURE:
<221> NAME/KEY: misc_feature

```
<222> LOCATION: (11)..(13)
<223> OTHER INFORMATION: 2'OMe modified
<220> FEATURE:
<221> NAME/KEY: misc_feature
<222> LOCATION: (10)..(12)
<223> OTHER INFORMATION: Phosphorothioate linkage
<220> FEATURE:
<221> NAME/KEY: misc_feature
<222> LOCATION: (12)..(13)
<223> OTHER INFORMATION: Phosphodiester linkage

<400> SEQUENCE: 9
gagaggcaug uua                                                              13

<210> SEQ ID NO 10
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: DY547 dye modified
<220> FEATURE:
<221> NAME/KEY: misc_feature
<222> LOCATION: (1)..(2)
<223> OTHER INFORMATION: 2'OMe modified
<220> FEATURE:
<221> NAME/KEY: misc_feature
<222> LOCATION: (1)..(12)
<223> OTHER INFORMATION: Phosphorothioate linkage
<220> FEATURE:
<221> NAME/KEY: misc_feature
<222> LOCATION: (7)..(7)
<223> OTHER INFORMATION: 2'OMe modified
<220> FEATURE:
<221> NAME/KEY: misc_feature
<222> LOCATION: (9)..(9)
<223> OTHER INFORMATION: 2'OMe modified
<220> FEATURE:
<221> NAME/KEY: misc_feature
<222> LOCATION: (11)..(13)
<223> OTHER INFORMATION: 2'OMe modified
<220> FEATURE:
<221> NAME/KEY: misc_feature
<222> LOCATION: (12)..(13)
<223> OTHER INFORMATION: Phosphodiester linkage

<400> SEQUENCE: 10
gagaggcaug uua                                                              13

<210> SEQ ID NO 11
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: DY547 dye modified
<220> FEATURE:
<221> NAME/KEY: misc_feature
<222> LOCATION: (1)..(2)
<223> OTHER INFORMATION: 2'OMe modified
<220> FEATURE:
<221> NAME/KEY: misc_feature
<222> LOCATION: (1)..(12)
<223> OTHER INFORMATION: Phosphorothioate linkage
<220> FEATURE:
<221> NAME/KEY: misc_feature
<222> LOCATION: (4)..(4)
<223> OTHER INFORMATION: Octyl modified
<220> FEATURE:
```

```
<221> NAME/KEY: misc_feature
<222> LOCATION: (4)..(4)
<223> OTHER INFORMATION: 2'OMe modified
<220> FEATURE:
<221> NAME/KEY: misc_feature
<222> LOCATION: (10)..(10)
<223> OTHER INFORMATION: Octyl modified
<220> FEATURE:
<221> NAME/KEY: misc_feature
<222> LOCATION: (10)..(10)
<223> OTHER INFORMATION: 2'OMe modified
<220> FEATURE:
<221> NAME/KEY: misc_feature
<222> LOCATION: (12)..(13)
<223> OTHER INFORMATION: 2'OMe modified
<220> FEATURE:
<221> NAME/KEY: misc_feature
<222> LOCATION: (12)..(13)
<223> OTHER INFORMATION: Phosphodiester linkage

<400> SEQUENCE: 11
agguggaaau gaa                                                          13

<210> SEQ ID NO 12
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: DY547 dye modified
<220> FEATURE:
<221> NAME/KEY: misc_feature
<222> LOCATION: (1)..(2)
<223> OTHER INFORMATION: 2'OMe modified
<220> FEATURE:
<221> NAME/KEY: misc_feature
<222> LOCATION: (1)..(12)
<223> OTHER INFORMATION: Phosphorothioate linkage
<220> FEATURE:
<221> NAME/KEY: misc_feature
<222> LOCATION: (4)..(4)
<223> OTHER INFORMATION: 5-methyl modified
<220> FEATURE:
<221> NAME/KEY: misc_feature
<222> LOCATION: (4)..(4)
<223> OTHER INFORMATION: 2'OMe modified
<220> FEATURE:
<221> NAME/KEY: misc_feature
<222> LOCATION: (10)..(10)
<223> OTHER INFORMATION: Octyl modified
<220> FEATURE:
<221> NAME/KEY: misc_feature
<222> LOCATION: (10)..(10)
<223> OTHER INFORMATION: 2'OMe modified
<220> FEATURE:
<221> NAME/KEY: misc_feature
<222> LOCATION: (12)..(13)
<223> OTHER INFORMATION: 2'OMe modified
<220> FEATURE:
<221> NAME/KEY: misc_feature
<222> LOCATION: (12)..(13)
<223> OTHER INFORMATION: Phosphodiester linkage

<400> SEQUENCE: 12
agguggaaau gaa                                                          13

<210> SEQ ID NO 13
<211> LENGTH: 13
<212> TYPE: RNA
<213> ORGANISM: Artificial Sequence
<220> FEATURE:
<223> OTHER INFORMATION: Synthetic Polynucleotide
```

```
<220> FEATURE:
<221> NAME/KEY: misc_feature
<222> LOCATION: (1)..(1)
<223> OTHER INFORMATION: DY547 dye modified
<220> FEATURE:
<221> NAME/KEY: misc_feature
<222> LOCATION: (1)..(2)
<223> OTHER INFORMATION: 2'OMe modified
<220> FEATURE:
<221> NAME/KEY: misc_feature
<222> LOCATION: (1)..(12)
<223> OTHER INFORMATION: Phosphorothioate linkage
<220> FEATURE:
<221> NAME/KEY: misc_feature
<222> LOCATION: (4)..(4)
<223> OTHER INFORMATION: Octyl modified
<220> FEATURE:
<221> NAME/KEY: misc_feature
<222> LOCATION: (4)..(4)
<223> OTHER INFORMATION: 2'OMe modified
<220> FEATURE:
<221> NAME/KEY: misc_feature
<222> LOCATION: (10)..(10)
<223> OTHER INFORMATION: 5-methyl modified
<220> FEATURE:
<221> NAME/KEY: misc_feature
<222> LOCATION: (10)..(10)
<223> OTHER INFORMATION: 2'OMe modified
<220> FEATURE:
<221> NAME/KEY: misc_feature
<222> LOCATION: (12)..(13)
<223> OTHER INFORMATION: 2'OMe modified
<220> FEATURE:
<221> NAME/KEY: misc_feature
<222> LOCATION: (12)..(13)
<223> OTHER INFORMATION: Phosphodiester linkage

<400> SEQUENCE: 13
agguggaaau gaa                                                          13

<210> SEQ ID NO 14
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: DY547 dye modified
<220> FEATURE:
<221> NAME/KEY: misc_feature
<222> LOCATION: (1)..(2)
<223> OTHER INFORMATION: 2'OMe modified
<220> FEATURE:
<221> NAME/KEY: misc_feature
<222> LOCATION: (1)..(12)
<223> OTHER INFORMATION: Phosphorothioate linkage
<220> FEATURE:
<221> NAME/KEY: misc_feature
<222> LOCATION: (4)..(4)
<223> OTHER INFORMATION: 5-methyl modified
<220> FEATURE:
<221> NAME/KEY: misc_feature
<222> LOCATION: (4)..(4)
<223> OTHER INFORMATION: 2'OMe modified
<220> FEATURE:
<221> NAME/KEY: misc_feature
<222> LOCATION: (10)..(10)
<223> OTHER INFORMATION: 5-methyl modified
<220> FEATURE:
<221> NAME/KEY: misc_feature
<222> LOCATION: (10)..(10)
<223> OTHER INFORMATION: 2'OMe modified
<220> FEATURE:
<221> NAME/KEY: misc_feature
<222> LOCATION: (12)..(13)
```

```
<223> OTHER INFORMATION: 2'OMe modified
<220> FEATURE:
<221> NAME/KEY: misc_feature
<222> LOCATION: (12)..(13)
<223> OTHER INFORMATION: Phosphodiester linkage

<400> SEQUENCE: 14
agguggaaau gaa                                                              13

<210> SEQ ID NO 15
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: DY547 dye modified
<220> FEATURE:
<221> NAME/KEY: misc_feature
<222> LOCATION: (1)..(2)
<223> OTHER INFORMATION: 2'OMe modified
<220> FEATURE:
<221> NAME/KEY: misc_feature
<222> LOCATION: (1)..(12)
<223> OTHER INFORMATION: Phosphorothioate linkage
<220> FEATURE:
<221> NAME/KEY: misc_feature
<222> LOCATION: (4)..(4)
<223> OTHER INFORMATION: 2'OMe modified
<220> FEATURE:
<221> NAME/KEY: misc_feature
<222> LOCATION: (10)..(10)
<223> OTHER INFORMATION: 2'OMe modified
<220> FEATURE:
<221> NAME/KEY: misc_feature
<222> LOCATION: (12)..(13)
<223> OTHER INFORMATION: 2'OMe modified
<220> FEATURE:
<221> NAME/KEY: misc_feature
<222> LOCATION: (12)..(13)
<223> OTHER INFORMATION: Phosphodiester linkage

<400> SEQUENCE: 15
agguggaaau gaa                                                              13

<210> SEQ ID NO 16
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: DY547 dye modified
<220> FEATURE:
<221> NAME/KEY: misc_feature
<222> LOCATION: (1)..(2)
<223> OTHER INFORMATION: 2'OMe modified
<220> FEATURE:
<221> NAME/KEY: misc_feature
<222> LOCATION: (1)..(12)
<223> OTHER INFORMATION: Phosphorothioate linkage
<220> FEATURE:
<221> NAME/KEY: misc_feature
<222> LOCATION: (4)..(4)
<223> OTHER INFORMATION: 2'OMe modified
<220> FEATURE:
<221> NAME/KEY: misc_feature
<222> LOCATION: (10)..(10)
<223> OTHER INFORMATION: 2'OMe modified
<220> FEATURE:
<221> NAME/KEY: misc_feature
```

```
<222> LOCATION: (12)..(13)
<223> OTHER INFORMATION: 2'OMe modified
<220> FEATURE:
<221> NAME/KEY: misc_feature
<222> LOCATION: (12)..(13)
<223> OTHER INFORMATION: Phosphodiester linkage

<400> SEQUENCE: 16
agguggaaau gaa                                                          13

<210> SEQ ID NO 17
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: DY547 dye modified
<220> FEATURE:
<221> NAME/KEY: misc_feature
<222> LOCATION: (1)..(2)
<223> OTHER INFORMATION: 2'OMe modified
<220> FEATURE:
<221> NAME/KEY: misc_feature
<222> LOCATION: (1)..(12)
<223> OTHER INFORMATION: Phosphorothioate linkage
<220> FEATURE:
<221> NAME/KEY: misc_feature
<222> LOCATION: (4)..(4)
<223> OTHER INFORMATION: 2'OMe modified
<220> FEATURE:
<221> NAME/KEY: misc_feature
<222> LOCATION: (10)..(10)
<223> OTHER INFORMATION: 2'OMe modified
<220> FEATURE:
<221> NAME/KEY: misc_feature
<222> LOCATION: (12)..(13)
<223> OTHER INFORMATION: 2'OMe modified
<220> FEATURE:
<221> NAME/KEY: misc_feature
<222> LOCATION: (12)..(13)
<223> OTHER INFORMATION: Phosphodiester linkage

<400> SEQUENCE: 17
agguggaaau gaa                                                          13

<210> SEQ ID NO 18
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: DY547 dye modified
<220> FEATURE:
<221> NAME/KEY: misc_feature
<222> LOCATION: (1)..(2)
<223> OTHER INFORMATION: 2'OMe modified
<220> FEATURE:
<221> NAME/KEY: misc_feature
<222> LOCATION: (1)..(12)
<223> OTHER INFORMATION: Phosphorothioate linkage
<220> FEATURE:
<221> NAME/KEY: misc_feature
<222> LOCATION: (4)..(4)
<223> OTHER INFORMATION: 2'OMe modified
<220> FEATURE:
<221> NAME/KEY: misc_feature
<222> LOCATION: (10)..(10)
<223> OTHER INFORMATION: 2'OMe modified
<220> FEATURE:
```

```
<221> NAME/KEY: misc_feature
<222> LOCATION: (12)..(13)
<223> OTHER INFORMATION: 2'OMe modified
<220> FEATURE:
<221> NAME/KEY: misc_feature
<222> LOCATION: (12)..(13)
<223> OTHER INFORMATION: Phosphodiester linkage

<400> SEQUENCE: 18
agguggaaau gaa                                                          13

<210> SEQ ID NO 19
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: DY547 dye modified
<220> FEATURE:
<221> NAME/KEY: misc_feature
<222> LOCATION: (1)..(2)
<223> OTHER INFORMATION: 2'OMe modified
<220> FEATURE:
<221> NAME/KEY: misc_feature
<222> LOCATION: (1)..(12)
<223> OTHER INFORMATION: Phosphorothioate linkage
<220> FEATURE:
<221> NAME/KEY: misc_feature
<222> LOCATION: (4)..(4)
<223> OTHER INFORMATION: 2'OMe modified
<220> FEATURE:
<221> NAME/KEY: misc_feature
<222> LOCATION: (10)..(10)
<223> OTHER INFORMATION: 2'OMe modified
<220> FEATURE:
<221> NAME/KEY: misc_feature
<222> LOCATION: (12)..(13)
<223> OTHER INFORMATION: 2'OMe modified
<220> FEATURE:
<221> NAME/KEY: misc_feature
<222> LOCATION: (12)..(13)
<223> OTHER INFORMATION: Phosphodiester linkage

<400> SEQUENCE: 19
agguggaaau gaa                                                          13

<210> SEQ ID NO 20
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: DY547 dye modified
<220> FEATURE:
<221> NAME/KEY: misc_feature
<222> LOCATION: (1)..(2)
<223> OTHER INFORMATION: 2'OMe modified
<220> FEATURE:
<221> NAME/KEY: misc_feature
<222> LOCATION: (1)..(12)
<223> OTHER INFORMATION: Phosphorothioate linkage
<220> FEATURE:
<221> NAME/KEY: misc_feature
<222> LOCATION: (4)..(4)
<223> OTHER INFORMATION: 5-methyl modified
<220> FEATURE:
<221> NAME/KEY: misc_feature
<222> LOCATION: (4)..(4)
<223> OTHER INFORMATION: 2'OMe modified
```

```
<220> FEATURE:
<221> NAME/KEY: misc_feature
<222> LOCATION: (10)..(10)
<223> OTHER INFORMATION: Thiophene modified
<220> FEATURE:
<221> NAME/KEY: misc_feature
<222> LOCATION: (10)..(10)
<223> OTHER INFORMATION: 2'OMe modified
<220> FEATURE:
<221> NAME/KEY: misc_feature
<222> LOCATION: (12)..(13)
<223> OTHER INFORMATION: 2'OMe modified
<220> FEATURE:
<221> NAME/KEY: misc_feature
<222> LOCATION: (12)..(13)
<223> OTHER INFORMATION: Phosphodiester linkage

<400> SEQUENCE: 20
agguggaaau gaa                                                          13

<210> SEQ ID NO 21
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: DY547 dye modified
<220> FEATURE:
<221> NAME/KEY: misc_feature
<222> LOCATION: (1)..(2)
<223> OTHER INFORMATION: 2'OMe modified
<220> FEATURE:
<221> NAME/KEY: misc_feature
<222> LOCATION: (1)..(12)
<223> OTHER INFORMATION: Phosphorothioate linkage
<220> FEATURE:
<221> NAME/KEY: misc_feature
<222> LOCATION: (4)..(4)
<223> OTHER INFORMATION: Thiophene modified
<220> FEATURE:
<221> NAME/KEY: misc_feature
<222> LOCATION: (4)..(4)
<223> OTHER INFORMATION: 2'OMe modified
<220> FEATURE:
<221> NAME/KEY: misc_feature
<222> LOCATION: (10)..(10)
<223> OTHER INFORMATION: 5-methyl modified
<220> FEATURE:
<221> NAME/KEY: misc_feature
<222> LOCATION: (10)..(10)
<223> OTHER INFORMATION: 2'OMe modified
<220> FEATURE:
<221> NAME/KEY: misc_feature
<222> LOCATION: (12)..(13)
<223> OTHER INFORMATION: 2'OMe modified
<220> FEATURE:
<221> NAME/KEY: misc_feature
<222> LOCATION: (12)..(13)
<223> OTHER INFORMATION: Phosphodiester linkage

<400> SEQUENCE: 21
agguggaaau gaa                                                          13

<210> SEQ ID NO 22
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
```

```
<223> OTHER INFORMATION: DY547 dye modified
<220> FEATURE:
<221> NAME/KEY: misc_feature
<222> LOCATION: (1)..(2)
<223> OTHER INFORMATION: 2'OMe modified
<220> FEATURE:
<221> NAME/KEY: misc_feature
<222> LOCATION: (1)..(12)
<223> OTHER INFORMATION: Phosphorothioate linkage
<220> FEATURE:
<221> NAME/KEY: misc_feature
<222> LOCATION: (4)..(4)
<223> OTHER INFORMATION: 5-methyl modified
<220> FEATURE:
<221> NAME/KEY: misc_feature
<222> LOCATION: (4)..(4)
<223> OTHER INFORMATION: 2'OMe modified
<220> FEATURE:
<221> NAME/KEY: misc_feature
<222> LOCATION: (10)..(10)
<223> OTHER INFORMATION: 5-methyl modified
<220> FEATURE:
<221> NAME/KEY: misc_feature
<222> LOCATION: (10)..(10)
<223> OTHER INFORMATION: 2'OMe modified
<220> FEATURE:
<221> NAME/KEY: misc_feature
<222> LOCATION: (12)..(13)
<223> OTHER INFORMATION: 2'OMe modified
<220> FEATURE:
<221> NAME/KEY: misc_feature
<222> LOCATION: (12)..(13)
<223> OTHER INFORMATION: Phosphodiester linkage

<400> SEQUENCE: 22
agguggaaau gaa                                                    13

<210> SEQ ID NO 23
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: DY547 dye modified
<220> FEATURE:
<221> NAME/KEY: misc_feature
<222> LOCATION: (1)..(2)
<223> OTHER INFORMATION: 2'OMe modified
<220> FEATURE:
<221> NAME/KEY: misc_feature
<222> LOCATION: (1)..(12)
<223> OTHER INFORMATION: Phosphorothioate linkage
<220> FEATURE:
<221> NAME/KEY: misc_feature
<222> LOCATION: (4)..(4)
<223> OTHER INFORMATION: 2'OMe modified
<220> FEATURE:
<221> NAME/KEY: misc_feature
<222> LOCATION: (10)..(10)
<223> OTHER INFORMATION: 2'OMe modified
<220> FEATURE:
<221> NAME/KEY: misc_feature
<222> LOCATION: (12)..(13)
<223> OTHER INFORMATION: 2'OMe modified
<220> FEATURE:
<221> NAME/KEY: misc_feature
<222> LOCATION: (12)..(13)
<223> OTHER INFORMATION: Phosphodiester linkage

<400> SEQUENCE: 23
agguggaaau gaa                                                    13
```

```
<210> SEQ ID NO 24
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: DY547 dye modified
<220> FEATURE:
<221> NAME/KEY: misc_feature
<222> LOCATION: (1)..(2)
<223> OTHER INFORMATION: 2'OMe modified
<220> FEATURE:
<221> NAME/KEY: misc_feature
<222> LOCATION: (1)..(12)
<223> OTHER INFORMATION: Phosphorothioate linkage
<220> FEATURE:
<221> NAME/KEY: misc_feature
<222> LOCATION: (4)..(4)
<223> OTHER INFORMATION: 2'OMe modified
<220> FEATURE:
<221> NAME/KEY: misc_feature
<222> LOCATION: (10)..(10)
<223> OTHER INFORMATION: 2'OMe modified
<220> FEATURE:
<221> NAME/KEY: misc_feature
<222> LOCATION: (12)..(13)
<223> OTHER INFORMATION: 2'OMe modified
<220> FEATURE:
<221> NAME/KEY: misc_feature
<222> LOCATION: (12)..(13)
<223> OTHER INFORMATION: Phosphodiester linkage

<400> SEQUENCE: 24
agguggaaau gaa                                                      13

<210> SEQ ID NO 25
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: DY547 dye modified
<220> FEATURE:
<221> NAME/KEY: misc_feature
<222> LOCATION: (1)..(2)
<223> OTHER INFORMATION: 2'OMe modified
<220> FEATURE:
<221> NAME/KEY: misc_feature
<222> LOCATION: (1)..(12)
<223> OTHER INFORMATION: Phosphorothioate linkage
<220> FEATURE:
<221> NAME/KEY: misc_feature
<222> LOCATION: (4)..(4)
<223> OTHER INFORMATION: Isobutyl modified
<220> FEATURE:
<221> NAME/KEY: misc_feature
<222> LOCATION: (4)..(4)
<223> OTHER INFORMATION: Deoxyribose modified
<220> FEATURE:
<221> NAME/KEY: misc_feature
<222> LOCATION: (10)..(10)
<223> OTHER INFORMATION: Isobutyl modified
<220> FEATURE:
<221> NAME/KEY: misc_feature
<222> LOCATION: (10)..(10)
<223> OTHER INFORMATION: Deoxyribose modified
<220> FEATURE:
<221> NAME/KEY: misc_feature
<222> LOCATION: (12)..(13)
<223> OTHER INFORMATION: 2'OMe modified
<220> FEATURE:
```

```
<221> NAME/KEY: misc_feature
<222> LOCATION: (12)..(13)
<223> OTHER INFORMATION: Phosphodiester linkage

<400> SEQUENCE: 25
agguggaaau gaa                                                        13

<210> SEQ ID NO 26
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: DY547 dye modified
<220> FEATURE:
<221> NAME/KEY: misc_feature
<222> LOCATION: (1)..(2)
<223> OTHER INFORMATION: 2'OMe modified
<220> FEATURE:
<221> NAME/KEY: misc_feature
<222> LOCATION: (1)..(12)
<223> OTHER INFORMATION: Phosphorothioate linkage
<220> FEATURE:
<221> NAME/KEY: misc_feature
<222> LOCATION: (4)..(4)
<223> OTHER INFORMATION: 5-methyl modified
<220> FEATURE:
<221> NAME/KEY: misc_feature
<222> LOCATION: (4)..(4)
<223> OTHER INFORMATION: 2'OMe modified
<220> FEATURE:
<221> NAME/KEY: misc_feature
<222> LOCATION: (10)..(10)
<223> OTHER INFORMATION: Isobutyl modified
<220> FEATURE:
<221> NAME/KEY: misc_feature
<222> LOCATION: (10)..(10)
<223> OTHER INFORMATION: Deoxyribose modified
<220> FEATURE:
<221> NAME/KEY: misc_feature
<222> LOCATION: (12)..(13)
<223> OTHER INFORMATION: 2'OMe modified
<220> FEATURE:
<221> NAME/KEY: misc_feature
<222> LOCATION: (12)..(13)
<223> OTHER INFORMATION: Phosphodiester linkage

<400> SEQUENCE: 26
agguggaaau gaa                                                        13

<210> SEQ ID NO 27
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: DY547 dye modified
<220> FEATURE:
<221> NAME/KEY: misc_feature
<222> LOCATION: (1)..(2)
<223> OTHER INFORMATION: 2'OMe modified
<220> FEATURE:
<221> NAME/KEY: misc_feature
<222> LOCATION: (1)..(12)
<223> OTHER INFORMATION: Phosphorothioate linkage
<220> FEATURE:
<221> NAME/KEY: misc_feature
<222> LOCATION: (4)..(4)
<223> OTHER INFORMATION: Isobutyl modified
```

```
<220> FEATURE:
<221> NAME/KEY: misc_feature
<222> LOCATION: (4)..(4)
<223> OTHER INFORMATION: Deoxyribose modified
<220> FEATURE:
<221> NAME/KEY: misc_feature
<222> LOCATION: (10)..(10)
<223> OTHER INFORMATION: 5-methyl modified
<220> FEATURE:
<221> NAME/KEY: misc_feature
<222> LOCATION: (10)..(10)
<223> OTHER INFORMATION: 2'OMe modified
<220> FEATURE:
<221> NAME/KEY: misc_feature
<222> LOCATION: (12)..(13)
<223> OTHER INFORMATION: 2'OMe modified
<220> FEATURE:
<221> NAME/KEY: misc_feature
<222> LOCATION: (12)..(13)
<223> OTHER INFORMATION: Phosphodiester linkage

<400> SEQUENCE: 27
agguggaaau gaa                                                              13

<210> SEQ ID NO 28
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: DY547 dye modified
<220> FEATURE:
<221> NAME/KEY: misc_feature
<222> LOCATION: (1)..(2)
<223> OTHER INFORMATION: 2'OMe modified
<220> FEATURE:
<221> NAME/KEY: misc_feature
<222> LOCATION: (1)..(12)
<223> OTHER INFORMATION: Phosphorothioate linkage
<220> FEATURE:
<221> NAME/KEY: misc_feature
<222> LOCATION: (4)..(4)
<223> OTHER INFORMATION: 2'OMe modified
<220> FEATURE:
<221> NAME/KEY: misc_feature
<222> LOCATION: (10)..(10)
<223> OTHER INFORMATION: 2'OMe modified
<220> FEATURE:
<221> NAME/KEY: misc_feature
<222> LOCATION: (12)..(13)
<223> OTHER INFORMATION: 2'OMe modified
<220> FEATURE:
<221> NAME/KEY: misc_feature
<222> LOCATION: (12)..(13)
<223> OTHER INFORMATION: Phosphodiester linkage

<400> SEQUENCE: 28
agguggaaau gaa                                                              13

<210> SEQ ID NO 29
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: DY547 dye modified
<220> FEATURE:
<221> NAME/KEY: misc_feature
<222> LOCATION: (1)..(2)
```

```
<223> OTHER INFORMATION: 2'OMe modified
<220> FEATURE:
<221> NAME/KEY: misc_feature
<222> LOCATION: (1)..(12)
<223> OTHER INFORMATION: Phosphorothioate linkage
<220> FEATURE:
<221> NAME/KEY: misc_feature
<222> LOCATION: (4)..(4)
<223> OTHER INFORMATION: 2'OMe modified
<220> FEATURE:
<221> NAME/KEY: misc_feature
<222> LOCATION: (10)..(10)
<223> OTHER INFORMATION: 2'OMe modified
<220> FEATURE:
<221> NAME/KEY: misc_feature
<222> LOCATION: (12)..(13)
<223> OTHER INFORMATION: 2'OMe modified
<220> FEATURE:
<221> NAME/KEY: misc_feature
<222> LOCATION: (12)..(13)
<223> OTHER INFORMATION: Phosphodiester linkage

<400> SEQUENCE: 29
agguggaaau gaa                                                          13

<210> SEQ ID NO 30
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: DY547 dye modified
<220> FEATURE:
<221> NAME/KEY: misc_feature
<222> LOCATION: (1)..(2)
<223> OTHER INFORMATION: 2'OMe modified
<220> FEATURE:
<221> NAME/KEY: misc_feature
<222> LOCATION: (1)..(12)
<223> OTHER INFORMATION: Phosphorothioate linkage
<220> FEATURE:
<221> NAME/KEY: misc_feature
<222> LOCATION: (4)..(4)
<223> OTHER INFORMATION: 2'OMe modified
<220> FEATURE:
<221> NAME/KEY: misc_feature
<222> LOCATION: (10)..(10)
<223> OTHER INFORMATION: 2'OMe modified
<220> FEATURE:
<221> NAME/KEY: misc_feature
<222> LOCATION: (12)..(13)
<223> OTHER INFORMATION: 2'OMe modified
<220> FEATURE:
<221> NAME/KEY: misc_feature
<222> LOCATION: (12)..(13)
<223> OTHER INFORMATION: Phosphodiester linkage

<400> SEQUENCE: 30
agguggaaau gaa                                                          13

<210> SEQ ID NO 31
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(2)
<223> OTHER INFORMATION: 2'OMe modified
<220> FEATURE:
<221> NAME/KEY: misc_feature
```

```
<222> LOCATION: (1)..(11)
<223> OTHER INFORMATION: Phosphodiester linkage
<220> FEATURE:
<221> NAME/KEY: misc_feature
<222> LOCATION: (4)..(4)
<223> OTHER INFORMATION: 2'OMe modified
<220> FEATURE:
<221> NAME/KEY: misc_feature
<222> LOCATION: (7)..(7)
<223> OTHER INFORMATION: 2'OMe modified
<220> FEATURE:
<221> NAME/KEY: misc_feature
<222> LOCATION: (9)..(9)
<223> OTHER INFORMATION: 2'OMe modified
<220> FEATURE:
<221> NAME/KEY: misc_feature
<222> LOCATION: (11)..(12)
<223> OTHER INFORMATION: Phosphorothioate linkage
<220> FEATURE:
<221> NAME/KEY: misc_feature
<222> LOCATION: (11)..(13)
<223> OTHER INFORMATION: 2'OMe modified
<220> FEATURE:
<221> NAME/KEY: misc_feature
<222> LOCATION: (12)..(13)
<223> OTHER INFORMATION: Phosphodiester linkage

<400> SEQUENCE: 31
gagaggcaug uua                                                            13

<210> SEQ ID NO 32
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(2)
<223> OTHER INFORMATION: 2'OMe modified
<220> FEATURE:
<221> NAME/KEY: misc_feature
<222> LOCATION: (1)..(11)
<223> OTHER INFORMATION: Phosphodiester linkage
<220> FEATURE:
<221> NAME/KEY: misc_feature
<222> LOCATION: (4)..(4)
<223> OTHER INFORMATION: 2'OMe modified
<220> FEATURE:
<221> NAME/KEY: misc_feature
<222> LOCATION: (7)..(7)
<223> OTHER INFORMATION: 2'OMe modified
<220> FEATURE:
<221> NAME/KEY: misc_feature
<222> LOCATION: (9)..(9)
<223> OTHER INFORMATION: 2'OMe modified
<220> FEATURE:
<221> NAME/KEY: misc_feature
<222> LOCATION: (11)..(12)
<223> OTHER INFORMATION: Phosphorothioate linkage
<220> FEATURE:
<221> NAME/KEY: misc_feature
<222> LOCATION: (11)..(13)
<223> OTHER INFORMATION: 2'OMe modified
<220> FEATURE:
<221> NAME/KEY: misc_feature
<222> LOCATION: (12)..(13)
<223> OTHER INFORMATION: Phosphodiester linkage

<400> SEQUENCE: 32
gagaggcaug uua                                                            13

<210> SEQ ID NO 33
<211> LENGTH: 13
<212> TYPE: RNA
```

```
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(2)
<223> OTHER INFORMATION: 2'OMe modified
<220> FEATURE:
<221> NAME/KEY: misc_feature
<222> LOCATION: (1)..(11)
<223> OTHER INFORMATION: Phosphodiester linkage
<220> FEATURE:
<221> NAME/KEY: misc_feature
<222> LOCATION: (4)..(4)
<223> OTHER INFORMATION: 2'OMe modified
<220> FEATURE:
<221> NAME/KEY: misc_feature
<222> LOCATION: (7)..(7)
<223> OTHER INFORMATION: 2'OMe modified
<220> FEATURE:
<221> NAME/KEY: misc_feature
<222> LOCATION: (9)..(9)
<223> OTHER INFORMATION: 2'OMe modified
<220> FEATURE:
<221> NAME/KEY: misc_feature
<222> LOCATION: (11)..(12)
<223> OTHER INFORMATION: Phosphorothioate linkage
<220> FEATURE:
<221> NAME/KEY: misc_feature
<222> LOCATION: (11)..(13)
<223> OTHER INFORMATION: 2'OMe modified
<220> FEATURE:
<221> NAME/KEY: misc_feature
<222> LOCATION: (12)..(13)
<223> OTHER INFORMATION: Phosphodiester linkage

<400> SEQUENCE: 33
gagaggcaug uua                                                        13

<210> SEQ ID NO 34
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(2)
<223> OTHER INFORMATION: 2'OMe modified
<220> FEATURE:
<221> NAME/KEY: misc_feature
<222> LOCATION: (1)..(12)
<223> OTHER INFORMATION: Phosphorothioate linkage
<220> FEATURE:
<221> NAME/KEY: misc_feature
<222> LOCATION: (4)..(4)
<223> OTHER INFORMATION: 2'OMe modified
<220> FEATURE:
<221> NAME/KEY: misc_feature
<222> LOCATION: (7)..(7)
<223> OTHER INFORMATION: 2'OMe modified
<220> FEATURE:
<221> NAME/KEY: misc_feature
<222> LOCATION: (9)..(9)
<223> OTHER INFORMATION: 2'OMe modified
<220> FEATURE:
<221> NAME/KEY: misc_feature
<222> LOCATION: (11)..(13)
<223> OTHER INFORMATION: 2'OMe modified
<220> FEATURE:
<221> NAME/KEY: misc_feature
<222> LOCATION: (12)..(13)
<223> OTHER INFORMATION: Phosphodiester linkage

<400> SEQUENCE: 34
gagaggcaug uua                                                        13
```

```
<210> SEQ ID NO 35
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(2)
<223> OTHER INFORMATION: 2'OMe modified
<220> FEATURE:
<221> NAME/KEY: misc_feature
<222> LOCATION: (1)..(12)
<223> OTHER INFORMATION: Phosphorothioate linkage
<220> FEATURE:
<221> NAME/KEY: misc_feature
<222> LOCATION: (4)..(4)
<223> OTHER INFORMATION: 2'OMe modified
<220> FEATURE:
<221> NAME/KEY: misc_feature
<222> LOCATION: (7)..(7)
<223> OTHER INFORMATION: 2'OMe modified
<220> FEATURE:
<221> NAME/KEY: misc_feature
<222> LOCATION: (9)..(9)
<223> OTHER INFORMATION: 2'OMe modified
<220> FEATURE:
<221> NAME/KEY: misc_feature
<222> LOCATION: (11)..(13)
<223> OTHER INFORMATION: 2'OMe modified
<220> FEATURE:
<221> NAME/KEY: misc_feature
<222> LOCATION: (12)..(13)
<223> OTHER INFORMATION: Phosphodiester linkage

<400> SEQUENCE: 35
gagaggcaug uua                                                          13

<210> SEQ ID NO 36
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(2)
<223> OTHER INFORMATION: 2'OMe modified
<220> FEATURE:
<221> NAME/KEY: misc_feature
<222> LOCATION: (1)..(11)
<223> OTHER INFORMATION: Phosphodiester linkage
<220> FEATURE:
<221> NAME/KEY: misc_feature
<222> LOCATION: (4)..(4)
<223> OTHER INFORMATION: 2'OMe modified
<220> FEATURE:
<221> NAME/KEY: misc_feature
<222> LOCATION: (7)..(7)
<223> OTHER INFORMATION: 2'OMe modified
<220> FEATURE:
<221> NAME/KEY: misc_feature
<222> LOCATION: (9)..(9)
<223> OTHER INFORMATION: 2'OMe modified
<220> FEATURE:
<221> NAME/KEY: misc_feature
<222> LOCATION: (11)..(12)
<223> OTHER INFORMATION: Phosphorothioate linkage
<220> FEATURE:
<221> NAME/KEY: misc_feature
<222> LOCATION: (11)..(13)
<223> OTHER INFORMATION: 2'OMe modified
<220> FEATURE:
<221> NAME/KEY: misc_feature
<222> LOCATION: (12)..(13)
```

<223> OTHER INFORMATION: Phosphodiester linkage

<400> SEQUENCE: 36
gagaggcaug uua                                                          13

<210> SEQ ID NO 37
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(2)
<223> OTHER INFORMATION: 2'OMe modified
<220> FEATURE:
<221> NAME/KEY: misc_feature
<222> LOCATION: (1)..(12)
<223> OTHER INFORMATION: Phosphorothioate linkage
<220> FEATURE:
<221> NAME/KEY: misc_feature
<222> LOCATION: (4)..(4)
<223> OTHER INFORMATION: 2'OMe modified
<220> FEATURE:
<221> NAME/KEY: misc_feature
<222> LOCATION: (7)..(7)
<223> OTHER INFORMATION: 2'OMe modified
<220> FEATURE:
<221> NAME/KEY: misc_feature
<222> LOCATION: (9)..(9)
<223> OTHER INFORMATION: 2'OMe modified
<220> FEATURE:
<221> NAME/KEY: misc_feature
<222> LOCATION: (11)..(13)
<223> OTHER INFORMATION: 2'OMe modified
<220> FEATURE:
<221> NAME/KEY: misc_feature
<222> LOCATION: (12)..(13)
<223> OTHER INFORMATION: Phosphodiester linkage

<400> SEQUENCE: 37
gagaggcaug uua                                                          13

<210> SEQ ID NO 38
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(2)
<223> OTHER INFORMATION: 2'OMe modified
<220> FEATURE:
<221> NAME/KEY: misc_feature
<222> LOCATION: (1)..(11)
<223> OTHER INFORMATION: Phosphodiester linkage
<220> FEATURE:
<221> NAME/KEY: misc_feature
<222> LOCATION: (4)..(4)
<223> OTHER INFORMATION: 2'OMe modified
<220> FEATURE:
<221> NAME/KEY: misc_feature
<222> LOCATION: (7)..(7)
<223> OTHER INFORMATION: 2'OMe modified
<220> FEATURE:
<221> NAME/KEY: misc_feature
<222> LOCATION: (9)..(9)
<223> OTHER INFORMATION: 2'OMe modified
<220> FEATURE:
<221> NAME/KEY: misc_feature
<222> LOCATION: (11)..(12)
<223> OTHER INFORMATION: Phosphorothioate linkage
<220> FEATURE:
<221> NAME/KEY: misc_feature

```
<222> LOCATION: (11)..(13)
<223> OTHER INFORMATION: 2'OMe modified
<220> FEATURE:
<221> NAME/KEY: misc_feature
<222> LOCATION: (12)..(13)
<223> OTHER INFORMATION: Phosphodiester linkage

<400> SEQUENCE: 38
gagaggcaug uua                                                             13

<210> SEQ ID NO 39
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(2)
<223> OTHER INFORMATION: 2'OMe modified
<220> FEATURE:
<221> NAME/KEY: misc_feature
<222> LOCATION: (1)..(12)
<223> OTHER INFORMATION: Phosphorothioate linkage
<220> FEATURE:
<221> NAME/KEY: misc_feature
<222> LOCATION: (7)..(7)
<223> OTHER INFORMATION: 2'OMe modified
<220> FEATURE:
<221> NAME/KEY: misc_feature
<222> LOCATION: (9)..(9)
<223> OTHER INFORMATION: 2'OMe modified
<220> FEATURE:
<221> NAME/KEY: misc_feature
<222> LOCATION: (11)..(13)
<223> OTHER INFORMATION: 2'OMe modified
<220> FEATURE:
<221> NAME/KEY: misc_feature
<222> LOCATION: (12)..(13)
<223> OTHER INFORMATION: Phosphodiester linkage

<400> SEQUENCE: 39
gagaggcaug uua                                                             13

<210> SEQ ID NO 40
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(2)
<223> OTHER INFORMATION: 2'OMe modified
<220> FEATURE:
<221> NAME/KEY: misc_feature
<222> LOCATION: (1)..(12)
<223> OTHER INFORMATION: Phosphorothioate linkage
<220> FEATURE:
<221> NAME/KEY: misc_feature
<222> LOCATION: (4)..(4)
<223> OTHER INFORMATION: Octyl modified
<220> FEATURE:
<221> NAME/KEY: misc_feature
<222> LOCATION: (4)..(4)
<223> OTHER INFORMATION: 2'OMe modified
<220> FEATURE:
<221> NAME/KEY: misc_feature
<222> LOCATION: (10)..(10)
<223> OTHER INFORMATION: Octyl modified
<220> FEATURE:
<221> NAME/KEY: misc_feature
<222> LOCATION: (10)..(10)
<223> OTHER INFORMATION: 2'OMe modified
<220> FEATURE:
```

-continued

```
<221> NAME/KEY: misc_feature
<222> LOCATION: (12)..(13)
<223> OTHER INFORMATION: 2'OMe modified
<220> FEATURE:
<221> NAME/KEY: misc_feature
<222> LOCATION: (12)..(13)
<223> OTHER INFORMATION: Phosphodiester linkage

<400> SEQUENCE: 40
agguggaaau gaa                                                              13

<210> SEQ ID NO 41
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(2)
<223> OTHER INFORMATION: 2'OMe modified
<220> FEATURE:
<221> NAME/KEY: misc_feature
<222> LOCATION: (1)..(12)
<223> OTHER INFORMATION: Phosphorothioate linkage
<220> FEATURE:
<221> NAME/KEY: misc_feature
<222> LOCATION: (4)..(4)
<223> OTHER INFORMATION: 5-methyl modified
<220> FEATURE:
<221> NAME/KEY: misc_feature
<222> LOCATION: (4)..(4)
<223> OTHER INFORMATION: 2'OMe modified
<220> FEATURE:
<221> NAME/KEY: misc_feature
<222> LOCATION: (10)..(10)
<223> OTHER INFORMATION: Octyl modified
<220> FEATURE:
<221> NAME/KEY: misc_feature
<222> LOCATION: (10)..(10)
<223> OTHER INFORMATION: 2'OMe modified
<220> FEATURE:
<221> NAME/KEY: misc_feature
<222> LOCATION: (12)..(13)
<223> OTHER INFORMATION: 2'OMe modified
<220> FEATURE:
<221> NAME/KEY: misc_feature
<222> LOCATION: (12)..(13)
<223> OTHER INFORMATION: Phosphodiester linkage

<400> SEQUENCE: 41
agguggaaau gaa                                                              13

<210> SEQ ID NO 42
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(2)
<223> OTHER INFORMATION: 2'OMe modified
<220> FEATURE:
<221> NAME/KEY: misc_feature
<222> LOCATION: (1)..(12)
<223> OTHER INFORMATION: Phosphorothioate linkage
<220> FEATURE:
<221> NAME/KEY: misc_feature
<222> LOCATION: (4)..(4)
<223> OTHER INFORMATION: Octyl modified
<220> FEATURE:
<221> NAME/KEY: misc_feature
<222> LOCATION: (4)..(4)
<223> OTHER INFORMATION: 2'OMe modified
```

```
<220> FEATURE:
<221> NAME/KEY: misc_feature
<222> LOCATION: (10)..(10)
<223> OTHER INFORMATION: 5-methyl modified
<220> FEATURE:
<221> NAME/KEY: misc_feature
<222> LOCATION: (10)..(10)
<223> OTHER INFORMATION: 2'OMe modified
<220> FEATURE:
<221> NAME/KEY: misc_feature
<222> LOCATION: (12)..(13)
<223> OTHER INFORMATION: 2'OMe modified
<220> FEATURE:
<221> NAME/KEY: misc_feature
<222> LOCATION: (12)..(13)
<223> OTHER INFORMATION: Phosphodiester linkage

<400> SEQUENCE: 42
agguggaaau gaa                                                           13

<210> SEQ ID NO 43
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(2)
<223> OTHER INFORMATION: 2'OMe modified
<220> FEATURE:
<221> NAME/KEY: misc_feature
<222> LOCATION: (1)..(12)
<223> OTHER INFORMATION: Phosphorothioate linkage
<220> FEATURE:
<221> NAME/KEY: misc_feature
<222> LOCATION: (4)..(4)
<223> OTHER INFORMATION: 5-methyl modified
<220> FEATURE:
<221> NAME/KEY: misc_feature
<222> LOCATION: (4)..(4)
<223> OTHER INFORMATION: 2'OMe modified
<220> FEATURE:
<221> NAME/KEY: misc_feature
<222> LOCATION: (10)..(10)
<223> OTHER INFORMATION: 5-methyl modified
<220> FEATURE:
<221> NAME/KEY: misc_feature
<222> LOCATION: (10)..(10)
<223> OTHER INFORMATION: 2'OMe modified
<220> FEATURE:
<221> NAME/KEY: misc_feature
<222> LOCATION: (12)..(13)
<223> OTHER INFORMATION: 2'OMe modified
<220> FEATURE:
<221> NAME/KEY: misc_feature
<222> LOCATION: (12)..(13)
<223> OTHER INFORMATION: Phosphodiester linkage

<400> SEQUENCE: 43
agguggaaau gaa                                                           13

<210> SEQ ID NO 44
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(2)
<223> OTHER INFORMATION: 2'OMe modified
<220> FEATURE:
<221> NAME/KEY: misc_feature
<222> LOCATION: (1)..(12)
```

-continued

```
<223> OTHER INFORMATION: Phosphorothioate linkage
<220> FEATURE:
<221> NAME/KEY: misc_feature
<222> LOCATION: (4)..(4)
<223> OTHER INFORMATION: 2'OMe modified
<220> FEATURE:
<221> NAME/KEY: misc_feature
<222> LOCATION: (10)..(10)
<223> OTHER INFORMATION: 2'OMe modified
<220> FEATURE:
<221> NAME/KEY: misc_feature
<222> LOCATION: (12)..(13)
<223> OTHER INFORMATION: 2'OMe modified
<220> FEATURE:
<221> NAME/KEY: misc_feature
<222> LOCATION: (12)..(13)
<223> OTHER INFORMATION: Phosphodiester linkage

<400> SEQUENCE: 44
agguggaaau gaa                                                              13

<210> SEQ ID NO 45
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(2)
<223> OTHER INFORMATION: 2'OMe modified
<220> FEATURE:
<221> NAME/KEY: misc_feature
<222> LOCATION: (1)..(12)
<223> OTHER INFORMATION: Phosphorothioate linkage
<220> FEATURE:
<221> NAME/KEY: misc_feature
<222> LOCATION: (4)..(4)
<223> OTHER INFORMATION: 2'OMe modified
<220> FEATURE:
<221> NAME/KEY: misc_feature
<222> LOCATION: (10)..(10)
<223> OTHER INFORMATION: 2'OMe modified
<220> FEATURE:
<221> NAME/KEY: misc_feature
<222> LOCATION: (12)..(13)
<223> OTHER INFORMATION: 2'OMe modified
<220> FEATURE:
<221> NAME/KEY: misc_feature
<222> LOCATION: (12)..(13)
<223> OTHER INFORMATION: Phosphodiester linkage

<400> SEQUENCE: 45
agguggaaau gaa                                                              13

<210> SEQ ID NO 46
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(2)
<223> OTHER INFORMATION: 2'OMe modified
<220> FEATURE:
<221> NAME/KEY: misc_feature
<222> LOCATION: (1)..(12)
<223> OTHER INFORMATION: Phosphorothioate linkage
<220> FEATURE:
<221> NAME/KEY: misc_feature
<222> LOCATION: (4)..(4)
<223> OTHER INFORMATION: 2'OMe modified
<220> FEATURE:
<221> NAME/KEY: misc_feature
```

```
<222> LOCATION: (10)..(10)
<223> OTHER INFORMATION: 2'OMe modified
<220> FEATURE:
<221> NAME/KEY: misc_feature
<222> LOCATION: (12)..(13)
<223> OTHER INFORMATION: 2'OMe modified
<220> FEATURE:
<221> NAME/KEY: misc_feature
<222> LOCATION: (12)..(13)
<223> OTHER INFORMATION: Phosphodiester linkage

<400> SEQUENCE: 46
agguggaaau gaa                                                     13

<210> SEQ ID NO 47
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(2)
<223> OTHER INFORMATION: 2'OMe modified
<220> FEATURE:
<221> NAME/KEY: misc_feature
<222> LOCATION: (1)..(12)
<223> OTHER INFORMATION: Phosphorothioate linkage
<220> FEATURE:
<221> NAME/KEY: misc_feature
<222> LOCATION: (4)..(4)
<223> OTHER INFORMATION: 2'OMe modified
<220> FEATURE:
<221> NAME/KEY: misc_feature
<222> LOCATION: (10)..(10)
<223> OTHER INFORMATION: 2'OMe modified
<220> FEATURE:
<221> NAME/KEY: misc_feature
<222> LOCATION: (12)..(13)
<223> OTHER INFORMATION: 2'OMe modified
<220> FEATURE:
<221> NAME/KEY: misc_feature
<222> LOCATION: (12)..(13)
<223> OTHER INFORMATION: Phosphodiester linkage

<400> SEQUENCE: 47
agguggaaau gaa                                                     13

<210> SEQ ID NO 48
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(2)
<223> OTHER INFORMATION: 2'OMe modified
<220> FEATURE:
<221> NAME/KEY: misc_feature
<222> LOCATION: (1)..(12)
<223> OTHER INFORMATION: Phosphorothioate linkage
<220> FEATURE:
<221> NAME/KEY: misc_feature
<222> LOCATION: (4)..(4)
<223> OTHER INFORMATION: 2'OMe modified
<220> FEATURE:
<221> NAME/KEY: misc_feature
<222> LOCATION: (10)..(10)
<223> OTHER INFORMATION: 2'OMe modified
<220> FEATURE:
<221> NAME/KEY: misc_feature
<222> LOCATION: (12)..(13)
<223> OTHER INFORMATION: 2'OMe modified
<220> FEATURE:
```

```
<221> NAME/KEY: misc_feature
<222> LOCATION: (12)..(13)
<223> OTHER INFORMATION: Phosphodiester linkage

<400> SEQUENCE: 48
agguggaaau gaa                                                          13

<210> SEQ ID NO 49
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(2)
<223> OTHER INFORMATION: 2'OMe modified
<220> FEATURE:
<221> NAME/KEY: misc_feature
<222> LOCATION: (1)..(12)
<223> OTHER INFORMATION: Phosphorothioate linkage
<220> FEATURE:
<221> NAME/KEY: misc_feature
<222> LOCATION: (4)..(4)
<223> OTHER INFORMATION: 5-methyl modified
<220> FEATURE:
<221> NAME/KEY: misc_feature
<222> LOCATION: (4)..(4)
<223> OTHER INFORMATION: 2'OMe modified
<220> FEATURE:
<221> NAME/KEY: misc_feature
<222> LOCATION: (10)..(10)
<223> OTHER INFORMATION: Thiophene modified
<220> FEATURE:
<221> NAME/KEY: misc_feature
<222> LOCATION: (10)..(10)
<223> OTHER INFORMATION: 2'OMe modified
<220> FEATURE:
<221> NAME/KEY: misc_feature
<222> LOCATION: (12)..(13)
<223> OTHER INFORMATION: 2'OMe modified
<220> FEATURE:
<221> NAME/KEY: misc_feature
<222> LOCATION: (12)..(13)
<223> OTHER INFORMATION: Phosphodiester linkage

<400> SEQUENCE: 49
agguggaaau gaa                                                          13

<210> SEQ ID NO 50
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(2)
<223> OTHER INFORMATION: 2'OMe modified
<220> FEATURE:
<221> NAME/KEY: misc_feature
<222> LOCATION: (1)..(12)
<223> OTHER INFORMATION: Phosphorothioate linkage
<220> FEATURE:
<221> NAME/KEY: misc_feature
<222> LOCATION: (4)..(4)
<223> OTHER INFORMATION: Thiophene modified
<220> FEATURE:
<221> NAME/KEY: misc_feature
<222> LOCATION: (4)..(4)
<223> OTHER INFORMATION: 2'OMe modified
<220> FEATURE:
<221> NAME/KEY: misc_feature
<222> LOCATION: (10)..(10)
<223> OTHER INFORMATION: 5-methyl modified
```

```
<220> FEATURE:
<221> NAME/KEY: misc_feature
<222> LOCATION: (10)..(10)
<223> OTHER INFORMATION: 2'OMe modified
<220> FEATURE:
<221> NAME/KEY: misc_feature
<222> LOCATION: (12)..(13)
<223> OTHER INFORMATION: 2'OMe modified
<220> FEATURE:
<221> NAME/KEY: misc_feature
<222> LOCATION: (12)..(13)
<223> OTHER INFORMATION: Phosphodiester linkage

<400> SEQUENCE: 50
agguggaaau gaa                                                          13

<210> SEQ ID NO 51
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(2)
<223> OTHER INFORMATION: 2'OMe modified
<220> FEATURE:
<221> NAME/KEY: misc_feature
<222> LOCATION: (1)..(12)
<223> OTHER INFORMATION: Phosphorothioate linkage
<220> FEATURE:
<221> NAME/KEY: misc_feature
<222> LOCATION: (4)..(4)
<223> OTHER INFORMATION: 5-methyl modified
<220> FEATURE:
<221> NAME/KEY: misc_feature
<222> LOCATION: (4)..(4)
<223> OTHER INFORMATION: 2'OMe modified
<220> FEATURE:
<221> NAME/KEY: misc_feature
<222> LOCATION: (10)..(10)
<223> OTHER INFORMATION: 5-methyl modified
<220> FEATURE:
<221> NAME/KEY: misc_feature
<222> LOCATION: (10)..(10)
<223> OTHER INFORMATION: 2'OMe modified
<220> FEATURE:
<221> NAME/KEY: misc_feature
<222> LOCATION: (12)..(13)
<223> OTHER INFORMATION: 2'OMe modified
<220> FEATURE:
<221> NAME/KEY: misc_feature
<222> LOCATION: (12)..(13)
<223> OTHER INFORMATION: Phosphodiester linkage

<400> SEQUENCE: 51
agguggaaau gaa                                                          13

<210> SEQ ID NO 52
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(2)
<223> OTHER INFORMATION: 2'OMe modified
<220> FEATURE:
<221> NAME/KEY: misc_feature
<222> LOCATION: (1)..(12)
<223> OTHER INFORMATION: Phosphorothioate linkage
<220> FEATURE:
<221> NAME/KEY: misc_feature
<222> LOCATION: (4)..(4)
```

```
<223> OTHER INFORMATION: 2'OMe modified
<220> FEATURE:
<221> NAME/KEY: misc_feature
<222> LOCATION: (10)..(10)
<223> OTHER INFORMATION: 2'OMe modified
<220> FEATURE:
<221> NAME/KEY: misc_feature
<222> LOCATION: (12)..(13)
<223> OTHER INFORMATION: 2'OMe modified
<220> FEATURE:
<221> NAME/KEY: misc_feature
<222> LOCATION: (12)..(13)
<223> OTHER INFORMATION: Phosphodiester linkage

<400> SEQUENCE: 52
agguggaaau gaa                                                           13

<210> SEQ ID NO 53
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(2)
<223> OTHER INFORMATION: 2'OMe modified
<220> FEATURE:
<221> NAME/KEY: misc_feature
<222> LOCATION: (1)..(12)
<223> OTHER INFORMATION: Phosphorothioate linkage
<220> FEATURE:
<221> NAME/KEY: misc_feature
<222> LOCATION: (4)..(4)
<223> OTHER INFORMATION: 2'OMe modified
<220> FEATURE:
<221> NAME/KEY: misc_feature
<222> LOCATION: (10)..(10)
<223> OTHER INFORMATION: 2'OMe modified
<220> FEATURE:
<221> NAME/KEY: misc_feature
<222> LOCATION: (12)..(13)
<223> OTHER INFORMATION: 2'OMe modified
<220> FEATURE:
<221> NAME/KEY: misc_feature
<222> LOCATION: (12)..(13)
<223> OTHER INFORMATION: Phosphodiester linkage

<400> SEQUENCE: 53
agguggaaau gaa                                                           13

<210> SEQ ID NO 54
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(2)
<223> OTHER INFORMATION: 2'OMe modified
<220> FEATURE:
<221> NAME/KEY: misc_feature
<222> LOCATION: (1)..(12)
<223> OTHER INFORMATION: Phosphorothioate linkage
<220> FEATURE:
<221> NAME/KEY: misc_feature
<222> LOCATION: (4)..(4)
<223> OTHER INFORMATION: Isobutyl modified
<220> FEATURE:
<221> NAME/KEY: misc_feature
<222> LOCATION: (4)..(4)
<223> OTHER INFORMATION: Deoxyribose modified
<220> FEATURE:
<221> NAME/KEY: misc_feature
```

```
<222> LOCATION: (10)..(10)
<223> OTHER INFORMATION: Isobutyl modified
<220> FEATURE:
<221> NAME/KEY: misc_feature
<222> LOCATION: (10)..(10)
<223> OTHER INFORMATION: Deoxyribose modified
<220> FEATURE:
<221> NAME/KEY: misc_feature
<222> LOCATION: (12)..(13)
<223> OTHER INFORMATION: 2'OMe modified
<220> FEATURE:
<221> NAME/KEY: misc_feature
<222> LOCATION: (12)..(13)
<223> OTHER INFORMATION: Phosphodiester linkage

<400> SEQUENCE: 54
agguggaaau gaa                                                          13

<210> SEQ ID NO 55
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(2)
<223> OTHER INFORMATION: 2'OMe modified
<220> FEATURE:
<221> NAME/KEY: misc_feature
<222> LOCATION: (1)..(12)
<223> OTHER INFORMATION: Phosphorothioate linkage
<220> FEATURE:
<221> NAME/KEY: misc_feature
<222> LOCATION: (4)..(4)
<223> OTHER INFORMATION: 5-methyl modified
<220> FEATURE:
<221> NAME/KEY: misc_feature
<222> LOCATION: (4)..(4)
<223> OTHER INFORMATION: 2'OMe modified
<220> FEATURE:
<221> NAME/KEY: misc_feature
<222> LOCATION: (10)..(10)
<223> OTHER INFORMATION: Isobutyl modified
<220> FEATURE:
<221> NAME/KEY: misc_feature
<222> LOCATION: (10)..(10)
<223> OTHER INFORMATION: Deoxyribose modified
<220> FEATURE:
<221> NAME/KEY: misc_feature
<222> LOCATION: (12)..(13)
<223> OTHER INFORMATION: 2'OMe modified
<220> FEATURE:
<221> NAME/KEY: misc_feature
<222> LOCATION: (12)..(13)
<223> OTHER INFORMATION: Phosphodiester linkage

<400> SEQUENCE: 55
agguggaaau gaa                                                          13

<210> SEQ ID NO 56
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(2)
<223> OTHER INFORMATION: 2'OMe modified
<220> FEATURE:
<221> NAME/KEY: misc_feature
<222> LOCATION: (1)..(12)
<223> OTHER INFORMATION: Phosphorothioate linkage
<220> FEATURE:
```

```
<221> NAME/KEY: misc_feature
<222> LOCATION: (4)..(4)
<223> OTHER INFORMATION: Isobutyl modified
<220> FEATURE:
<221> NAME/KEY: misc_feature
<222> LOCATION: (4)..(4)
<223> OTHER INFORMATION: Deoxyribose modified
<220> FEATURE:
<221> NAME/KEY: misc_feature
<222> LOCATION: (10)..(10)
<223> OTHER INFORMATION: 5-methyl modified
<220> FEATURE:
<221> NAME/KEY: misc_feature
<222> LOCATION: (10)..(10)
<223> OTHER INFORMATION: 2'OMe modified
<220> FEATURE:
<221> NAME/KEY: misc_feature
<222> LOCATION: (12)..(13)
<223> OTHER INFORMATION: 2'OMe modified
<220> FEATURE:
<221> NAME/KEY: misc_feature
<222> LOCATION: (12)..(13)
<223> OTHER INFORMATION: Phosphodiester linkage

<400> SEQUENCE: 56
agguggaaau gaa                                                              13

<210> SEQ ID NO 57
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(2)
<223> OTHER INFORMATION: 2'OMe modified
<220> FEATURE:
<221> NAME/KEY: misc_feature
<222> LOCATION: (1)..(12)
<223> OTHER INFORMATION: Phosphorothioate linkage
<220> FEATURE:
<221> NAME/KEY: misc_feature
<222> LOCATION: (4)..(4)
<223> OTHER INFORMATION: 2'OMe modified
<220> FEATURE:
<221> NAME/KEY: misc_feature
<222> LOCATION: (10)..(10)
<223> OTHER INFORMATION: 2'OMe modified
<220> FEATURE:
<221> NAME/KEY: misc_feature
<222> LOCATION: (12)..(13)
<223> OTHER INFORMATION: 2'OMe modified
<220> FEATURE:
<221> NAME/KEY: misc_feature
<222> LOCATION: (12)..(13)
<223> OTHER INFORMATION: Phosphodiester linkage

<400> SEQUENCE: 57
agguggaaau gaa                                                              13

<210> SEQ ID NO 58
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(2)
<223> OTHER INFORMATION: 2'OMe modified
<220> FEATURE:
<221> NAME/KEY: misc_feature
<222> LOCATION: (1)..(12)
<223> OTHER INFORMATION: Phosphorothioate linkage
```

```
<220> FEATURE:
<221> NAME/KEY: misc_feature
<222> LOCATION: (4)..(4)
<223> OTHER INFORMATION: 2'OMe modified
<220> FEATURE:
<221> NAME/KEY: misc_feature
<222> LOCATION: (10)..(10)
<223> OTHER INFORMATION: 2'OMe modified
<220> FEATURE:
<221> NAME/KEY: misc_feature
<222> LOCATION: (12)..(13)
<223> OTHER INFORMATION: 2'OMe modified
<220> FEATURE:
<221> NAME/KEY: misc_feature
<222> LOCATION: (12)..(13)
<223> OTHER INFORMATION: Phosphodiester linkage

<400> SEQUENCE: 58
agguggaaau gaa                                                              13

<210> SEQ ID NO 59
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(2)
<223> OTHER INFORMATION: 2'OMe modified
<220> FEATURE:
<221> NAME/KEY: misc_feature
<222> LOCATION: (1)..(12)
<223> OTHER INFORMATION: Phosphorothioate linkage
<220> FEATURE:
<221> NAME/KEY: misc_feature
<222> LOCATION: (4)..(4)
<223> OTHER INFORMATION: 2'OMe modified
<220> FEATURE:
<221> NAME/KEY: misc_feature
<222> LOCATION: (10)..(10)
<223> OTHER INFORMATION: 2'OMe modified
<220> FEATURE:
<221> NAME/KEY: misc_feature
<222> LOCATION: (12)..(13)
<223> OTHER INFORMATION: 2'OMe modified
<220> FEATURE:
<221> NAME/KEY: misc_feature
<222> LOCATION: (12)..(13)
<223> OTHER INFORMATION: Phosphodiester linkage

<400> SEQUENCE: 59
agguggaaau gaa                                                              13

<210> SEQ ID NO 60
<211> LENGTH: 21
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: 5' Phosphate modified
<220> FEATURE:
<221> NAME/KEY: misc_feature
<222> LOCATION: (1)..(1)
<223> OTHER INFORMATION: 2'OMe modified
<220> FEATURE:
<221> NAME/KEY: misc_feature
<222> LOCATION: (1)..(20)
<223> OTHER INFORMATION: Phosphorothioate linkage
<220> FEATURE:
<221> NAME/KEY: misc_feature
<222> LOCATION: (4)..(4)
```

```
<223> OTHER INFORMATION: 2'Fluoro modified
<220> FEATURE:
<221> NAME/KEY: misc_feature
<222> LOCATION: (6)..(6)
<223> OTHER INFORMATION: 2'Fluoro modified
<220> FEATURE:
<221> NAME/KEY: misc_feature
<222> LOCATION: (8)..(12)
<223> OTHER INFORMATION: 2'Fluoro modified
<220> FEATURE:
<221> NAME/KEY: misc_feature
<222> LOCATION: (14)..(16)
<223> OTHER INFORMATION: 2'Fluoro modified
<220> FEATURE:
<221> NAME/KEY: misc_feature
<222> LOCATION: (18)..(20)
<223> OTHER INFORMATION: 2'Fluoro modified
<220> FEATURE:
<221> NAME/KEY: misc_feature
<222> LOCATION: (20)..(21)
<223> OTHER INFORMATION: Phosphodiester linkage

<400> SEQUENCE: 60
uaacaugccu cucuucaucc u                                              21

<210> SEQ ID NO 61
<211> LENGTH: 21
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: 5' Phosphate modified
<220> FEATURE:
<221> NAME/KEY: misc_feature
<222> LOCATION: (1)..(1)
<223> OTHER INFORMATION: 2'OMe modified
<220> FEATURE:
<221> NAME/KEY: misc_feature
<222> LOCATION: (1)..(13)
<223> OTHER INFORMATION: Phosphodiester linkage
<220> FEATURE:
<221> NAME/KEY: misc_feature
<222> LOCATION: (4)..(4)
<223> OTHER INFORMATION: 2'Fluoro modified
<220> FEATURE:
<221> NAME/KEY: misc_feature
<222> LOCATION: (6)..(6)
<223> OTHER INFORMATION: 2'Fluoro modified
<220> FEATURE:
<221> NAME/KEY: misc_feature
<222> LOCATION: (8)..(16)
<223> OTHER INFORMATION: 2'Fluoro modified
<220> FEATURE:
<221> NAME/KEY: misc_feature
<222> LOCATION: (13)..(20)
<223> OTHER INFORMATION: Phosphorothioate linkage
<220> FEATURE:
<221> NAME/KEY: misc_feature
<222> LOCATION: (18)..(20)
<223> OTHER INFORMATION: 2'Fluoro modified
<220> FEATURE:
<221> NAME/KEY: misc_feature
<222> LOCATION: (20)..(21)
<223> OTHER INFORMATION: Phosphodiester linkage

<400> SEQUENCE: 61
uaacaugccu cucuucaucc u                                              21

<210> SEQ ID NO 62
<211> LENGTH: 19
<212> TYPE: RNA
<213> ORGANISM: Artificial Sequence
```

-continued

```
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: 5' Phosphate modified
<220> FEATURE:
<221> NAME/KEY: misc_feature
<222> LOCATION: (1)..(1)
<223> OTHER INFORMATION: 2'OMe modified
<220> FEATURE:
<221> NAME/KEY: misc_feature
<222> LOCATION: (1)..(13)
<223> OTHER INFORMATION: Phosphodiester linkage
<220> FEATURE:
<221> NAME/KEY: misc_feature
<222> LOCATION: (4)..(4)
<223> OTHER INFORMATION: 2'Fluoro modified
<220> FEATURE:
<221> NAME/KEY: misc_feature
<222> LOCATION: (6)..(6)
<223> OTHER INFORMATION: 2'Fluoro modified
<220> FEATURE:
<221> NAME/KEY: misc_feature
<222> LOCATION: (8)..(16)
<223> OTHER INFORMATION: 2'Fluoro modified
<220> FEATURE:
<221> NAME/KEY: misc_feature
<222> LOCATION: (13)..(18)
<223> OTHER INFORMATION: Phosphorothioate linkage
<220> FEATURE:
<221> NAME/KEY: misc_feature
<222> LOCATION: (18)..(18)
<223> OTHER INFORMATION: 2'Fluoro modified
<220> FEATURE:
<221> NAME/KEY: misc_feature
<222> LOCATION: (18)..(19)
<223> OTHER INFORMATION: Phosphodiester linkage

<400> SEQUENCE: 62
uaacaugccu cucuucauc                                               19

<210> SEQ ID NO 63
<211> LENGTH: 21
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: 5' Phosphate modified
<220> FEATURE:
<221> NAME/KEY: misc_feature
<222> LOCATION: (1)..(1)
<223> OTHER INFORMATION: 2'OMe modified
<220> FEATURE:
<221> NAME/KEY: misc_feature
<222> LOCATION: (1)..(13)
<223> OTHER INFORMATION: Phosphodiester linkage
<220> FEATURE:
<221> NAME/KEY: misc_feature
<222> LOCATION: (4)..(4)
<223> OTHER INFORMATION: 2'Fluoro modified
<220> FEATURE:
<221> NAME/KEY: misc_feature
<222> LOCATION: (6)..(6)
<223> OTHER INFORMATION: 2'Fluoro modified
<220> FEATURE:
<221> NAME/KEY: misc_feature
<222> LOCATION: (8)..(16)
<223> OTHER INFORMATION: 2'Fluoro modified
<220> FEATURE:
<221> NAME/KEY: misc_feature
<222> LOCATION: (13)..(20)
<223> OTHER INFORMATION: Phosphorothioate linkage
<220> FEATURE:
```

<221> NAME/KEY: misc_feature
<222> LOCATION: (18)..(20)
<223> OTHER INFORMATION: 2'Fluoro modified
<220> FEATURE:
<221> NAME/KEY: misc_feature
<222> LOCATION: (20)..(21)
<223> OTHER INFORMATION: Phosphodiester linkage

<400> SEQUENCE: 63
uaacaugccu cucuucaucc u                                              21

<210> SEQ ID NO 64
<211> LENGTH: 21
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: 5' Phosphate modified
<220> FEATURE:
<221> NAME/KEY: misc_feature
<222> LOCATION: (1)..(1)
<223> OTHER INFORMATION: 2'OMe modified
<220> FEATURE:
<221> NAME/KEY: misc_feature
<222> LOCATION: (1)..(20)
<223> OTHER INFORMATION: Phosphorothioate linkage
<220> FEATURE:
<221> NAME/KEY: misc_feature
<222> LOCATION: (4)..(4)
<223> OTHER INFORMATION: 2'Fluoro modified
<220> FEATURE:
<221> NAME/KEY: misc_feature
<222> LOCATION: (6)..(6)
<223> OTHER INFORMATION: 2'Fluoro modified
<220> FEATURE:
<221> NAME/KEY: misc_feature
<222> LOCATION: (8)..(12)
<223> OTHER INFORMATION: 2'Fluoro modified
<220> FEATURE:
<221> NAME/KEY: misc_feature
<222> LOCATION: (14)..(16)
<223> OTHER INFORMATION: 2'Fluoro modified
<220> FEATURE:
<221> NAME/KEY: misc_feature
<222> LOCATION: (18)..(20)
<223> OTHER INFORMATION: 2'Fluoro modified
<220> FEATURE:
<221> NAME/KEY: misc_feature
<222> LOCATION: (20)..(21)
<223> OTHER INFORMATION: Phosphodiester linkage

<400> SEQUENCE: 64
uaacaugccu cucuucaucc u                                              21

<210> SEQ ID NO 65
<211> LENGTH: 21
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: 5' Phosphate modified
<220> FEATURE:
<221> NAME/KEY: misc_feature
<222> LOCATION: (1)..(1)
<223> OTHER INFORMATION: 2'OMe modified
<220> FEATURE:
<221> NAME/KEY: misc_feature
<222> LOCATION: (1)..(13)
<223> OTHER INFORMATION: Phosphodiester linkage

```
<220> FEATURE:
<221> NAME/KEY: misc_feature
<222> LOCATION: (4)..(4)
<223> OTHER INFORMATION: 2'Fluoro modified
<220> FEATURE:
<221> NAME/KEY: misc_feature
<222> LOCATION: (6)..(6)
<223> OTHER INFORMATION: 2'Fluoro modified
<220> FEATURE:
<221> NAME/KEY: misc_feature
<222> LOCATION: (8)..(16)
<223> OTHER INFORMATION: 2'Fluoro modified
<220> FEATURE:
<221> NAME/KEY: misc_feature
<222> LOCATION: (13)..(20)
<223> OTHER INFORMATION: Phosphorothioate linkage
<220> FEATURE:
<221> NAME/KEY: misc_feature
<222> LOCATION: (18)..(20)
<223> OTHER INFORMATION: 2'Fluoro modified
<220> FEATURE:
<221> NAME/KEY: misc_feature
<222> LOCATION: (20)..(21)
<223> OTHER INFORMATION: Phosphodiester linkage

<400> SEQUENCE: 65
uaacaugccu cucuucaucc u                                           21

<210> SEQ ID NO 66
<211> LENGTH: 19
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: 5' Phosphate modified
<220> FEATURE:
<221> NAME/KEY: misc_feature
<222> LOCATION: (1)..(1)
<223> OTHER INFORMATION: 2'OMe modified
<220> FEATURE:
<221> NAME/KEY: misc_feature
<222> LOCATION: (1)..(18)
<223> OTHER INFORMATION: Phosphorothioate linkage
<220> FEATURE:
<221> NAME/KEY: misc_feature
<222> LOCATION: (4)..(4)
<223> OTHER INFORMATION: 2'Fluoro modified
<220> FEATURE:
<221> NAME/KEY: misc_feature
<222> LOCATION: (6)..(6)
<223> OTHER INFORMATION: 2'Fluoro modified
<220> FEATURE:
<221> NAME/KEY: misc_feature
<222> LOCATION: (8)..(16)
<223> OTHER INFORMATION: 2'Fluoro modified
<220> FEATURE:
<221> NAME/KEY: misc_feature
<222> LOCATION: (18)..(18)
<223> OTHER INFORMATION: 2'Fluoro modified
<220> FEATURE:
<221> NAME/KEY: misc_feature
<222> LOCATION: (18)..(19)
<223> OTHER INFORMATION: Phosphodiester linkage

<400> SEQUENCE: 66
uaacaugccu cucuucauc                                              19

<210> SEQ ID NO 67
<211> LENGTH: 19
<212> TYPE: RNA
<213> ORGANISM: Artificial Sequence
<220> FEATURE:
```

```
<223> OTHER INFORMATION: Synthetic Polynucleotide
<220> FEATURE:
<221> NAME/KEY: misc_feature
<222> LOCATION: (1)..(1)
<223> OTHER INFORMATION: 5' Phosphate modified
<220> FEATURE:
<221> NAME/KEY: misc_feature
<222> LOCATION: (1)..(1)
<223> OTHER INFORMATION: 2'OMe modified
<220> FEATURE:
<221> NAME/KEY: misc_feature
<222> LOCATION: (1)..(18)
<223> OTHER INFORMATION: Phosphorothioate linkage
<220> FEATURE:
<221> NAME/KEY: misc_feature
<222> LOCATION: (4)..(4)
<223> OTHER INFORMATION: 2'Fluoro modified
<220> FEATURE:
<221> NAME/KEY: misc_feature
<222> LOCATION: (6)..(6)
<223> OTHER INFORMATION: 2'Fluoro modified
<220> FEATURE:
<221> NAME/KEY: misc_feature
<222> LOCATION: (8)..(16)
<223> OTHER INFORMATION: 2'Fluoro modified
<220> FEATURE:
<221> NAME/KEY: misc_feature
<222> LOCATION: (18)..(18)
<223> OTHER INFORMATION: 2'Fluoro modified
<220> FEATURE:
<221> NAME/KEY: misc_feature
<222> LOCATION: (18)..(19)
<223> OTHER INFORMATION: Phosphodiester linkage

<400> SEQUENCE: 67
uaacaugccu cucuucauc                                                    19

<210> SEQ ID NO 68
<211> LENGTH: 21
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: 5' Phosphate modified
<220> FEATURE:
<221> NAME/KEY: misc_feature
<222> LOCATION: (1)..(1)
<223> OTHER INFORMATION: 2'OMe modified
<220> FEATURE:
<221> NAME/KEY: misc_feature
<222> LOCATION: (1)..(20)
<223> OTHER INFORMATION: Phosphorothioate linkage
<220> FEATURE:
<221> NAME/KEY: misc_feature
<222> LOCATION: (4)..(4)
<223> OTHER INFORMATION: 2'Fluoro modified
<220> FEATURE:
<221> NAME/KEY: misc_feature
<222> LOCATION: (6)..(6)
<223> OTHER INFORMATION: 2'Fluoro modified
<220> FEATURE:
<221> NAME/KEY: misc_feature
<222> LOCATION: (8)..(16)
<223> OTHER INFORMATION: 2'Fluoro modified
<220> FEATURE:
<221> NAME/KEY: misc_feature
<222> LOCATION: (18)..(20)
<223> OTHER INFORMATION: 2'Fluoro modified
<220> FEATURE:
<221> NAME/KEY: misc_feature
<222> LOCATION: (20)..(21)
<223> OTHER INFORMATION: Phosphodiester linkage

<400> SEQUENCE: 68
```
uaacaugccu cucuucaucc u                                              21

<210> SEQ ID NO 69
<211> LENGTH: 21
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: 5' Phosphate modified
<220> FEATURE:
<221> NAME/KEY: misc_feature
<222> LOCATION: (1)..(1)
<223> OTHER INFORMATION: 2'OMe modified
<220> FEATURE:
<221> NAME/KEY: misc_feature
<222> LOCATION: (1)..(20)
<223> OTHER INFORMATION: Phosphorothioate linkage
<220> FEATURE:
<221> NAME/KEY: misc_feature
<222> LOCATION: (4)..(4)
<223> OTHER INFORMATION: 2'Fluoro modified
<220> FEATURE:
<221> NAME/KEY: misc_feature
<222> LOCATION: (6)..(6)
<223> OTHER INFORMATION: 2'Fluoro modified
<220> FEATURE:
<221> NAME/KEY: misc_feature
<222> LOCATION: (8)..(12)
<223> OTHER INFORMATION: 2'Fluoro modified
<220> FEATURE:
<221> NAME/KEY: misc_feature
<222> LOCATION: (14)..(16)
<223> OTHER INFORMATION: 2'Fluoro modified
<220> FEATURE:
<221> NAME/KEY: misc_feature
<222> LOCATION: (18)..(20)
<223> OTHER INFORMATION: 2'Fluoro modified
<220> FEATURE:
<221> NAME/KEY: misc_feature
<222> LOCATION: (20)..(21)
<223> OTHER INFORMATION: Phosphodiester linkage

<400> SEQUENCE: 69
uaacaugccu cucuucaucc u                                              21

<210> SEQ ID NO 70
<211> LENGTH: 21
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: 5' Phosphate modified
<220> FEATURE:
<221> NAME/KEY: misc_feature
<222> LOCATION: (1)..(1)
<223> OTHER INFORMATION: 2'OMe modified
<220> FEATURE:
<221> NAME/KEY: misc_feature
<222> LOCATION: (1)..(20)
<223> OTHER INFORMATION: Phosphorothioate linkage
<220> FEATURE:
<221> NAME/KEY: misc_feature
<222> LOCATION: (2)..(3)
<223> OTHER INFORMATION: 2'Fluoro modified
<220> FEATURE:
<221> NAME/KEY: misc_feature
<222> LOCATION: (5)..(9)
<223> OTHER INFORMATION: 2'Fluoro modified
<220> FEATURE:

```
<221> NAME/KEY: misc_feature
<222> LOCATION: (11)..(11)
<223> OTHER INFORMATION: 2'Fluoro modified
<220> FEATURE:
<221> NAME/KEY: misc_feature
<222> LOCATION: (12)..(15)
<223> OTHER INFORMATION: 2'OMe modified
<220> FEATURE:
<221> NAME/KEY: misc_feature
<222> LOCATION: (17)..(18)
<223> OTHER INFORMATION: 2'OMe modified
<220> FEATURE:
<221> NAME/KEY: misc_feature
<222> LOCATION: (19)..(19)
<223> OTHER INFORMATION: 2'Fluoro modified
<220> FEATURE:
<221> NAME/KEY: misc_feature
<222> LOCATION: (20)..(21)
<223> OTHER INFORMATION: Phosphodiester linkage

<400> SEQUENCE: 70
uucauuucca ccuuugccca a                                              21

<210> SEQ ID NO 71
<211> LENGTH: 21
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: 5' Phosphate modified
<220> FEATURE:
<221> NAME/KEY: misc_feature
<222> LOCATION: (1)..(1)
<223> OTHER INFORMATION: 2'OMe modified
<220> FEATURE:
<221> NAME/KEY: misc_feature
<222> LOCATION: (1)..(20)
<223> OTHER INFORMATION: Phosphorothioate linkage
<220> FEATURE:
<221> NAME/KEY: misc_feature
<222> LOCATION: (2)..(3)
<223> OTHER INFORMATION: 2'Fluoro modified
<220> FEATURE:
<221> NAME/KEY: misc_feature
<222> LOCATION: (5)..(9)
<223> OTHER INFORMATION: 2'Fluoro modified
<220> FEATURE:
<221> NAME/KEY: misc_feature
<222> LOCATION: (11)..(11)
<223> OTHER INFORMATION: 2'Fluoro modified
<220> FEATURE:
<221> NAME/KEY: misc_feature
<222> LOCATION: (12)..(15)
<223> OTHER INFORMATION: 2'OMe modified
<220> FEATURE:
<221> NAME/KEY: misc_feature
<222> LOCATION: (17)..(18)
<223> OTHER INFORMATION: 2'OMe modified
<220> FEATURE:
<221> NAME/KEY: misc_feature
<222> LOCATION: (19)..(19)
<223> OTHER INFORMATION: 2'Fluoro modified
<220> FEATURE:
<221> NAME/KEY: misc_feature
<222> LOCATION: (20)..(21)
<223> OTHER INFORMATION: Phosphodiester linkage

<400> SEQUENCE: 71
uucauuucca ccuuugccca a                                              21

<210> SEQ ID NO 72
<211> LENGTH: 21
```

```
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: 5' Phosphate modified
<220> FEATURE:
<221> NAME/KEY: misc_feature
<222> LOCATION: (1)..(1)
<223> OTHER INFORMATION: 2'OMe modified
<220> FEATURE:
<221> NAME/KEY: misc_feature
<222> LOCATION: (1)..(20)
<223> OTHER INFORMATION: Phosphorothioate linkage
<220> FEATURE:
<221> NAME/KEY: misc_feature
<222> LOCATION: (2)..(3)
<223> OTHER INFORMATION: 2'Fluoro modified
<220> FEATURE:
<221> NAME/KEY: misc_feature
<222> LOCATION: (5)..(9)
<223> OTHER INFORMATION: 2'Fluoro modified
<220> FEATURE:
<221> NAME/KEY: misc_feature
<222> LOCATION: (11)..(11)
<223> OTHER INFORMATION: 2'Fluoro modified
<220> FEATURE:
<221> NAME/KEY: misc_feature
<222> LOCATION: (12)..(15)
<223> OTHER INFORMATION: 2'OMe modified
<220> FEATURE:
<221> NAME/KEY: misc_feature
<222> LOCATION: (17)..(18)
<223> OTHER INFORMATION: 2'OMe modified
<220> FEATURE:
<221> NAME/KEY: misc_feature
<222> LOCATION: (19)..(19)
<223> OTHER INFORMATION: 2'Fluoro modified
<220> FEATURE:
<221> NAME/KEY: misc_feature
<222> LOCATION: (20)..(21)
<223> OTHER INFORMATION: Phosphodiester linkage

<400> SEQUENCE: 72
uucauuucca ccuuugccca a                                            21

<210> SEQ ID NO 73
<211> LENGTH: 21
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: 5' Phosphate modified
<220> FEATURE:
<221> NAME/KEY: misc_feature
<222> LOCATION: (1)..(1)
<223> OTHER INFORMATION: 2'OMe modified
<220> FEATURE:
<221> NAME/KEY: misc_feature
<222> LOCATION: (1)..(20)
<223> OTHER INFORMATION: Phosphorothioate linkage
<220> FEATURE:
<221> NAME/KEY: misc_feature
<222> LOCATION: (2)..(3)
<223> OTHER INFORMATION: 2'Fluoro modified
<220> FEATURE:
<221> NAME/KEY: misc_feature
<222> LOCATION: (5)..(9)
<223> OTHER INFORMATION: 2'Fluoro modified
<220> FEATURE:
<221> NAME/KEY: misc_feature
<222> LOCATION: (11)..(11)
```

```
<223> OTHER INFORMATION: 2'Fluoro modified
<220> FEATURE:
<221> NAME/KEY: misc_feature
<222> LOCATION: (12)..(15)
<223> OTHER INFORMATION: 2'OMe modified
<220> FEATURE:
<221> NAME/KEY: misc_feature
<222> LOCATION: (17)..(18)
<223> OTHER INFORMATION: 2'OMe modified
<220> FEATURE:
<221> NAME/KEY: misc_feature
<222> LOCATION: (19)..(19)
<223> OTHER INFORMATION: 2'Fluoro modified
<220> FEATURE:
<221> NAME/KEY: misc_feature
<222> LOCATION: (20)..(21)
<223> OTHER INFORMATION: Phosphodiester linkage

<400> SEQUENCE: 73
uucauuucca ccuuugccca a                                              21

<210> SEQ ID NO 74
<211> LENGTH: 21
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: 5-methyl modified
<220> FEATURE:
<221> NAME/KEY: misc_feature
<222> LOCATION: (1)..(1)
<223> OTHER INFORMATION: 5' Phosphate modified
<220> FEATURE:
<221> NAME/KEY: misc_feature
<222> LOCATION: (1)..(1)
<223> OTHER INFORMATION: 2'OMe modified
<220> FEATURE:
<221> NAME/KEY: misc_feature
<222> LOCATION: (1)..(20)
<223> OTHER INFORMATION: Phosphorothioate linkage
<220> FEATURE:
<221> NAME/KEY: misc_feature
<222> LOCATION: (2)..(2)
<223> OTHER INFORMATION: Octyl modified
<220> FEATURE:
<221> NAME/KEY: misc_feature
<222> LOCATION: (2)..(3)
<223> OTHER INFORMATION: 2'Fluoro modified
<220> FEATURE:
<221> NAME/KEY: misc_feature
<222> LOCATION: (3)..(3)
<223> OTHER INFORMATION: 5-methyl modified
<220> FEATURE:
<221> NAME/KEY: misc_feature
<222> LOCATION: (5)..(6)
<223> OTHER INFORMATION: 5-methyl modified
<220> FEATURE:
<221> NAME/KEY: misc_feature
<222> LOCATION: (5)..(9)
<223> OTHER INFORMATION: 2'Fluoro modified
<220> FEATURE:
<221> NAME/KEY: misc_feature
<222> LOCATION: (7)..(7)
<223> OTHER INFORMATION: Octyl modified
<220> FEATURE:
<221> NAME/KEY: misc_feature
<222> LOCATION: (8)..(9)
<223> OTHER INFORMATION: 5-methyl modified
<220> FEATURE:
<221> NAME/KEY: misc_feature
<222> LOCATION: (11)..(11)
<223> OTHER INFORMATION: 2'Fluoro modified
<220> FEATURE:
<221> NAME/KEY: misc_feature
```

```
<222> LOCATION: (11)..(12)
<223> OTHER INFORMATION: 5-methyl modified
<220> FEATURE:
<221> NAME/KEY: misc_feature
<222> LOCATION: (12)..(15)
<223> OTHER INFORMATION: 2'OMe modified
<220> FEATURE:
<221> NAME/KEY: misc_feature
<222> LOCATION: (13)..(13)
<223> OTHER INFORMATION: Octyl modified
<220> FEATURE:
<221> NAME/KEY: misc_feature
<222> LOCATION: (14)..(15)
<223> OTHER INFORMATION: 5-methyl modified
<220> FEATURE:
<221> NAME/KEY: misc_feature
<222> LOCATION: (17)..(18)
<223> OTHER INFORMATION: 2'OMe modified
<220> FEATURE:
<221> NAME/KEY: misc_feature
<222> LOCATION: (17)..(19)
<223> OTHER INFORMATION: 5-methyl modified
<220> FEATURE:
<221> NAME/KEY: misc_feature
<222> LOCATION: (19)..(19)
<223> OTHER INFORMATION: 2'Fluoro modified
<220> FEATURE:
<221> NAME/KEY: misc_feature
<222> LOCATION: (20)..(21)
<223> OTHER INFORMATION: Phosphodiester linkage

<400> SEQUENCE: 74
uucauuucca ccuuugccca a                                             21

<210> SEQ ID NO 75
<211> LENGTH: 21
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: 5' Phosphate modified
<220> FEATURE:
<221> NAME/KEY: misc_feature
<222> LOCATION: (1)..(1)
<223> OTHER INFORMATION: 2'OMe modified
<220> FEATURE:
<221> NAME/KEY: misc_feature
<222> LOCATION: (1)..(2)
<223> OTHER INFORMATION: 5-methyl modified
<220> FEATURE:
<221> NAME/KEY: misc_feature
<222> LOCATION: (1)..(20)
<223> OTHER INFORMATION: Phosphorothioate linkage
<220> FEATURE:
<221> NAME/KEY: misc_feature
<222> LOCATION: (2)..(3)
<223> OTHER INFORMATION: 2'Fluoro modified
<220> FEATURE:
<221> NAME/KEY: misc_feature
<222> LOCATION: (3)..(3)
<223> OTHER INFORMATION: Octyl modified
<220> FEATURE:
<221> NAME/KEY: misc_feature
<222> LOCATION: (5)..(6)
<223> OTHER INFORMATION: 5-methyl modified
<220> FEATURE:
<221> NAME/KEY: misc_feature
<222> LOCATION: (5)..(9)
<223> OTHER INFORMATION: 2'Fluoro modified
<220> FEATURE:
<221> NAME/KEY: misc_feature
<222> LOCATION: (7)..(7)
<223> OTHER INFORMATION: Octyl modified
<220> FEATURE:
```

```
<221> NAME/KEY: misc_feature
<222> LOCATION: (8)..(9)
<223> OTHER INFORMATION: 5-methyl modified
<220> FEATURE:
<221> NAME/KEY: misc_feature
<222> LOCATION: (11)..(11)
<223> OTHER INFORMATION: 2'Fluoro modified
<220> FEATURE:
<221> NAME/KEY: misc_feature
<222> LOCATION: (11)..(12)
<223> OTHER INFORMATION: 5-methyl modified
<220> FEATURE:
<221> NAME/KEY: misc_feature
<222> LOCATION: (12)..(15)
<223> OTHER INFORMATION: 2'OMe modified
<220> FEATURE:
<221> NAME/KEY: misc_feature
<222> LOCATION: (13)..(13)
<223> OTHER INFORMATION: Octyl modified
<220> FEATURE:
<221> NAME/KEY: misc_feature
<222> LOCATION: (14)..(15)
<223> OTHER INFORMATION: 5-methyl modified
<220> FEATURE:
<221> NAME/KEY: misc_feature
<222> LOCATION: (17)..(18)
<223> OTHER INFORMATION: 2'OMe modified
<220> FEATURE:
<221> NAME/KEY: misc_feature
<222> LOCATION: (17)..(19)
<223> OTHER INFORMATION: 5-methyl modified
<220> FEATURE:
<221> NAME/KEY: misc_feature
<222> LOCATION: (19)..(19)
<223> OTHER INFORMATION: 2'Fluoro modified
<220> FEATURE:
<221> NAME/KEY: misc_feature
<222> LOCATION: (20)..(21)
<223> OTHER INFORMATION: Phosphodiester linkage

<400> SEQUENCE: 75
uucauuucca ccuuugccca a                                        21

<210> SEQ ID NO 76
<211> LENGTH: 21
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: 5' Phosphate modified
<220> FEATURE:
<221> NAME/KEY: misc_feature
<222> LOCATION: (1)..(1)
<223> OTHER INFORMATION: 2'OMe modified
<220> FEATURE:
<221> NAME/KEY: misc_feature
<222> LOCATION: (1)..(1)
<223> OTHER INFORMATION: 5-methyl modified
<220> FEATURE:
<221> NAME/KEY: misc_feature
<222> LOCATION: (1)..(20)
<223> OTHER INFORMATION: Phosphorothioate linkage
<220> FEATURE:
<221> NAME/KEY: misc_feature
<222> LOCATION: (2)..(2)
<223> OTHER INFORMATION: Octyl modified
<220> FEATURE:
<221> NAME/KEY: misc_feature
<222> LOCATION: (2)..(3)
<223> OTHER INFORMATION: 2'Fluoro modified
<220> FEATURE:
<221> NAME/KEY: misc_feature
<222> LOCATION: (3)..(3)
<223> OTHER INFORMATION: 5-methyl modified
```

```
<220> FEATURE:
<221> NAME/KEY: misc_feature
<222> LOCATION: (5)..(9)
<223> OTHER INFORMATION: 5-methyl modified
<220> FEATURE:
<221> NAME/KEY: misc_feature
<222> LOCATION: (5)..(9)
<223> OTHER INFORMATION: 2'Fluoro modified
<220> FEATURE:
<221> NAME/KEY: misc_feature
<222> LOCATION: (11)..(11)
<223> OTHER INFORMATION: 2'Fluoro modified
<220> FEATURE:
<221> NAME/KEY: misc_feature
<222> LOCATION: (11)..(12)
<223> OTHER INFORMATION: 5-methyl modified
<220> FEATURE:
<221> NAME/KEY: misc_feature
<222> LOCATION: (12)..(15)
<223> OTHER INFORMATION: 2'OMe modified
<220> FEATURE:
<221> NAME/KEY: misc_feature
<222> LOCATION: (13)..(13)
<223> OTHER INFORMATION: Octyl modified
<220> FEATURE:
<221> NAME/KEY: misc_feature
<222> LOCATION: (14)..(15)
<223> OTHER INFORMATION: 5-methyl modified
<220> FEATURE:
<221> NAME/KEY: misc_feature
<222> LOCATION: (17)..(18)
<223> OTHER INFORMATION: 2'OMe modified
<220> FEATURE:
<221> NAME/KEY: misc_feature
<222> LOCATION: (17)..(19)
<223> OTHER INFORMATION: 5-methyl modified
<220> FEATURE:
<221> NAME/KEY: misc_feature
<222> LOCATION: (19)..(19)
<223> OTHER INFORMATION: 2'Fluoro modified
<220> FEATURE:
<221> NAME/KEY: misc_feature
<222> LOCATION: (20)..(21)
<223> OTHER INFORMATION: Phosphodiester linkage

<400> SEQUENCE: 76
uucauuucca ccuuugccca a                                              21

<210> SEQ ID NO 77
<211> LENGTH: 21
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: 5' Phosphate modified
<220> FEATURE:
<221> NAME/KEY: misc_feature
<222> LOCATION: (1)..(1)
<223> OTHER INFORMATION: 2'OMe modified
<220> FEATURE:
<221> NAME/KEY: misc_feature
<222> LOCATION: (1)..(1)
<223> OTHER INFORMATION: 5-methyl modified
<220> FEATURE:
<221> NAME/KEY: misc_feature
<222> LOCATION: (1)..(20)
<223> OTHER INFORMATION: Phosphorothioate linkage
<220> FEATURE:
<221> NAME/KEY: misc_feature
<222> LOCATION: (2)..(2)
<223> OTHER INFORMATION: Octyl modified
<220> FEATURE:
<221> NAME/KEY: misc_feature
<222> LOCATION: (2)..(3)
```

```
<223> OTHER INFORMATION: 2'Fluoro modified
<220> FEATURE:
<221> NAME/KEY: misc_feature
<222> LOCATION: (3)..(3)
<223> OTHER INFORMATION: 5-methyl modified
<220> FEATURE:
<221> NAME/KEY: misc_feature
<222> LOCATION: (5)..(6)
<223> OTHER INFORMATION: 5-methyl modified
<220> FEATURE:
<221> NAME/KEY: misc_feature
<222> LOCATION: (5)..(9)
<223> OTHER INFORMATION: 2'Fluoro modified
<220> FEATURE:
<221> NAME/KEY: misc_feature
<222> LOCATION: (7)..(7)
<223> OTHER INFORMATION: Octyl modified
<220> FEATURE:
<221> NAME/KEY: misc_feature
<222> LOCATION: (8)..(9)
<223> OTHER INFORMATION: 5-methyl modified
<220> FEATURE:
<221> NAME/KEY: misc_feature
<222> LOCATION: (11)..(11)
<223> OTHER INFORMATION: 2'Fluoro modified
<220> FEATURE:
<221> NAME/KEY: misc_feature
<222> LOCATION: (11)..(15)
<223> OTHER INFORMATION: 5-methyl modified
<220> FEATURE:
<221> NAME/KEY: misc_feature
<222> LOCATION: (12)..(15)
<223> OTHER INFORMATION: 2'OMe modified
<220> FEATURE:
<221> NAME/KEY: misc_feature
<222> LOCATION: (17)..(18)
<223> OTHER INFORMATION: 2'OMe modified
<220> FEATURE:
<221> NAME/KEY: misc_feature
<222> LOCATION: (17)..(19)
<223> OTHER INFORMATION: 5-methyl modified
<220> FEATURE:
<221> NAME/KEY: misc_feature
<222> LOCATION: (19)..(19)
<223> OTHER INFORMATION: 2'Fluoro modified
<220> FEATURE:
<221> NAME/KEY: misc_feature
<222> LOCATION: (20)..(21)
<223> OTHER INFORMATION: Phosphodiester linkage

<400> SEQUENCE: 77
uucauuucca ccuuugccca a                                                   21

<210> SEQ ID NO 78
<211> LENGTH: 21
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: 5' Phosphate modified
<220> FEATURE:
<221> NAME/KEY: misc_feature
<222> LOCATION: (1)..(1)
<223> OTHER INFORMATION: 2'OMe modified
<220> FEATURE:
<221> NAME/KEY: misc_feature
<222> LOCATION: (1)..(3)
<223> OTHER INFORMATION: 5-methyl modified
<220> FEATURE:
<221> NAME/KEY: misc_feature
<222> LOCATION: (1)..(20)
<223> OTHER INFORMATION: Phosphorothioate linkage
<220> FEATURE:
<221> NAME/KEY: misc_feature
```

```
<222> LOCATION: (2)..(3)
<223> OTHER INFORMATION: 2'Fluoro modified
<220> FEATURE:
<221> NAME/KEY: misc_feature
<222> LOCATION: (5)..(9)
<223> OTHER INFORMATION: 5-methyl modified
<220> FEATURE:
<221> NAME/KEY: misc_feature
<222> LOCATION: (5)..(9)
<223> OTHER INFORMATION: 2'Fluoro modified
<220> FEATURE:
<221> NAME/KEY: misc_feature
<222> LOCATION: (11)..(11)
<223> OTHER INFORMATION: 2'Fluoro modified
<220> FEATURE:
<221> NAME/KEY: misc_feature
<222> LOCATION: (11)..(15)
<223> OTHER INFORMATION: 5-methyl modified
<220> FEATURE:
<221> NAME/KEY: misc_feature
<222> LOCATION: (12)..(15)
<223> OTHER INFORMATION: 2'OMe modified
<220> FEATURE:
<221> NAME/KEY: misc_feature
<222> LOCATION: (17)..(18)
<223> OTHER INFORMATION: 2'OMe modified
<220> FEATURE:
<221> NAME/KEY: misc_feature
<222> LOCATION: (17)..(19)
<223> OTHER INFORMATION: 5-methyl modified
<220> FEATURE:
<221> NAME/KEY: misc_feature
<222> LOCATION: (19)..(19)
<223> OTHER INFORMATION: 2'Fluoro modified
<220> FEATURE:
<221> NAME/KEY: misc_feature
<222> LOCATION: (20)..(21)
<223> OTHER INFORMATION: Phosphodiester linkage

<400> SEQUENCE: 78
uucauuucca ccuuugccca a                                      21

<210> SEQ ID NO 79
<211> LENGTH: 21
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: 5' Phosphate modified
<220> FEATURE:
<221> NAME/KEY: misc_feature
<222> LOCATION: (1)..(1)
<223> OTHER INFORMATION: 2'OMe modified
<220> FEATURE:
<221> NAME/KEY: misc_feature
<222> LOCATION: (1)..(20)
<223> OTHER INFORMATION: Phosphorothioate linkage
<220> FEATURE:
<221> NAME/KEY: misc_feature
<222> LOCATION: (2)..(3)
<223> OTHER INFORMATION: 2'Fluoro modified
<220> FEATURE:
<221> NAME/KEY: misc_feature
<222> LOCATION: (5)..(9)
<223> OTHER INFORMATION: 2'Fluoro modified
<220> FEATURE:
<221> NAME/KEY: misc_feature
<222> LOCATION: (11)..(11)
<223> OTHER INFORMATION: 2'Fluoro modified
<220> FEATURE:
<221> NAME/KEY: misc_feature
<222> LOCATION: (12)..(15)
<223> OTHER INFORMATION: 2'OMe modified
<220> FEATURE:
```

```
<221> NAME/KEY: misc_feature
<222> LOCATION: (17)..(18)
<223> OTHER INFORMATION: 2'OMe modified
<220> FEATURE:
<221> NAME/KEY: misc_feature
<222> LOCATION: (19)..(19)
<223> OTHER INFORMATION: 2'Fluoro modified
<220> FEATURE:
<221> NAME/KEY: misc_feature
<222> LOCATION: (20)..(21)
<223> OTHER INFORMATION: Phosphodiester linkage

<400> SEQUENCE: 79
uucauuucca ccuuugccca a                                              21

<210> SEQ ID NO 80
<211> LENGTH: 21
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: 5' Phosphate modified
<220> FEATURE:
<221> NAME/KEY: misc_feature
<222> LOCATION: (1)..(1)
<223> OTHER INFORMATION: 2'OMe modified
<220> FEATURE:
<221> NAME/KEY: misc_feature
<222> LOCATION: (1)..(20)
<223> OTHER INFORMATION: Phosphorothioate linkage
<220> FEATURE:
<221> NAME/KEY: misc_feature
<222> LOCATION: (2)..(3)
<223> OTHER INFORMATION: 2'Fluoro modified
<220> FEATURE:
<221> NAME/KEY: misc_feature
<222> LOCATION: (5)..(9)
<223> OTHER INFORMATION: 2'Fluoro modified
<220> FEATURE:
<221> NAME/KEY: misc_feature
<222> LOCATION: (11)..(11)
<223> OTHER INFORMATION: 2'Fluoro modified
<220> FEATURE:
<221> NAME/KEY: misc_feature
<222> LOCATION: (12)..(15)
<223> OTHER INFORMATION: 2'OMe modified
<220> FEATURE:
<221> NAME/KEY: misc_feature
<222> LOCATION: (17)..(18)
<223> OTHER INFORMATION: 2'OMe modified
<220> FEATURE:
<221> NAME/KEY: misc_feature
<222> LOCATION: (19)..(19)
<223> OTHER INFORMATION: 2'Fluoro modified
<220> FEATURE:
<221> NAME/KEY: misc_feature
<222> LOCATION: (20)..(21)
<223> OTHER INFORMATION: Phosphodiester linkage

<400> SEQUENCE: 80
uucauuucca ccuuugccca a                                              21

<210> SEQ ID NO 81
<211> LENGTH: 21
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: 5' Phosphate modified
```

```
<220> FEATURE:
<221> NAME/KEY: misc_feature
<222> LOCATION: (1)..(1)
<223> OTHER INFORMATION: 2'OMe modified
<220> FEATURE:
<221> NAME/KEY: misc_feature
<222> LOCATION: (1)..(20)
<223> OTHER INFORMATION: Phosphorothioate linkage
<220> FEATURE:
<221> NAME/KEY: misc_feature
<222> LOCATION: (2)..(3)
<223> OTHER INFORMATION: 2'Fluoro modified
<220> FEATURE:
<221> NAME/KEY: misc_feature
<222> LOCATION: (5)..(9)
<223> OTHER INFORMATION: 2'Fluoro modified
<220> FEATURE:
<221> NAME/KEY: misc_feature
<222> LOCATION: (11)..(11)
<223> OTHER INFORMATION: 2'Fluoro modified
<220> FEATURE:
<221> NAME/KEY: misc_feature
<222> LOCATION: (12)..(15)
<223> OTHER INFORMATION: 2'OMe modified
<220> FEATURE:
<221> NAME/KEY: misc_feature
<222> LOCATION: (17)..(18)
<223> OTHER INFORMATION: 2'OMe modified
<220> FEATURE:
<221> NAME/KEY: misc_feature
<222> LOCATION: (19)..(19)
<223> OTHER INFORMATION: 2'Fluoro modified
<220> FEATURE:
<221> NAME/KEY: misc_feature
<222> LOCATION: (20)..(21)
<223> OTHER INFORMATION: Phosphodiester linkage

<400> SEQUENCE: 81
uucauuucca ccuuugccca a                                          21

<210> SEQ ID NO 82
<211> LENGTH: 21
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: 5' Phosphate modified
<220> FEATURE:
<221> NAME/KEY: misc_feature
<222> LOCATION: (1)..(1)
<223> OTHER INFORMATION: 2'OMe modified
<220> FEATURE:
<221> NAME/KEY: misc_feature
<222> LOCATION: (1)..(1)
<223> OTHER INFORMATION: 5-methyl modified
<220> FEATURE:
<221> NAME/KEY: misc_feature
<222> LOCATION: (1)..(20)
<223> OTHER INFORMATION: Phosphorothioate linkage
<220> FEATURE:
<221> NAME/KEY: misc_feature
<222> LOCATION: (2)..(2)
<223> OTHER INFORMATION: Thiophene modified
<220> FEATURE:
<221> NAME/KEY: misc_feature
<222> LOCATION: (2)..(3)
<223> OTHER INFORMATION: 2'Fluoro modified
<220> FEATURE:
<221> NAME/KEY: misc_feature
<222> LOCATION: (3)..(3)
<223> OTHER INFORMATION: 5-methyl modified
<220> FEATURE:
<221> NAME/KEY: misc_feature
<222> LOCATION: (5)..(6)
```

```
<223> OTHER INFORMATION: 5-methyl modified
<220> FEATURE:
<221> NAME/KEY: misc_feature
<222> LOCATION: (5)..(9)
<223> OTHER INFORMATION: 2'Fluoro modified
<220> FEATURE:
<221> NAME/KEY: misc_feature
<222> LOCATION: (7)..(7)
<223> OTHER INFORMATION: Thiophene modified
<220> FEATURE:
<221> NAME/KEY: misc_feature
<222> LOCATION: (8)..(9)
<223> OTHER INFORMATION: 5-methyl modified
<220> FEATURE:
<221> NAME/KEY: misc_feature
<222> LOCATION: (11)..(11)
<223> OTHER INFORMATION: 2'Fluoro modified
<220> FEATURE:
<221> NAME/KEY: misc_feature
<222> LOCATION: (11)..(15)
<223> OTHER INFORMATION: 5-methyl modified
<220> FEATURE:
<221> NAME/KEY: misc_feature
<222> LOCATION: (12)..(15)
<223> OTHER INFORMATION: 2'OMe modified
<220> FEATURE:
<221> NAME/KEY: misc_feature
<222> LOCATION: (17)..(18)
<223> OTHER INFORMATION: 2'OMe modified
<220> FEATURE:
<221> NAME/KEY: misc_feature
<222> LOCATION: (17)..(19)
<223> OTHER INFORMATION: 5-methyl modified
<220> FEATURE:
<221> NAME/KEY: misc_feature
<222> LOCATION: (19)..(19)
<223> OTHER INFORMATION: 2'Fluoro modified
<220> FEATURE:
<221> NAME/KEY: misc_feature
<222> LOCATION: (20)..(21)
<223> OTHER INFORMATION: Phosphodiester linkage

<400> SEQUENCE: 82
uucauuucca ccuuugccca a                                           21

<210> SEQ ID NO 83
<211> LENGTH: 21
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: 5' Phosphate modified
<220> FEATURE:
<221> NAME/KEY: misc_feature
<222> LOCATION: (1)..(1)
<223> OTHER INFORMATION: 2'OMe modified
<220> FEATURE:
<221> NAME/KEY: misc_feature
<222> LOCATION: (1)..(3)
<223> OTHER INFORMATION: 5-methyl modified
<220> FEATURE:
<221> NAME/KEY: misc_feature
<222> LOCATION: (1)..(20)
<223> OTHER INFORMATION: Phosphorothioate linkage
<220> FEATURE:
<221> NAME/KEY: misc_feature
<222> LOCATION: (2)..(3)
<223> OTHER INFORMATION: 2'Fluoro modified
<220> FEATURE:
<221> NAME/KEY: misc_feature
<222> LOCATION: (5)..(9)
<223> OTHER INFORMATION: 5-methyl modified
<220> FEATURE:
<221> NAME/KEY: misc_feature
```

```
<222> LOCATION: (5)..(9)
<223> OTHER INFORMATION: 2'Fluoro modified
<220> FEATURE:
<221> NAME/KEY: misc_feature
<222> LOCATION: (11)..(11)
<223> OTHER INFORMATION: 2'Fluoro modified
<220> FEATURE:
<221> NAME/KEY: misc_feature
<222> LOCATION: (11)..(15)
<223> OTHER INFORMATION: 5-methyl modified
<220> FEATURE:
<221> NAME/KEY: misc_feature
<222> LOCATION: (12)..(15)
<223> OTHER INFORMATION: 2'OMe modified
<220> FEATURE:
<221> NAME/KEY: misc_feature
<222> LOCATION: (17)..(18)
<223> OTHER INFORMATION: 2'OMe modified
<220> FEATURE:
<221> NAME/KEY: misc_feature
<222> LOCATION: (17)..(19)
<223> OTHER INFORMATION: 5-methyl modified
<220> FEATURE:
<221> NAME/KEY: misc_feature
<222> LOCATION: (19)..(19)
<223> OTHER INFORMATION: 2'Fluoro modified
<220> FEATURE:
<221> NAME/KEY: misc_feature
<222> LOCATION: (20)..(21)
<223> OTHER INFORMATION: Phosphodiester linkage

<400> SEQUENCE: 83
uucauuucca ccuuugccca a                                              21

<210> SEQ ID NO 84
<211> LENGTH: 21
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: 5' Phosphate modified
<220> FEATURE:
<221> NAME/KEY: misc_feature
<222> LOCATION: (1)..(1)
<223> OTHER INFORMATION: 2'OMe modified
<220> FEATURE:
<221> NAME/KEY: misc_feature
<222> LOCATION: (1)..(20)
<223> OTHER INFORMATION: Phosphorothioate linkage
<220> FEATURE:
<221> NAME/KEY: misc_feature
<222> LOCATION: (2)..(3)
<223> OTHER INFORMATION: 2'Fluoro modified
<220> FEATURE:
<221> NAME/KEY: misc_feature
<222> LOCATION: (5)..(9)
<223> OTHER INFORMATION: 2'Fluoro modified
<220> FEATURE:
<221> NAME/KEY: misc_feature
<222> LOCATION: (11)..(11)
<223> OTHER INFORMATION: 2'Fluoro modified
<220> FEATURE:
<221> NAME/KEY: misc_feature
<222> LOCATION: (12)..(15)
<223> OTHER INFORMATION: 2'OMe modified
<220> FEATURE:
<221> NAME/KEY: misc_feature
<222> LOCATION: (17)..(18)
<223> OTHER INFORMATION: 2'OMe modified
<220> FEATURE:
<221> NAME/KEY: misc_feature
<222> LOCATION: (19)..(19)
<223> OTHER INFORMATION: 2'Fluoro modified
<220> FEATURE:
```

```
<221> NAME/KEY: misc_feature
<222> LOCATION: (20)..(21)
<223> OTHER INFORMATION: Phosphodiester linkage

<400> SEQUENCE: 84
uucauuucca ccuuugccca a                                              21

<210> SEQ ID NO 85
<211> LENGTH: 21
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: 5' Phosphate modified
<220> FEATURE:
<221> NAME/KEY: misc_feature
<222> LOCATION: (1)..(1)
<223> OTHER INFORMATION: 2'OMe modified
<220> FEATURE:
<221> NAME/KEY: misc_feature
<222> LOCATION: (1)..(20)
<223> OTHER INFORMATION: Phosphorothioate linkage
<220> FEATURE:
<221> NAME/KEY: misc_feature
<222> LOCATION: (2)..(3)
<223> OTHER INFORMATION: 2'Fluoro modified
<220> FEATURE:
<221> NAME/KEY: misc_feature
<222> LOCATION: (5)..(9)
<223> OTHER INFORMATION: 2'Fluoro modified
<220> FEATURE:
<221> NAME/KEY: misc_feature
<222> LOCATION: (11)..(11)
<223> OTHER INFORMATION: 2'Fluoro modified
<220> FEATURE:
<221> NAME/KEY: misc_feature
<222> LOCATION: (12)..(15)
<223> OTHER INFORMATION: 2'OMe modified
<220> FEATURE:
<221> NAME/KEY: misc_feature
<222> LOCATION: (17)..(18)
<223> OTHER INFORMATION: 2'OMe modified
<220> FEATURE:
<221> NAME/KEY: misc_feature
<222> LOCATION: (19)..(19)
<223> OTHER INFORMATION: 2'Fluoro modified
<220> FEATURE:
<221> NAME/KEY: misc_feature
<222> LOCATION: (20)..(21)
<223> OTHER INFORMATION: Phosphodiester linkage

<400> SEQUENCE: 85
uucauuucca ccuuugccca a                                              21

<210> SEQ ID NO 86
<211> LENGTH: 21
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: 5' Phosphate modified
<220> FEATURE:
<221> NAME/KEY: misc_feature
<222> LOCATION: (1)..(1)
<223> OTHER INFORMATION: 2'OMe modified
<220> FEATURE:
<221> NAME/KEY: misc_feature
<222> LOCATION: (1)..(20)
<223> OTHER INFORMATION: Phosphorothioate linkage
```

```
<220> FEATURE:
<221> NAME/KEY: misc_feature
<222> LOCATION: (2)..(3)
<223> OTHER INFORMATION: 2'Fluoro modified
<220> FEATURE:
<221> NAME/KEY: misc_feature
<222> LOCATION: (5)..(9)
<223> OTHER INFORMATION: 2'Fluoro modified
<220> FEATURE:
<221> NAME/KEY: misc_feature
<222> LOCATION: (11)..(11)
<223> OTHER INFORMATION: 2'Fluoro modified
<220> FEATURE:
<221> NAME/KEY: misc_feature
<222> LOCATION: (12)..(15)
<223> OTHER INFORMATION: 2'OMe modified
<220> FEATURE:
<221> NAME/KEY: misc_feature
<222> LOCATION: (17)..(18)
<223> OTHER INFORMATION: 2'OMe modified
<220> FEATURE:
<221> NAME/KEY: misc_feature
<222> LOCATION: (19)..(19)
<223> OTHER INFORMATION: 2'Fluoro modified
<220> FEATURE:
<221> NAME/KEY: misc_feature
<222> LOCATION: (20)..(21)
<223> OTHER INFORMATION: Phosphodiester linkage

<400> SEQUENCE: 86
uucauuucca ccuuugccca a                                              21

<210> SEQ ID NO 87
<211> LENGTH: 21
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: 5-methyl modified
<220> FEATURE:
<221> NAME/KEY: misc_feature
<222> LOCATION: (1)..(1)
<223> OTHER INFORMATION: 5' Phosphate modified
<220> FEATURE:
<221> NAME/KEY: misc_feature
<222> LOCATION: (1)..(1)
<223> OTHER INFORMATION: 2'OMe modified
<220> FEATURE:
<221> NAME/KEY: misc_feature
<222> LOCATION: (1)..(20)
<223> OTHER INFORMATION: Phosphorothioate linkage
<220> FEATURE:
<221> NAME/KEY: misc_feature
<222> LOCATION: (2)..(2)
<223> OTHER INFORMATION: Isobutyl modified
<220> FEATURE:
<221> NAME/KEY: misc_feature
<222> LOCATION: (2)..(2)
<223> OTHER INFORMATION: Deoxyribose modified
<220> FEATURE:
<221> NAME/KEY: misc_feature
<222> LOCATION: (2)..(3)
<223> OTHER INFORMATION: 2'Fluoro modified
<220> FEATURE:
<221> NAME/KEY: misc_feature
<222> LOCATION: (3)..(3)
<223> OTHER INFORMATION: 5-methyl modified
<220> FEATURE:
<221> NAME/KEY: misc_feature
<222> LOCATION: (5)..(6)
<223> OTHER INFORMATION: 5-methyl modified
<220> FEATURE:
<221> NAME/KEY: misc_feature
<222> LOCATION: (5)..(9)
```

```
<223> OTHER INFORMATION: 2'Fluoro modified
<220> FEATURE:
<221> NAME/KEY: misc_feature
<222> LOCATION: (7)..(7)
<223> OTHER INFORMATION: Isobutyl modified
<220> FEATURE:
<221> NAME/KEY: misc_feature
<222> LOCATION: (7)..(7)
<223> OTHER INFORMATION: Deoxyribose modified
<220> FEATURE:
<221> NAME/KEY: misc_feature
<222> LOCATION: (8)..(9)
<223> OTHER INFORMATION: 5-methyl modified
<220> FEATURE:
<221> NAME/KEY: misc_feature
<222> LOCATION: (11)..(11)
<223> OTHER INFORMATION: 2'Fluoro modified
<220> FEATURE:
<221> NAME/KEY: misc_feature
<222> LOCATION: (11)..(12)
<223> OTHER INFORMATION: 5-methyl modified
<220> FEATURE:
<221> NAME/KEY: misc_feature
<222> LOCATION: (12)..(15)
<223> OTHER INFORMATION: 2'OMe modified
<220> FEATURE:
<221> NAME/KEY: misc_feature
<222> LOCATION: (13)..(13)
<223> OTHER INFORMATION: Isobutyl modified
<220> FEATURE:
<221> NAME/KEY: misc_feature
<222> LOCATION: (13)..(13)
<223> OTHER INFORMATION: Deoxyribose modified
<220> FEATURE:
<221> NAME/KEY: misc_feature
<222> LOCATION: (14)..(15)
<223> OTHER INFORMATION: 5-methyl modified
<220> FEATURE:
<221> NAME/KEY: misc_feature
<222> LOCATION: (17)..(18)
<223> OTHER INFORMATION: 2'OMe modified
<220> FEATURE:
<221> NAME/KEY: misc_feature
<222> LOCATION: (17)..(19)
<223> OTHER INFORMATION: 5-methyl modified
<220> FEATURE:
<221> NAME/KEY: misc_feature
<222> LOCATION: (19)..(19)
<223> OTHER INFORMATION: 2'Fluoro modified
<220> FEATURE:
<221> NAME/KEY: misc_feature
<222> LOCATION: (20)..(21)
<223> OTHER INFORMATION: Phosphodiester linkage

<400> SEQUENCE: 87
uucauuucca ccuuugccca a                                            21

<210> SEQ ID NO 88
<211> LENGTH: 21
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: 5' Phosphate modified
<220> FEATURE:
<221> NAME/KEY: misc_feature
<222> LOCATION: (1)..(1)
<223> OTHER INFORMATION: 2'OMe modified
<220> FEATURE:
<221> NAME/KEY: misc_feature
<222> LOCATION: (1)..(2)
<223> OTHER INFORMATION: 5-methyl modified
<220> FEATURE:
<221> NAME/KEY: misc_feature
```

```
<222> LOCATION: (1)..(20)
<223> OTHER INFORMATION: Phosphorothioate linkage
<220> FEATURE:
<221> NAME/KEY: misc_feature
<222> LOCATION: (2)..(3)
<223> OTHER INFORMATION: 2'Fluoro modified
<220> FEATURE:
<221> NAME/KEY: misc_feature
<222> LOCATION: (3)..(3)
<223> OTHER INFORMATION: Octyl modified
<220> FEATURE:
<221> NAME/KEY: misc_feature
<222> LOCATION: (5)..(6)
<223> OTHER INFORMATION: 5-methyl modified
<220> FEATURE:
<221> NAME/KEY: misc_feature
<222> LOCATION: (5)..(9)
<223> OTHER INFORMATION: 2'Fluoro modified
<220> FEATURE:
<221> NAME/KEY: misc_feature
<222> LOCATION: (7)..(7)
<223> OTHER INFORMATION: Isobutyl modified
<220> FEATURE:
<221> NAME/KEY: misc_feature
<222> LOCATION: (7)..(7)
<223> OTHER INFORMATION: Deoxyribose modified
<220> FEATURE:
<221> NAME/KEY: misc_feature
<222> LOCATION: (8)..(9)
<223> OTHER INFORMATION: 5-methyl modified
<220> FEATURE:
<221> NAME/KEY: misc_feature
<222> LOCATION: (11)..(11)
<223> OTHER INFORMATION: 2'Fluoro modified
<220> FEATURE:
<221> NAME/KEY: misc_feature
<222> LOCATION: (11)..(12)
<223> OTHER INFORMATION: 5-methyl modified
<220> FEATURE:
<221> NAME/KEY: misc_feature
<222> LOCATION: (12)..(15)
<223> OTHER INFORMATION: 2'OMe modified
<220> FEATURE:
<221> NAME/KEY: misc_feature
<222> LOCATION: (13)..(13)
<223> OTHER INFORMATION: Isobutyl modified
<220> FEATURE:
<221> NAME/KEY: misc_feature
<222> LOCATION: (13)..(13)
<223> OTHER INFORMATION: Deoxyribose modified
<220> FEATURE:
<221> NAME/KEY: misc_feature
<222> LOCATION: (14)..(15)
<223> OTHER INFORMATION: 5-methyl modified
<220> FEATURE:
<221> NAME/KEY: misc_feature
<222> LOCATION: (17)..(18)
<223> OTHER INFORMATION: 2'OMe modified
<220> FEATURE:
<221> NAME/KEY: misc_feature
<222> LOCATION: (17)..(19)
<223> OTHER INFORMATION: 5-methyl modified
<220> FEATURE:
<221> NAME/KEY: misc_feature
<222> LOCATION: (19)..(19)
<223> OTHER INFORMATION: 2'Fluoro modified
<220> FEATURE:
<221> NAME/KEY: misc_feature
<222> LOCATION: (20)..(21)
<223> OTHER INFORMATION: Phosphodiester linkage

<400> SEQUENCE: 88
uucauuucca ccuuugccca a                                    21

<210> SEQ ID NO 89
<211> LENGTH: 21
<212> TYPE: RNA
```

<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: 5' Phosphate modified
<220> FEATURE:
<221> NAME/KEY: misc_feature
<222> LOCATION: (1)..(1)
<223> OTHER INFORMATION: 2'OMe modified
<220> FEATURE:
<221> NAME/KEY: misc_feature
<222> LOCATION: (1)..(20)
<223> OTHER INFORMATION: Phosphorothioate linkage
<220> FEATURE:
<221> NAME/KEY: misc_feature
<222> LOCATION: (2)..(3)
<223> OTHER INFORMATION: 2'Fluoro modified
<220> FEATURE:
<221> NAME/KEY: misc_feature
<222> LOCATION: (5)..(9)
<223> OTHER INFORMATION: 2'Fluoro modified
<220> FEATURE:
<221> NAME/KEY: misc_feature
<222> LOCATION: (11)..(11)
<223> OTHER INFORMATION: 2'Fluoro modified
<220> FEATURE:
<221> NAME/KEY: misc_feature
<222> LOCATION: (12)..(15)
<223> OTHER INFORMATION: 2'OMe modified
<220> FEATURE:
<221> NAME/KEY: misc_feature
<222> LOCATION: (17)..(18)
<223> OTHER INFORMATION: 2'OMe modified
<220> FEATURE:
<221> NAME/KEY: misc_feature
<222> LOCATION: (19)..(19)
<223> OTHER INFORMATION: 2'Fluoro modified
<220> FEATURE:
<221> NAME/KEY: misc_feature
<222> LOCATION: (20)..(21)
<223> OTHER INFORMATION: Phosphodiester linkage

<400> SEQUENCE: 89
uucauuucca ccuuugccca a                                              21

<210> SEQ ID NO 90
<211> LENGTH: 21
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: 5' Phosphate modified
<220> FEATURE:
<221> NAME/KEY: misc_feature
<222> LOCATION: (1)..(1)
<223> OTHER INFORMATION: 2'OMe modified
<220> FEATURE:
<221> NAME/KEY: misc_feature
<222> LOCATION: (1)..(20)
<223> OTHER INFORMATION: Phosphorothioate linkage
<220> FEATURE:
<221> NAME/KEY: misc_feature
<222> LOCATION: (4)..(4)
<223> OTHER INFORMATION: 2'Fluoro modified
<220> FEATURE:
<221> NAME/KEY: misc_feature
<222> LOCATION: (6)..(6)
<223> OTHER INFORMATION: 2'Fluoro modified
<220> FEATURE:
<221> NAME/KEY: misc_feature
<222> LOCATION: (8)..(12)
<223> OTHER INFORMATION: 2'Fluoro modified

```
<220> FEATURE:
<221> NAME/KEY: misc_feature
<222> LOCATION: (14)..(16)
<223> OTHER INFORMATION: 2'Fluoro modified
<220> FEATURE:
<221> NAME/KEY: misc_feature
<222> LOCATION: (18)..(20)
<223> OTHER INFORMATION: 2'Fluoro modified
<220> FEATURE:
<221> NAME/KEY: misc_feature
<222> LOCATION: (20)..(21)
<223> OTHER INFORMATION: Phosphodiester linkage

<400> SEQUENCE: 90
uaacaugccu cucuucaucc u                                              21

<210> SEQ ID NO 91
<211> LENGTH: 21
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: 5' Phosphate modified
<220> FEATURE:
<221> NAME/KEY: misc_feature
<222> LOCATION: (1)..(1)
<223> OTHER INFORMATION: 2'OMe modified
<220> FEATURE:
<221> NAME/KEY: misc_feature
<222> LOCATION: (1)..(13)
<223> OTHER INFORMATION: Phosphodiester linkage
<220> FEATURE:
<221> NAME/KEY: misc_feature
<222> LOCATION: (4)..(4)
<223> OTHER INFORMATION: 2'Fluoro modified
<220> FEATURE:
<221> NAME/KEY: misc_feature
<222> LOCATION: (6)..(6)
<223> OTHER INFORMATION: 2'Fluoro modified
<220> FEATURE:
<221> NAME/KEY: misc_feature
<222> LOCATION: (8)..(16)
<223> OTHER INFORMATION: 2'Fluoro modified
<220> FEATURE:
<221> NAME/KEY: misc_feature
<222> LOCATION: (13)..(20)
<223> OTHER INFORMATION: Phosphorothioate linkage
<220> FEATURE:
<221> NAME/KEY: misc_feature
<222> LOCATION: (18)..(20)
<223> OTHER INFORMATION: 2'Fluoro modified
<220> FEATURE:
<221> NAME/KEY: misc_feature
<222> LOCATION: (20)..(21)
<223> OTHER INFORMATION: Phosphodiester linkage

<400> SEQUENCE: 91
uaacaugccu cucuucaucc u                                              21

<210> SEQ ID NO 92
<211> LENGTH: 19
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: 5' Phosphate modified
<220> FEATURE:
<221> NAME/KEY: misc_feature
<222> LOCATION: (1)..(1)
```

<223> OTHER INFORMATION: 2'OMe modified
<220> FEATURE:
<221> NAME/KEY: misc_feature
<222> LOCATION: (1)..(13)
<223> OTHER INFORMATION: Phosphodiester linkage
<220> FEATURE:
<221> NAME/KEY: misc_feature
<222> LOCATION: (4)..(4)
<223> OTHER INFORMATION: 2'Fluoro modified
<220> FEATURE:
<221> NAME/KEY: misc_feature
<222> LOCATION: (6)..(6)
<223> OTHER INFORMATION: 2'Fluoro modified
<220> FEATURE:
<221> NAME/KEY: misc_feature
<222> LOCATION: (8)..(16)
<223> OTHER INFORMATION: 2'Fluoro modified
<220> FEATURE:
<221> NAME/KEY: misc_feature
<222> LOCATION: (13)..(18)
<223> OTHER INFORMATION: Phosphorothioate linkage
<220> FEATURE:
<221> NAME/KEY: misc_feature
<222> LOCATION: (18)..(18)
<223> OTHER INFORMATION: 2'Fluoro modified
<220> FEATURE:
<221> NAME/KEY: misc_feature
<222> LOCATION: (18)..(19)
<223> OTHER INFORMATION: Phosphodiester linkage

<400> SEQUENCE: 92
uaacaugccu cucuucauc                                              19

<210> SEQ ID NO 93
<211> LENGTH: 21
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: 5' Phosphate modified
<220> FEATURE:
<221> NAME/KEY: misc_feature
<222> LOCATION: (1)..(1)
<223> OTHER INFORMATION: 2'OMe modified
<220> FEATURE:
<221> NAME/KEY: misc_feature
<222> LOCATION: (1)..(13)
<223> OTHER INFORMATION: Phosphodiester linkage
<220> FEATURE:
<221> NAME/KEY: misc_feature
<222> LOCATION: (4)..(4)
<223> OTHER INFORMATION: 2'Fluoro modified
<220> FEATURE:
<221> NAME/KEY: misc_feature
<222> LOCATION: (6)..(6)
<223> OTHER INFORMATION: 2'Fluoro modified
<220> FEATURE:
<221> NAME/KEY: misc_feature
<222> LOCATION: (8)..(16)
<223> OTHER INFORMATION: 2'Fluoro modified
<220> FEATURE:
<221> NAME/KEY: misc_feature
<222> LOCATION: (13)..(20)
<223> OTHER INFORMATION: Phosphorothioate linkage
<220> FEATURE:
<221> NAME/KEY: misc_feature
<222> LOCATION: (18)..(20)
<223> OTHER INFORMATION: 2'Fluoro modified
<220> FEATURE:
<221> NAME/KEY: misc_feature
<222> LOCATION: (20)..(21)
<223> OTHER INFORMATION: Phosphodiester linkage

<400> SEQUENCE: 93
uaacaugccu cucuucaucc u                                                21

<210> SEQ ID NO 94
<211> LENGTH: 21
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: 5' Phosphate modified
<220> FEATURE:
<221> NAME/KEY: misc_feature
<222> LOCATION: (1)..(1)
<223> OTHER INFORMATION: 2'OMe modified
<220> FEATURE:
<221> NAME/KEY: misc_feature
<222> LOCATION: (1)..(13)
<223> OTHER INFORMATION: Phosphodiester linkage
<220> FEATURE:
<221> NAME/KEY: misc_feature
<222> LOCATION: (4)..(4)
<223> OTHER INFORMATION: 2'Fluoro modified
<220> FEATURE:
<221> NAME/KEY: misc_feature
<222> LOCATION: (6)..(6)
<223> OTHER INFORMATION: 2'Fluoro modified
<220> FEATURE:
<221> NAME/KEY: misc_feature
<222> LOCATION: (8)..(16)
<223> OTHER INFORMATION: 2'Fluoro modified
<220> FEATURE:
<221> NAME/KEY: misc_feature
<222> LOCATION: (13)..(20)
<223> OTHER INFORMATION: Phosphorothioate linkage
<220> FEATURE:
<221> NAME/KEY: misc_feature
<222> LOCATION: (18)..(20)
<223> OTHER INFORMATION: 2'Fluoro modified
<220> FEATURE:
<221> NAME/KEY: misc_feature
<222> LOCATION: (20)..(21)
<223> OTHER INFORMATION: Phosphodiester linkage

<400> SEQUENCE: 94
uaacaugccu cucuucaucc u                                                21

<210> SEQ ID NO 95
<211> LENGTH: 19
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: 5' Phosphate modified
<220> FEATURE:
<221> NAME/KEY: misc_feature
<222> LOCATION: (1)..(1)
<223> OTHER INFORMATION: 2'OMe modified
<220> FEATURE:
<221> NAME/KEY: misc_feature
<222> LOCATION: (1)..(18)
<223> OTHER INFORMATION: Phosphorothioate linkage
<220> FEATURE:
<221> NAME/KEY: misc_feature
<222> LOCATION: (4)..(4)
<223> OTHER INFORMATION: 2'Fluoro modified
<220> FEATURE:
<221> NAME/KEY: misc_feature
<222> LOCATION: (6)..(6)
<223> OTHER INFORMATION: 2'Fluoro modified
<220> FEATURE:

```
<221> NAME/KEY: misc_feature
<222> LOCATION: (8)..(16)
<223> OTHER INFORMATION: 2'Fluoro modified
<220> FEATURE:
<221> NAME/KEY: misc_feature
<222> LOCATION: (18)..(18)
<223> OTHER INFORMATION: 2'Fluoro modified
<220> FEATURE:
<221> NAME/KEY: misc_feature
<222> LOCATION: (18)..(19)
<223> OTHER INFORMATION: Phosphodiester linkage

<400> SEQUENCE: 95
uaacaugccu cucuucauc                                                19

<210> SEQ ID NO 96
<211> LENGTH: 19
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: 5' Phosphate modified
<220> FEATURE:
<221> NAME/KEY: misc_feature
<222> LOCATION: (1)..(1)
<223> OTHER INFORMATION: 2'OMe modified
<220> FEATURE:
<221> NAME/KEY: misc_feature
<222> LOCATION: (1)..(18)
<223> OTHER INFORMATION: Phosphorothioate linkage
<220> FEATURE:
<221> NAME/KEY: misc_feature
<222> LOCATION: (4)..(4)
<223> OTHER INFORMATION: 2'Fluoro modified
<220> FEATURE:
<221> NAME/KEY: misc_feature
<222> LOCATION: (6)..(6)
<223> OTHER INFORMATION: 2'Fluoro modified
<220> FEATURE:
<221> NAME/KEY: misc_feature
<222> LOCATION: (8)..(16)
<223> OTHER INFORMATION: 2'Fluoro modified
<220> FEATURE:
<221> NAME/KEY: misc_feature
<222> LOCATION: (18)..(18)
<223> OTHER INFORMATION: 2'Fluoro modified
<220> FEATURE:
<221> NAME/KEY: misc_feature
<222> LOCATION: (18)..(19)
<223> OTHER INFORMATION: Phosphodiester linkage

<400> SEQUENCE: 96
uaacaugccu cucuucauc                                                19

<210> SEQ ID NO 97
<211> LENGTH: 21
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: 5' Phosphate modified
<220> FEATURE:
<221> NAME/KEY: misc_feature
<222> LOCATION: (1)..(1)
<223> OTHER INFORMATION: 2'OMe modified
<220> FEATURE:
<221> NAME/KEY: misc_feature
<222> LOCATION: (1)..(20)
<223> OTHER INFORMATION: Phosphorothioate linkage
```

```
<220> FEATURE:
<221> NAME/KEY: misc_feature
<222> LOCATION: (4)..(4)
<223> OTHER INFORMATION: 2'Fluoro modified
<220> FEATURE:
<221> NAME/KEY: misc_feature
<222> LOCATION: (6)..(6)
<223> OTHER INFORMATION: 2'Fluoro modified
<220> FEATURE:
<221> NAME/KEY: misc_feature
<222> LOCATION: (8)..(16)
<223> OTHER INFORMATION: 2'Fluoro modified
<220> FEATURE:
<221> NAME/KEY: misc_feature
<222> LOCATION: (18)..(20)
<223> OTHER INFORMATION: 2'Fluoro modified
<220> FEATURE:
<221> NAME/KEY: misc_feature
<222> LOCATION: (20)..(21)
<223> OTHER INFORMATION: Phosphodiester linkage

<400> SEQUENCE: 97
uaacaugccu cucuucaucc u                                                 21

<210> SEQ ID NO 98
<211> LENGTH: 21
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: 5' Phosphate modified
<220> FEATURE:
<221> NAME/KEY: misc_feature
<222> LOCATION: (1)..(1)
<223> OTHER INFORMATION: 2'OMe modified
<220> FEATURE:
<221> NAME/KEY: misc_feature
<222> LOCATION: (1)..(20)
<223> OTHER INFORMATION: Phosphorothioate linkage
<220> FEATURE:
<221> NAME/KEY: misc_feature
<222> LOCATION: (4)..(4)
<223> OTHER INFORMATION: 2'Fluoro modified
<220> FEATURE:
<221> NAME/KEY: misc_feature
<222> LOCATION: (6)..(6)
<223> OTHER INFORMATION: 2'Fluoro modified
<220> FEATURE:
<221> NAME/KEY: misc_feature
<222> LOCATION: (8)..(12)
<223> OTHER INFORMATION: 2'Fluoro modified
<220> FEATURE:
<221> NAME/KEY: misc_feature
<222> LOCATION: (14)..(16)
<223> OTHER INFORMATION: 2'Fluoro modified
<220> FEATURE:
<221> NAME/KEY: misc_feature
<222> LOCATION: (18)..(20)
<223> OTHER INFORMATION: 2'Fluoro modified
<220> FEATURE:
<221> NAME/KEY: misc_feature
<222> LOCATION: (20)..(21)
<223> OTHER INFORMATION: Phosphodiester linkage

<400> SEQUENCE: 98
uaacaugccu cucuucaucc u                                                 21

<210> SEQ ID NO 99
<211> LENGTH: 21
<212> TYPE: RNA
<213> ORGANISM: Artificial Sequence
<220> FEATURE:
```

```
<223> OTHER INFORMATION: Synthetic Polynucleotide
<220> FEATURE:
<221> NAME/KEY: misc_feature
<222> LOCATION: (1)..(1)
<223> OTHER INFORMATION: 5' Phosphate modified
<220> FEATURE:
<221> NAME/KEY: misc_feature
<222> LOCATION: (1)..(1)
<223> OTHER INFORMATION: 2'OMe modified
<220> FEATURE:
<221> NAME/KEY: misc_feature
<222> LOCATION: (1)..(20)
<223> OTHER INFORMATION: Phosphorothioate linkage
<220> FEATURE:
<221> NAME/KEY: misc_feature
<222> LOCATION: (2)..(3)
<223> OTHER INFORMATION: 2'Fluoro modified
<220> FEATURE:
<221> NAME/KEY: misc_feature
<222> LOCATION: (5)..(9)
<223> OTHER INFORMATION: 2'Fluoro modified
<220> FEATURE:
<221> NAME/KEY: misc_feature
<222> LOCATION: (11)..(11)
<223> OTHER INFORMATION: 2'Fluoro modified
<220> FEATURE:
<221> NAME/KEY: misc_feature
<222> LOCATION: (12)..(15)
<223> OTHER INFORMATION: 2'OMe modified
<220> FEATURE:
<221> NAME/KEY: misc_feature
<222> LOCATION: (17)..(18)
<223> OTHER INFORMATION: 2'OMe modified
<220> FEATURE:
<221> NAME/KEY: misc_feature
<222> LOCATION: (19)..(19)
<223> OTHER INFORMATION: 2'Fluoro modified
<220> FEATURE:
<221> NAME/KEY: misc_feature
<222> LOCATION: (20)..(21)
<223> OTHER INFORMATION: Phosphodiester linkage

<400> SEQUENCE: 99
uucauuucca ccuuugccca a                                              21

<210> SEQ ID NO 100
<211> LENGTH: 21
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: 5' Phosphate modified
<220> FEATURE:
<221> NAME/KEY: misc_feature
<222> LOCATION: (1)..(1)
<223> OTHER INFORMATION: 2'OMe modified
<220> FEATURE:
<221> NAME/KEY: misc_feature
<222> LOCATION: (1)..(20)
<223> OTHER INFORMATION: Phosphorothioate linkage
<220> FEATURE:
<221> NAME/KEY: misc_feature
<222> LOCATION: (2)..(3)
<223> OTHER INFORMATION: 2'Fluoro modified
<220> FEATURE:
<221> NAME/KEY: misc_feature
<222> LOCATION: (5)..(9)
<223> OTHER INFORMATION: 2'Fluoro modified
<220> FEATURE:
<221> NAME/KEY: misc_feature
<222> LOCATION: (11)..(11)
<223> OTHER INFORMATION: 2'Fluoro modified
<220> FEATURE:
<221> NAME/KEY: misc_feature
```

```
<222> LOCATION: (12)..(15)
<223> OTHER INFORMATION: 2'OMe modified
<220> FEATURE:
<221> NAME/KEY: misc_feature
<222> LOCATION: (17)..(18)
<223> OTHER INFORMATION: 2'OMe modified
<220> FEATURE:
<221> NAME/KEY: misc_feature
<222> LOCATION: (19)..(19)
<223> OTHER INFORMATION: 2'Fluoro modified
<220> FEATURE:
<221> NAME/KEY: misc_feature
<222> LOCATION: (20)..(21)
<223> OTHER INFORMATION: Phosphodiester linkage

<400> SEQUENCE: 100
uucauuucca ccuuugccca a                                              21

<210> SEQ ID NO 101
<211> LENGTH: 21
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: 5' Phosphate modified
<220> FEATURE:
<221> NAME/KEY: misc_feature
<222> LOCATION: (1)..(1)
<223> OTHER INFORMATION: 2'OMe modified
<220> FEATURE:
<221> NAME/KEY: misc_feature
<222> LOCATION: (1)..(20)
<223> OTHER INFORMATION: Phosphorothioate linkage
<220> FEATURE:
<221> NAME/KEY: misc_feature
<222> LOCATION: (2)..(3)
<223> OTHER INFORMATION: 2'Fluoro modified
<220> FEATURE:
<221> NAME/KEY: misc_feature
<222> LOCATION: (5)..(9)
<223> OTHER INFORMATION: 2'Fluoro modified
<220> FEATURE:
<221> NAME/KEY: misc_feature
<222> LOCATION: (11)..(11)
<223> OTHER INFORMATION: 2'Fluoro modified
<220> FEATURE:
<221> NAME/KEY: misc_feature
<222> LOCATION: (12)..(15)
<223> OTHER INFORMATION: 2'OMe modified
<220> FEATURE:
<221> NAME/KEY: misc_feature
<222> LOCATION: (17)..(18)
<223> OTHER INFORMATION: 2'OMe modified
<220> FEATURE:
<221> NAME/KEY: misc_feature
<222> LOCATION: (19)..(19)
<223> OTHER INFORMATION: 2'Fluoro modified
<220> FEATURE:
<221> NAME/KEY: misc_feature
<222> LOCATION: (20)..(21)
<223> OTHER INFORMATION: Phosphodiester linkage

<400> SEQUENCE: 101
uucauuucca ccuuugccca a                                              21

<210> SEQ ID NO 102
<211> LENGTH: 21
<212> TYPE: RNA
<213> ORGANISM: Artificial Sequence
<220> FEATURE:
<223> OTHER INFORMATION: Synthetic Polynucleotide
<220> FEATURE:
```

```
<221> NAME/KEY: misc_feature
<222> LOCATION: (1)..(1)
<223> OTHER INFORMATION: 5' Phosphate modified
<220> FEATURE:
<221> NAME/KEY: misc_feature
<222> LOCATION: (1)..(1)
<223> OTHER INFORMATION: 2'OMe modified
<220> FEATURE:
<221> NAME/KEY: misc_feature
<222> LOCATION: (1)..(20)
<223> OTHER INFORMATION: Phosphorothioate linkage
<220> FEATURE:
<221> NAME/KEY: misc_feature
<222> LOCATION: (2)..(3)
<223> OTHER INFORMATION: 2'Fluoro modified
<220> FEATURE:
<221> NAME/KEY: misc_feature
<222> LOCATION: (5)..(9)
<223> OTHER INFORMATION: 2'Fluoro modified
<220> FEATURE:
<221> NAME/KEY: misc_feature
<222> LOCATION: (11)..(11)
<223> OTHER INFORMATION: 2'Fluoro modified
<220> FEATURE:
<221> NAME/KEY: misc_feature
<222> LOCATION: (12)..(15)
<223> OTHER INFORMATION: 2'OMe modified
<220> FEATURE:
<221> NAME/KEY: misc_feature
<222> LOCATION: (17)..(18)
<223> OTHER INFORMATION: 2'OMe modified
<220> FEATURE:
<221> NAME/KEY: misc_feature
<222> LOCATION: (19)..(19)
<223> OTHER INFORMATION: 2'Fluoro modified
<220> FEATURE:
<221> NAME/KEY: misc_feature
<222> LOCATION: (20)..(21)
<223> OTHER INFORMATION: Phosphodiester linkage

<400> SEQUENCE: 102
uucauuucca ccuuugccca a                                           21

<210> SEQ ID NO 103
<211> LENGTH: 21
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: 5-methyl modified
<220> FEATURE:
<221> NAME/KEY: misc_feature
<222> LOCATION: (1)..(1)
<223> OTHER INFORMATION: 5' Phosphate modified
<220> FEATURE:
<221> NAME/KEY: misc_feature
<222> LOCATION: (1)..(1)
<223> OTHER INFORMATION: 2'OMe modified
<220> FEATURE:
<221> NAME/KEY: misc_feature
<222> LOCATION: (1)..(20)
<223> OTHER INFORMATION: Phosphorothioate linkage
<220> FEATURE:
<221> NAME/KEY: misc_feature
<222> LOCATION: (2)..(2)
<223> OTHER INFORMATION: Octyl modified
<220> FEATURE:
<221> NAME/KEY: misc_feature
<222> LOCATION: (2)..(3)
<223> OTHER INFORMATION: 2'Fluoro modified
<220> FEATURE:
<221> NAME/KEY: misc_feature
<222> LOCATION: (3)..(3)
<223> OTHER INFORMATION: 5-methyl modified
```

```
<220> FEATURE:
<221> NAME/KEY: misc_feature
<222> LOCATION: (5)..(6)
<223> OTHER INFORMATION: 5-methyl modified
<220> FEATURE:
<221> NAME/KEY: misc_feature
<222> LOCATION: (5)..(9)
<223> OTHER INFORMATION: 2'Fluoro modified
<220> FEATURE:
<221> NAME/KEY: misc_feature
<222> LOCATION: (7)..(7)
<223> OTHER INFORMATION: Octyl modified
<220> FEATURE:
<221> NAME/KEY: misc_feature
<222> LOCATION: (8)..(9)
<223> OTHER INFORMATION: 5-methyl modified
<220> FEATURE:
<221> NAME/KEY: misc_feature
<222> LOCATION: (11)..(11)
<223> OTHER INFORMATION: 2'Fluoro modified
<220> FEATURE:
<221> NAME/KEY: misc_feature
<222> LOCATION: (11)..(12)
<223> OTHER INFORMATION: 5-methyl modified
<220> FEATURE:
<221> NAME/KEY: misc_feature
<222> LOCATION: (12)..(15)
<223> OTHER INFORMATION: 2'OMe modified
<220> FEATURE:
<221> NAME/KEY: misc_feature
<222> LOCATION: (13)..(13)
<223> OTHER INFORMATION: Octyl modified
<220> FEATURE:
<221> NAME/KEY: misc_feature
<222> LOCATION: (14)..(15)
<223> OTHER INFORMATION: 5-methyl modified
<220> FEATURE:
<221> NAME/KEY: misc_feature
<222> LOCATION: (17)..(18)
<223> OTHER INFORMATION: 2'OMe modified
<220> FEATURE:
<221> NAME/KEY: misc_feature
<222> LOCATION: (17)..(19)
<223> OTHER INFORMATION: 5-methyl modified
<220> FEATURE:
<221> NAME/KEY: misc_feature
<222> LOCATION: (19)..(19)
<223> OTHER INFORMATION: 2'Fluoro modified
<220> FEATURE:
<221> NAME/KEY: misc_feature
<222> LOCATION: (20)..(21)
<223> OTHER INFORMATION: Phosphodiester linkage

<400> SEQUENCE: 103
uucauuucca ccuuugccca a                                              21

<210> SEQ ID NO 104
<211> LENGTH: 21
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: 5' Phosphate modified
<220> FEATURE:
<221> NAME/KEY: misc_feature
<222> LOCATION: (1)..(1)
<223> OTHER INFORMATION: 2'OMe modified
<220> FEATURE:
<221> NAME/KEY: misc_feature
<222> LOCATION: (1)..(2)
<223> OTHER INFORMATION: 5-methyl modified
<220> FEATURE:
<221> NAME/KEY: misc_feature
<222> LOCATION: (1)..(20)
```

```
<223> OTHER INFORMATION: Phosphorothioate linkage
<220> FEATURE:
<221> NAME/KEY: misc_feature
<222> LOCATION: (2)..(3)
<223> OTHER INFORMATION: 2'Fluoro modified
<220> FEATURE:
<221> NAME/KEY: misc_feature
<222> LOCATION: (3)..(3)
<223> OTHER INFORMATION: Octyl modified
<220> FEATURE:
<221> NAME/KEY: misc_feature
<222> LOCATION: (5)..(6)
<223> OTHER INFORMATION: 5-methyl modified
<220> FEATURE:
<221> NAME/KEY: misc_feature
<222> LOCATION: (5)..(9)
<223> OTHER INFORMATION: 2'Fluoro modified
<220> FEATURE:
<221> NAME/KEY: misc_feature
<222> LOCATION: (7)..(7)
<223> OTHER INFORMATION: Octyl modified
<220> FEATURE:
<221> NAME/KEY: misc_feature
<222> LOCATION: (8)..(9)
<223> OTHER INFORMATION: 5-methyl modified
<220> FEATURE:
<221> NAME/KEY: misc_feature
<222> LOCATION: (11)..(11)
<223> OTHER INFORMATION: 2'Fluoro modified
<220> FEATURE:
<221> NAME/KEY: misc_feature
<222> LOCATION: (11)..(12)
<223> OTHER INFORMATION: 5-methyl modified
<220> FEATURE:
<221> NAME/KEY: misc_feature
<222> LOCATION: (12)..(15)
<223> OTHER INFORMATION: 2'OMe modified
<220> FEATURE:
<221> NAME/KEY: misc_feature
<222> LOCATION: (13)..(13)
<223> OTHER INFORMATION: Octyl modified
<220> FEATURE:
<221> NAME/KEY: misc_feature
<222> LOCATION: (14)..(15)
<223> OTHER INFORMATION: 5-methyl modified
<220> FEATURE:
<221> NAME/KEY: misc_feature
<222> LOCATION: (17)..(18)
<223> OTHER INFORMATION: 2'OMe modified
<220> FEATURE:
<221> NAME/KEY: misc_feature
<222> LOCATION: (17)..(19)
<223> OTHER INFORMATION: 5-methyl modified
<220> FEATURE:
<221> NAME/KEY: misc_feature
<222> LOCATION: (19)..(19)
<223> OTHER INFORMATION: 2'Fluoro modified
<220> FEATURE:
<221> NAME/KEY: misc_feature
<222> LOCATION: (20)..(21)
<223> OTHER INFORMATION: Phosphodiester linkage

<400> SEQUENCE: 104
uucauuucca ccuuugccca a                                         21

<210> SEQ ID NO 105
<211> LENGTH: 21
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: 5' Phosphate modified
<220> FEATURE:
<221> NAME/KEY: misc_feature
```

```
<222> LOCATION: (1)..(1)
<223> OTHER INFORMATION: 2'OMe modified
<220> FEATURE:
<221> NAME/KEY: misc_feature
<222> LOCATION: (1)..(1)
<223> OTHER INFORMATION: 5-methyl modified
<220> FEATURE:
<221> NAME/KEY: misc_feature
<222> LOCATION: (1)..(20)
<223> OTHER INFORMATION: Phosphorothioate linkage
<220> FEATURE:
<221> NAME/KEY: misc_feature
<222> LOCATION: (2)..(2)
<223> OTHER INFORMATION: Octyl modified
<220> FEATURE:
<221> NAME/KEY: misc_feature
<222> LOCATION: (2)..(3)
<223> OTHER INFORMATION: 2'Fluoro modified
<220> FEATURE:
<221> NAME/KEY: misc_feature
<222> LOCATION: (3)..(3)
<223> OTHER INFORMATION: 5-methyl modified
<220> FEATURE:
<221> NAME/KEY: misc_feature
<222> LOCATION: (5)..(9)
<223> OTHER INFORMATION: 5-methyl modified
<220> FEATURE:
<221> NAME/KEY: misc_feature
<222> LOCATION: (5)..(9)
<223> OTHER INFORMATION: 2'Fluoro modified
<220> FEATURE:
<221> NAME/KEY: misc_feature
<222> LOCATION: (11)..(11)
<223> OTHER INFORMATION: 2'Fluoro modified
<220> FEATURE:
<221> NAME/KEY: misc_feature
<222> LOCATION: (11)..(12)
<223> OTHER INFORMATION: 5-methyl modified
<220> FEATURE:
<221> NAME/KEY: misc_feature
<222> LOCATION: (12)..(15)
<223> OTHER INFORMATION: 2'OMe modified
<220> FEATURE:
<221> NAME/KEY: misc_feature
<222> LOCATION: (13)..(13)
<223> OTHER INFORMATION: Octyl modified
<220> FEATURE:
<221> NAME/KEY: misc_feature
<222> LOCATION: (14)..(15)
<223> OTHER INFORMATION: 5-methyl modified
<220> FEATURE:
<221> NAME/KEY: misc_feature
<222> LOCATION: (17)..(18)
<223> OTHER INFORMATION: 2'OMe modified
<220> FEATURE:
<221> NAME/KEY: misc_feature
<222> LOCATION: (17)..(19)
<223> OTHER INFORMATION: 5-methyl modified
<220> FEATURE:
<221> NAME/KEY: misc_feature
<222> LOCATION: (19)..(19)
<223> OTHER INFORMATION: 2'Fluoro modified
<220> FEATURE:
<221> NAME/KEY: misc_feature
<222> LOCATION: (20)..(21)
<223> OTHER INFORMATION: Phosphodiester linkage

<400> SEQUENCE: 105
uucauuucca ccuuugccca a                                            21

<210> SEQ ID NO 106
<211> LENGTH: 21
<212> TYPE: RNA
<213> ORGANISM: Artificial Sequence
<220> FEATURE:
<223> OTHER INFORMATION: Synthetic Polynucleotide
<220> FEATURE:
```

```
<221> NAME/KEY: misc_feature
<222> LOCATION: (1)..(1)
<223> OTHER INFORMATION: 5' Phosphate modified
<220> FEATURE:
<221> NAME/KEY: misc_feature
<222> LOCATION: (1)..(1)
<223> OTHER INFORMATION: 2'OMe modified
<220> FEATURE:
<221> NAME/KEY: misc_feature
<222> LOCATION: (1)..(1)
<223> OTHER INFORMATION: 5-methyl modified
<220> FEATURE:
<221> NAME/KEY: misc_feature
<222> LOCATION: (1)..(20)
<223> OTHER INFORMATION: Phosphorothioate linkage
<220> FEATURE:
<221> NAME/KEY: misc_feature
<222> LOCATION: (2)..(2)
<223> OTHER INFORMATION: Octyl modified
<220> FEATURE:
<221> NAME/KEY: misc_feature
<222> LOCATION: (2)..(3)
<223> OTHER INFORMATION: 2'Fluoro modified
<220> FEATURE:
<221> NAME/KEY: misc_feature
<222> LOCATION: (3)..(3)
<223> OTHER INFORMATION: 5-methyl modified
<220> FEATURE:
<221> NAME/KEY: misc_feature
<222> LOCATION: (5)..(6)
<223> OTHER INFORMATION: 5-methyl modified
<220> FEATURE:
<221> NAME/KEY: misc_feature
<222> LOCATION: (5)..(9)
<223> OTHER INFORMATION: 2'Fluoro modified
<220> FEATURE:
<221> NAME/KEY: misc_feature
<222> LOCATION: (7)..(7)
<223> OTHER INFORMATION: Octyl modified
<220> FEATURE:
<221> NAME/KEY: misc_feature
<222> LOCATION: (8)..(9)
<223> OTHER INFORMATION: 5-methyl modified
<220> FEATURE:
<221> NAME/KEY: misc_feature
<222> LOCATION: (11)..(11)
<223> OTHER INFORMATION: 2'Fluoro modified
<220> FEATURE:
<221> NAME/KEY: misc_feature
<222> LOCATION: (11)..(15)
<223> OTHER INFORMATION: 5-methyl modified
<220> FEATURE:
<221> NAME/KEY: misc_feature
<222> LOCATION: (12)..(15)
<223> OTHER INFORMATION: 2'OMe modified
<220> FEATURE:
<221> NAME/KEY: misc_feature
<222> LOCATION: (17)..(18)
<223> OTHER INFORMATION: 2'OMe modified
<220> FEATURE:
<221> NAME/KEY: misc_feature
<222> LOCATION: (17)..(19)
<223> OTHER INFORMATION: 5-methyl modified
<220> FEATURE:
<221> NAME/KEY: misc_feature
<222> LOCATION: (19)..(19)
<223> OTHER INFORMATION: 2'Fluoro modified
<220> FEATURE:
<221> NAME/KEY: misc_feature
<222> LOCATION: (20)..(21)
<223> OTHER INFORMATION: Phosphodiester linkage

<400> SEQUENCE: 106
uucauuucca ccuuugccca a                                      21

<210> SEQ ID NO 107
<211> LENGTH: 21
```

```
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: 5' Phosphate modified
<220> FEATURE:
<221> NAME/KEY: misc_feature
<222> LOCATION: (1)..(1)
<223> OTHER INFORMATION: 2'OMe modified
<220> FEATURE:
<221> NAME/KEY: misc_feature
<222> LOCATION: (1)..(3)
<223> OTHER INFORMATION: 5-methyl modified
<220> FEATURE:
<221> NAME/KEY: misc_feature
<222> LOCATION: (1)..(20)
<223> OTHER INFORMATION: Phosphorothioate linkage
<220> FEATURE:
<221> NAME/KEY: misc_feature
<222> LOCATION: (2)..(3)
<223> OTHER INFORMATION: 2'Fluoro modified
<220> FEATURE:
<221> NAME/KEY: misc_feature
<222> LOCATION: (5)..(9)
<223> OTHER INFORMATION: 5-methyl modified
<220> FEATURE:
<221> NAME/KEY: misc_feature
<222> LOCATION: (5)..(9)
<223> OTHER INFORMATION: 2'Fluoro modified
<220> FEATURE:
<221> NAME/KEY: misc_feature
<222> LOCATION: (11)..(11)
<223> OTHER INFORMATION: 2'Fluoro modified
<220> FEATURE:
<221> NAME/KEY: misc_feature
<222> LOCATION: (11)..(15)
<223> OTHER INFORMATION: 5-methyl modified
<220> FEATURE:
<221> NAME/KEY: misc_feature
<222> LOCATION: (12)..(15)
<223> OTHER INFORMATION: 2'OMe modified
<220> FEATURE:
<221> NAME/KEY: misc_feature
<222> LOCATION: (17)..(18)
<223> OTHER INFORMATION: 2'OMe modified
<220> FEATURE:
<221> NAME/KEY: misc_feature
<222> LOCATION: (17)..(19)
<223> OTHER INFORMATION: 5-methyl modified
<220> FEATURE:
<221> NAME/KEY: misc_feature
<222> LOCATION: (19)..(19)
<223> OTHER INFORMATION: 2'Fluoro modified
<220> FEATURE:
<221> NAME/KEY: misc_feature
<222> LOCATION: (20)..(21)
<223> OTHER INFORMATION: Phosphodiester linkage

<400> SEQUENCE: 107
uucauuucca ccuuugccca a                                               21

<210> SEQ ID NO 108
<211> LENGTH: 21
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: 5' Phosphate modified
<220> FEATURE:
<221> NAME/KEY: misc_feature
<222> LOCATION: (1)..(1)
```

```
<223> OTHER INFORMATION: 2'OMe modified
<220> FEATURE:
<221> NAME/KEY: misc_feature
<222> LOCATION: (1)..(20)
<223> OTHER INFORMATION: Phosphorothioate linkage
<220> FEATURE:
<221> NAME/KEY: misc_feature
<222> LOCATION: (2)..(3)
<223> OTHER INFORMATION: 2'Fluoro modified
<220> FEATURE:
<221> NAME/KEY: misc_feature
<222> LOCATION: (5)..(9)
<223> OTHER INFORMATION: 2'Fluoro modified
<220> FEATURE:
<221> NAME/KEY: misc_feature
<222> LOCATION: (11)..(11)
<223> OTHER INFORMATION: 2'Fluoro modified
<220> FEATURE:
<221> NAME/KEY: misc_feature
<222> LOCATION: (12)..(15)
<223> OTHER INFORMATION: 2'OMe modified
<220> FEATURE:
<221> NAME/KEY: misc_feature
<222> LOCATION: (17)..(18)
<223> OTHER INFORMATION: 2'OMe modified
<220> FEATURE:
<221> NAME/KEY: misc_feature
<222> LOCATION: (19)..(19)
<223> OTHER INFORMATION: 2'Fluoro modified
<220> FEATURE:
<221> NAME/KEY: misc_feature
<222> LOCATION: (20)..(21)
<223> OTHER INFORMATION: Phosphodiester linkage

<400> SEQUENCE: 108
uucauuucca ccuuugccca a                                      21

<210> SEQ ID NO 109
<211> LENGTH: 21
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: 5' Phosphate modified
<220> FEATURE:
<221> NAME/KEY: misc_feature
<222> LOCATION: (1)..(1)
<223> OTHER INFORMATION: 2'OMe modified
<220> FEATURE:
<221> NAME/KEY: misc_feature
<222> LOCATION: (1)..(20)
<223> OTHER INFORMATION: Phosphorothioate linkage
<220> FEATURE:
<221> NAME/KEY: misc_feature
<222> LOCATION: (2)..(3)
<223> OTHER INFORMATION: 2'Fluoro modified
<220> FEATURE:
<221> NAME/KEY: misc_feature
<222> LOCATION: (5)..(9)
<223> OTHER INFORMATION: 2'Fluoro modified
<220> FEATURE:
<221> NAME/KEY: misc_feature
<222> LOCATION: (11)..(11)
<223> OTHER INFORMATION: 2'Fluoro modified
<220> FEATURE:
<221> NAME/KEY: misc_feature
<222> LOCATION: (12)..(15)
<223> OTHER INFORMATION: 2'OMe modified
<220> FEATURE:
<221> NAME/KEY: misc_feature
<222> LOCATION: (17)..(18)
<223> OTHER INFORMATION: 2'OMe modified
<220> FEATURE:
<221> NAME/KEY: misc_feature
```

```
<222> LOCATION: (19)..(19)
<223> OTHER INFORMATION: 2'Fluoro modified
<220> FEATURE:
<221> NAME/KEY: misc_feature
<222> LOCATION: (20)..(21)
<223> OTHER INFORMATION: Phosphodiester linkage

<400> SEQUENCE: 109
uucauuucca ccuuugccca a                                              21

<210> SEQ ID NO 110
<211> LENGTH: 21
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: 5' Phosphate modified
<220> FEATURE:
<221> NAME/KEY: misc_feature
<222> LOCATION: (1)..(1)
<223> OTHER INFORMATION: 2'OMe modified
<220> FEATURE:
<221> NAME/KEY: misc_feature
<222> LOCATION: (1)..(20)
<223> OTHER INFORMATION: Phosphorothioate linkage
<220> FEATURE:
<221> NAME/KEY: misc_feature
<222> LOCATION: (2)..(3)
<223> OTHER INFORMATION: 2'Fluoro modified
<220> FEATURE:
<221> NAME/KEY: misc_feature
<222> LOCATION: (5)..(9)
<223> OTHER INFORMATION: 2'Fluoro modified
<220> FEATURE:
<221> NAME/KEY: misc_feature
<222> LOCATION: (11)..(11)
<223> OTHER INFORMATION: 2'Fluoro modified
<220> FEATURE:
<221> NAME/KEY: misc_feature
<222> LOCATION: (12)..(15)
<223> OTHER INFORMATION: 2'OMe modified
<220> FEATURE:
<221> NAME/KEY: misc_feature
<222> LOCATION: (17)..(18)
<223> OTHER INFORMATION: 2'OMe modified
<220> FEATURE:
<221> NAME/KEY: misc_feature
<222> LOCATION: (19)..(19)
<223> OTHER INFORMATION: 2'Fluoro modified
<220> FEATURE:
<221> NAME/KEY: misc_feature
<222> LOCATION: (20)..(21)
<223> OTHER INFORMATION: Phosphodiester linkage

<400> SEQUENCE: 110
uucauuucca ccuuugccca a                                              21

<210> SEQ ID NO 111
<211> LENGTH: 21
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: 5' Phosphate modified
<220> FEATURE:
<221> NAME/KEY: misc_feature
<222> LOCATION: (1)..(1)
<223> OTHER INFORMATION: 2'OMe modified
<220> FEATURE:
```

```
<221> NAME/KEY: misc_feature
<222> LOCATION: (1)..(1)
<223> OTHER INFORMATION: 5-methyl modified
<220> FEATURE:
<221> NAME/KEY: misc_feature
<222> LOCATION: (1)..(20)
<223> OTHER INFORMATION: Phosphorothioate linkage
<220> FEATURE:
<221> NAME/KEY: misc_feature
<222> LOCATION: (2)..(2)
<223> OTHER INFORMATION: Thiophene modified
<220> FEATURE:
<221> NAME/KEY: misc_feature
<222> LOCATION: (2)..(3)
<223> OTHER INFORMATION: 2'Fluoro modified
<220> FEATURE:
<221> NAME/KEY: misc_feature
<222> LOCATION: (3)..(3)
<223> OTHER INFORMATION: 5-methyl modified
<220> FEATURE:
<221> NAME/KEY: misc_feature
<222> LOCATION: (5)..(6)
<223> OTHER INFORMATION: 5-methyl modified
<220> FEATURE:
<221> NAME/KEY: misc_feature
<222> LOCATION: (5)..(9)
<223> OTHER INFORMATION: 2'Fluoro modified
<220> FEATURE:
<221> NAME/KEY: misc_feature
<222> LOCATION: (7)..(7)
<223> OTHER INFORMATION: Thiophene modified
<220> FEATURE:
<221> NAME/KEY: misc_feature
<222> LOCATION: (8)..(9)
<223> OTHER INFORMATION: 5-methyl modified
<220> FEATURE:
<221> NAME/KEY: misc_feature
<222> LOCATION: (11)..(11)
<223> OTHER INFORMATION: 2'Fluoro modified
<220> FEATURE:
<221> NAME/KEY: misc_feature
<222> LOCATION: (11)..(15)
<223> OTHER INFORMATION: 5-methyl modified
<220> FEATURE:
<221> NAME/KEY: misc_feature
<222> LOCATION: (12)..(15)
<223> OTHER INFORMATION: 2'OMe modified
<220> FEATURE:
<221> NAME/KEY: misc_feature
<222> LOCATION: (17)..(18)
<223> OTHER INFORMATION: 2'OMe modified
<220> FEATURE:
<221> NAME/KEY: misc_feature
<222> LOCATION: (17)..(19)
<223> OTHER INFORMATION: 5-methyl modified
<220> FEATURE:
<221> NAME/KEY: misc_feature
<222> LOCATION: (19)..(19)
<223> OTHER INFORMATION: 2'Fluoro modified
<220> FEATURE:
<221> NAME/KEY: misc_feature
<222> LOCATION: (20)..(21)
<223> OTHER INFORMATION: Phosphodiester linkage

<400> SEQUENCE: 111
uucauuucca ccuuugccca a                                            21

<210> SEQ ID NO 112
<211> LENGTH: 21
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: 5' Phosphate modified
```

```
<220> FEATURE:
<221> NAME/KEY: misc_feature
<222> LOCATION: (1)..(1)
<223> OTHER INFORMATION: 2'OMe modified
<220> FEATURE:
<221> NAME/KEY: misc_feature
<222> LOCATION: (1)..(3)
<223> OTHER INFORMATION: 5-methyl modified
<220> FEATURE:
<221> NAME/KEY: misc_feature
<222> LOCATION: (1)..(20)
<223> OTHER INFORMATION: Phosphorothioate linkage
<220> FEATURE:
<221> NAME/KEY: misc_feature
<222> LOCATION: (2)..(3)
<223> OTHER INFORMATION: 2'Fluoro modified
<220> FEATURE:
<221> NAME/KEY: misc_feature
<222> LOCATION: (5)..(9)
<223> OTHER INFORMATION: 5-methyl modified
<220> FEATURE:
<221> NAME/KEY: misc_feature
<222> LOCATION: (5)..(9)
<223> OTHER INFORMATION: 2'Fluoro modified
<220> FEATURE:
<221> NAME/KEY: misc_feature
<222> LOCATION: (11)..(11)
<223> OTHER INFORMATION: 2'Fluoro modified
<220> FEATURE:
<221> NAME/KEY: misc_feature
<222> LOCATION: (11)..(15)
<223> OTHER INFORMATION: 5-methyl modified
<220> FEATURE:
<221> NAME/KEY: misc_feature
<222> LOCATION: (12)..(15)
<223> OTHER INFORMATION: 2'OMe modified
<220> FEATURE:
<221> NAME/KEY: misc_feature
<222> LOCATION: (17)..(18)
<223> OTHER INFORMATION: 2'OMe modified
<220> FEATURE:
<221> NAME/KEY: misc_feature
<222> LOCATION: (17)..(19)
<223> OTHER INFORMATION: 5-methyl modified
<220> FEATURE:
<221> NAME/KEY: misc_feature
<222> LOCATION: (19)..(19)
<223> OTHER INFORMATION: 2'Fluoro modified
<220> FEATURE:
<221> NAME/KEY: misc_feature
<222> LOCATION: (20)..(21)
<223> OTHER INFORMATION: Phosphodiester linkage

<400> SEQUENCE: 112
uucauuucca ccuuugccca a                                              21

<210> SEQ ID NO 113
<211> LENGTH: 21
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: 5' Phosphate modified
<220> FEATURE:
<221> NAME/KEY: misc_feature
<222> LOCATION: (1)..(1)
<223> OTHER INFORMATION: 2'OMe modified
<220> FEATURE:
<221> NAME/KEY: misc_feature
<222> LOCATION: (1)..(20)
<223> OTHER INFORMATION: Phosphorothioate linkage
<220> FEATURE:
<221> NAME/KEY: misc_feature
<222> LOCATION: (2)..(3)
```

```
<223> OTHER INFORMATION: 2'Fluoro modified
<220> FEATURE:
<221> NAME/KEY: misc_feature
<222> LOCATION: (5)..(9)
<223> OTHER INFORMATION: 2'Fluoro modified
<220> FEATURE:
<221> NAME/KEY: misc_feature
<222> LOCATION: (11)..(11)
<223> OTHER INFORMATION: 2'Fluoro modified
<220> FEATURE:
<221> NAME/KEY: misc_feature
<222> LOCATION: (12)..(15)
<223> OTHER INFORMATION: 2'OMe modified
<220> FEATURE:
<221> NAME/KEY: misc_feature
<222> LOCATION: (17)..(18)
<223> OTHER INFORMATION: 2'OMe modified
<220> FEATURE:
<221> NAME/KEY: misc_feature
<222> LOCATION: (19)..(19)
<223> OTHER INFORMATION: 2'Fluoro modified
<220> FEATURE:
<221> NAME/KEY: misc_feature
<222> LOCATION: (20)..(21)
<223> OTHER INFORMATION: Phosphodiester linkage

<400> SEQUENCE: 113
uucauuucca ccuuugccca a                                              21

<210> SEQ ID NO 114
<211> LENGTH: 21
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: 5' Phosphate modified
<220> FEATURE:
<221> NAME/KEY: misc_feature
<222> LOCATION: (1)..(1)
<223> OTHER INFORMATION: 2'OMe modified
<220> FEATURE:
<221> NAME/KEY: misc_feature
<222> LOCATION: (1)..(20)
<223> OTHER INFORMATION: Phosphorothioate linkage
<220> FEATURE:
<221> NAME/KEY: misc_feature
<222> LOCATION: (2)..(3)
<223> OTHER INFORMATION: 2'Fluoro modified
<220> FEATURE:
<221> NAME/KEY: misc_feature
<222> LOCATION: (5)..(9)
<223> OTHER INFORMATION: 2'Fluoro modified
<220> FEATURE:
<221> NAME/KEY: misc_feature
<222> LOCATION: (11)..(11)
<223> OTHER INFORMATION: 2'Fluoro modified
<220> FEATURE:
<221> NAME/KEY: misc_feature
<222> LOCATION: (12)..(15)
<223> OTHER INFORMATION: 2'OMe modified
<220> FEATURE:
<221> NAME/KEY: misc_feature
<222> LOCATION: (17)..(18)
<223> OTHER INFORMATION: 2'OMe modified
<220> FEATURE:
<221> NAME/KEY: misc_feature
<222> LOCATION: (19)..(19)
<223> OTHER INFORMATION: 2'Fluoro modified
<220> FEATURE:
<221> NAME/KEY: misc_feature
<222> LOCATION: (20)..(21)
<223> OTHER INFORMATION: Phosphodiester linkage

<400> SEQUENCE: 114
```
uucauuucca ccuuugccca a					21

<210> SEQ ID NO 115
<211> LENGTH: 21
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: 5' Phosphate modified
<220> FEATURE:
<221> NAME/KEY: misc_feature
<222> LOCATION: (1)..(1)
<223> OTHER INFORMATION: 2'OMe modified
<220> FEATURE:
<221> NAME/KEY: misc_feature
<222> LOCATION: (1)..(20)
<223> OTHER INFORMATION: Phosphorothioate linkage
<220> FEATURE:
<221> NAME/KEY: misc_feature
<222> LOCATION: (2)..(3)
<223> OTHER INFORMATION: 2'Fluoro modified
<220> FEATURE:
<221> NAME/KEY: misc_feature
<222> LOCATION: (5)..(9)
<223> OTHER INFORMATION: 2'Fluoro modified
<220> FEATURE:
<221> NAME/KEY: misc_feature
<222> LOCATION: (11)..(11)
<223> OTHER INFORMATION: 2'Fluoro modified
<220> FEATURE:
<221> NAME/KEY: misc_feature
<222> LOCATION: (12)..(15)
<223> OTHER INFORMATION: 2'OMe modified
<220> FEATURE:
<221> NAME/KEY: misc_feature
<222> LOCATION: (17)..(18)
<223> OTHER INFORMATION: 2'OMe modified
<220> FEATURE:
<221> NAME/KEY: misc_feature
<222> LOCATION: (19)..(19)
<223> OTHER INFORMATION: 2'Fluoro modified
<220> FEATURE:
<221> NAME/KEY: misc_feature
<222> LOCATION: (20)..(21)
<223> OTHER INFORMATION: Phosphodiester linkage

<400> SEQUENCE: 115
uucauuucca ccuuugccca a					21

<210> SEQ ID NO 116
<211> LENGTH: 21
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: 5-methyl modified
<220> FEATURE:
<221> NAME/KEY: misc_feature
<222> LOCATION: (1)..(1)
<223> OTHER INFORMATION: 5' Phosphate modified
<220> FEATURE:
<221> NAME/KEY: misc_feature
<222> LOCATION: (1)..(1)
<223> OTHER INFORMATION: 2'OMe modified
<220> FEATURE:
<221> NAME/KEY: misc_feature
<222> LOCATION: (1)..(20)
<223> OTHER INFORMATION: Phosphorothioate linkage
<220> FEATURE:

```
<221> NAME/KEY: misc_feature
<222> LOCATION: (2)..(2)
<223> OTHER INFORMATION: Isobutyl modified
<220> FEATURE:
<221> NAME/KEY: misc_feature
<222> LOCATION: (2)..(2)
<223> OTHER INFORMATION: Deoxyribose modified
<220> FEATURE:
<221> NAME/KEY: misc_feature
<222> LOCATION: (2)..(3)
<223> OTHER INFORMATION: 2'Fluoro modified
<220> FEATURE:
<221> NAME/KEY: misc_feature
<222> LOCATION: (3)..(3)
<223> OTHER INFORMATION: 5-methyl modified
<220> FEATURE:
<221> NAME/KEY: misc_feature
<222> LOCATION: (5)..(6)
<223> OTHER INFORMATION: 5-methyl modified
<220> FEATURE:
<221> NAME/KEY: misc_feature
<222> LOCATION: (5)..(9)
<223> OTHER INFORMATION: 2'Fluoro modified
<220> FEATURE:
<221> NAME/KEY: misc_feature
<222> LOCATION: (7)..(7)
<223> OTHER INFORMATION: Isobutyl modified
<220> FEATURE:
<221> NAME/KEY: misc_feature
<222> LOCATION: (7)..(7)
<223> OTHER INFORMATION: Deoxyribose modified
<220> FEATURE:
<221> NAME/KEY: misc_feature
<222> LOCATION: (8)..(9)
<223> OTHER INFORMATION: 5-methyl modified
<220> FEATURE:
<221> NAME/KEY: misc_feature
<222> LOCATION: (11)..(11)
<223> OTHER INFORMATION: 2'Fluoro modified
<220> FEATURE:
<221> NAME/KEY: misc_feature
<222> LOCATION: (11)..(12)
<223> OTHER INFORMATION: 5-methyl modified
<220> FEATURE:
<221> NAME/KEY: misc_feature
<222> LOCATION: (12)..(15)
<223> OTHER INFORMATION: 2'OMe modified
<220> FEATURE:
<221> NAME/KEY: misc_feature
<222> LOCATION: (13)..(13)
<223> OTHER INFORMATION: Isobutyl modified
<220> FEATURE:
<221> NAME/KEY: misc_feature
<222> LOCATION: (13)..(13)
<223> OTHER INFORMATION: Deoxyribose modified
<220> FEATURE:
<221> NAME/KEY: misc_feature
<222> LOCATION: (14)..(15)
<223> OTHER INFORMATION: 5-methyl modified
<220> FEATURE:
<221> NAME/KEY: misc_feature
<222> LOCATION: (17)..(18)
<223> OTHER INFORMATION: 2'OMe modified
<220> FEATURE:
<221> NAME/KEY: misc_feature
<222> LOCATION: (17)..(19)
<223> OTHER INFORMATION: 5-methyl modified
<220> FEATURE:
<221> NAME/KEY: misc_feature
<222> LOCATION: (19)..(19)
<223> OTHER INFORMATION: 2'Fluoro modified
<220> FEATURE:
<221> NAME/KEY: misc_feature
<222> LOCATION: (20)..(21)
<223> OTHER INFORMATION: Phosphodiester linkage

<400> SEQUENCE: 116
uucauuucca ccuuugccca a                                        21
```

```
<210> SEQ ID NO 117
<211> LENGTH: 21
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: 5' Phosphate modified
<220> FEATURE:
<221> NAME/KEY: misc_feature
<222> LOCATION: (1)..(1)
<223> OTHER INFORMATION: 2'OMe modified
<220> FEATURE:
<221> NAME/KEY: misc_feature
<222> LOCATION: (1)..(2)
<223> OTHER INFORMATION: 5-methyl modified
<220> FEATURE:
<221> NAME/KEY: misc_feature
<222> LOCATION: (1)..(20)
<223> OTHER INFORMATION: Phosphorothioate linkage
<220> FEATURE:
<221> NAME/KEY: misc_feature
<222> LOCATION: (2)..(3)
<223> OTHER INFORMATION: 2'Fluoro modified
<220> FEATURE:
<221> NAME/KEY: misc_feature
<222> LOCATION: (3)..(3)
<223> OTHER INFORMATION: Octyl modified
<220> FEATURE:
<221> NAME/KEY: misc_feature
<222> LOCATION: (5)..(6)
<223> OTHER INFORMATION: 5-methyl modified
<220> FEATURE:
<221> NAME/KEY: misc_feature
<222> LOCATION: (5)..(9)
<223> OTHER INFORMATION: 2'Fluoro modified
<220> FEATURE:
<221> NAME/KEY: misc_feature
<222> LOCATION: (7)..(7)
<223> OTHER INFORMATION: Isobutyl modified
<220> FEATURE:
<221> NAME/KEY: misc_feature
<222> LOCATION: (7)..(7)
<223> OTHER INFORMATION: Deoxyribose modified
<220> FEATURE:
<221> NAME/KEY: misc_feature
<222> LOCATION: (8)..(9)
<223> OTHER INFORMATION: 5-methyl modified
<220> FEATURE:
<221> NAME/KEY: misc_feature
<222> LOCATION: (11)..(11)
<223> OTHER INFORMATION: 2'Fluoro modified
<220> FEATURE:
<221> NAME/KEY: misc_feature
<222> LOCATION: (11)..(12)
<223> OTHER INFORMATION: 5-methyl modified
<220> FEATURE:
<221> NAME/KEY: misc_feature
<222> LOCATION: (12)..(15)
<223> OTHER INFORMATION: 2'OMe modified
<220> FEATURE:
<221> NAME/KEY: misc_feature
<222> LOCATION: (13)..(13)
<223> OTHER INFORMATION: Isobutyl modified
<220> FEATURE:
<221> NAME/KEY: misc_feature
<222> LOCATION: (13)..(13)
<223> OTHER INFORMATION: Deoxyribose modified
<220> FEATURE:
<221> NAME/KEY: misc_feature
<222> LOCATION: (14)..(15)
<223> OTHER INFORMATION: 5-methyl modified
<220> FEATURE:
<221> NAME/KEY: misc_feature
<222> LOCATION: (17)..(18)
```

<223> OTHER INFORMATION: 2'OMe modified
<220> FEATURE:
<221> NAME/KEY: misc_feature
<222> LOCATION: (17)..(19)
<223> OTHER INFORMATION: 5-methyl modified
<220> FEATURE:
<221> NAME/KEY: misc_feature
<222> LOCATION: (19)..(19)
<223> OTHER INFORMATION: 2'Fluoro modified
<220> FEATURE:
<221> NAME/KEY: misc_feature
<222> LOCATION: (20)..(21)
<223> OTHER INFORMATION: Phosphodiester linkage

<400> SEQUENCE: 117
uucauuucca ccuuugccca a                                               21

<210> SEQ ID NO 118
<211> LENGTH: 21
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: 5' Phosphate modified
<220> FEATURE:
<221> NAME/KEY: misc_feature
<222> LOCATION: (1)..(1)
<223> OTHER INFORMATION: 2'OMe modified
<220> FEATURE:
<221> NAME/KEY: misc_feature
<222> LOCATION: (1)..(20)
<223> OTHER INFORMATION: Phosphorothioate linkage
<220> FEATURE:
<221> NAME/KEY: misc_feature
<222> LOCATION: (2)..(3)
<223> OTHER INFORMATION: 2'Fluoro modified
<220> FEATURE:
<221> NAME/KEY: misc_feature
<222> LOCATION: (5)..(9)
<223> OTHER INFORMATION: 2'Fluoro modified
<220> FEATURE:
<221> NAME/KEY: misc_feature
<222> LOCATION: (11)..(11)
<223> OTHER INFORMATION: 2'Fluoro modified
<220> FEATURE:
<221> NAME/KEY: misc_feature
<222> LOCATION: (12)..(15)
<223> OTHER INFORMATION: 2'OMe modified
<220> FEATURE:
<221> NAME/KEY: misc_feature
<222> LOCATION: (17)..(18)
<223> OTHER INFORMATION: 2'OMe modified
<220> FEATURE:
<221> NAME/KEY: misc_feature
<222> LOCATION: (19)..(19)
<223> OTHER INFORMATION: 2'Fluoro modified
<220> FEATURE:
<221> NAME/KEY: misc_feature
<222> LOCATION: (20)..(21)
<223> OTHER INFORMATION: Phosphodiester linkage

<400> SEQUENCE: 118
uucauuucca ccuuugccca a                                               21

<210> SEQ ID NO 119
<211> LENGTH: 981
<212> TYPE: DNA
<213> ORGANISM: Homo sapiens

<400> SEQUENCE: 119
gtttggggcc agagtgggcg aggcgcggag gtctggccta taaagtagtc gcggagacgg     60

-continued

```
ggtgctggtt tgcgtcgtag tctcctgcag cgtctggggt ttccgttgca gtcctcggaa      120
ccaggacctc ggcgtggcct agcgagttat ggcgacgaag gccgtgtgcg tgctgaaggg      180
cgacggccca gtgcagggca tcatcaattt cgagcagaag gaaagtaatg gaccagtgaa      240
ggtgtgggga agcattaaag gactgactga aggcctgcat ggattccatg ttcatgagtt      300
tggagataat acagcaggct gtaccagtgc aggtcctcac tttaatcctc tatccagaaa      360
acacggtggg ccaaaggatg aagagaggca tgttggagac ttgggcaatg tgactgctga      420
caaagatggt gtggccgatg tgtctattga agattctgtg atctcactct caggagacca      480
ttgcatcatt ggccgcacac tggtggtcca tgaaaaagca gatgacttgg gcaaaggtgg      540
aaatgaagaa agtacaaaga caggaaacgc tggaagtcgt ttggcttgtg gtgtaattgg      600
gatcgcccaa taaacattcc cttggatgta gtctgaggcc ccttaactca tctgttatcc      660
tgctagctgt agaaatgtat cctgataaac attaaacact gtaatcttaa aagtgtaatt      720
gtgtgacttt ttcagagttg cttaaagta cctgtagtga gaaactgatt tatgatcact      780
tggaagattt gtatagtttt ataaaactca gttaaaatgt ctgtttcaat gacctgtatt      840
ttgccagact taaatcacag atgggtatta aacttgtcag aatttctttg tcattcaagc      900
ctgtgaataa aaaccctgta tggcacttat tatgaggcta ttaaaagaat ccaaattcaa      960
actaaaaaaa aaaaaaaaa a                                                  981
```